(12) United States Patent
Duan et al.

(10) Patent No.: US 12,337,040 B2
(45) Date of Patent: Jun. 24, 2025

(54) DYSTROPHIN R16/R17 SYNTROPHIN PDZ FUSION PROTEINS

(71) Applicant: THE CURATORS OF THE UNIVERSITY OF MISSOURI, Columbia, MO (US)

(72) Inventors: Dongsheng Duan, Columbia, MO (US); Yi Lai, Columbia, MO (US); Junling Zhao, Columbia, MO (US); Yongping Yue, Columbia, MO (US)

(73) Assignee: THE CURATORS OF THE UNIVERSITY OF MISSOURI, Columbia, MO (US)

(*) Notice: Subject to any disclaimer, the term of this patent is extended or adjusted under 35 U.S.C. 154(b) by 756 days.

(21) Appl. No.: 17/555,233

(22) Filed: Dec. 17, 2021

(65) Prior Publication Data

US 2022/0175964 A1   Jun. 9, 2022

Related U.S. Application Data

(63) Continuation of application No. 16/311,236, filed as application No. PCT/US2017/038418 on Jun. 21, 2017, now Pat. No. 11,202,840.

(60) Provisional application No. 62/367,559, filed on Jul. 27, 2016, provisional application No. 62/357,865, filed on Jul. 1, 2016, provisional application No. 62/352,927, filed on Jun. 21, 2016.

(51) Int. Cl.
| | |
|---|---|
| *A61K 48/00* | (2006.01) |
| *A61K 9/00* | (2006.01) |
| *A61K 35/00* | (2006.01) |
| *A61K 35/28* | (2015.01) |
| *A61K 38/00* | (2006.01) |
| *A61P 25/14* | (2006.01) |
| *C07K 14/47* | (2006.01) |
| *C12N 5/0775* | (2010.01) |
| *C12N 15/62* | (2006.01) |
| *C12N 15/85* | (2006.01) |
| *C12N 15/86* | (2006.01) |

(52) U.S. Cl.
CPC .......... *A61K 48/005* (2013.01); *A61K 9/0019* (2013.01); *A61K 35/28* (2013.01); *A61K 48/00* (2013.01); *A61P 25/14* (2018.01); *C07K 14/4716* (2013.01); *C12N 5/0663* (2013.01); *C12N 15/62* (2013.01); *C12N 15/85* (2013.01); *C12N 15/86* (2013.01); *A61K 35/00* (2013.01); *A61K 38/00* (2013.01); *C07K 2319/00* (2013.01); *C07K 2319/01* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,580,859 A | 12/1996 | Felgner et al. | |
| 11,202,840 B2 * | 12/2021 | Duan ................ | C12N 15/62 |
| 2004/0033604 A1 | 2/2004 | Kobinger et al. | |
| 2007/0042462 A1 | 2/2007 | Hildinger | |
| 2008/0044393 A1 | 2/2008 | White et al. | |
| 2008/0249052 A1 | 10/2008 | Duan et al. | |
| 2014/0140969 A1 | 5/2014 | Beausejour et al. | |
| 2014/0234255 A1 | 8/2014 | Lai et al. | |
| 2016/0115488 A1 | 4/2016 | Zhang et al. | |
| 2016/0153004 A1 | 6/2016 | Zhang et al. | |
| 2016/0175462 A1 | 6/2016 | Zhang et al. | |

OTHER PUBLICATIONS

Duan, et al. (2021) "Primer: Duchenne muscular dystrophy", Nature Reviews, 7:13. (Year: 2021).*
Tidball, et al. (2014) "Nitric oxide synthase deficiency and the pathophysiology of muscular dystrophy", Journal of Physiology, DOI: 10.1113/jphysiol,2014,274878, pp. 4627-4638. (Year: 2014).*
Banks et al., "Functional capacity of dystrophins carrying deletions in the N-terminal actin-binding domain", Human Molecular Genetics, 2007, pp. 2105-2113, vol. 16, No. 17.
Boehler et al., "Clinical potential of microdystrophin as a surrogate endpoint", Neuromuscular Disorders, 2023, pp. 40-49, vol. 33.
Duan, "Systemic AAV Micro-dystrophin Gene Therapy for Duchenne Muscular Dystrophy", Molecular Therapy, Oct. 2018, pp. 2337-2356, vol. 26, No. 10.
Fabb et al., "Adeno-associated virus vector gene transfer and sarcolemmal expression of a 144 kDa micro-dystrophin effectively restores the dystrophin-associated protein complex and inhibits myofibre degeneration in nude/mdx mice", Human Molecular Genetics, 2002, pp. 733-741, vol. 11, No. 7.
Foster et al., "Codon and mRNA Sequence Optimization of Microdystrophin Transgenes Improves Expression and Physiological Outcome in Dystrophic mdx Mice Following AAV2/8 Gene Transfer", Molecular Therapy, Nov. 2008, pp. 1825-1832, vol. 16, No. 11.
Hakim et al., "A Five-Repeat Micro-Dystrophin Gene Ameliorated Dystrophic Phenotype in the Severe DBA/2J-mdx Model of Duchenne Muscular Dystrophy", Molecular Therapy: Methods & Clinical Development, 2017, pp. 216-230, vol. 6.

(Continued)

*Primary Examiner* — Robert M Kelly
(74) *Attorney, Agent, or Firm* — Thompson Coburn LLP; William A. J. Holtz D.

(57) ABSTRACT

Synthetic nucleic acids encoding mini and microdystrophin genes comprising the membrane binding motifs or domains of the R10-R11-R12 region are provided. Also provided are vectors, host cells, and related methods of using the same to treat a subject suffering from Duchenne muscular dystrophy (DMD), Becker muscular dystrophy (BMD) or X-linked dilated cardiomyopathy (XLDC), or for ameliorating one or more adverse effects of DMD, BMD, or XLDC. Also provided are a fusion protein comprising a nNOS binding domain of dystrophin R16-R17 that is operably linked to a syntrophin PDZ domain and synthetic nucleic acids comprising the same that can be used to treat subjects with diseases characterized by loss of sarcolemmal neuronal nitric oxide synthase (nNOS) activity.

20 Claims, 28 Drawing Sheets

Specification includes a Sequence Listing.

(56) References Cited

OTHER PUBLICATIONS

JØrgensen et al., "Efficient and Fast Functional Screening of Microdystrophin Constructs In Vivo and In Vitro for Therapy of Duchenne Muscular Dystrophy", Human Gene Therapy, Jun. 2009, pp. 641-650, vol. 20.
Koo et al., "Delivery of AAV2/9-Microdystrophin Genes Incorporating Helix 1 of the Coiled-Coil Motif in the C-Terminal Domain of Dystrophin Improves Muscle Pathology and Restores the Level of a1-Syntrophin and a-Dystrobrevin in Skeletal Muscles of mdx Mice", Human Gene Therapy, Nov. 2011, pp. 1379-1388, vol. 22.
Sakamoto et al., "Micro-dystrophin cDNA ameliorates dystrophic phenotypes when introduced into mdx mice as a transgene", Biochemical and Biophysical Research Communications, 2002, pp. 1265-1272, vol. 293.
Shin et al., "Improvement of cardiac fibrosis in dystrophic mice by rAAV9-mediated microdystrophin transduction", Gene Therapy, 2011, pp. 910-919, vol. 18, No. 9.
Yoshimura et al., "AAV Vector-Mediated Microdystrophin Expression in a Relatively Small Percentage of mdx Myofibers Improved the mdx Phenotype", Molecular Therapy, Nov. 2004, pp. 821-828, vol. 10, No. 5.
Yuasa et al., "Effective restoration of dystrophin-associated proteins in vivo by adenovirus-mediated transfer of truncated dystrophin cDNAs", FEBS Letters, 1998, pp. 329-336, vol. 425.
"Sequence 137006 from Patent EP1716227", Database EPO Proteins [Online], Oct. 11, 2013, XP002810809, retrieved from EBI accession No. EP0P:JB557990.
Legardinier et al., "Mapping of the Lipid-Binding and Stability Properties of the Central Rod Domain of Human Dystrophin", Journal of Molecular Biology, 2009, pp. 546-558, vol. 389.
Legardinier et al., "Sub-Domains of the Dystrophin Rod Domain Display Contrasting Lipid-Binding and Stability Properties", Biochimica et Biophysica Acta, 2008, pp. 672-682, vol. 1784.
Levitt et al., "Definition of an Efficient Synthetic Poly(A) Site", Genes & Development, 1989, pp. 1019-1025, vol. 3.
Li et al., "A highly functional mini-dystrophin/GFP fusion gene for cell and gene therapy studies of Duchenne muscular dystrophy", Human Molecular Genetics, 2006, pp. 1610-1622, vol. 15, No. 10.
Liadaki et al., "Co-Detection of GFP and Dystrophin in Skeletal Muscle Tissue Sections", Bio Techniques, 2007, pp. 699-700, vol. 42, No. 6.
Linder et al., "Palmitoylation: Policing Protein Stability and Traffic", Nature Reviews Molecular Cell Biology, 2007, pp. 74-78, vol. 8, No. 1.
Liu et al., "Adeno-Associated Virus-Mediated Microdystrophin Expression Protects Young mdx Muscle from Contraction-Induced Injury", Mol Ther., 2005, pp. 245-256, vol. 11, No. 2.
Luna et al., "Cytoskeleton-Plasma Membrane Interactions", Science, 1992, pp. 955-964, vol. 258, No. 5084.
Maconochie et al., "The Cysteine-Rich and C-Terminal Domains of Dystrophin are not Required for Normal Costameric Localization in the Mouse", Transgenic Research, 1996, pp. 123-130, vol. 5.
Mariani et al., "A Tightly Membrane-Associated Subpopulation of Spectrin Is $^3$H-Palmitoylated", The Journal of Biological Chemistry, 1993, pp. 12996-13001, vol. 268, No. 17.
Mendell et al., "Dystrophin Immunity in Duchenne's Muscular Dystrophy", The New England Journal of Medicine, 2010, pp. 1429-1437, vol. 363, No. 15.
Odom et al., "Gene Therapy of mdx Mice with Large Truncated Dystrophins Generated by Recombination Using rAAV6", Molecular Therapy, 2011, pp. 36-45, vol. 19, No. 1.
Oku et al., "In Silico Screening for Palmitoyl Substrates Reveals a Role for DHHC1/3/10 (zDHHC1/3/11)-Mediated Neurochondrin Palmitoylation in Its Targeting to Rab5-Positive Endosomes", The Journal of Biological Chemistry, 2013, pp. 19816-19829, vol. 299, No. 27.

Petrof et al., "Dystrophin Protects the Sarcolemma from Stresses Developed During Muscle Contraction", Proc. Natl. Acad. Sci. USA, 1993, pp. 3710-3714, vol. 90.
Prior et al., "Spectrum of Small Mutations in the Dystrophin Coding Region", Am. J. Hum. Genet., 1995, pp. 22-33, vol. 57.
Rafael et al., "Forced Expression of Dystrophin Deletion Constructs Reveals Structure-Function Correlations", The Journal of Cell Biology, 1996, pp. 93-102, vol. 134, No. 1.
Rapaport et al., "Dp71, the Nonmuscle product of the Duchenne Musuclar Dystrophy Gene is Associated with the Cell Membrane", FEBS Letters, 1993, pp. 197-202, vol. 328, No. 12.
Recan et al., "Are Cysteine-Rich and COOH-Terminal Domains of Dystrophin Cirical for Sarcolemmal Localization?", J. Clin. Invest., 1992, pp. 712-716, vol. 89.
Ren et al., "CSS-Palm 2.0: An Updated Software for Palmitoylation Sites Prediction", Protein Engineering, Design & Selection, 2008, pp. 639-644, vol. 21, No. 11.
Rumeur et al., "Binding of the Dystrophin Second Repeat to Membrane Di-Oleyl Phospholipids is Dependent Upon Lipid Packing", Biochimica et Biophysica Acta, 2007, pp. 648-654, vol. 1768.
Rumeur et al., "Dystrophin: More Than Just the Sum of its Parts", Biochimica et Biophysica Acta, 2010, pp. 1713-1722, vol. 1804, No. 9.
Rumeur et al., "Interaction of Dystrophin Rod Domain with Membrane Phospholipids", The Journal of Biological Chemistry, 2003, pp. 5993-6001, vol. 278, No. 8.
Rybakova et al., "A New Model for the Interaction of Dystrophin with F-Actin", The Journal of Cell Biology, 1996, pp. 661-672, vol. 135, No. 3.
Sadoulet-Puccio et al., "Dystrobrevin and Dystrophin: An Interaction Through Coiled-Coil Motifs", Proc. Natl. Acad. Sci. USA, 1997, pp. 12413-12418, vol. 94.
Sarkis et al., "Resisting Sarcolemmal Rupture: Dystrophin Repeats Increase Membrane-Actin Stiffness", The FASEB Journal, 2013, pp. 359-367, vol. 27.
Sarkis et al., "Spectrin-Like Repeats 11-15 of Human Dystrophin Show Adaptations to a Lipidic Envrionment", The Journal of Biological Chemistry, 2011, pp. 30481-30491, vol. 286, No. 35.
Sheetz et al., "Continuous Membrane-Cytoskeleton Adhesion Requires Continuous Accommodation to Lipid and Cytoskeleton Dynamics", Annu. Rev. Biophys. Biomol. Struct., 2006, pp. 417-434, vol. 35.
Shin et al., "A Simplified Immune Suppression Scheme Leads to Persistent Micro-Dystrophin Expression in Duchenne Muscular Dystrophy Dogs", Human Gene Therapy, 2012, pp. 202-209, vol. 23.
Shin et al., "Microdystrophin Ameliorates Muscular Dystrophy in the Canine Model of Duchenne Muscular Dystrophy", Molecular Therapy, 2013, pp. 750-757, vol. 21, No. 4.
Shin et al., "Recombinant Adeno-Associated Viral Vector Production and Purification", Methods Mol Biol., 2012, pp. 267-284, vol. 798.
Straub et al., "Animal Models for Musuclar Dystrophy Show Different patterns of Sarcolemmal Disruption", Cell Biology, 1997, pp. 375-385, vol. 139, No. 2.
Suminaga et al., "C-Terminal Truncated Dystrophin Identified in Skeletal Muscle of an Asymptomatic Boy with a Novel Nonsense Mutation of the Dystrophin Gene", Pediatric Research, 2004, pp. 739-743, vol. 56, No. 5.
Sun et al., "Overcoming Adeno-Associated Virus Vector Size Limitation Through Viral DNA Heterodimerization", Nature Medicine, 2000, pp. 599-602, vol. 6, No. 5.
Suzuki et al., "Glycoprotein-Binding Site of Dystrophin is Confined to the Cysteine-Rich Domain and the First Half of the Carboxy-Terminal Domain", Federation of European Biochemical Societies, 1992, pp. 154-160, vol. 308, No. 2.
Suzuki et al., "Mammalian a1- and b1-Syntrophin Bind to the Alternative Splice-Prone Region of the Dystrophin COOH Terminus", The Journal of Cell Biology, 1995, pp. 373-381, vol. 128, No. 3.
Suzuki et al., "Molecular Organization at the Glycoprotein-Complex-Binding Site of Dystrophin", Eur. J. Biochem., 1994, pp. 283-292, vol. 220.

(56) References Cited

OTHER PUBLICATIONS

Topinka et al., "N-Terminal Palmitoylation of PSD-95 Regulates Association with Cell Membranes and Interactions with K+ Channel Kv1.4", Neuron, 1998, pp. 125-134, vol. 20.
Wang et al., "Adeno-Associated Virus Vector Carrying Human Minidystrophin Genes Effectively Ameliorates Muscular Dystrophy in mdx Mouse Model", PNAS, 2000, pp. 13714-13719, vol. 97, No. 25.
Wang et al., "Construction and Analysis of Compact Muscle-Specific Promoters for AAV Vectors", Gene Therapy, 2008, pp. 1489-1499, vol. 15.
Wang et al., "Successful Regional Delivery and Long-Term Expression of a Dystrophin Gene in Canine Muscular Dystrophy: A Preclinical Model for Human Therapies", Molecular Therapy, 2012, pp. 1501-1507, vol. 20, No. 8.
Yan et al., "Trans-Splicing Vectors Expand the Utility of Adeno-Associated Virus for Gene Therapy", PNAS, 2000, pp. 6716-6721, vol. 97, No. 12.
Yanai et al., "Palmitoylation of Huntingtin by HIP14 is Essential for Its Trafficking and Function", Nat Neurosci., 2006, pp. 824-831, vol. 9, No. 6.
Yang et al., "Dystrophin Deficiency Compromises Force Production of the Extensor Carpi Ulnaris Muscle in the Canine Model of Duchenne Muscular Dystrophy", PLOS One, 2012, pp. 1-7, vol. 7, No. 9.
Yang et al., "Identification of a-Syntrophin Binding to Syntrophin Triplet, Dystrophin, and Utrophin", The Journal of Biological Chemistry, 1995, pp. 4975-4978, vol. 270, No. 10.
Yoshida et al., "Biochemical Evidence for Association of Dystrobrevin with the Sarcoglycan-Sarcospan Complex as a Basis for Understanding Sarcoglycanopathy", Human Molecular Genetics, 2000, pp. 1033-1040, vol. 9, No. 7.
Yue et al., "C-Terminal-Truncated Microdystrophin Recruits Dystrobrevin and Syntrophin to the Dystrophin-Associated Glycoprotein Complex and Reduces Muscular Dystrophy in Symptomatic Utrophin/Dystrophin Double-Knockout Mice", Mol Ther., 2006, pp. 79-87, vol. 14, No. 1.
Yue et al., "Safe and Bodywide Muscle Transduction in Young Adult Duchenne Muscular Dystrophy Dogs with Adeno-Associated Virus", Human Molecular Genetics, 2015, pp. 5880-5890, vol. 24, No. 20.
Zhang et al. "Novel Mini-Dystrophin Gene Dual Adeno-Associated Virus Vectors Restore Neuronal Nitric Oxide Synthase Expression at the Sarcolemma", Human Gene Therapy (2012) pp. 98-103, vol. 23, No. 1; XP055619093, GB ISSN: 1043-0342, DOI: 101089/hum. 2011.131 *p. 98 col. 2, p. 99 col. 2 para. 2, 3, Fig. 1*.
Zhang et al., "Dual AAV Therapy Ameliorates Exercise-Induced Muscle Injury and Functional Ischemia in Murine Models of Duchenne Muscular Dystrophy", Human Molecular Genetics, May 15, 2013, pp. 3720-3729, vol. 22.
Zhao et al., "Dystrophin contains multiple independent membrane-binding domains", Human Molecular Genetics, 2016, pp. 3647-3653, vol. 25, No. 17.
Zhong et al., "Next Generation of Adeno-Associated Virus 2 Vectors: Point Mutations in Tyrosines Lead to High-Efficiency Transduction at Lower Doses", PNAS, 2008, pp. 7827-7832, vol. 105, No. 22.
Allen et al., "Absence of Dystrophin Disrupts Skeletal Muscle Signaling: Roles of $Ca^{2+}$, Reactive Oxygen Species, and Nitric Oxide in the Development of Muscular Dystrophy", Physiological Reviews, 2016, pp. 253-305, vol. 96, No. 1.
Amann et al., "A Cluster of Basic Repeats in the Dystrophin Rod Domain Binds F-Actin Through an Electrostatic Interaction", The Journal of Biological Chemistry, 1998, pp. 28419-28423, vol. 273, No. 43.
Bajanca et al., "In Vivo Dynamics of Skeletal Muscle Dystrophin in Zebrafish Embryos Revealed by Improved FRAP Analysis", 2015, pp. 1-32.

Banks et al., "The Polyproline Site in Hinge 2 Influences the Functional Capacity of Truncated Dystrophins", Plos Genetics, 2010, pp. 1-10, vol. 6, No. 5.
Barnabei et al., "Severe Dystrophic Cardiomyopathy Caused by the Enteroviral Protease 2A-Mediated C-Terminal Dystrophin Cleavage Fragment", Science Translational Medicine, 2015, pp. 1-11, vol. 7.
Bennett et al., "An Adaptable Spectrin/Ankyrin-Based Mechanism for Long-Range Organization of Plasma Membranes in Vertebrate Tissues", Current Topics in Membranes, 2016, pp. 143-184, vol. 77.
Bok et al., "Lipid-Binding Role of bII-Spectrin Ankyrin-Binding Domain", Cell Biology International, 2007, pp. 1482-1494, vol. 31.
Bostick et al., "AAV Micro-Dystrophin Gene Therapy Alleviates Stress-Induced Cardiac Death but not Myocardial Fibrosis in > 21-m-Old mdx Mice, an End-Stage Model of Duchenne Muscular Dystrophy Cardiomyopathy", Journal of Molecular and Cellular Cardiology, May 12, 2012, pp. 217-222, vol. 53.
Bostick et al., "Cardiac Expression of a Mini-Dystrophin That Normalizes Skeletal Muscle Force Only Partially Restores Heart Function in Aged Mdx Mice", Molecular Therapy, 2009, pp. 253-261, vol. 17, No. 2.
Bunnell et al., "Destabilization of the Dystrophin-Glycoprotein Complex without Functional Deficits in a-Dystrobrevin Null Muscle", PLOS One, 2008, pp. 1-6, vol. 3, No. 7.
Campbell et al., "Association of Dystrophin and an Integral Membrane Glycoprotein", Nature, 1989, pp. 259-262, vol. 338.
Chandrasekharan et al., "Introduction of a Human-Specific Deletion in Mouse Cmah Increases Disease Severity in the mdx Model of Duchenne Muscular Dystrophy", Sci Transl Med., 2010, pp. 1-34, vol. 2, No. 42.
Constantin, "Dystrophin Complex Functions as a Scaffold for Signalling Proteins", Biochimica et Biophysica Acta, 2014, pp. 635-642, vol. 1838.
Cox et al., "Dp71 can Restore the Dystrophin-Associated Glycoprotein Complex in Muscle but Fails to Prevent Dystrophy", Nature Genetics, 1994, pp. 333-339, vol. 8.
Crawford et al., "Assembly of the Dystrophin-Associated Protein Complex Does Not Require the Dystrophin COOH-Terminal Domain", The Journal of Cell Biology, 2000, pp. 1399-1409, vol. 150, No. 6.
Das et al., "Purification and Biochemical Characterization of a Protein-Palmitoyl Acyltransferase from Human Erythrocytes", The Journal of Biological Chemistry, 1997, pp. 11021-11025, vol. 272, No. 17.
Dewolf et al., "Interaction of Dystrophin Fragments with Model Membranes", Biophysical Journal, 1997, pp. 2599-2604, vol. 72.
Draviam et al., "Mini-Dystrophin Efficiently Incorporates into the Dystrophin Protein Complex in Living Cells", Journal of Muscle Research and Cell Motility, 2006, pp. 53-67, vol. 27.
Duan et al., "Expanding AAV Packaging Capacity with Trans-Splicing or Overlapping Vectors: A Quantitative Comparison", Molecular Therapy, 2001, pp. 383-391, vol. 4, No. 4.
Dunckley et al., "Independent Localization of Dystrophin N- and C-Terminal Regions to the Sarcolemma of mdx Mouse Myofibres In Vivo", Journal of Cell Science, 1994, pp. 1469-1475, vol. 107.
Einbond et al., "Towards Prediction of Cognate Complexes Between the WW Domain and Proline-Rich Ligands", FEBS Letters, 1996, pp. 1-8, vol. 384.
Ervasti et al., "Membrane Organization of the Dystrophin-Glycoprotein Complex", Cell, 1991, pp. 1121-1131, vol. 66.
Fine et al., "Age-Matched Comparison Reveals Early Electrocardiogramand Echocardiography Changes in Dystrophin-Deficient Dog", Neuromuscul Disord., 2011, pp. 453-461, vol. 21, No. 7.
Fritz et al., "Expression of Deletion-Containing Dystrophins in mdx Muscle: Implicatons for Gene Therapy and Dystrophin Function", Pediatric Research, 1995, pp. 693-700, vol. 37, No. 6.
Gao et al., "The Dystrophin Complex: Structure, Function, and Implications for Therapy", Compr Physiol., 2015, pp. 1223-1239, vol. 5, No. 3.
Gardner et al., "Restoration of all Dystrophin Protein Interactions by Functional Domains in Trans Does Not Rescue Dystrophy", Gene Therapy, 2006, pp. 744-751, vol. 13.

(56) References Cited

OTHER PUBLICATIONS

Ghosh et al., "A Hybrid Vector System Expands Adeno-Associated Viral Vector Packaging Capacity in a Transgene-Independent Manner", Molecular Therapy, 2008, pp. 124-130, vol. 16, No. 1.

Ghosh et al., "Expanding Adeno-Associated Viral Vector Capacity: A Tale of Two Vectors", Biotechnology and Genetic Engineering Reviews, 2007, pp. 165-178, vol. 24.

Halbert et al., "Efficient Mouse Airway Transduction Following Recombination Between AAV Vectors Carrying Parts of a Larger Gene", Nature Biotechnology, 2002, pp. 697-701, vol. 20.

Harper et al., "Modular Flexibility of Dystrophin: Implications for Gene Therapy of Duchenne Muscular Dystrophy", Nature Medicine, 2002, pp. 253-261, vol. 8, No. 3.

Helliwell et al., "A Truncated Dystrophin Lacking the C-Terminal Domains is Localized at the Muscle Membrane", American Journal of Human Genetics, 1992, pp. 508-514, vol. 50.

Hillier et al., "Unexpected Modes of PDZ Domain Scaffolding Revealed by Structure of nNOS-Syntrophin Complex", Science, Apr. 30, 1999, pp. 812-815, vol. 284.

Hir et al., "Cholesterol Favors the Anchorage of Human Dystrophin Repeats 16 to 21 in Membrane at Physiological Surface Pressure", Biochimica et Biophysica Acta, 2014, pp. 1266-1273, vol. 1838, No. 5.

Hoffman et al., "Dystrophin: The Protein Product of the Duchenne Muscular Dystrophy Locus", Cell, 1987, pp. 919-928, vol. 51.

Hoffman et al., "Is the Carboxyl-Terminus of Dystrophin Required for Membrane Association? A Novel, Severe Case of Duchenne Muscular Dystrophy", Annals of Neurology, 1991, pp. 605-610, vol. 30, No. 4.

Huang et al., "Structure of a WW Domain Containing Fragment of Dystrophin in Complex with b-Dystroglycan", Nature Structural Biology, 2000, pp. 634-638, vol. 7, No. 8.

Ipsaro et al., "Structural Basis for Spectrin Recognition by Ankyrin", Blood, 2010, pp. 4093-4101, vol. 115, No. 20.

Ipsaro et al., "Structures of the Spectrin-Ankyrin Interaction Binding Domains", Blood, 2009, pp. 5385-5393, vol. 113, No. 22.

Ishikawa-Sakurai et al., "ZZ Domain is Essentially Required for the Physiological Binding of Dystrophin and Utrophin to b-Dystroglycan", Human Molecular Genetics, 2004, pp. 693-702, vol. 13, No. 7.

Johnson et al., "Identification of New Dystroglycan Complexes in Skeletal Muscle", PLOS One, 2013, pp. 1-17, vol. 8, No. 8.

Johnson et al., "Proteomic Analysis Reveals New Cardiac-Specific Dystrophin-Associated Proteins", PLOS One, 2012, pp. 1-12, vol. 7, No. 8.

Judge et al., "Dissecting the Signaling and Mechanical Functions of the Dystrophin-Glycoprotein Complex", Journal of Cell Science, 2006, pp. 1537-1546, vol. 119.

Judge et al., "Expression of the Dystrophin Isoform Dp116 Preserves Functional Muscle Mass and Extends Lifespan Without Preventing Dystrophy in Severely Dystrophic Mice", Human Molecular Genetics, 2011, pp. 4978-4990, vol. 20, No. 24.

Jung et al., "Identification and Characterization of the Dystrophin Anchoring Site on b-Dystroglycan", The Journal of Biological Chemistry, 1995, pp. 27305-27310, vol. 270, No. 45.

Koenig et al., "Detailed Analysis of the Repeat Domain of Dystrophin Reveals Four Potential Hinge Segments That May Confer Flexibility", The Journal of Biological Chemistry, 1990, pp. 4560-4566, vol. 265.

Lai et al., "a2 and a3 Helices of Dystrophin R16 and R17 Frame a Microdomain in the a1 Helix of Dystrophin R17 for Neuronal NOS Binding", PNAS, 2013, pp. 525-530, vol. 110, No. 2.

Lai et al., "Dystrophins Carrying Spectrin-Like Repeats 16 and 17 Anchor nNOS to the Sarcolemma and Enhance Exercise Performance in a Mouse Model of Muscular Dystrophy", The Journal of Clinical Investigation, 2009, pp.624-635, vol. 119, No. 3.

Lai et al., "Efficient In Vivo Gene Expression by Trans-Splicing Adeno-Associated Viral Vectors", Nat Biotechnol., 2005, pp. 1435-1439, vol. 23, No. 11.

Lai et al., "Partial Restoration of Cardiac Function with DPDZ nNOS in Aged mdx Model of Duchenne Cardiomyopathy", Human Molecular Genetics, Jan. 25, 2014, pp. 3189-3199, vol. 23.

Lai et al., "Synthetic Intron Improves Transduction Efficiency of Trans-Splicing Adeno-Associated Viral Vectors", Human Gene Therapy, 2006, pp. 1036-1042, vol. 17, No. 10.

\* cited by examiner

A. Full-length dystrophin

B. CR-deleted dystrophins that were found at the sarcolemma in human patients

C. Synthetic CR-deleted dystrophins that are found at the sarcolemma in mdx mice D. Dystrophin membrane binding domains identified by *in vitro* studies

ΔR4-R23/ΔCR

ΔR4-R23/ΔCT

| | | | |
|---|---|---|---|
| NT-H1 | 1-336 [NT-H1 | GFP] | 65.9 kD | YL376 |
| R1-3 | 337-667 [R1-3 | GFP] | 65.7 kD | YL375 |
| R4-6 | 718-1045 [R4-6 | GFP] | 65.5 kD | YL367 |
| R7-9 | 1046-1367 [R7-9 | GFP] | 64.9 kD | YL368 |
| R10-12 | 1368-1676 [R10-12 | GFP] | 62.6 kD | YL369 |
| R13-15 | 1677-1973 [R13-15 | GFP] | 62.4 kD | YL370 |
| R16-19 | 1992-2423 [R16-19 | GFP] | 77.8 kD | YL371 |
| R20-24 | 2471-3040 [R20-24 | GFP] | 94.1 kD | YL372 |
| H4-CR | 3041-3408 [H4-CR | GFP] | 69.9 kD | YL410 |
| CT | 3422-3685 [CT | GFP] | 57 kD | YL411 |

Figure 5

| Domain | Human | Mouse |
| --- | --- | --- |
| R1 | C433 | C435 |
| R2 | C544 | C490, C546 |
| R3 | C569, C650 | C571 |
| R11 | C1505 | C1507 |
| R12 | C1569 | C1571 |
| CT | C3476 | C3469 |

Figure 12

| Position | Peptide | Score | Cutoff | Cluster |
|---|---|---|---|---|
| R1 | LLNSRWECLRVASME | 0.929 | 0.196 | Cluster A |
| R3 | QRLTEEQCLFSAWLS | 1.537 | 0.951 | Cluster C |
| R3 | WLDNFARCWDNLVQK | 0.648 | 0.196 | Cluster A |
| R12 | CLKLSRKM | 1.452 | 0.196 | Cluster A |

Figure 13

R1-3 (Cys mut)  R10-12 (Cys mut)  CT (Cys mut)

μDys-1

μDys-2

μDys-3

PCR-based Cloning

AAV production & purification

Intramuscular injection

Staining for protein detection

Individual Membrane-Binding Domains of Dystrophin

| Membrane Binding | | | | |
|---|---|---|---|---|
| No | NT-H1 | 1-336 NT-H1 GFP | 65.9 kD | YL376 |
| Yes | R1-3 | 337-667 R1-3 GFP | 65.7 kD | YL375 |
| No | R4-6 | 718-1045 R4-6 GFP | 65.5 kD | YL367 |
| No | R7-9 | 1046-1367 R7-9 GFP | 64.9 kD | YL368 |
| Yes | R10-12 | 1368-1676 R10-12 GFP | 62.6 kD | YL369 |
| No | R13-15 | 1677-1973 R13-15 GFP | 62.4 kD | YL370 |
| No | R16-19 | 1992-2423 R16-19 GFP | 77.8 kD | YL371 |
| No | R20-24 | 2471-3040 R20-24 GFP | 94.1 kD | YL372 |
| Yes | H4-CR | 3041-3408 H4-CR GFP | 69.9 kD | YL410 |
| Yes | CT | 3422-3685 CT GFP | 57 kD | YL411 |

Figure 26

DYSTROPHIN R16/R17 SYNTROPHIN PDZ FUSION PROTEINS

CROSS REFERENCE TO RELATED APPLICATIONS

This application is a Continuation of U.S. application Ser. No. 16/311,236, filed on Dec. 19, 2018, issued as U.S. Pat. No. 11,202,840, which is a U.S. National Phase application of International Patent Application PCT/US2017/038418, filed on Jun. 21, 2017, which claims the benefit of U.S. Provisional Patent Application No. 62/367,559, filed on Jul. 27, 2016; U.S. Provisional Patent Application No. 62/357,865, filed on Jul. 1, 2016; and U.S. Provisional Patent Application No. 62/352,927, filed on Jun. 21, 2016, each of which is incorporated herein by reference in its entirety.

STATEMENT REGARDING FEDERALLY-SPONSORED RESEARCH AND DEVELOPMENT

This invention was made with government support under AR067985, AR049419, and NS090634 awarded by the National Institutes of Health. The government has certain rights in the invention.

INCORPORATION OF SEQUENCE LISTINGS

A sequence listing containing the file named "17UMC006_SEQ LST_TC167044_ST25.txt", which is 263,001 bytes (measured in MS-Windows®), contains 67 sequences, and was created on Jun. 14, 2017, is provided herewith via the USPTO's EFS system, and is incorporated herein by reference in its entirety.

BACKGROUND

Dystrophin is an essential cytoskeletal protein in the muscle. It constitutes a primary linkage between the extracellular matrix (ECM) and the actin cytoskeleton (1, 2). In muscle cells, dystrophin plays an important role in maintaining membrane integrity and preventing membrane rupture. Loss of dystrophin, as seen in Duchenne muscular dystrophy (DMD) (3), leads to sarcolemmal leakage, myofiber degeneration and necrosis. Full-length dystrophin is a large rod-shaped protein. It contains four functional domains including N-terminus (NT), the mid-rod domain, the cysteine-rich (CR) domain and C-terminus (CT). The mid-rod domain consists of 24 spectrin-like repeats. Four hinges (H) are interspersed in the mid-rod domain (4). Dystrophin NT and spectrin-like repeats R11-17 bind to cytoskeletal filamentous actin (5, 6). The CR domain anchors dystrophin to the muscle membrane via interaction with the transmembrane protein β-dystroglycan (7-9). β-dystroglycan further connects with basal lamina proteins to complete the axis from the ECM to the cytoskeleton (10). This mechanical linkage protects the muscle membrane from contraction-induced damages. In this well-established model, the dystrophin CR domain is solely responsible for dystrophin membrane binding (FIG. 1).

Despite compelling evidence suggesting that the CR domain mediates dystrophin-sarcolemma interaction, case reports from some rare-occurring patients suggest that dystrophin can bind to the sarcolemma through CR domain-independent mechanisms. In these patients, biochemical and genetic analyses confirmed a complete deletion of the CR domain. Yet, immunostaining showed clear sarcolemmal localization of the truncated dystrophin protein (FIG. 2B) (11-13).

SUMMARY

Synthetic nucleic acid molecules encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17; wherein the domains and the MBM are arranged from N to C terminus in the order in which they occur in a wild-type dystrophin protein and are operably linked are provided. Synthetic nucleic acid molecules encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17 that is operably linked to a syntrophin PDZ domain; wherein the dystrophin domains and the MBM are arranged from N to C terminus in the order in which they occur in a wild-type dystrophin protein and are operably linked are also provided. A synthetic nucleic acid molecule comprising a sequence encoding a fusion protein comprising a nNOS binding domain of dystrophin R16-R17 that is operably linked to a syntrophin PDZ domain are also provided. In certain embodiments, the nNOS binding domain of dystrophin R16-R17 is operably linked to a syntrophin PDZ domain with a hinge region in the fusion protein. In certain embodiments, the nNOS binding domain of dystrophin R16-R17 is operably linked to a syntrophin PDZ domain with a hinge region selected from the group consisting of a synthetic hinge, a semi-synthetic hinge, dystrophin H1, dystrophin H2, dystrophin H3, dystrophin H4, and variants thereof. In certain embodiments, the MBM of R1-R2-R3 comprises at least one S-palmitoylation site peptide selected from the group consisting of SEQ ID NO: 54, SEQ ID NO: 55, and SEQ ID NO:56. In certain embodiments, the R3 repeat or R2-R3 repeats are absent from the non-full length dystrophin protein. In certain embodiments, the R1, R2, R3, R1 and R2, R2 and R3, or R1, R2, and R3 repeats are present in the non-full length dystrophin protein. In certain embodiments, the MBM of R10-R11-R12 comprises an S-palmitoylation site peptide of SEQ ID NO:57. In certain embodiments, the R10 repeat, the R11 repeat, the R12 repeat, the R10-R11 repeats, the R11-R12, or the R10 and R12 repeats are present in the non-full length dystrophin protein. In certain embodiments, the R17 domain is present in the non-full length dystrophin protein. In certain embodiments, the n-terminal alpha helix of the R16 domain (SEQ ID NO:59) or a portion thereof is absent from the non-full length dystrophin protein. In certain embodiments, alpha-helix 2 and alpha-helix 3 of the R16 domain is present and alpha-helix 1, alpha-helix 2, and alpha-helix 3 of the R17 domain is present in the non-full length dystrophin protein. In certain embodiments, alpha-helix 2 and alpha-helix 3 of the R16 domain is present and alpha-helix 1, alpha-helix 2, and alpha-helix 3 of the R17 domain is present in the non-full length dystrophin protein. In certain embodiments, the N-terminal helix one of the R16 domain is substituted with the MBM of the R1-R2-R3 MBD or with the MBM of the R10-R11-R12 MBD. In certain embodiments, the R16 domain and the R17 domain are present in the non-full length dystrophin protein. In certain embodiments, the MBM of the CR membrane binding domain is absent, wherein the CR membrane binding domain is absent, or wherein the CR domain is absent from the non-full length dystrophin protein. In certain embodiments, the MBM of the CT MBD comprises residues 3422 to 3535 of SEQ ID NO: 1. In certain embodiments, the MBM of the CT MBD comprises residues 3501 to 3685 of SEQ ID NO:1. In certain embodiments, at least one domain and at least one MBM are operably linked with a hinge region selected from the group consisting of a synthetic hinge, a semi-synthetic hinge, dystrophin H1, dystrophin H2, dystrophin H3, dystrophin H4, and variants thereof. In certain embodiments, the dystrophin H1 hinge or a variant thereof operably links the C-terminus of the NT domain to the N-terminus of an MBM or domain containing an MBM, wherein the dystrophin H2 hinge or a variant thereof operably links the C-terminus of a MBM or domain containing an MBM to the N-terminus of another MBM or domain containing another MBM, wherein the dystrophin H3 hinge or a variant thereof operably links the C-terminus of an MBM or domain containing an MBM to the N-terminus of another MBM or domain containing another MBM, wherein the dystrophin H4 hinge or a variant thereof operably links the C-terminus of an MBM to the N-terminus of the CR MBM or the CR domain, or any combination thereof. In certain embodiments, the dystrophin H4 hinge or a variant thereof operably links the C-terminus of an MBM to the N-terminus of the CR MBM or the CR domain. In certain embodiments of any of the aforementioned synthetic nucleic acid molecules, the mini- or micro-dystrophin gene is between 5 kb to about 8 kb in length or less than 5 kb in length, respectively. In certain embodiments of any of the aforementioned synthetic nucleic acid molecules, the mini- or micro-dystrophin gene is operably linked to a heterologous promoter, a heterologous 5' untranslated region (UTR), a heterologous 3' UTR, a heterologous polyadenylation site, or any combination thereof. In certain embodiments of any of the aforementioned synthetic nucleic acid molecules, the molecule is integrated within an endogenous dystrophin gene locus in an X-chromosome.

Lentiviral vectors comprising any of the aforementioned synthetic nucleic acid molecules, wherein the nucleic acid molecule is operably linked to an expression cassette, 5' and 3' long terminal repeats (LTR), and a psi sequence in the lentiviral vector are also provided.

Single recombinant adeno-associated virus (AAV) vector comprising any of the aforementioned synthetic nucleic acid molecules, wherein said nucleic acid molecule is operably linked to an expression cassette and viral inverted terminal repeats (ITRs) in the AAVare also provided.

Dual recombinant AAV vector system, comprising two AAV vectors, wherein one of the two AAV vectors comprises a part of the nucleic acid molecule of any one of the aforementioned synthetic nucleic acid molecules, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Composition comprising any one of the aforementioned synthetic nucleic acid molecules or vectors and a pharmaceutically acceptable carrier are also provided. In certain embodiments, the synthetic nucleic acid molecule is operably linked to an expression cassette, 5' and 3' long terminal repeats (LTR), and a psi sequence in a lentiviral vector. In certain embodiments, the nucleic acid molecule is operably linked to an expression cassette and viral inverted terminal repeats (ITRs) in an AAV. In certain embodiments, the composition comprises the aforementioned dual recombinant AAV vector system.

Isolated host cells comprising any one of the aforementioned synthetic nucleic acid molecules or vectors are also provided. In certain embodiments, the nucleic acid molecule is integrated within an endogenous dystrophin gene locus in a chromosome of the host cell. In certain embodiments, the nucleic acid molecule is operably linked to an expression cassette, 5' and 3' long terminal repeats (LTR), and a psi element in a lentiviral vector. In certain embodiments, the nucleic acid molecule is operably linked to an expression cassette and ITRs in an AAV. In certain embodiments, the host cell is a myogenic stem cell.

Methods for the treating or ameliorating one or more adverse effects of Duchenne muscular dystrophy (DMD), Becker muscular dystrophy (BMD), X-linked dilated cardiomyopathy (XLDC), age-related muscle atrophy, cancer cachexia, or other neuromuscular disorders characterized by loss of sarcolemmal neuronal nitric oxide synthase (nNOS) activity in a subject in need thereof comprising the step of administering to the subject a therapeutically effective amount of: (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells to a subject in need thereof. In certain embodiments, the administration is by injection into muscle, systemic delivery, or local delivery. In certain embodiments, the host cell is a stem cell or myogenic stem cell. In certain embodiments, the host cell is derived from an autologous cell of the subject. In certain aforementioned methods, a defective endogenous dystrophin gene of the host cell or a defective portion thereof is edited to provide the synthetic nucleic acid molecule within the host cell's X-chromosome.

Use of (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells for making a composition for administration to a subject suffering from Duchenne muscular dystrophy (DMD), Becker muscular dystrophy (BMD), X-linked dilated cardiomyopathy (XLDC) age-related muscle atrophy, cancer cachexia, or other neuromuscular disorders characterized by loss of sarcolemmal neuronal nitric oxide synthase (nNOS) activity is also provided.

Use of (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells for treating a subject suffering from Duchenne muscular dystrophy (DMD), Becker muscular dystrophy (BMD) or X-linked dilated cardiomyopathy (XLDC), or for ameliorating one or more adverse effects of DMD, BMD, XLDC, age-related muscle atrophy, cancer cachexia, or other neuromuscular disorders characterized by loss of sarcolemmal neuronal nitric oxide synthase (nNOS) activity is also provided.

BRIEF DESCRIPTION OF THE DRAWINGS

FIG. 5. Cartoon illustration of ten GFP-fused dystrophin subdomains used in the study. The full-length human dystrophin molecule is split into ten subdomains. The numerical number range above each cartoon illustration refers to amino acid sequence numbering in the full-length human dystrophin protein. The predicted molecular weight of each fusion protein is marked. The YL numbers refer to the construct name in the Duan/Lai laboratory.

FIG. 12. Position of cysteine residues in R1-3, R10-12 and CT is conserved between human and mouse dystrophin.

FIG. 13. Identification of potential palmitoylated site peptides in R1-3 and R10-12 by CSS-Palm 2.0 program. The predicted palmitoylation sites are the sole cysteine residues in the sequences. From top to bottom, the palmitoylation site peptide sequences are

LLNSRWECLRVASME, (SEQ ID NO: 54)

QRLTEEQCLFSAWLS, (SEQ ID NO: 55)

WLDNFARCWDNLVQK, (SEQ ID NO: 56)
and

CLKLSRKM. (SEQ ID NO: 57)

Figure 14:
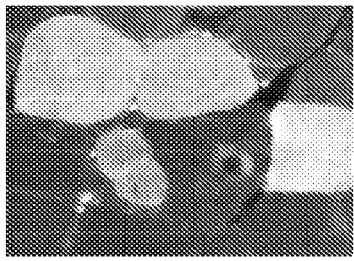
Figure 14:
Figure 14:

FIG. 14. Shows that cysteine mutations (C to S mutation) disrupt membrane binding of R1-3, R10-12 and CT. In R10-12, cysteine mutations also causes protein aggregates. Images shown as the GFP signal. Cys mut: cysteine mutant.

Figure 15:
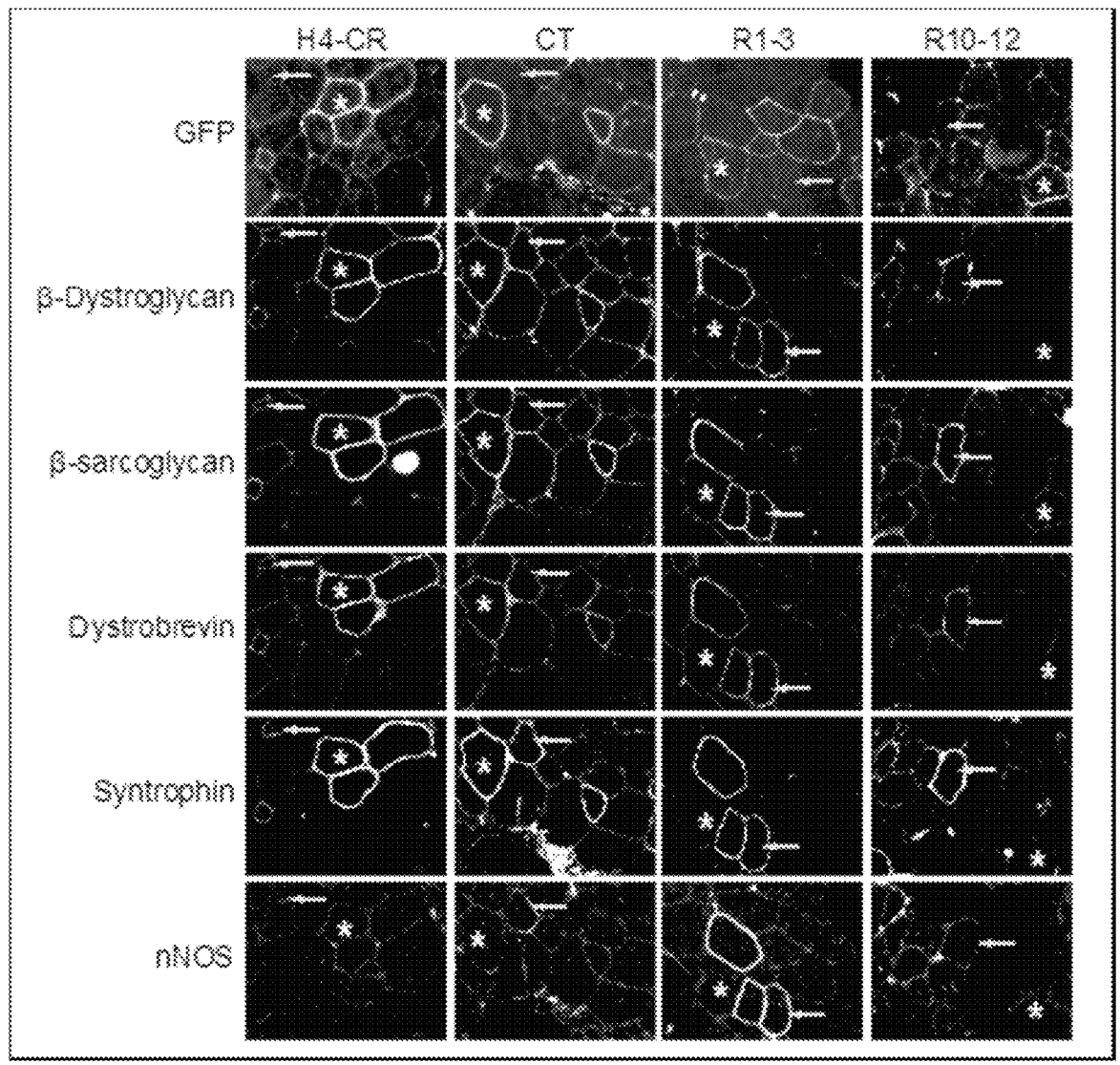

FIG. 15. Both CR and CT domain are associated with the DGC components. The DGC staining was performed in the sections expressed with H4-CR.GFP, CT.GFP, R1-3.GFP and R10-12.GFP. Both CR and CT domain are associated with the DGC at the muscle membrane, while R1-3 and R10-12 are not co-localized with the DGC at the sarcolemma. White asterisk: the GFP-positive fiber; arrow: the revertant fiber.

Figure 16A:
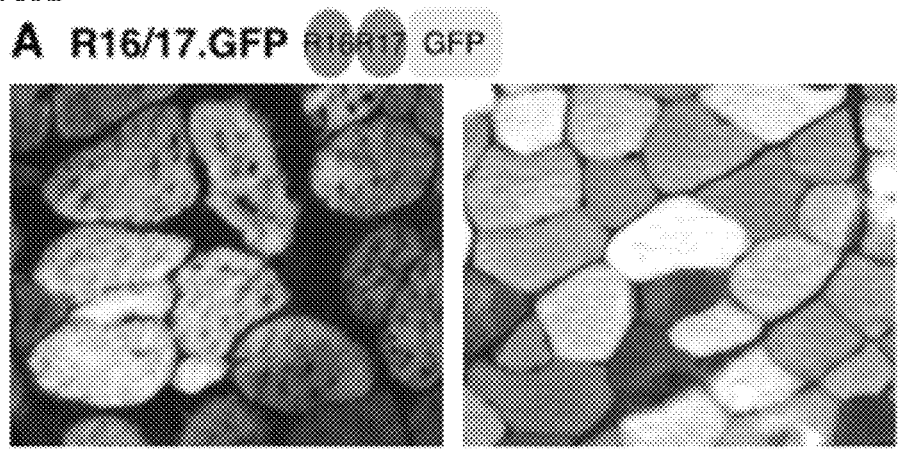

FIG. 16A,B. The constructs for detecting whether individual repeats from R1-3 and R10-12 maintain the membrane-binding ability. A. Cytosolic distribution of R16/17.GFP in the muscle of mdx and ΔH2-R19 mini-dystrophin transgenic mice. B. The construct design for the example.

Figure 17:
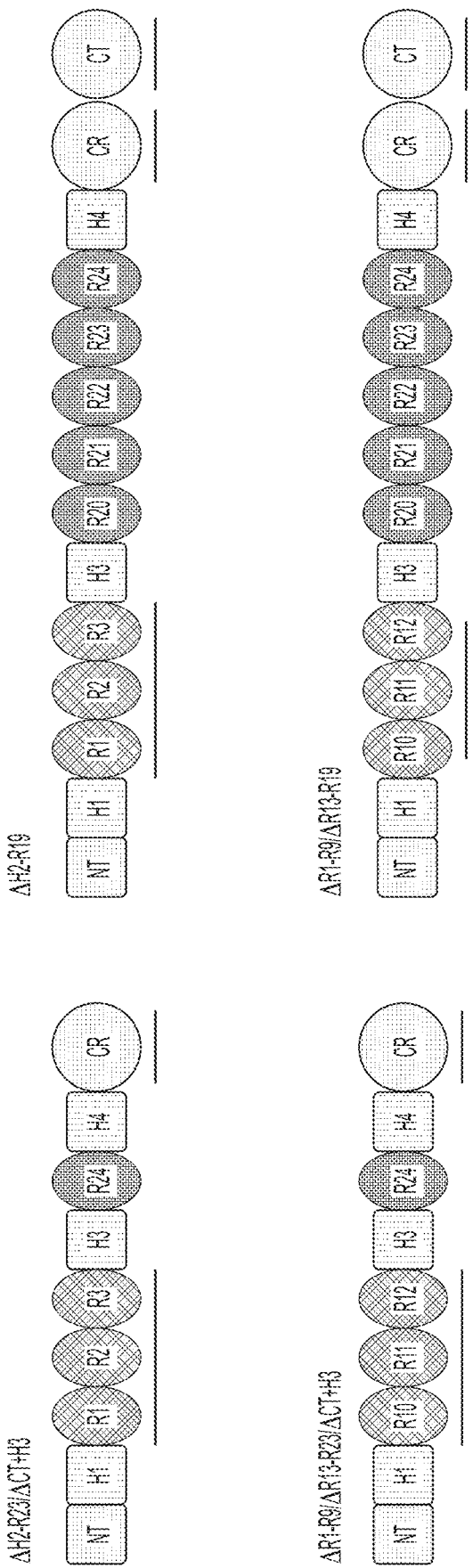

FIG. 17. Comparison of the functional roles of R1-3 and R10-12. R1-3 is replaced with R10-12 in micro- and mini-dystrophin. The membrane binding is marked by underlining.

Figure 18:
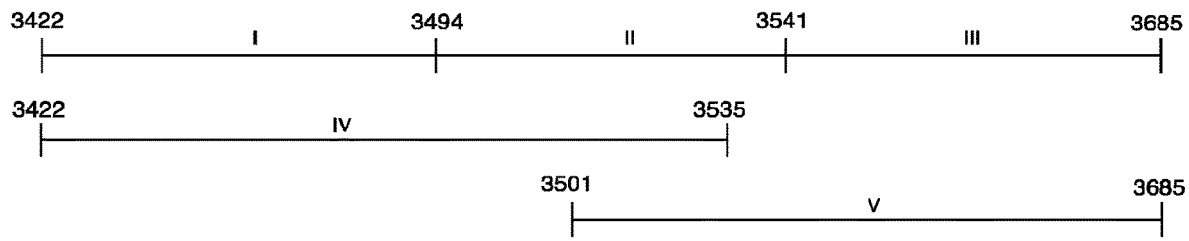

FIG. 18. The constructs with partial deletion of the CT domain for detecting the membrane-binding motif in CT. The CT domain tested here is from amino acid 3422 to 3685. The Roman numerals indicate the partial CT domains with different boundaries. The boundary of the constructs is labeled by the number of amino acid. These partial CT domains will be fused to GFP and expressed by AAV gene transfer.

Figure 19:
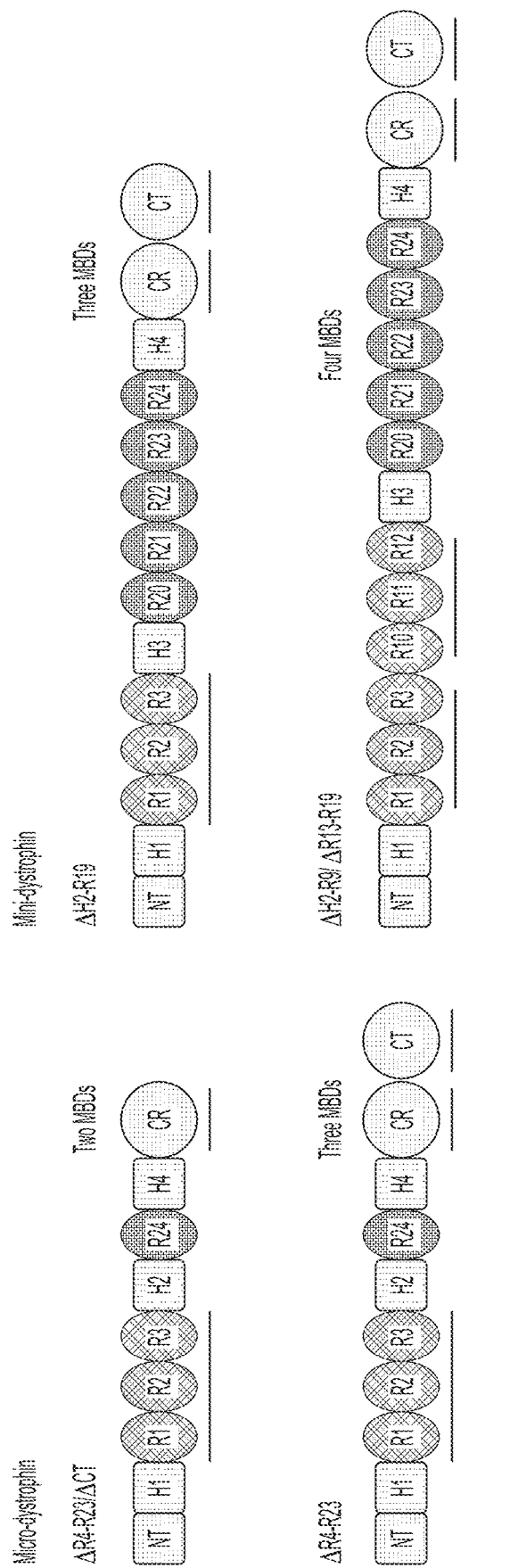

FIG. 19. The new micro- and mini-dystrophins. The original ΔR4-R23/ΔCT only contains two MBDs. We will generate ΔR4-R23 micro-dystrophin with three MBDs. The mini-dystrophin ΔH2-R19 contains three MBDs. We will add R10-12 to ΔH2-R19 minigene to make ΔH2-R9/ΔR13-R19 new minigene with four MBDs. The MBDs are marked by underlining.

Figure 20:
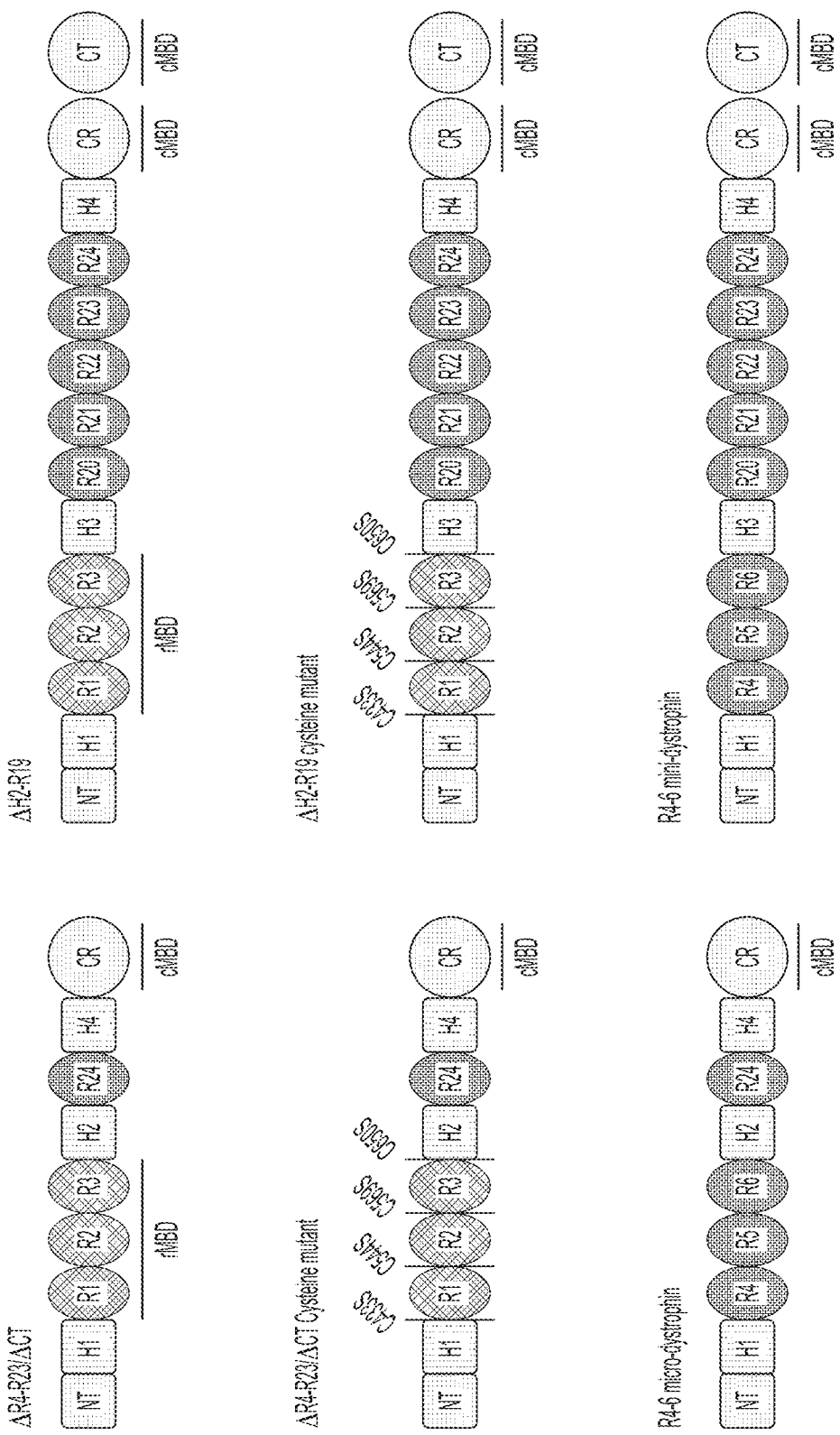

FIG. 20. Membrane binding of the rMBD, R1-3 was disrupted by cysteine mutations, or by replacement with R4-6 in micro- and mini-dystrophin. The membrane binding is marked by red underline.

Figure 21:
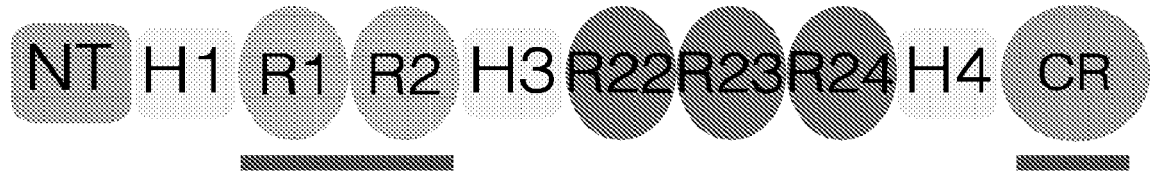
Figure 21:
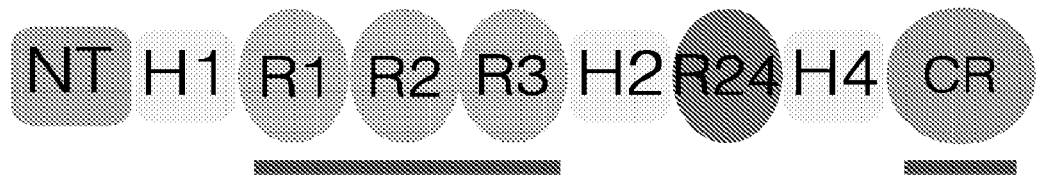
Figure 21:

FIG. 21. Currently available micro-dystrophins used in a clinical trial (μDys-1; Mendell, J. R. et al. *N Engl. J. Med.* 363, 1429-1437 (2010)) or in large animal models (μDys-2; Wang, Z. et al., *Mol Ther* 20, 1501-1507 (2012) and μDys-3; Yue, Y. et al. *Hum. Mol. Genet.* 24, 5880-5890 (2015)). They contain a partial or complete rMBD and a complete cMBD, indicated by underlining.

Figure 22:
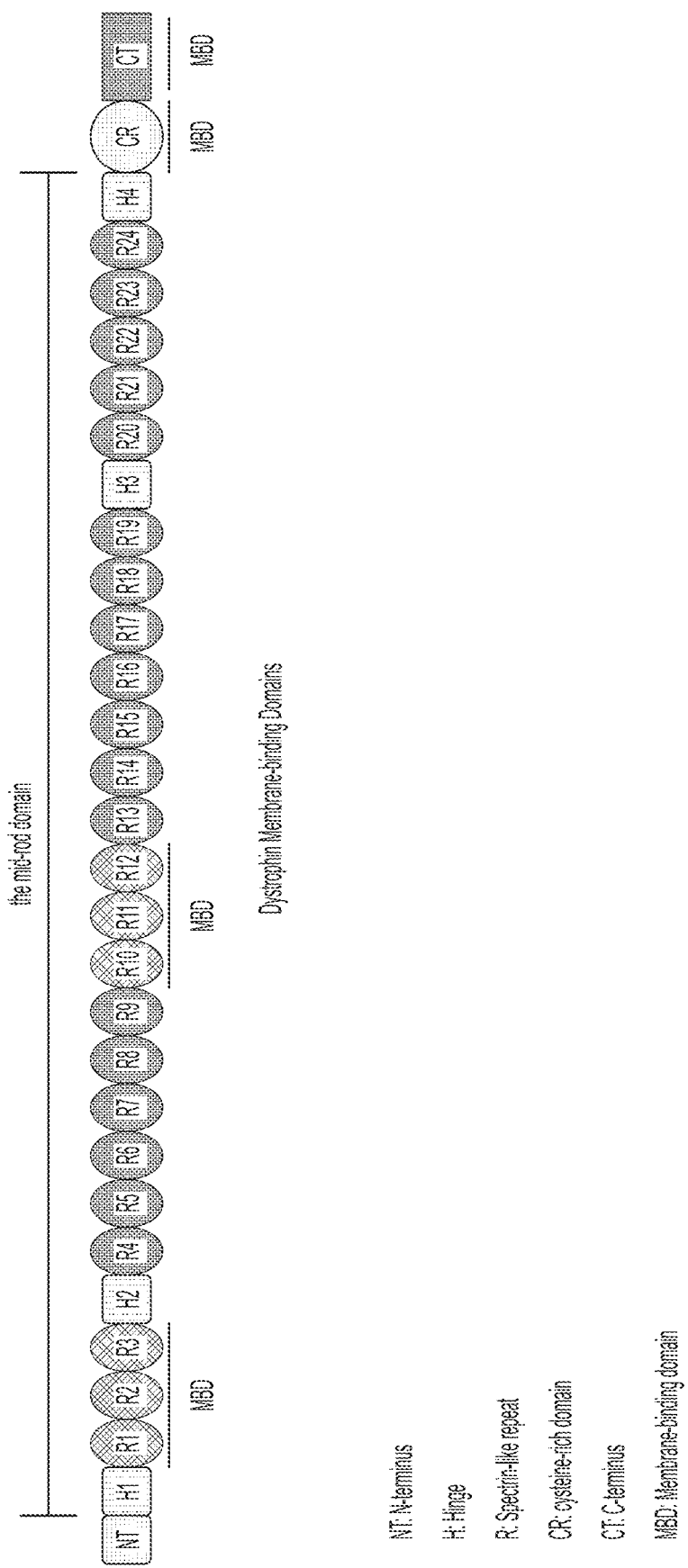

FIG. 22. Schematic diagram of dystrophin and its membrane binding domains.

Figure 23:
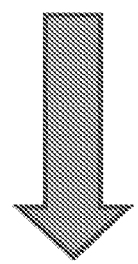
Figure 23:
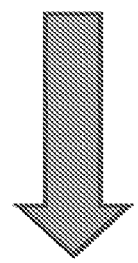
Figure 23:
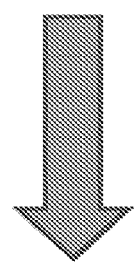

FIG. 23. Methodology for evaluating synthetic mini-dystrophin gene or micro-dystrophin gene constructs.

Figure 24:

FIG. 24. The construct design of AAV.R16/17.Syn.GFP-.Pal. To induce the expression of R16/17.Syn PDZ.GFP.Pal in the muscle, we will engineer an AAV construct. Syntrophin PDZ domain is fused to the C-terminus of dystrophin R16/17. We add green fluorescent protein (GFP) as the tag to help detection of R16/17.Syn fusion protein. Pal is the signal for membrane targeting. The expression of R16/17.Syn.GFP.Pal is driven by CMV promoter and SV40 polyA. ITR (inverted terminal repeat) is the sequence for AAV virus production.

Figure 25:
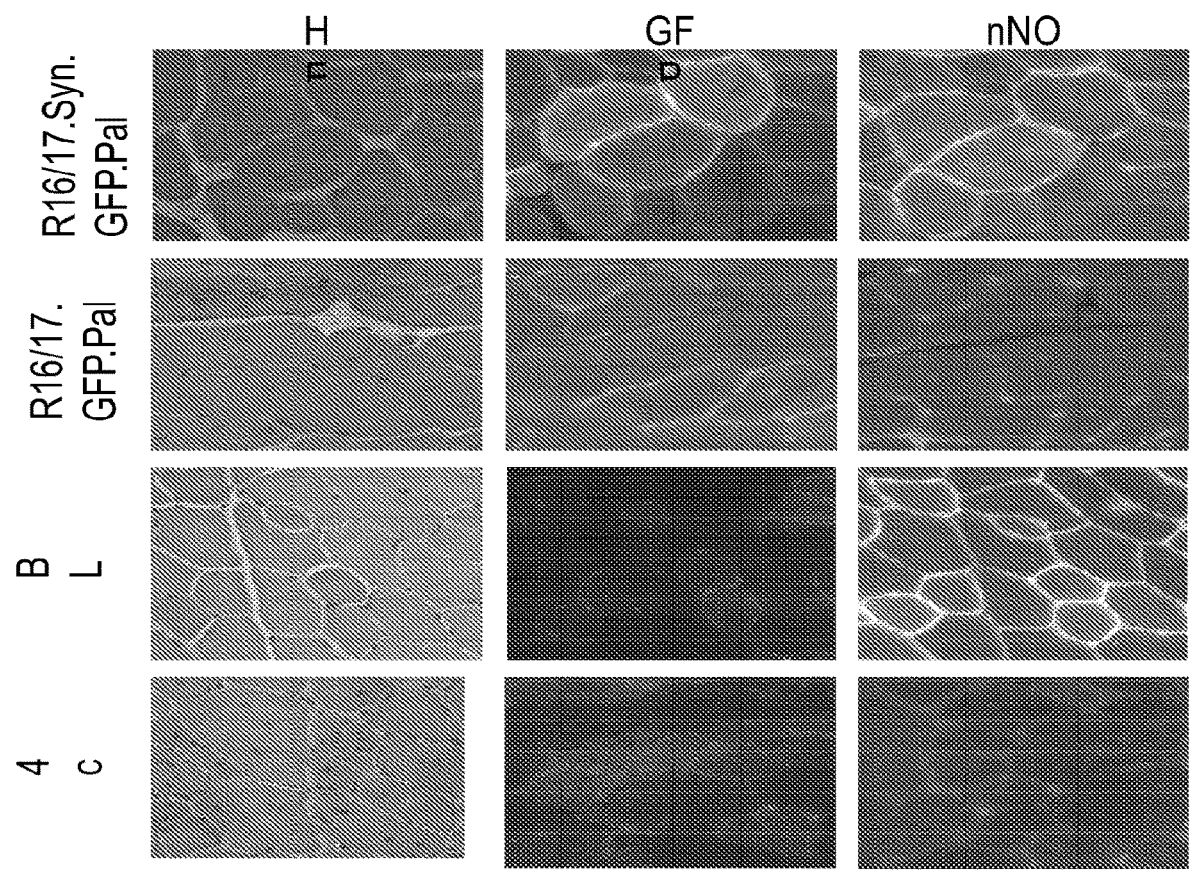

FIG. 25. Sarcolemmal nNOS was recovered successfully in a mdx mouse with the use of the R16/17-syntrophin PDZ fusion protein. Illustrated above are the expression levels of nNOS in different mice controls.

FIG. 26. Schematic diagram of dystrophin domains that do or do not exhibit membrane binding.

Figure 27A:
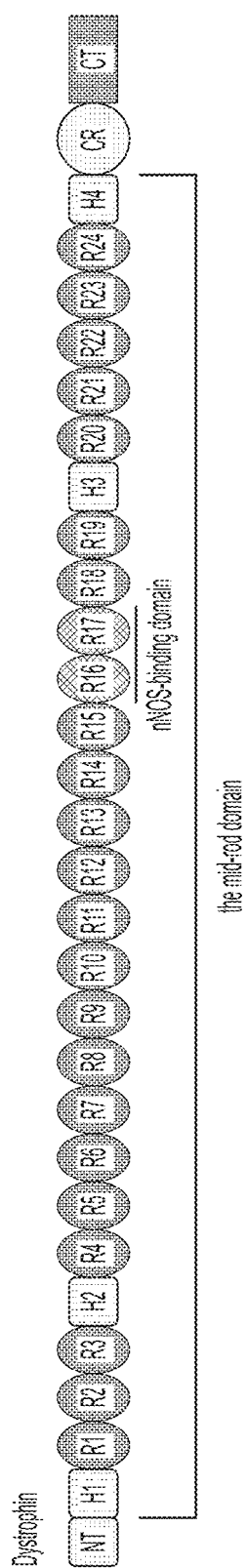
Figure 27B:
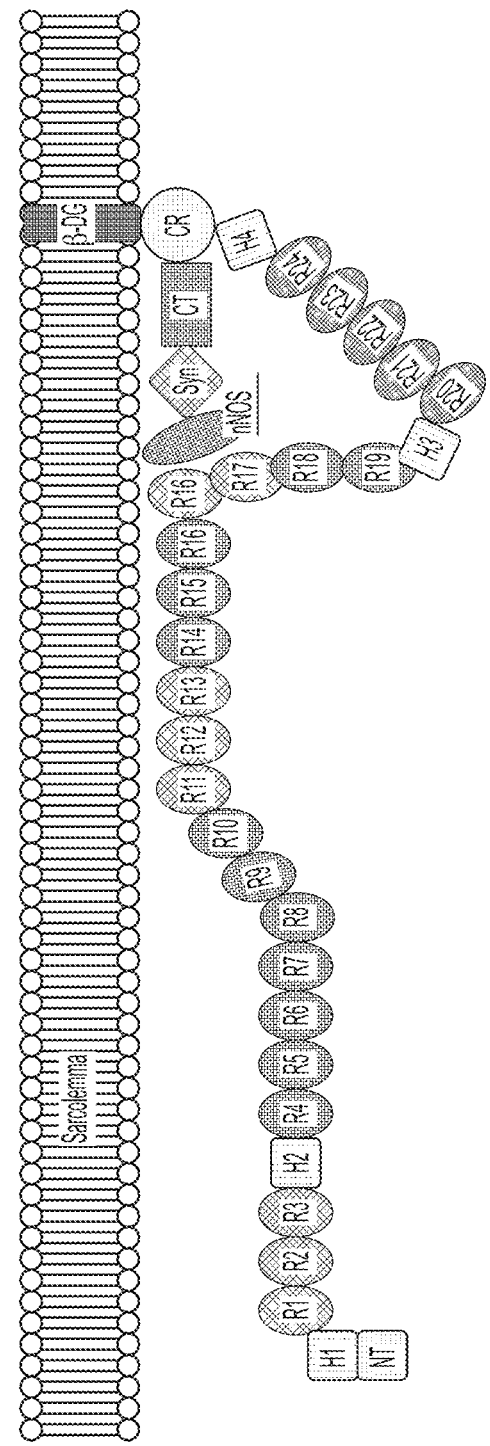

FIG. 27A,B. A Dystrophin functional domains and dystrophin nNOS-binding domain. Dystrophin is composed of four functional domains: NT: N-terminus; the mid rod domain; CR: cysteine-rich domain; and CT: C-terminus. The mid-rod domain contains 24 spectrin-like repeats and four hinge (H) regions. Dystrophin spectrin-like repeats 16 and 17 (R16/17) are identified as the nNOS-binding domain. B. Sarcolemmal localization of nNOS is dependent on interactions with dystrophin R16/17 and syntrophin. Both dystrophin R16/17 and Syntrophin (Syn) bind to nNOS. The interaction of nNOS with dystrophin R16/17 and syntrophin anchors nNOS to the sarcolemma. Syn: Syntrophin; DG: Dystroglycan.

DETAILED DESCRIPTION

The present disclosure identifies a novel series of dystrophin minigenes and microgenes that are small enough to be packaged into AAV or lentiviral vectors, and yet retain functions of a full-length, wild type dystrophin gene, including, but not limited to, the membrane binding functions and signal functions (such as sarcolemmal nNOS-related functions), needed for protecting muscle from dystrophic injury. The present disclosure recognizes that the inclusion of membrane binding motifs and/or the entire membrane binding domains contained in the spectrin repeats R10-R11-R12 of the mid-rod domain of a dystrophin protein in a synthetic mini/micro-dystrophin gene provide useful membrane binding functions. Mini or micro-dystrophin genes retaining the membrane binding motifs or membrane binding domains of the R10-R11-R12 can exhibit improved membrane binding and biological activity in comparison to mini or micro-dystrophin genes that lack the membrane binding motifs or membrane binding domains of the R10-R11-R12.

By "domain" is meant a portion of a protein structure. For example, the "N-terminal domain" or "NT" of a human dystrophin protein, as referred to herein, includes amino acid residues from approximately 1 to approximately 252, particularly, from amino acid residues methionine 1 to glutamate 252 of SEQ ID NO: 1, more particularly, amino acid sequence encoded by a nucleotide sequence as set forth in SEQ ID NO: 17. Similarly, the "mid-rod domain" or "rod domain" of a dystrophin protein, as referred to herein, includes amino acid residues approximately from 253 to approximately 3112 of SEQ ID NO: 1, particularly, from amino acid residues methionine 253 to leucine 3112 as set forth in SEQ ID NO: 1; the "cysteine-rich domain" or "CR" of a dystrophin protein, as referred to herein, includes amino acid residues from approximately 3113 to approximately 3408 of SEQ ID NO: 1, particularly, from amino acid residues arginine 3113 to threonine 3048 as set forth in SEQ ID NO: 1, more particularly, amino acid sequence encoded by a nucleotide sequence as set forth in SEQ ID NO: 46 and the "C-terminal domain" or "CT" of a dystrophin protein, as referred to herein, includes amino acid residues from approximately 3409 to 3685 of SEQ ID NO: 1, particularly, from amino acid residues proline 3409 to methionine 3685 as set forth in SEQ ID NO: 47.

By "dystrophin microgene" or "micro-dystrophin gene" or "microgene" is meant a nucleic acid molecule that is 5 kb or less in length and encodes a modified or non-full-length dystrophin polypeptide (also referred to as micro-dystrophin in the present application) that retains the N-terminal domain, the cysteine-rich domain, two or more repeats of the mid-rod domain, and two or more hinges of the mid-rod domain of a full-length dystrophin protein. By "micro-dystrophin" is meant a modified or non-full-length dystrophin protein molecule that retains biological function of a full-length dystrophin protein and the coding sequence of which is 5 kb or less.

By "dystrophin minigene," "mini-dystrophin gene" or "minigene" is meant a nucleic acid molecule that is more than 5 kb in length but less than the full-length of dystrophin coding sequence, between 5 kb to about 10 kb in length, about 5 kb to about 8 kb in length, or about 7 kb in length, and encodes a modified or non-full-length dystrophin polypeptide (also referred to as mini-dystrophin in the present application) that retains the N-terminal domain, the cysteine-rich domain, two or more repeats (also referred to by R and a number, e.g., R16 means repeat number 16) of the mid-rod domain, and two or more hinges of the mid-rod domain of a full-length dystrophin protein. By "mini-dystrophin" is meant a modified or non-full-length dystrophin protein molecule that retains the biological functions of a full-length dystrophin protein and the coding sequence of which is more than 5 kb in length but less than the full-length of dystrophin coding sequence.

By "biological functions" of a dystrophin protein is meant functions which include, but are not limited, at least one of providing a mechanical link between the sarcolemma, cytoskeleton or the extracellular matrix and/or providing a signaling function such as recruiting nNOS to the sarcolemma.

By "modified" in connection with dystrophin gene or dystrophin protein is meant a wild-type (or naturally-occurring) full-length dystrophin gene or dystrophin protein molecule is changed so that the modified dystrophin gene or dystrophin protein molecule does not include the full-length coding sequence of a dystrophin gene or the full-length amino acid sequence of a dystrophin protein, yet retain or substantially retain certain biological functions of a full-length gene or protein.

By "modified N-terminal domain" is meant an N-terminal domain that is different in structure and/or sequence from that of wild type or naturally occurred but retain the function of a wild type or naturally occurred N-terminus. By "modifications or variations" is meant any changes to a nucleic acid molecule or polypeptide, such as by mutation, that retains substantial function of the nucleic acid molecule or polypeptides and/or is substantially homologous with, or similar/identical to, the nucleic acid molecule or polypeptide.

In the classic model, dystrophin stabilizes the sarcolemma by interacting with a transmembrane protein β-dystroglycan and the F-actin cytoskeleton via its CR and NT domains, respectively. β-dystroglycan further connects with basal lamina proteins to complete the axis from the extracellular matrix (ECM) to intracellular cytoskeleton. However, this model completely ignores the direct interaction between dystrophin and membrane lipid bilayer, a major mechanism underlying spectrin-mediated membrane stabilization (Luna & Hitt, A. L. *Science* 258, 955-964 (1992); Le Rumeur et al. *Biochim. Biophys. Acta* 1804, 1713-1722 (2010); Sheetz, et al. *Annu Rev Biophys Biomol Struct* 35, 417-434 (2006)). Several lines of evidence suggest that dystrophin-lipid bilayer interaction can play a critical role for sarcolemma protection. First, in vitro studies suggest that the rod domain can contain putative lipid binding regions (LBRs) in R1-3 and R4-19 (Luna & Hitt, A. L. *Science* 258, 955-964 (1992); Le Rumeur et al. *Biochim. Biophys. Acta* 1804, 1713-1722 (2010); Sheetz, et al. *Annu Rev Biophys Biomol Struct* 35, 417-434 (2006)). Second, deletion of all putative rod domain LBRs abolishes the ability of dystrophin to protect muscle (Harper, S. Q. et al. *Nat. Med.* 8, 253-261 (2002)). Third, a series of in vitro studies demonstrated that binding of dystrophin LBRs to phospholipids considerably contributes to stiffness and stability of lipid monolayer (Sarkis, J. et al. *FASEB J.* 27, 359-367 (2013); Sarkis, J. et al. *J. Biol. Chem.* (2011)).

To better understand how dystrophin interacts with the sarcolemma in the absence of the CR domain, a comprehensive in vivo screening for alternative membrane binding domains (MBDs) in dystrophin was performed. The R1-3, R10-12 and CT domains were identified as new dystrophin MBDs in mouse muscle. We further confirmed that these MBDs are conserved in dog muscle. To determine whether these MBDs are functionally equivalent, we evaluated their ability to establish the dystrophin-associated glycoprotein complex (DGC) at the sarcolemma. Our results showed that only the CR domain and CT are capable of restoring the DGC. We also evaluated these newly discovered MBDs in the heart. We found that R1-3 and CT interact with the sarcolemma in cardiac muscle. Taken together, our studies suggest that dystrophin-sarcolemma interaction is much more complex than it has been perceived. Without seeking to be limited by theory, a new model to explain how dystrophin stabilizes the sarcolemma is proposed. In this model, dystrophin maintains sarcolemmal stability through two distinctive mechanisms: (i) dystrophin stabilizes the muscle membrane through the cytoskeleton (F-actin)-NT-CR-ECM axis; (ii) dystrophin strengthens the sarcolemma through the membrane association of its lipid binding regions LBRs. Both mechanisms involve the binding of dystrophin to the muscle membrane. Through the close association with the muscle membrane, dystrophin then tethers intracellular cytoskeleton to the sarcolemma, and stabilizes and strengthens the sarcolemma.

It is well established that dystrophin interacts with a congregation of cellular proteins (FIG. 3) (Johnson, E. K. et al. *PLoS One* 8, e73224 (2013); Johnson, E. K. et al. *PLoS One* 7, e43515 (2012); Allen, D. G. et al. *Physiol. Rev.* 96, 253-305 (2016); Constantin, B. Dystrophin complex functions as a scaffold for signaling proteins. *Biochim. Biophys. Acta* 1838, 635-642 (2014); Gao, Q. Q. & McNally, E. M. *Compr Physiol* 5, 1223-1239 (2015)). Besides the well known dystrophin-associated glycoprotein complex (DGC) (which includes dystroglycans, nNOS, syntrophin, dystrobrevins, sarcoglycans and sarcospan), dystrophin also interacts with cytoskeleton proteins (such as actin, tubulin, keratin, synemin and plectin), signaling proteins (such as Grb2, PAR-1b, cypher and ahnakl), channel proteins (such as TRPC1, TRPC4 and Nav1.5), caveolae proteins (such as caveolin-3 and cavin-1), tripartite motif proteins (e.g. myospryn) and chaperones (e.g. CRYAB). R10-12 belongs to the second actin-binding domain of dystrophin, and the CT-domain has the syntrophin and dystrobrevin binding motifs (Sadoulet-Puccio, et al. *Proc. Natl. Acad. Sci. USA* 94, 12413-12418 (1997). In certain embodiments provided herein, protein binding determinants in R10-R12 (F-actin), R16-R17 (nNOS), CR (beta-dystroglycan), and/or in CT (sarcoglycan, dystrobrevin, syntropin) are retained in the synthetic mini and micro dystrophin proteins and nucleic acids encoding the same that are provided herein.

In certain embodiments, the synthetic nucleic acid molecules provided herein comprise membrane binding motifs or membrane binding domains from the R10-R11-R12 regions of dystrophin that can be coupled with at least two membrane binding motifs or membrane binding domains from the R1-R2-R3, CR, and CT regions of dystrophin protein.

Membrane binding motifs of the R1-R2-R3 region used in the synthetic mini or micro dystrophins provided herein include, but are not limited to, the S-palmitoylation site peptide of SEQ ID NO: 54, SEQ ID NO: 55, and SEQ ID NO:56. In certain embodiments, the membrane binding domain of the R1-R2-R3 region used in the synthetic mini or micro dystrophins comprises the R1 repeat or the R1 and the R2 repeats.

Membrane binding motifs of the R10-R11-R12 region used in the synthetic mini or micro dystrophins provided herein include, but are not limited to, the S-palmitoylation site peptide of SEQ ID NO:57. In certain embodiments, the membrane binding domains of R10-R11-R12 can comprise any one of the R10 repeat, the R11 repeat, the R12 repeat, the R10-R11 repeats, the R11-R12, or the R10 and R12 repeats.

Membrane binding motifs of the CT domain used in the synthetic mini or micro dystrophins provided herein include, but are not limited to, the MBM of the CT MBD comprises residues 3422 to 3535 of SEQ ID NO: 1 or residues 3501 to 3685 of SEQ ID NO:1.

In certain embodiments, the synthetic nucleic acid molecules provided herein can comprise a nNOS binding domain of R16-R17. Such nNOS binding domains of the R16-R17 domains can comprise an R16-R17 peptide wherein the N-terminal alpha-helix of R16 (i.e., the sequence PSTYLTEITHVSQALLEVEQL (SEQ ID NO: 59) has been deleted where alpha-helices 2 and 3 of both of R16 and R17 are present. In certain embodiments, the N-terminal helix one of the R16 domain is substituted with the MBM of the R1-R2-R3 MBD or with the MBM of the R10-R11-R12 MBD. The remaining alpha-helices 2 and 3 of both of R16 and R17 along with the alpha-helix 1 of R17 that binds nNOS binding alpha-helix in vitro are sufficient to provide for in vivo nNOS binding (Lai, Y., et al., *Proc. Natl. Acad. Sci. USA* 110, 525-530 (2013).

In certain embodiments, the aforementioned dystrophin NT domain, repeats (e.g., R1, R2, R3, R10, R11, R12, R16, R17), CR domain, and CT domain are operably linked with a hinge region selected from the group consisting of a synthetic hinge, a semi-synthetic hinge, dystrophin H1, dystrophin H2, dystrophin H3, dystrophin H4, and variants thereof. A synthetic hinge can comprise or consist of one, two, or three, four, five or more "Gly-Gly-Ser-Gly" (SEQ ID NO:62) units. Other useful synthetic hinges that can be used include, but are not limited to: (i) [Gly-Ser]x linkers where x=2-10; (ii) one, two, or three, four, five or more "Gly-Gly-Gly-Ser" (SEQ ID NO:63) units; (iii) one, two, or three, four, five or more "Gly-Gly-Gly-Gly-Ser" (SEQ ID NO:64) units; (iv) one, two, or three, four, five or more "Ser-Glu-Gly" units; (v) one, two, or three, four, five or more "Gly-Ser-Ala-Thr" (SEQ ID NO:65) units; and (vi) any combination of (i)-(v) and/or of one, two, or three, four, five or more "Gly-Gly-Ser-Gly" (SEQ ID NO:62) units. A semi-sythetic hinge can comprise a dystrophin H1, H2, H3, or H4 hinge or portion thereof that incorporates a synthetic hinge.

Nucleic acids that encode the aforementioned syntrophin PDZ domain and/or dystrophin NT domain, repeats (e.g., R1, R2, R3, R10, R11, R12, R16, R17), CR domain, and CT domain that can be used include, but are not limited to, the nucleic acids provided in the sequence listing provided herein as well as by degenerate versions of those sequences that encode the same dystrophin polypeptide sequences. In certain embodiments, synthetic nucleic acids provided herein encode variants of the sequences of the aforementioned syntrophin PDZ domain and/or dystrophin NT domain, repeats (e.g., R1, R2, R3, R10, R11, R12, R16, R17), CR domain, and CT domain, or polypeptides contained therein that are listed in the sequence listing provided herewith or that are encoded by the nucleic acids listed in the sequence listing that: (i) exhibit at least 85%, 90%, 95%, 98%, or 99% sequence identity to the polypeptide sequence or encoded polypeptide sequence; (ii) contain 1, 2, 3, 4, 5, 6, or 7 conservative amino acid substitutions, insertions, or deletions; or (iii) incorporate one or more allelic variants of the sequence found in individuals with functional syntrophin PDZ domain or dystrophin genes that do not exhibit disease associated with loss or reductions in syntrophin PDZ domain or dystrophin activity.

In certain embodiments, the present disclosure provides vectors that can deliver the synthetic nucleic acid molecules encoding the micro or mini dystrophins or other fusion proteins provided herein. Any vector suitable for the purpose is contemplated by the present disclosure. In particular, the present disclosure provides a series of recombinant adeno-associated viral vectors (AAVs) and lentiviral vectors to deliver the nucleic acid molecules of the present disclosure (mini/micro-dystrophin genes) that exhibit improved membrane binding and biological activity. In certain embodiments, recombinant AAV vector (single vector or dual vectors) in accordance with the present disclosure includes any one of the nucleic acid molecule of the present disclosure (the mini/micro-dystrophin genes) that exhibit improved membrane binding and biological activity, operably linked to an expression cassette (a promoter and a polyA) and viral inverted terminal repeats (ITRs).

Numerous expression cassettes and vectors can be used with the micro and minidystrophin genes provided herein. By "expression cassette" is meant a complete set of control sequences including, but not limited to, initiation, promoter and termination sequences which function in a cell when they flank a structural gene in the proper reading frame. Expression cassettes frequently contain an assortment of restriction sites suitable for cleavage and insertion of any structural gene, e.g., the microgene or minigene of the present disclosure. In certain embodiments, the cloned gene will have a start codon in the correct reading frame for the structural synthetic dystrophin-encoding sequence. In addition, the expression cassette for the present disclosure can in certain embodiments includes, but not limited to, a constitutive promoter sequence, e.g., a CMV, RSV, CMV, SV40, CAG, CK6, or MCK promoters, at one end to cause the gene to be transcribed, and a poly-A recognition sequence at the other end for proper processing and transport of the messenger RNA. Examples of such a useful (empty) expression cassette into which the microgene of the present disclosure can be inserted are pcis.RSVmcs, pcis.CMVmcs, pcis.CMVmcs-intron, pcis.SV40mcs, pcis.SV40mcs-intron, pcis.CK6mcs, and pcis.CAGmcs as described in Yue et al (Yue & Duan 2002 Biotechniques 33(3):672-678). Examples of such a useful (empty) expression cassette into which the minigene of the present disclosure can be inserted are pDD188, pDD293 and pDD295 as described in Duan et al (Duan, Yue and Engelhardt 2003 Methods in Molecular Biology 219:29-51) and pAG15, and pAG21 as described in Ghosh et al (Ghosh, Yue, Lai and Duan 2008 Molecular Therapy 16:124-130). In certain embodiments, the expression cassette will provide for a muscle-specific promoter that is operably linked to the nucleic acid encoding the synthetic dystrophin. In certain embodiments, a muscle creatine kinase (MCK) promoter or variant thereof that retains muscle-specific activity is operably linked to the nucleic acid encoding the synthetic dystrophin (Wang et al.; Gene Ther. 2008 November; 15(22):1489-99). In certain embodiments, a muscle creatine kinase, troponin I, a skeletal alpha-actin, a desmin muscle-specific promoter or a derivative or chimera thereof is used (US20110212529, incorporated herein by reference in its entirety with respect to these promoters). Other useful muscle-specific promoters that can be used include, but are not limited to, CKS, CK6, CK7, CK8, myoglobin, CSK, Pitx3, and HAS promoters, derivatives thereof, or chimeras thereof. Other useful expression cassettes that can be used in certain vectors in conjunction with the mini and microdystrophin gene expression cassettes include, but are not limited to, expression cassettes that incorporate one or more selectable marker genes, such as a kanamycin, chlorosulfuron, phosphonothricin, hygromycin, or methotrexate resistance gene.

The term "vector" refers to a DNA or RNA sequence which is able to replicate and express a foreign gene in a host cell. Typically, vector has one or more endonuclease recognition sites which can be cut in a predictable fashion by use of the appropriate enzyme. Such vectors are can further comprise additional structural gene sequences imparting markers for identifying and separating transformed cells.

Useful markers/selection agents include, but are not limited to, kanamycin, chlorosulfuron, phosphonothricin, hygromycin and methotrexate. A cell in which the foreign genetic material in a vector is functionally expressed has been "transformed" by the vector and is referred to as a "transformant." Useful vectors include, but are not limited to, a nAAV vector, by which is a single-stranded DNA molecule which derives from the genome of Adeno-associated viruses but is non-pathogenic.

The expression cassette containing a minigene or microgene operably linked to the control sequences can be ligated into a suitable vector for delivery. In certain embodiments, AAV and lentiviral vectors containing replication and control sequences compatible with the host cell are used. A suitable vector, such as a single AAV vector will typically carry viral inverted terminal repeats (ITR) at the ends, the promoters, and microgene and polyA site.

By "dual vector system" meant a vector system composed of two vectors, e.g., AAV vectors, in which system both vector carry a part of a gene or sequence to be delivered and the entire gene is reconstituted by interaction between the two vectors. In one embodiment, the two vectors of dual vector system, e.g., AAV dual vector system, of the present disclosure are trans-splicing vectors (ts vectors, e.g., tsAAV vectors). In another embodiment, the two vectors of dual vector system, e.g., AAV dual vector system, of the present disclosure are hybrid vectors (e.g., hybrid AAV vectors). Trans-splicing AAV vectors typically carry (in addition to what are presented in a single AAV vector) a splicing donor signal and a splicing acceptor signal. Hybrid AAV vector will typically carry (in addition to what are presented in a single AAV vector and in the trans-splicing vector) a homologous overlapping sequence, such as from the middle one-third of human placental alkaline phosphotase gene. A lentiviral vector will typically carry the 5' long terminal repeats (LTR), the 3' LTR and the packaging signal.

By "operably linked" is meant that a nucleic acid molecule or polypeptide is placed in a functional relationship with another nucleic acid molecule or polypeptide. For example, expression cassette (a promoter and a polyA) is operably linked to a mini/micro-dystrophin gene if the expression cassette provided for transcription and polyadenylation of the sequence.

Dual AAV vectors of the present disclosure have large, e.g., at least 10 kb, packaging capacity. Three classical dual vectors are the cis-activation, trans-splicing (ts) and overlapping vectors (reviewed in Duan, D., Z. Yan, and J. F. Engelhardt. 2006. Expanding the capacity of AAV vectors, p. pp 525-32. In M. E. Bloom, S. F. Cotmore, R. M. Linden, C. R. Parrish, and J. R. Kerr (ed.), Parvoviruses. Hodder Arnold; Distributed in the U.S.A. by Oxford University Press, London, New York. Ghosh, A., and D. Duan. 2007. Expending Adeno-associated Viral Vector Capacity: A Tale of Two Vectors. Biotechnology and Genetic Engineering Reviews 24: 165-177, 2007.) The ts and overlapping vectors can deliver the 6 kb minigene. In tsAAV, a large therapeutic gene is split into a donor vector and an acceptor vector. The donor vector carries the 5' part of the gene and a splicing donor signal. The acceptor vector carries a splicing acceptor signal and the 3' part of the gene. Expression is achieved by AAV inverted terminal repeat (ITR)-mediated intermolecular recombination and subsequent splicing of the recombinant genome (FIG. 4) See Duan, D., Y. Yue, and J. F. Engelhardt. 2001. Expanding AAV Packaging Capacity With Transsplicing Or Overlapping Vectors: A Quantitative Comparison. Mol Ther 4:383-91, Sun, L., J. Li, and X. Xiao. 2000. Overcoming adeno-associated virus vector size limitation through viral DNA heterodimerization. Nat. Med. 6:599-602, and Yan, Z., Y. Zhang, D. Duan, and J. F. Engelhardt. 2000. From the Cover: Trans-splicing vectors expand the utility of adeno-associated virus for gene therapy. Proc. Natl. Acad. Sci. USA 97:6716-6721.

Figure 4:
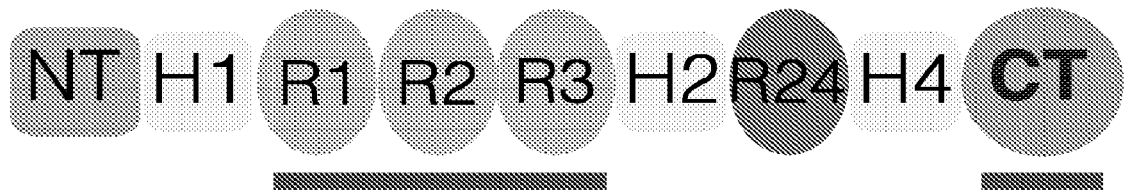
FIG. 4. The CR domain in ΔR4-R23/ΔCT is replaced with the CT domain. The membrane binding is marked by underlining.
Figure 4:
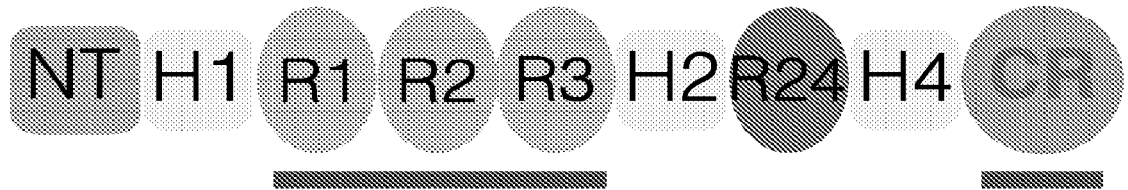

In the overlapping vectors, a large therapeutic gene is split into an upstream vector and a downstream vector. The upstream and the downstream vectors share a region of homology (Duan, D., Y. Yue, and J. F. Engelhardt. 2001., Halbert, C. L., J. M. Allen, and A. D. Miller. 2002. Efficient mouse airway transduction following recombination between AAV vectors carrying parts of a larger gene. Nat Biotechnol 20:697-701.) Transgene reconstitution is achieved through homologous recombination (FIG. 4). By rational vector design, such as optimizing the gene splitting site, the transduction efficiency from tsAAV vectors can reach that of a single AAV vector (Lai et al 2005 Nature Biotechnique; Lai et al 2006 Human Gene Therapy). Furthermore, systemic delivery of the tsAAV vectors has been shown to efficiently transduce whole body muscle in rodents (Ghosh, Yue, Long, Bostic and Duan 2007 Molecular Therapy 16:124-130). tsAAV-mediated minigene therapy was demonstrated to reduce muscle pathology, improve muscle force and prevent contraction-induced injury in a single mdx muscle (Lai, Y., D. Li, Y. Yue, and D. Duan. 2007. Design of trans-splicing adeno-associated viral vectors for Duchenne muscular dystrophy gene therapy. Method in Molecular Medicine:In-press., Lai, Y., Y. Yue, M. Liu, and D. Duan. 2006. Synthetic intron improves transduction efficiency of transsplicing adeno-associated viral vectors. Hum Gene Ther 17:1036-42, and Lai, Y., Y. Yue, M. Liu, A. Ghosh, J. F. Engelhardt, J. S. Chamberlain, and D. Duan. 2005. Efficient in vivo gene expression by trans-splicing adeno-associated viral vectors. Nat Biotechnol 23:1435-9.)

Besides the classic dual AAV vectors, a hybrid AAV dual vector system has been developed recently (Ghosh, Yue, Lai and Duan 2008 Molecular Therapy 16:124-130). The tsAAV is highly dependent on the optimal gene splitting site. This limitation is overcome in the hybrid vector system. In hybrid AAV vectors, transgene reconstitution can be achieved either through the traditional trans-splicing pathway as described in the tsAAV vectors or through homologous recombination via a highly recombinogenic foreign DNA sequence.

Accordingly, in still another embodiment, the present disclosure is directed to a method for the treatments of DMD, BMD and/or XLDC in a subject by administering to the subject a therapeutically effective amount of the minigene and/or microgene of the present disclosure, by administering a vector carrying the minigene and/or microgene, by administering to the subject a therapeutically effective amount of a AAV vector containing the minigene and/or microgene of the present disclosure. The term "subject" refers to any mammalian (e.g., human) or avian subject.

One route of the administration accordance with the method of the present disclosure includes, but is not limited to, local or regional muscle injection or forms of delivery to improve local muscle function in patients, systemic delivery (such as intravenous, intraartery, intraperitoneal) to all or most muscles in a region or in the whole body in patients, in vitro infection of myogenic stem cells with AAV or lentiviral vector followed by local and/or systemic delivery.

By "therapeutically effective amount" is meant an amount high enough to significantly positively modify the condition to be treated but low enough to avoid serious side effects (at reasonable benefit/risk ratio) within the scope of sound medical judgment. The therapeutically effective amount will vary with the particular condition being treated, or the condition of the subject being treated and his/her physical condition, as well as the type of preparation, vector, or composition being used.

In a particular embodiment, the present disclosure contemplates intravascular administration. For example, in AAV-9 gene therapy with micro-dystrophin gene containing R16 and R17, the dosage to newborn mice (1 week or younger in age) is about 0.5 to about $1.5 \times 10^{11}$ vg particles/gram body weight or about 50 to about 75 $\mu$l/gram body weight; the dosage to young mice (1 week to 1 month in age) is about 0.5 to about $1.5 \times 10^{11}$ vg particles/gram body weight or about 75 to about 200 $\mu$l/gram body weight; the dosage to adult mice (1 to 20-month-old) is about 0.5 to about $1.5 \times 10^{11}$ vg particles/gram body weight or about 200 to about 400 $\mu$l/gram body weight; the dosage for newborn dog (three days or younger in age) is about 0.5 to about $2 \times 10^{11}$ vg particles/gram body weight or about 10 to about 25 $\mu$l/gram body weight; the dosage for young dog (3 days to 3 months in age) is about 0.5 to about $2 \times 10^{11}$ vg particles/gram body weight or about 10 to about 25 $\mu$l/gram body weight; the dosage for adult dog (3-month-old or older) is about 1 to about $3 \times 10^{11}$ vg particles/gram body weight or about 15 to about 30 $\mu$l/gram body weight.

According to the present disclosure, after engineering the membrane binding motifs or membrane binding domains of the R10-R11-R12 repeat into the mini/micro dystrophin protein encoding sequence, the resultant synthetic nucleic acid molecule can be incorporated into non-viral and/or viral gene therapy vectors, and/or cell therapy for the treatment of dystrophin deficient diseases such as DMD, BMD and XLDC. The present disclosure provides a series of AAV mini/micro-dystrophin vectors that can exhibit improved membrane binding and biological activity in a dystrophin-deficient muscle. An recombinant AAV vector includes, but is not limited to, any one of the mini/micro-dystrophin genes provided herein, an expression cassette (a promoter and a polyA), and viral inverted terminal repeats (ITRs).

In yet another embodiment, the present disclosure is directed to a pharmaceutical composition containing one or more of the AAV vectors and lentiviral vectors of the present disclosure and unmodified plasmid DNA molecules and a pharmaceutically acceptable carrier.

Pharmaceutical formulations, dosages and routes of administration for nucleic acids are generally disclosed, for example, in U.S. Pat. No. 5,580,859 to Felgner et al. Both local and systemic administration are contemplated by the present disclosure. In certain embodiments where the molecules of the disclosure are employed for prophylactic purposes, agents of the disclosure are amenable to chronic use, such as by systemic administration. One or more suitable unit dosage forms comprising the therapeutic agents of the disclosure, which can optionally be formulated for sustained release, can be administered by a variety of routes including, but not limited to, oral, parenteral, including by rectal, transdermal, subcutaneous, intravenous, intramuscular, intraperitoneal, intrathoracic, intrapulmonary, and intranasal routes. The formulations can, where appropriate, be conveniently presented in discrete unit dosage forms and can be prepared. Such methods can include the step of bringing into association the synthetic dystrophin encoding nucleic acid or synthetic dystrophin with liquid carriers, solid matrices, semi-solid carriers, finely divided solid carriers or combinations thereof, and then, optionally, introducing or shaping the product into the delivery system.

In certain embodiments where a synthetic dystrophin encoding nucleic acid, synthetic dystrophins, or vectors comprising or encoding the same are prepared for oral administration, they can be combined with a pharmaceutically acceptable carrier, diluent or excipient to form a pharmaceutical formulation, or unit dosage form.

By "pharmaceutically acceptable" is meant the carrier, diluent, excipient, and/or salt is compatible with the other ingredients of the formulation, and not deleterious to the recipient thereof. The active ingredient for oral administration can be present as a powder or as granules; as a solution, a suspension or an emulsion; or in achievable base such as a synthetic resin for ingestion of the active ingredients from a chewing gum. The active ingredient can also be presented as a bolus, electuary or paste.

Pharmaceutical formulations containing the a therapeutic agent of this disclosure including, but not limited to, synthetic dystrophin encoding nucleic acids, synthetic dystrophins, vectors or viral vector particle comprising or encoding the same, can be prepared. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The therapeutic agents of the disclosure can also be formulated as elixirs or solutions for convenient oral administration or as solutions appropriate for parenteral administration, for instance by intramuscular, subcutaneous or intravenous routes.

The pharmaceutical formulations of the therapeutic agents of the disclosure can also take the form of an aqueous or anhydrous solution or dispersion, or alternatively the form of an emulsion or suspension.

Thus, the therapeutic agent of this disclosure can be formulated for parenteral administration (e.g., by injection, for example, bolus injection or continuous infusion) and can be presented in unit dose form in ampules, pre-filled syringes, small volume infusion containers or in multi-dose containers with an added preservative. The active ingredients can take such forms as suspensions, solutions, or emulsions in oily or aqueous vehicles, and can contain formulatory agents such as suspending, stabilizing and/or dispersing agents. Alternatively, the active ingredients can be in powder form, obtained by aseptic isolation of sterile solid or by lyophilization from solution, for constitution with a suitable vehicle, e.g., sterile, pyrogen-free water, before use.

The compositions according to the disclosure can also contain thickening agents such as cellulose and/or cellulose derivatives. They can also contain gums such as xanthan, guar or carbo gum or gum arabic, or alternatively polyethylene glycols, bentones and montmorillonites, and the like.

In certain embodiments, an adjuvant chosen from anti-oxidants, surfactants, other preservatives, film-forming, keratolytic or comedolytic agents, perfumes and colorings can be added to the composition. Also, other active ingredients can be added, whether for the conditions described or some other condition.

The local delivery of the pharmaceutical composition of the present disclosure can also be by a variety of techniques which administer the agent at or near the site of disease. Examples of site-specific or targeted local delivery techniques are not intended to be limiting but to be illustrative of the techniques available. Examples include local delivery catheters, such as an infusion or in-dwelling catheter, e.g., a needle infusion catheter, shunts and stents or other implantable devices, site specific carriers, direct injection, or direct applications.

In particular, for delivery of a vector of the disclosure to a tissue such as muscle, any physical or biological method that will introduce the vector into the muscle tissue of a host animal can be employed. Vector means both a bare recombinant vector and vector DNA packaged into viral coat proteins to form a viral vector particle. Simply dissolving an AAV vector in phosphate buffered saline (PBS) or in N-2-Hydroxyethylpiperazine-N'-2-ethanesulfonic acid (HEPES) buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). The pharmaceutical compositions can be prepared as injectable formulations or as topical formulations to be delivered to the muscles by transdermal transport. Numerous formulations for both intramuscular injection and transdermal transport have been previously developed and can be used in the practice of the disclosure. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. In certain embodiments, such aqueous solutions can be buffered and the liquid diluent first rendered isotonic with saline or glucose. Solutions of the synthetic nucleic acid or vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms.

In certain embodiments, the Pharmaceutical forms or compositions suitable for injectable use include, but are not limited to, sterile aqueous solutions or dispersions and sterile powders for the extemporaneous preparation of sterile injectable solutions or dispersions. In certain embodiments, the form is sterile and fluid to the extent that easy syringability exists. It is typically stable under the conditions of manufacture and storage and is preserved against the contaminating action of microorganisms such as bacteria and fungi. In certain embodiments, the carrier can be a solvent or dispersion medium containing, for example, water, ethanol, polyol (for example, glycerol, propylene glycol, liquid polyethylene glycol and the like), suitable mixtures thereof, and vegetable oils. In certain embodiments, the proper fluidity can be maintained, for example, by the use of a coating such as lecithin, by the maintenance of a given particle size in the case of a dispersion and by the use of surfactants. In certain embodiments, the prevention of the action of microorganisms can be brought about by various antibacterial and antifungal agents that include, but are not limited to, parabens, chlorobutanol, phenol, sorbic acid, thimerosal and the like. In certain embodiments, isotonic agents, for example, sugars or sodium chloride are included. Prolonged absorption of the injectable compositions can be brought about by use of agents delaying absorption, for example, aluminum monostearate and gelatin.

In certain embodiments, sterile injectable solutions are prepared by incorporating the synthetic nucleic acid or vector in the desired amount in the appropriate solvent with various of the other ingredients enumerated above, followed by filtered sterilization. In certain embodiments, dispersions are prepared by incorporating the sterilized active ingredient into a sterile vehicle which contains the basic dispersion medium and the other ingredients from those enumerated above. In the case of sterile powders for the preparation of sterile injectable solutions, the preferred methods of preparation are vacuum drying and the freeze drying technique which yield a powder of the active ingredient plus any additional ingredient from the previously sterile-filtered solution thereof.

Also provided herein are methods and resultant host cells wherein a defective endogenous dystrophin gene of the host cell or a defective portion thereof is edited to provide the synthetic nucleic acid molecule within the host cell's X-chromosome. Such methods of gene editing include, but are not limited to, those that employ a clustered regularly interspaced short palindromic repeats (CRISPR)-associated (Cas)-guide RNA or source thereof and a Cas endonuclease or source thereof, wherein the guide RNA and Cas endonuclease can form a complex that can introduce a double strand break at a target site in a nuclear genome of the host cell that provides for incorporation of the synthetic nucleic acid or portion thereof into the endogenous dystrophin locus. Methods that can be adapted for this purpose are disclosed in US Patent Application publications US20160175462, US20160115488, and US20160153004, which are each incorporated herein by reference in their entireties.

Abbreviations

DMD: Duchenne muscular dystrophy
CR: Cysteine-rich
NT: N-terminus
CT: C-terminus
R: Spectrin-like repeat
DGC: Dystrophin-associated glycoprotein complex
ECM: Extracellular matrix
H: Hinge region
MBD: Membrane binding domain
GFP: Green fluorescent protein
TA: Tibialis anterior
AAV: Adeno-associated virus To the extent to which any of the preceding abbreviations or definitions is inconsistent with abbreviations or definitions provided in any patent or non-patent reference incorporated herein by reference, any patent or non-patent reference cited herein, or in any patent or non-patent reference found elsewhere, it is understood that the preceding definition will be used herein.

Non-limiting embodiments provided herein include:
Embodiment 1. A synthetic nucleic acid molecule encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17; wherein the domains and the MBM are arranged from N to C terminus in the order in which they occur in a wild-type dystrophin protein and are operably linked.

Embodiment 2. The synthetic nucleic acid molecule of embodiment 1, wherein the MBM of R1-R2-R3 comprises at least one S-palmitoylation site peptide selected from the group consisting of SEQ ID NO: 54, SEQ ID NO: 55, and SEQ ID NO:56.

Embodiment 3. The synthetic nucleic acid molecule of embodiment 1, wherein R3 repeat or R2-R3 repeats are absent from the non-full length dystrophin protein.

Embodiment 4. The synthetic nucleic acid molecule of embodiment 1, wherein the R1, R2, R3, R1 and R2, R2 and R3, or R1, R2, and R3 repeats are present in the non-full length dystrophin protein.

Embodiment 5. The synthetic nucleic acid molecule of embodiment 1, wherein the MBM of R10-R11-R12 comprises an S-palmitoylation site peptide of SEQ ID NO:57.

Embodiment 6. The synthetic nucleic acid molecule of embodiment 1, wherein the R10 repeat, the R11 repeat, the R12 repeat, the R10-R11 repeats, the R11-R12, or the R10 and R12 repeats are present in the non-full length dystrophin protein.

Embodiment 7. The synthetic nucleic acid molecule of embodiment 1, wherein the R17 domain is present in the non-full length dystrophin protein.

Embodiment 8. The synthetic nucleic acid molecule of embodiment 1, wherein the n-terminal alpha helix of the R16 domain (SEQ ID NO:59) or a portion thereof is absent from the non-full length dystrophin protein.

Embodiment 9. The synthetic nucleic acid molecule of embodiment 8, wherein alpha-helix 2 and alpha-helix 3 of the R16 domain is present and alpha-helix 1, alpha-helix 2, and alpha-helix 3 of the R17 domain is present in the non-full length dystrophin protein.

Embodiment 10. The synthetic nucleic acid molecule of embodiment 8, wherein alpha-helix 2 and alpha-helix 3 of the R16 domain is present and alpha-helix 1, alpha-helix 2, and alpha-helix 3 of the R17 domain is present in the non-full length dystrophin protein.

Embodiment 11. The synthetic nucleic acid molecule of embodiment 8, wherein N-terminal helix one of the R16 domain is substituted with the MBM of the R1-R2-R3 MBD or with the MBM of the R10-R11-R12 MBD.

Embodiment 12. The synthetic nucleic acid molecule of embodiment 1, wherein the R16 domain and the R17 domain are present in the non-full length dystrophin protein.

Embodiment 13. The synthetic nucleic acid molecule of embodiment 1, wherein the MBM of the CR membrane binding domain is absent, wherein the CR membrane binding domain is absent, or wherein the CR domain is absent from the non-full length dystrophin protein.

Embodiment 14. The synthetic nucleic acid molecule of embodiment 1, wherein the MBM of the CT MBD comprises residues 3422 to 3535 of SEQ ID NO: 1.

Embodiment 15. The synthetic nucleic acid molecule of embodiment 1, wherein the MBM of the CT MBD comprises residues 3501 to 3685 of SEQ ID NO: 1.

Embodiment 16. The synthetic nucleic acid of embodiment 1, wherein at least one domain and at least one MBM are operably linked with a hinge region selected from the group consisting of a synthetic hinge, a semi-synthetic hinge, dystrophin H1, dystrophin H2, dystrophin H3, dystrophin H4, and variants thereof.

Embodiment 17. The synthetic nucleic acid of embodiment 1, wherein the dystrophin H1 hinge or a variant thereof operably links the C-terminus of the NT domain to the N-terminus of an MBM or domain containing an MBM, wherein the dystrophin H2 hinge or a variant thereof operably links the C-terminus of a MBM or domain containing an MBM to the N-terminus of another MBM or domain containing another MBM, wherein the dystrophin H3 hinge or a variant thereof operably links the C-terminus of an MBM or domain containing an MBM to the N-terminus of another MBM or domain containing another MBM, wherein the dystrophin H4 hinge or a variant thereof operably links the C-terminus of an MBM to the N-terminus of the CR MBM or the CR domain, or any combination thereof.

Embodiment 18. The synthetic nucleic acid of embodiment 1, wherein the dystrophin H4 hinge or a variant thereof operably links the C-terminus of an MBM to the N-terminus of the CR MBM or the CR domain.

Embodiment 19. The synthetic nucleic acid molecule of any one of embodiments 1 to 18, wherein the mini- or micro-dystrophin gene is between 5 kb to about 8 kb in length or less than 5 kb in length, respectively.

Embodiment 20. The synthetic nucleic acid molecule of any one of embodiments 1 to 18, wherein the mini- or micro-dystrophin gene is operably linked to a heterologous promoter, a heterologous 5' untranslated region (UTR), a heterologous 3' UTR, a heterologous polyadenylation site, or any combination thereof.

Embodiment 21. The synthetic nucleic acid molecule of any one of embodiments 1 to 18, wherein said molecule is integrated within an endogenous dystrophin gene locus in an X-chromosome.

Embodiment 22. A lentiviral vector comprising the synthetic nucleic acid molecule of any one of embodiments 1 to 20, wherein the nucleic acid molecule is operably linked to an expression cassette, 5' and 3' long terminal repeats (LTR), and a psi sequence in the lentiviral vector.

Embodiment 23. A single recombinant adeno-associated virus (AAV) vector comprising the nucleic acid of any one of embodiments 1 to 20, wherein said nucleic acid molecule is operably linked to an expression cassette and viral inverted terminal repeats (ITRs) in the AAV.

Embodiment 24. A dual recombinant AAV vector system, comprising two AAV vectors, wherein one of the two AAV vectors comprises a part of the nucleic acid molecule of any one of embodiments 1 to 20, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Embodiment 25. A composition comprising the synthetic nucleic acid molecule of any one of embodiments 1 to 20 and a pharmaceutically acceptable carrier.

Embodiment 26. The composition of embodiment 25, wherein the nucleic acid molecule is operably linked to an expression cassette, 5' and 3' long terminal repeats (LTR), and a psi sequence in a lentiviral vector.

Embodiment 27. The composition of embodiment 25, wherein said nucleic acid molecule is operably linked to an expression cassette and viral inverted terminal repeats (ITRs) in an AAV Embodiment 28. The composition of embodiment 25 comprising the dual recombinant AAV vector system of embodiment 24.

Embodiment 29. An isolated host cell comprising the synthetic nucleic acid molecule of any one of embodiments 1 to 21.

Embodiment 30. The host cell of embodiment 29, wherein said nucleic acid molecule is integrated within an endogenous dystrophin gene locus in a chromosome of the host cell.

Embodiment 31. The host cell of embodiment 29, wherein the nucleic acid molecule is operably linked to an expression cassette, 5' and 3' long terminal repeats (LTR), and a psi element in a lentiviral vector.

Embodiment 32. The host cell of embodiment 29, wherein said nucleic acid molecule is operably linked to an expression cassette and ITRs in an AAV.

Embodiment 33. The host cell of embodiment 29, wherein the host cell is a myogenic stem cell.

Embodiment 34. A method for the treating or ameliorating one or more adverse effects of Duchenne muscular dystrophy (DMD), Becker muscular dystrophy (BMD) or X-linked dilated cardiomyopathy (XLDC) in a subject in need thereof comprising the step of administering to the subject a therapeutically effective amount of: (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 to a subject in need thereof.

Embodiment 35. The method of embodiment 34, wherein the administration is by injection into muscle, systemic delivery, or local delivery.

Embodiment 36. The method of embodiment 34, wherein the host cell is a stem cell or myogenic stem cell.

Embodiment 37. The method of embodiment 34 or 36, wherein the host cell is derived from an autologous cell of the subject.

Embodiment 38. The method of any one of embodiments 34, 35, 36, or 37, wherein a defective endogenous dystrophin gene of the host cell or a defective portion thereof is edited to provide the synthetic nucleic acid molecule within the host cell's X-chromosome.

Embodiment 39. Use of (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 for making a composition for administration to a subject suffering from Duchenne muscular dystrophy (DMD), Becker muscular dystrophy (BMD) or X-linked dilated cardiomyopathy (XLDC).

Embodiment 40. Use of (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 for treating a subject suffering from Duchenne muscular dystrophy (DMD), Becker muscular dystrophy (BMD) or X-linked dilated cardiomyopathy (XLDC), or for ameliorating one or more adverse effects of DMD, BMD, or XLDC.

Embodiment 41. A synthetic nucleic acid molecule encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17 or an nNOS binding domain of R16-R17 that is operably linked to a syntrophin PDZ domain; wherein the dystrophin domains and the MBM are arranged from N to C terminus in the order in which they occur in a wild-type dystrophin protein and are operably linked.

Embodiment 42. A synthetic nucleic acid molecule comprising a sequence encoding a fusion protein comprising a nNOS binding domain of dystrophin R16-R17 that is operably linked to a syntrophin PDZ domain.

Embodiment 43. A single recombinant adeno-associated virus (AAV) vector comprising the nucleic acid molecule of embodiment 41 or 42, wherein said nucleic acid molecule is operably linked to an expression cassette and viral inverted terminal repeats (ITRs) in the AAV.

Embodiment 44. A dual recombinant AAV vector system, comprising two AAV vectors, wherein one of the two AAV vectors comprises a part of the nucleic acid molecule of embodiment 41 or 42, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Embodiment 45. A lentiviral vector comprising the synthetic nucleic acid molecule of embodiment 41 or 42, wherein the nucleic acid molecule is operably linked to an expression cassette, 5' and 3' long terminal repeats (LTR), and a psi sequence in the lentiviral vector.

Embodiment 46. A fusion protein comprising dystrophin nNOS binding domain of R16-R17 that is operably linked to a syntrophin PDZ domain.

Embodiment 47. A composition comprising (i) the synthetic nucleic acid molecule of embodiment 41 or 42, the vector of embodiment 43, 44, or 45, or the protein of embodiment 46; and (ii) a pharmaceutically acceptable carrier.

Embodiment 48. An isolated host cell comprising the synthetic nucleic acid molecule of embodiment 41 or 42, or the vector of embodiment 43, 44, or 45.

Embodiment 49. A method for the treating or ameliorating one or more adverse effects of Duchenne muscular dystrophy (DMD), age-related muscle atrophy, cancer cachexia, or other neuromuscular disorders characterized by loss of sarcolemmal neuronal nitric oxide synthase (nNOS) activity in a subject in need thereof comprising the step of administering to the subject a therapeutically effective amount of: (i) the synthetic nucleic acid molecule of any one of embodiments 41 or 42; (ii) the lentiviral vector of embodiment 45; (iii) the AAV vector of embodiment 43 or 44; (iv) the composition of embodiment 47; or (iv) the host cell of embodiment 48 to a subject in need thereof.

Embodiment 50. The method of embodiment 49, wherein the administration is by injection into muscle, systemic delivery, or local delivery.

EXAMPLES

The following examples are included to demonstrate various embodiments. It will be appreciated by those of skill in the art that the techniques disclosed in the following examples represent techniques discovered by the Applicants to function well. However, those of skill in the art should, in light of the instant disclosure, appreciate that many changes can be made in the specific embodiments that are disclosed, while still obtaining like or similar results, without departing from the scope of the disclosure.

Example 1. Identification of Dystrophin R1-3, R10-12 and CT as New Dystrophin MBDs To thoroughly understand how dystrophin interacts with the sarcolemma, we performed a comprehensive screening in mouse muscle. According to the fact that dystrophin has four functional domains and its mid-rod domain can be further divided into sub-regions (14), we split the full-length human dystrophin protein into ten subdomains, including NT-H1, R1-3, R4-6, R7-9, R10-12, R13-15, R16-19, R20-24, H4-CR and CT. We fused each subdomain with a green fluorescent protein (GFP) tag and individually expressed them in the tibialis anterior (TA) muscle of dystrophin-null mdx mice by adeno-associated virus (AAV)-mediated gene transfer (FIG. 5).

Figure 6:
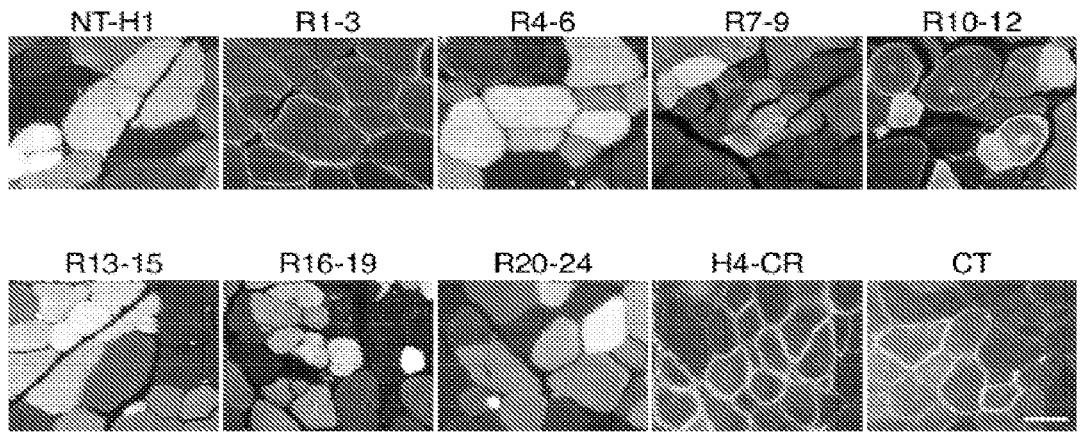
FIG. 6. Dystrophin R1-3, R10-12, CR and CT are independent membrane-binding domains. Full-length human dystrophin was split into ten subdomains and each subdomain fused with a GFP tag. The fusion proteins were individually expressed in mdx muscle by AAV gene transfer. Representative GFP photomicrographs of each indicated dystrophin subdomain are shown. Dystrophin R1-3, H4-CR and CT were exclusively localized at the sarcolemma. R10-12 was found at the sarcolemma and in the cytosol. NT-H1, R4-6, R7-9, R13-15, R16-19 and R20-24 were exclusively localized in the cytosol. Scale bar: 50 µm.

To determine subcellular localizations of each dystrophin subdomain, we visualized the GFP signal under a fluorescence microscope (FIG. 6). In line with the literature, we observed sarcolemmal localization of the H4-CR subdomain. Unexpectedly, we found that subdomains R1-3 and CT were exclusively restricted at the muscle cell membrane. Subdomains NT-H1, R4-6, R7-9, R13-15, R16-19, and R20-24 were only detected in the cytosol. Interestingly, the R10-12 subdomain was found both at the sarcolemma and in the cytoplasm (FIG. 6).

Figure 7A:
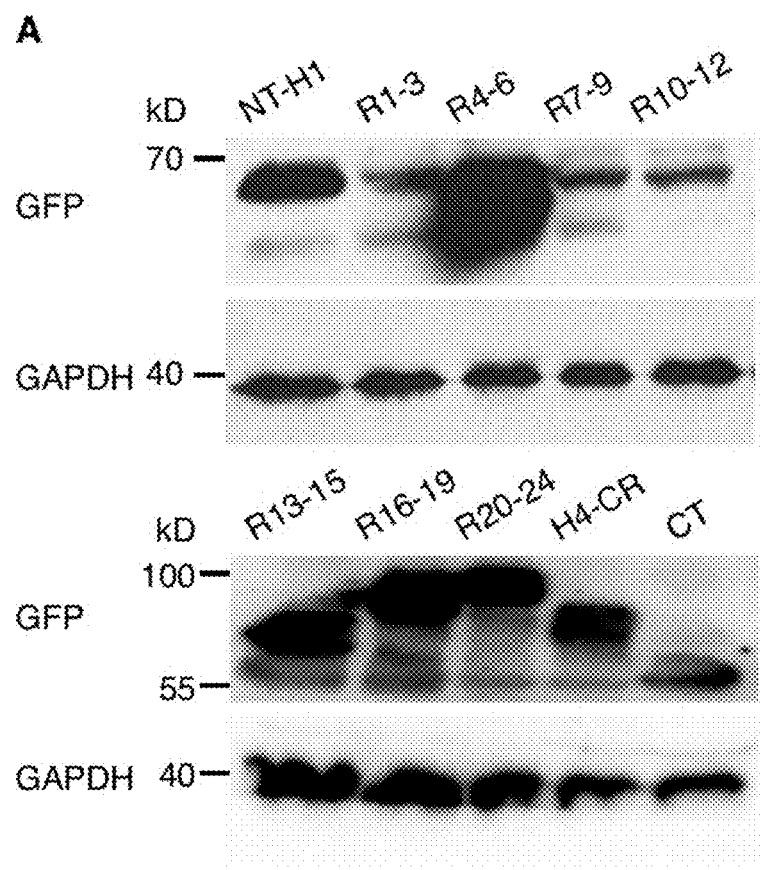
FIG. 7A,B. Microsomal western blot suggests the association of R1-3, R10-12, CR and CT with the sarcolemma. A. Whole muscle lysate western blots revealing AAV-mediated expression of GFP-fused dystrophin subdomains in mdx muscle. B. Detection of dystrophin R1-3, R10-12, CR and CT in the membrane fraction by microsomal western blots. GAPDH marks the cytosolic fraction. C, cytosolic fraction; M, membrane fraction.
Figure 7B:
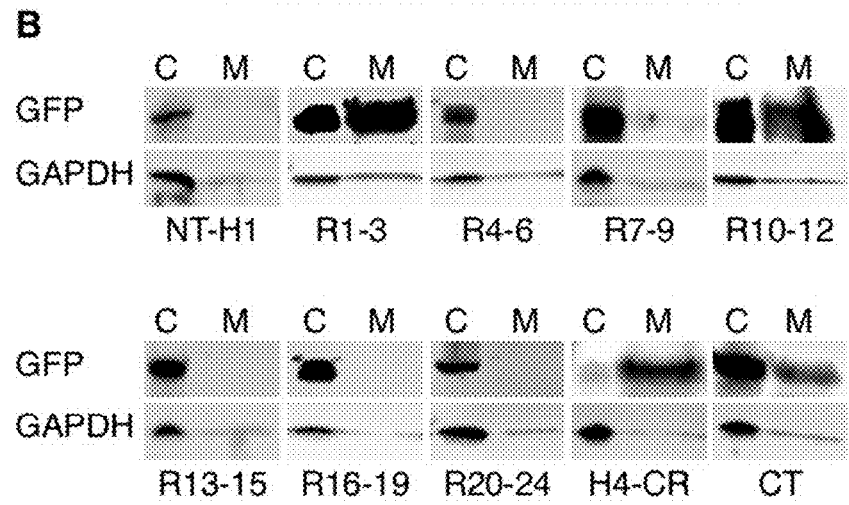

To confirm these intriguing observations, we performed immunoblot with whole muscle lysates and microsomal preparations (FIG. 7). In whole muscle lysates, we found efficient expression of all ten dystrophin subdomains (FIG. 7A). However, only subdomains R1-3, R10-12, CR and CT were detected in membrane-enriched microsomal preparations (FIG. 7B). These data are in agreement with immunostaining results suggesting that these subdomains are indeed dystrophin MBDs.

Figure 8:
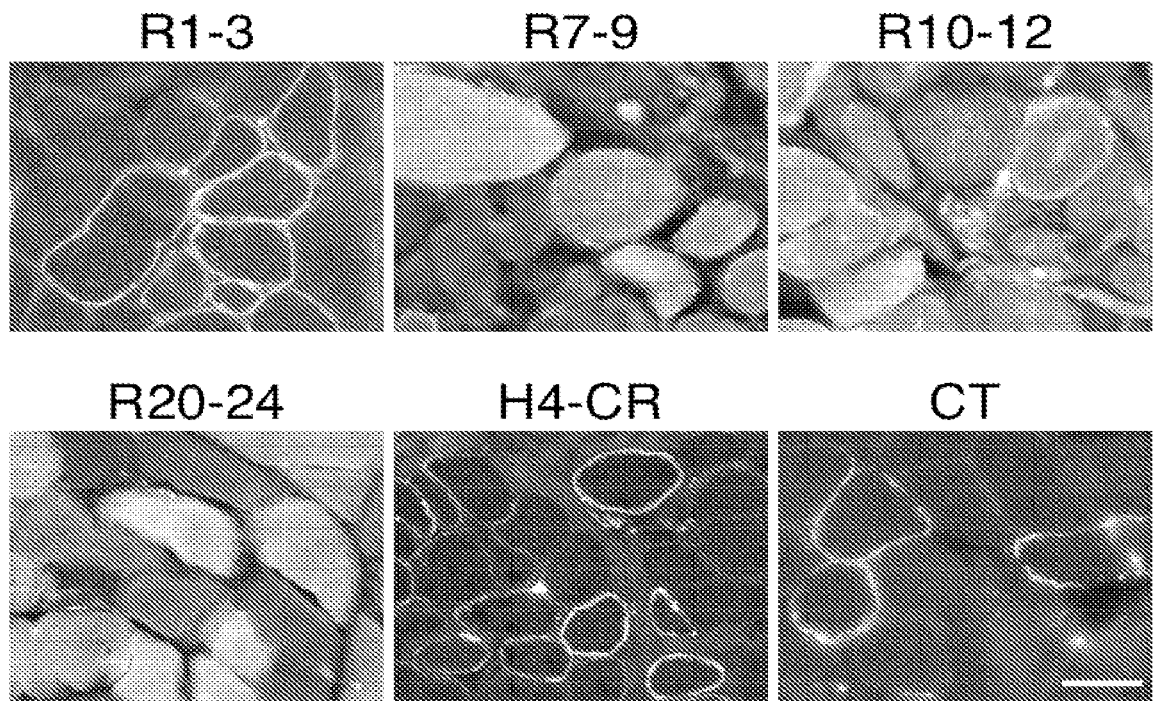
FIG. 8. Dystrophin R1-3, R10-12, CR and CT bind to the sarcolemma in canine muscle. Indicated GFP fusion dystrophin subdomains were expressed in dystrophic dog muscle by AAV gene transfer. Representative GFP photomicrographs show the membrane binding of R1-3, R10-12, CR and CT and cytosolic localization of R7-9 and R20-24. R10-12 is also seen in the cytosol. Scale bar: 50 µm.

Preservation of the membrane-binding property of R1-3, R10-12, CR and CT in canine muscle. To examine whether the membrane-binding property of R1-3, R10-12, CR and CT is conserved in different species, next we delivered the corresponding AAV vectors to dystrophic dog muscle by local injection. As controls, we also injected R7-9 and R20-24 AAV vectors. Two months later, we examined GFP expression under a fluorescence microscope. Similar to what we saw in mdx muscle, R1-3, CR and CT subdomains were exclusively localized at the muscle membrane, while the R10-12 subdomain was found both at the sarcolemma and in the cytoplasm. Subdomains R7-9 and R20-24, which localized exclusively in the cytosol in mdx muscle, were only detected in the cytosol of dystrophic dog muscle (FIG. 8)

Figure 1:
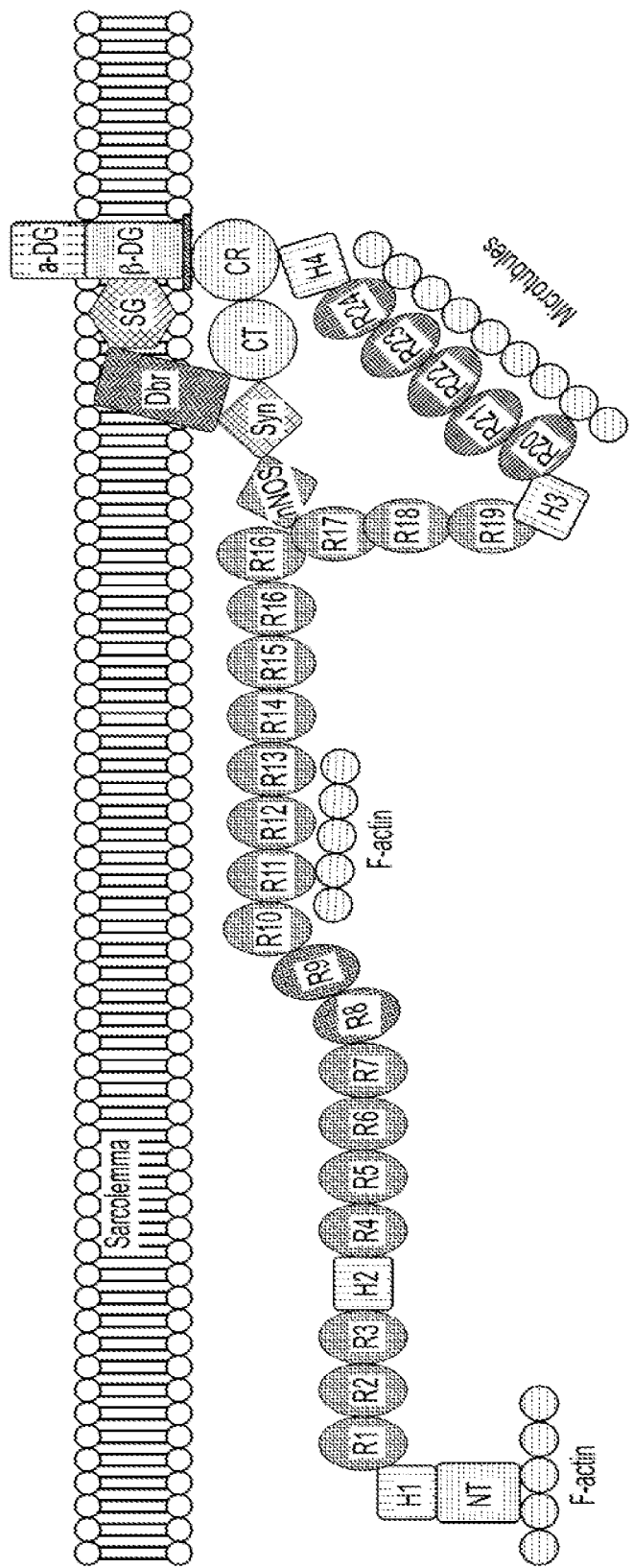
FIG. 1. The classic model of dystrophin-sarcolemma interaction. Numerous studies suggest that dystrophin binds to the sarcolemma via its CR domain (1-8). See Supplementary References provided herein for full citation.
Figure 9:
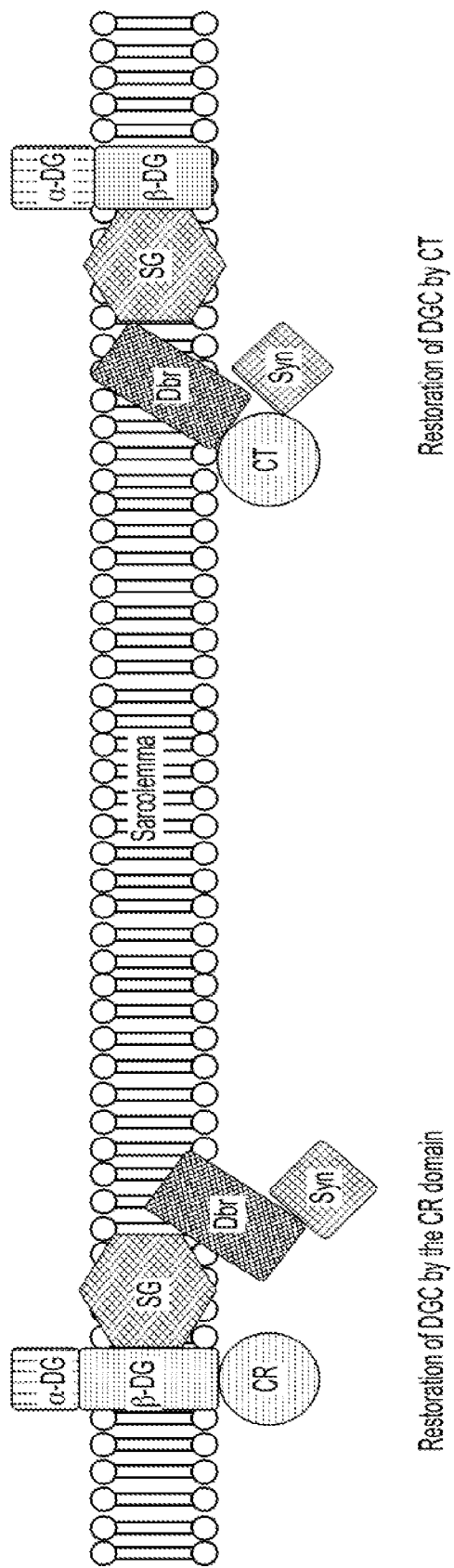
FIG. 9. The hypothetical mechanism of CT-mediated DGC restoration. Left side cartoon illustrates the CR domain mediated DGC restoration. Right side cartoon illustrates the hypothetical mechanism of CT-mediated DGC restoration. Specifically, direct membrane binding of the CT domain restores syntrophin and dystrobrevin to the sarcolemma (24, 25). Membrane-localized syntrophin and dystrobrevin then recruit sarcoglycans and dystroglycan to the sarcolemma (26-29). DG, dystroglycan; SG, sarcoglycans; Dbr, dystrobrevin; Syn, syntrophin.
Figure 10:
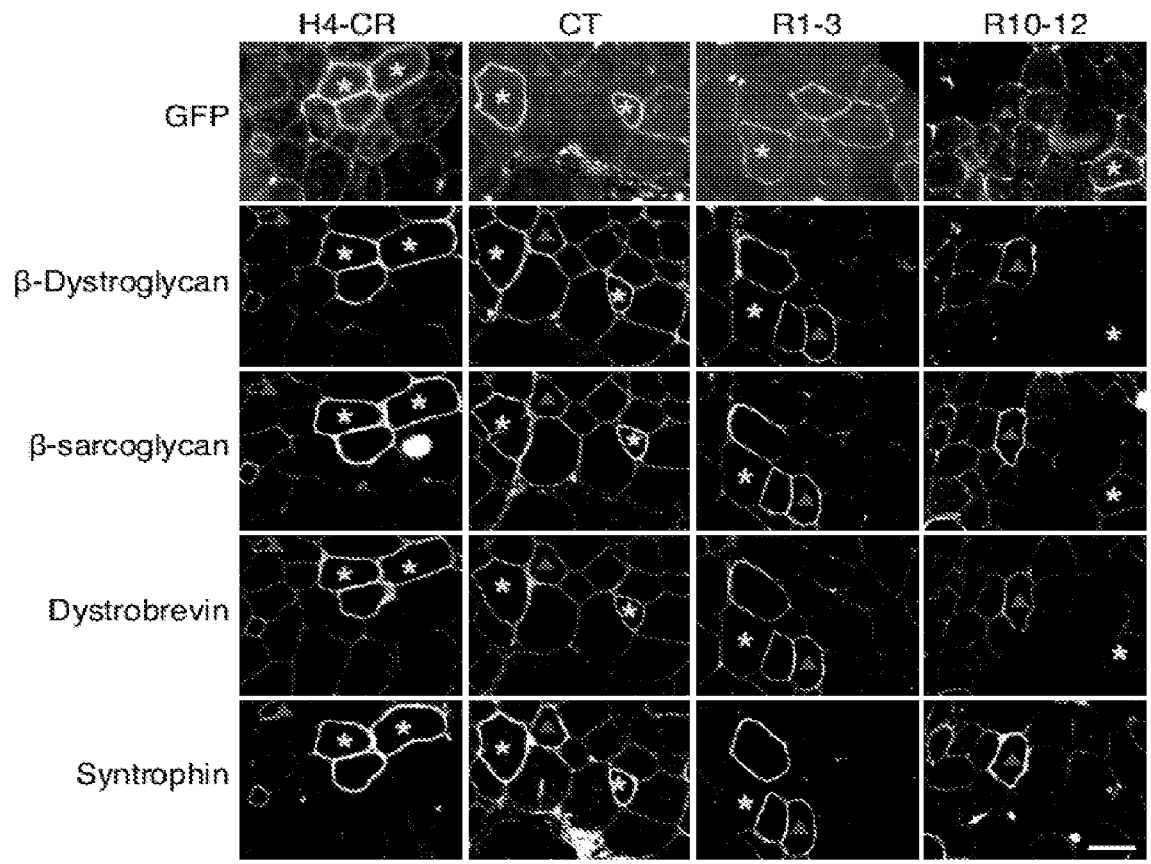
FIG. 10. Dystrophin CT restores the DGC at the sarcolemma. Representative serial section photomicrographs of GFP and immunostaining for β-dystroglycan, β-sarcoglycan, dystrobrevin and syntrophin in mdx muscle expressing the indicated GFP-dystrophin subdomain fusion proteins. Asterisk, the GFP-positive myofiber in serial sections; triangle, the GFP-negative revertant fiber in serial sections. GFP signals co-localize with DGC components in myofibers transduced by the H4-CR and CT but not R1-3 and R10-12 subdomain AAV vectors. Scale bar: 50 µm.

Independent restoration of the DGC by the CR domain and CT. In the canonical model (FIGS. 1 and 9), the CR domain is solely responsible for nucleating dystroglycan, sarcoglycans, dystrobrevin and syntrophin into the DGC at the sarcolemma (15-18). To determine whether the newly identified MBDs had similar functions, we evaluated DGC components on serial muscle sections by immunostaining (FIG. 10). As expected, the H4-CR subdomain successfully restored β-dystroglycan, β-sarcoglycan, dystrobrevin and syntrophin to the sarcolemma. Myofibers that were transduced with the CT subdomain AAV vector also resulted in sarcolemmal localization of these DGC components. In muscles infected with R1-3 and R10-12 AAV vectors, DGC components were detected in GFP-negative revertant fibers but not in transduced GFP-positive myofibers (FIG. 10).

Figure 3:
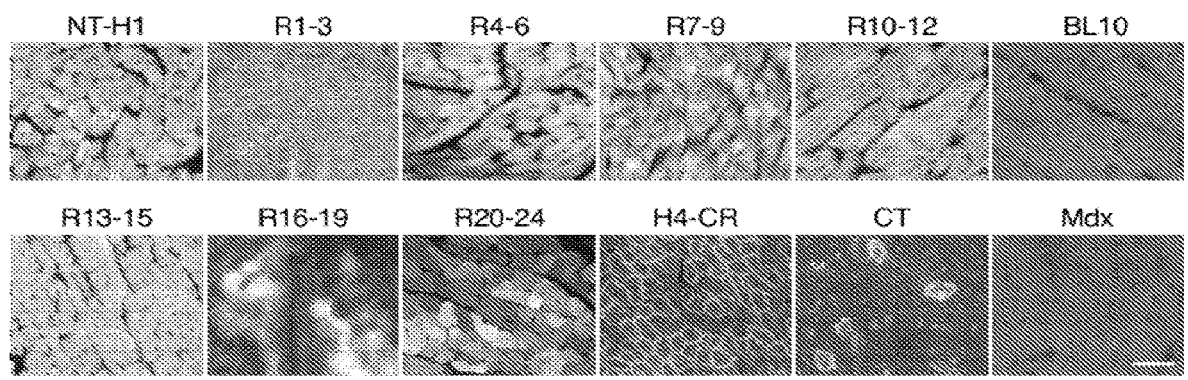
FIG. 3. Dystrophin R1-3, CR and CT bind to the sarcolemma in the heart. Indicated GFP fusion dystrophin subdomains were delivered to the mdx heart by systemic AAV injection. Uninjected BL10 and mdx hearts were used as negative controls. Subdomain H4-CR and CT showed membrane localization. Subdomain R1-3 was found in the intercalated disk and cytosol. Remaining subdomains were only seen in the cytosol. Scale bar: 50 µm.

Conservation of the membrane-binding property of R1-3, CR and CT in cardiac muscle. To determine whether our findings in skeletal muscle can be extended to cardiac muscle, we delivered GFP-fusion subdomain AAV vectors via the tail vein (FIG. 3). Compared with un-injected BL10 and mdx controls, systemic AAV injection resulted in robust GFP signals in the myocardium. Several different patterns were observed. The H4-CR subdomain was restricted at the sarcolemma while subdomains NT-H1, R4-6, R10-12, R13-15, R16-19 showed exclusive cytosolic expression. The R1-3 subdomain was found in the cytosol and the intercalated disk. In the mice infected with the CT-GFP AAV vector, we only detected a few GFP positive cardiomyocytes. Interestingly, GFP signals in these cells were found predominantly at the sarcolemma (FIG. 3).

Discussion

Figure 11A:
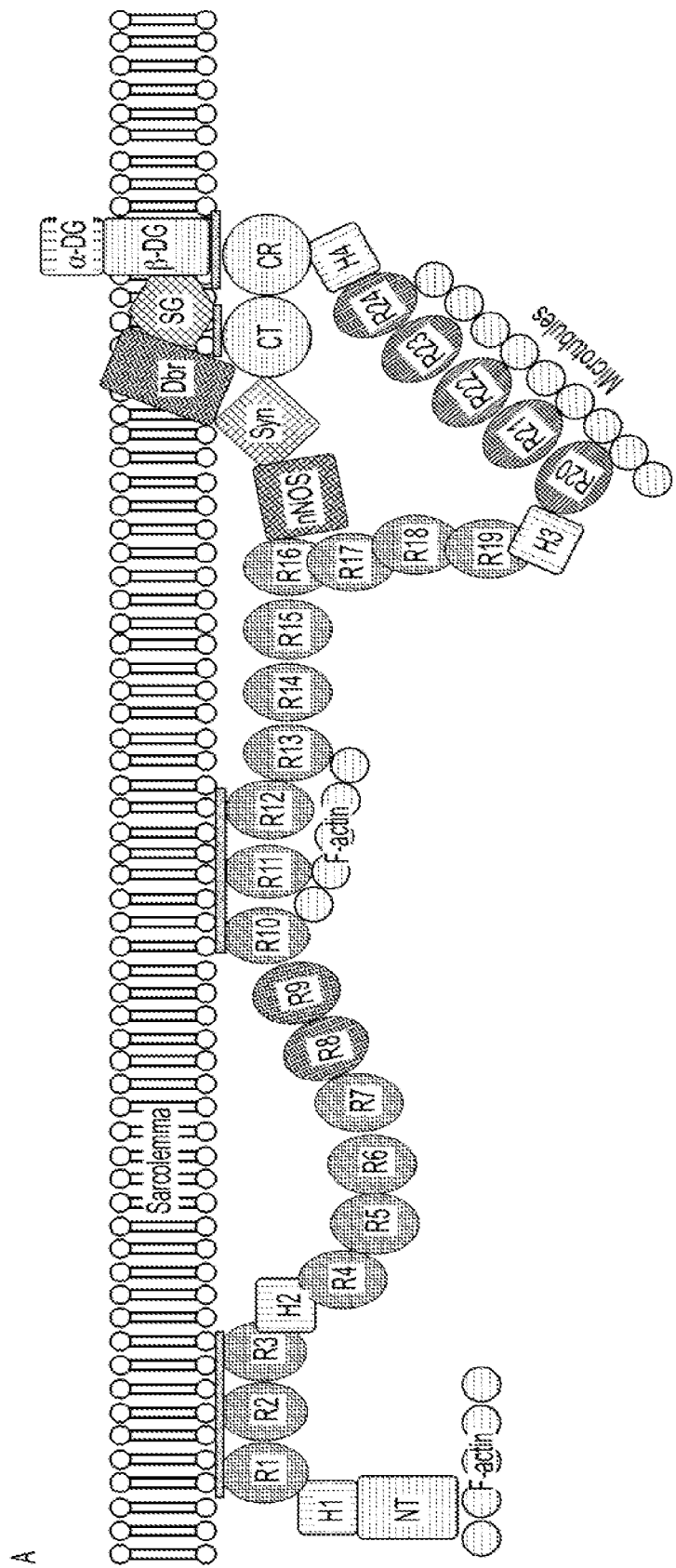
FIG. 11A,B. A new model of dystrophin-sarcolemma interaction. A. In muscle, dystrophin binds to the sarcolemma through four independent membrane-binding subdomains; B. In the heart, dystrophin binds to the sarcolemma through three independent membrane-binding domains. These subdomains are marked by thick red lines.
Figure 11B:
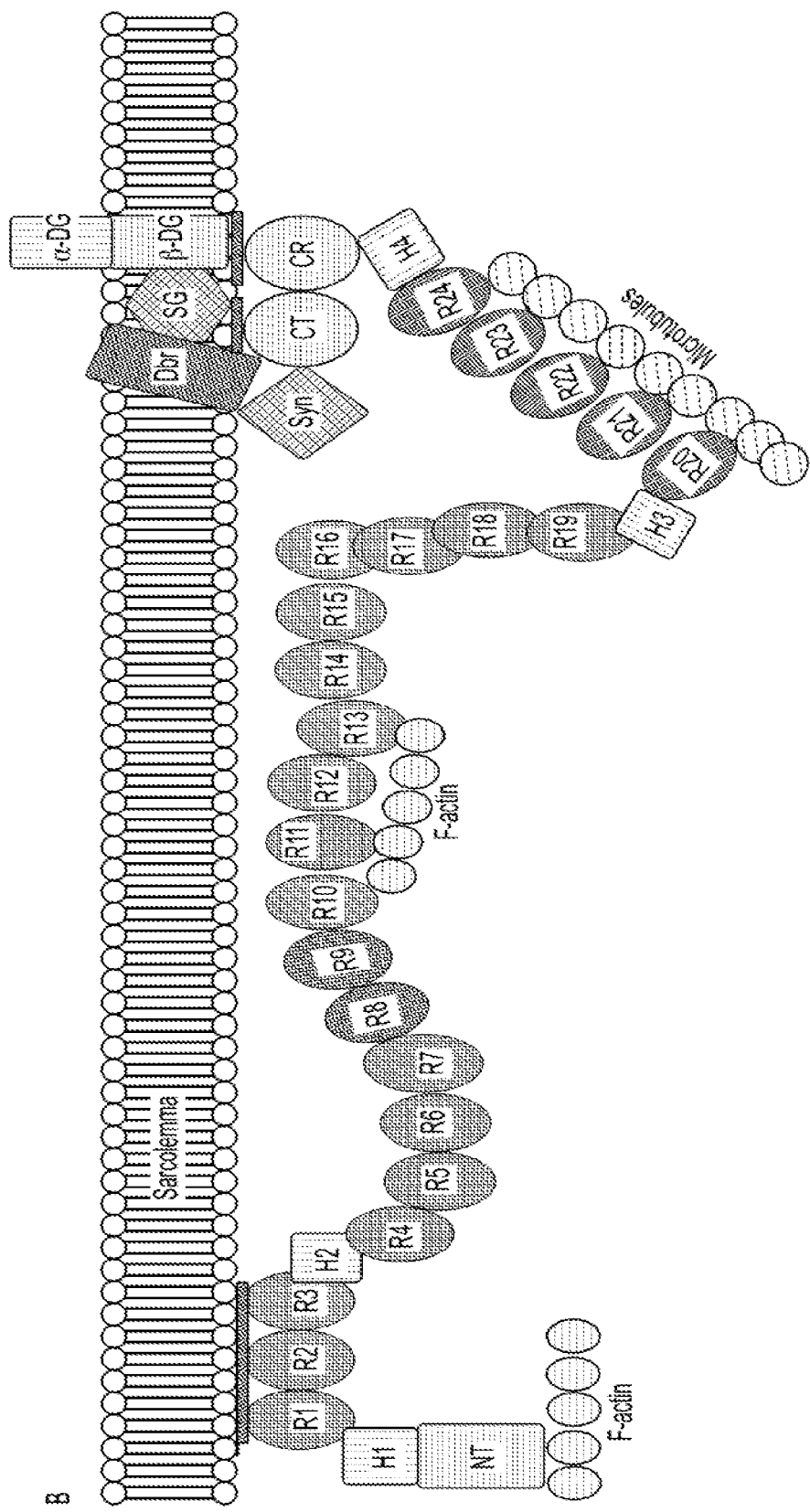

In this study, we performed the first comprehensive in vivo evaluation of the subcellular localizations of dystrophin subdomains. We demonstrated that in addition to the CR domain, dystrophin contains several highly conserved MBDs that can independently interact with the sarcolemma. These newly identified MBDs are R1-3, R10-12 and CT (FIG. 11). The CT subdomain bound to the sarcolemma in both skeletal muscle and cardiac muscle. Further it restored the DGC. Subdomain R1-3 showed exclusive membrane binding in skeletal muscle (FIG. 11A) but a preference for the intercalated disk in the heart (FIG. 11B). Subdomain R10-12 only demonstrated partial membrane localization in skeletal muscle (FIG. 11A).

Figure 2A:
FIG. 2A,B,C,D. Evidence of dystrophin sarcolemmal binding in the absence of the CR domain. A, Cartoon illustration of the structure of full-length dystrophin. B, Cartoon illustration of CR-deleted dystrophins that were found at the sarcolemma in patients (9-11). C, Cartoon illustration of synthetic CR-deleted dystrophin fragments that showed sarcolemmal localization in mdx mice (12-17). D, Cartoon illustration dystrophin membrane binding domains identified by in vitro interaction assays (18-23). Related references are marked next to the cartoon illustrations and the full citation is available in Supplementary References provided herein. Filled shapes: domains present; open shapes: domains absent.
Figure 2B:
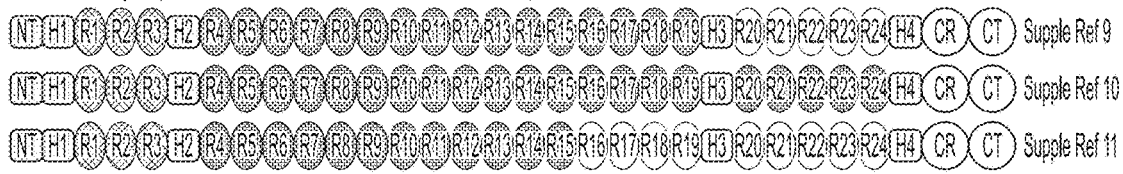
Figure 2C:
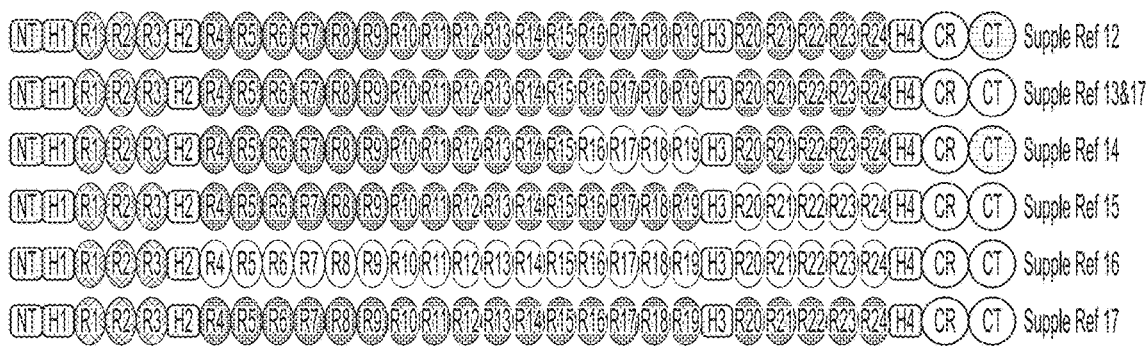

Interaction with the sarcolemma is central to how dystrophin protects muscle. A wealth of molecular, biochemical and structural studies has provided unequivocal proof that the CR domain anchors dystrophin to the sarcolemma via the formation of the DGC (7-9). Hence it has been quite puzzling why dystrophins that lack the CR domain still appear to bind to the sarcolemma in some atypical patients (11-13). Studies performed in mdx mice suggest that these puzzling patient observations can well be true. Of notice, forced expression of fragmented dystrophins that lack the CR domain has been repeatedly detected at the sarcolemma in mdx mice (FIG. 2C) (19-24). Collectively, it is reasonable to hypothesize that dystrophin can carry additional membrane localization domain(s).

Figure 2D:
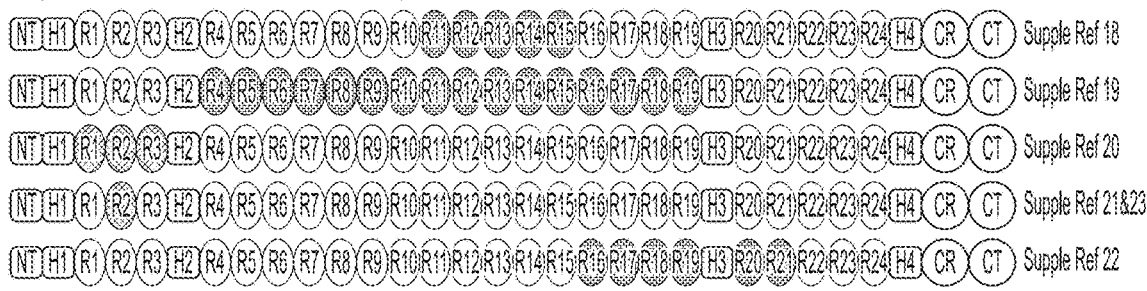

To better understand dystrophin-sarcolemma interaction, investigators have turned to the artificial in vitro systems. These studies identified a number of potential regions capable of membrane binding such as R2, R1-3, R4-19, R11-15, R16-21 (FIG. 2D) (14, 25-30). Essentially, 21 out of 24 spectrin-like repeats in the rod domain were found to carry the membrane binding property in these in vitro studies. Such a broad range makes it almost impossible to pinpoint the identity of true dystrophin MBDs. Considering the fact that in vivo performance of dystrophin spectrin-like repeats cannot be accurately predicted by in vitro analysis (31), it becomes even more challenging to characterize the CR domain-independent dystrophin-sarcolemma interaction in test tubes. Here we took a systematic and unbiased approach with an emphasis on the in vivo interaction in rodents and large mammals. We found four structurally defined regions in dystrophin that are capable of interacting with the sarcolemma. These include the well-studied CR domain and three new MBDs (two in the rod domain and one in CT). While R1-3 and R10-12 have been implicated in some in vitro studies, direct binding of CT to the sarcolemma has never been reported. Intriguingly, CT also restores the DGC (FIG. 10). It is intriguing that we observed striking differences in the membrane binding behavior of the newly identified rod domain MBDs. Specifically, R1-3 is not restricted to the sarcolemma in the heart and R10-12 has no membrane binding activity in the heart (FIG. 3). This is reminiscent of different nNOS-binding properties of dystrophin in the muscle and the heart (32, 33). Collectively, these data suggest that dystrophin can have different functional roles in the muscle and the heart.

The mechanism(s) by which these newly identified MBDs bind to the sarcolemma await future investigations. It is possible that electrostatic and/or hydrophobic interactions can play a role. However, considering what is known about other spectrin family proteins, we suspect that such interactions can likely involve specified membrane domains (such as lipid rafts) and palmitoylation (34).

Restoration of the DGC by CT is another unexpected finding in this study. We speculate that CT can utilize its syntrophin/dystrobrevin binding motifs to recruit syntrophin and dystrobrevin first. Subsequently, these two proteins scaffold sarcoglycans and dystroglycan to the complex (FIG. 9) (35-38).

Another area that requires further analysis is the kinetic mode of interaction between different MBDs and the sarcolemma. A recent study in the zebrafish suggests that dystrophin can associate with the sarcolemma either via stable tight interaction or via reversible dynamic shuttling between the sarcolemma and the cytosol (39). While additional studies are needed, the results of our microsomal preparation western blot seem to hint that the CR domain is responsible for stable membrane binding (GFP signals were barely detected in the cytosolic fraction) and three newly discovered MBDs can contribute to dynamic membrane binding (abundant GFP signals also presented in the cytosol) (FIG. 7B).

There are a few limitations in our study. First, we have not included hinges 2 and 3 in our constructs. Due to the structural properties of hinges (proline-rich, neither α-helix nor β-sheet), we suspect that these hinge regions can play a nominal role in membrane binding. Nevertheless, future studies are needed to confirm this. Second, we have used an over-expression system in our studies and also the fragmented dystrophin domains are not in their natural protein environment. It remains to be determined whether the membrane binding properties of the newly discovered MBDs are preserved under physiological concentration of dystrophin in wild type animals.

Taken together, we have discovered a new model for dystrophin membrane binding (FIG. 11). Our results offer insights into dystrophin function, DMD pathogenesis and gene therapy.

Materials and Methods

Animals. All animal experiments were approved by the Animal Care and Use Committee of the University of Missouri, and the animal use and handling were strictly in accordance with the National Institutes of Health guidelines. Dystrophin-null mdx mice were purchased from The Jackson Laboratory (Bar Harbor, ME). Dystrophin-deficient dogs were generated in house by artificial insemination.

AAV production and delivery. The GFP gene was fused in-frame to the C-terminal ends of the human dystrophin subdomains (FIG. 5). The fusion constructs were cloned into the cis AAV packaging constructs by PCR and confirmed by sequencing. Expression was driven by the cytomegalovirus promoter and the SV40 poly-adenylation signal. Y731F AAV-9 vectors were generated by transient transfection and purified through two rounds of CsCl gradient ultracentrifugation (40, 41). The viral titer was determined by quantitative PCR.

AAV vectors were delivered by intramuscular injection to limb muscles to adult mdx mice ($4$-$7 \times 10^{11}$ vg particles/muscle) and adult dystrophic dogs ($0.8$-$4 \times 10^{14}$ vg particles/muscle). In dog studies, we applied 5-week transient immune suppression with cyclosporine and mycophenolate mofetil according to our published protocol (42).

Muscle harvesting, microscopic examination and western blot. Eight weeks after injection, animals were euthanized and muscles were harvested according to Liadaki et al through serial sucrose gradient to preserve the GFP signal (43). GFP was visualized directly under the fluorescein isothiocyanate channel using a fluorescence microscope. Immunostaining was performed as we published before (31, 44). Whole muscle lysates were generated as we published before (31, 44). The cytosolic and microsomal preparations were obtained with the Plasma Membrane Protein Extraction kit (ab65400, Abcam). Muscle lysates were resolved in a 6% sodium dodecyl sulfate polyacrylamide gel and transferred to a polyvinylidene difluoride membrane. Antibodies used in immunostaining and western blot are listed in Table S1.

TABLE 1

Antibodies used in the study.

| Antigen | Host | Catalog # | Company | Dilution | Experiment |
|---|---|---|---|---|---|
| β-Dystroglycan | Mouse | NCL-B-DG | Novocastra | 1:50 | IF |
| Syntrophin | Mouse | ab11425 | Abcam | 1:200 | IF |
| β-sarcoglycan | Mouse | NCL-B-SARC | Novocastra | 1:50 | IF |
| Dystrobrevin | Mouse | 610766 | BD Bioscience | 1:200 | IF |
| GFP | Mouse | 33-2600 | Invitrogen | 1:100 | WB |
| GAPDH | Mouse | MAB374 | Millipore | 1:5,000 | WB |

IF: Immunofluorescence staining;
WB: western blot.

Example 2. Molecular Mechanisms for Membrane Binding of R1-3, R10-12 and the CT Domain The data in Example 1 showed unequivocal evidence that R1-3, R10-12 and CT localize to the sarcolemma on their own. Two mechanisms can result in membrane localization: (A) direct binding to the membrane lipid bilayer via S-palmitoylation and (B) through interaction with other transmembrane proteins (e.g. the binding of the dystrophin CR-domain to β-dystroglycan). S-palmitoylation-mediated mechanism has been shown for other spectrin super-family proteins such as β-spectrin (Das, A. K. et al., *J. Biol. Chem.* 272, 11021-11025 (1997); Mariani et al., *J. Biol. Chem.* 268, 12996-13001 (1993)). Specifically, S-palmitoylation involves the addition of palmitate (a 16-carbon saturated fatty acid) to the cysteine residues of the target proteins through a reversible thioester linkage during the process of posttranslational modification (Linder, M. E. et al., *Nat. Rev. Mol. Cell. Biol.* 8, 74-84 (2007)). Insertion of palmitate to the lipid bilayer brings the target proteins to the plasma membrane.

To distinguish these two potential mechanisms (direct binding via S-palmitoylation and indirect membrane binding via other membrane proteins), we examined the cysteine residues in new MBDs, and found that cysteine residues are very conserved in dystrophin R1-3, R10-12 and CT between human and mouse dystrophin (FIG. 12), indicating that cysteine residues can have an important role in the dystrophin function. In silico screening of palmitoylated sites with the CSS-Palm 2.0 program, a software for prediction of palmitoylated sites (Oku, S. et al., *J. Biol. Chem.* (2013); Ren, J. et al., *Protein Eng Des Sel* 21, 639-644 (2008)), successfully identified some palmitoylated sites in R1-3 and R10-12 (FIG. 13). Then we carried out a pilot study in which we mutated all cysteine residues in R1-3, R10-12 and the CT domain to serine (FIG. 14). Cysteine-to-serine mutation has been used by others to abolish S-palmitoylation (Topinka, J. R., et al., *Neuron* 20, 125-134 (1998); Yanai, A. et al. *Nat. Neurosci.* 9, 824-831 (2006)). We hypothesized that if S-palmitoylation mediated mechanism is responsible for sarcolemma anchoring of R1-3, R10-12 and the CT domain, cysteine-to-serine mutation should abolish S-palmitoylation and result in cytosolic location of R1-3, R10-12 and the CT domain. We made AAV vectors to express cysteine-to-serine mutated R1-3, R10-12 and the CT domain GFP fusion proteins. Following intramuscular injection to the muscle of mdx mice, we only detected cytosolic GFP signal (FIG. 14). This is in sharp contrast to what we see in FIG. 6. These results strongly suggest that S-palmitoylation is likely the predominant molecular mechanism for membrane localization of R1-3, R10-12 and the CT domain.

There are a total of four cysteine residues in R1-3, two in R10-12, and one in the CT domain. There are located in R1 (C433), R2 (C544), R3 (C569 and C650), R11 (C1505), R12 (C1569) and CT (C3476) (FIG. 12). In our preliminary study (FIG. 14), we found that mutation of all cysteine residues in each fragment abolished sarcolemmal binding.

Example 3. Further Identification of Protein Binding Partners, Membrane Binding Motifs (MBM), Membrane Binding Repeats, and Membrane Binding Sub-Domains As the first step to identify protein partners of our newly discovered MBDs, we performed immunofluorescence staining using antibodies against several DGC components. These included β-dystroglycan, β-sarcoglycan, dystrobrevin, syntrophin and nNOS. We also included H4-CR.GFP as a control. We have previously shown that nNOS-binding requires R16/17, (Lai, Y. et al., *J. Clin. Invest.* 119, 624-635 (2009)) or an nNOS binding domain of R16/17 (Lai, Y., et al., *Proc. Natl. Acad. Sci. USA* 110, 525-530 (2013). As a consequence, none of the MBDs was able to restore sarcolemmal nNOS expression. Previous studies suggest that the interaction of the CR domain with β-dystroglycan is sufficient for restoration of the DGC components (Crawford, G. E. et al., *J Cell Biol.* 150, 1399-1410 (2000); Yue, Y. et al., *Mol Ther* 14, 79-87 (2006)). As expected, H4-CR restored all DGC components. We also found that R1-3 and R10-12 did not interact with the DGC components. The CT domain by itself is associated with all the DGC components at the muscle membrane (FIG. 15).

Figure 16B:
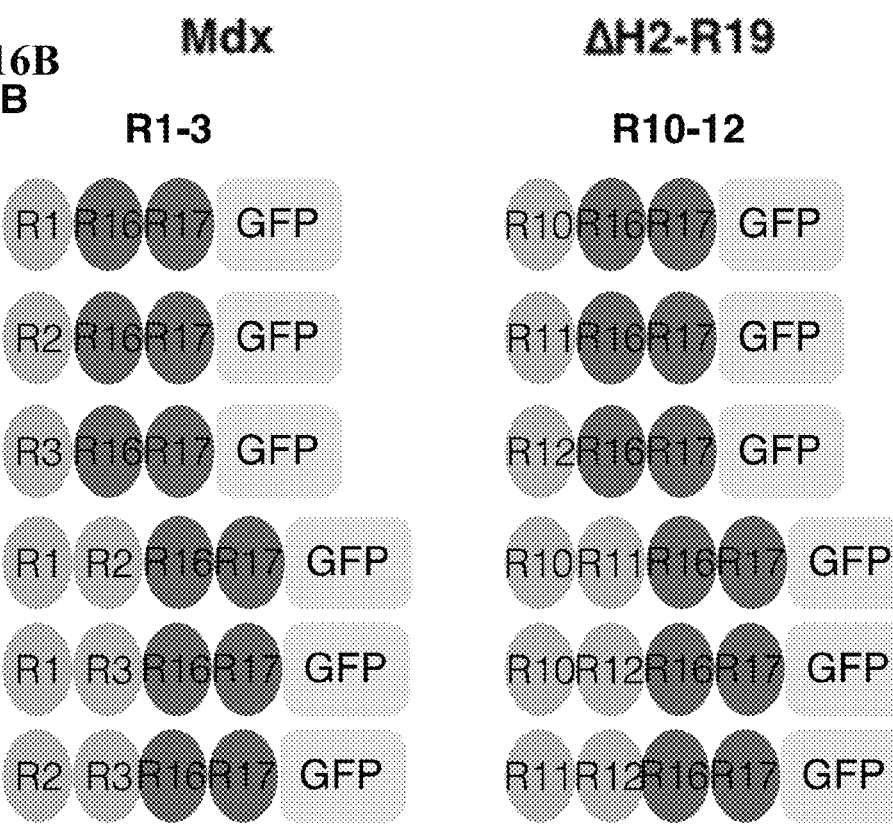

A typical feature of dystrophin membrane binding is that dystrophin MBDs are confined to two regions. Two MBDs R1-3 and R10-12 are located at the mid-rod domain, while the other two MBDs CR and CT are at the C-terminal part of dystrophin (FIG. 16). Through our preliminary data, both C-terminal MBDs (cMBDs), CR and CT, are associated with the DGC, while both rod MBDs (rMBDs), R1-3 and R10-12, are not co-localized with the components of the DGC (FIG. 17), suggesting that rMBDs and cMBDs have different functional roles. Dystrophin stabilizes and strengthens the sarcolemma by two different mechanisms: the axis from the ECM to intracellular cytoskeleton, and the membrane association from newly identified MBDs. Membrane binding of the CR domain establishes the axis from the ECM to intracellular cytoskeleton, and, in certain contexts and embodiments, the CR domain is involved in dystrophin function (Rafael, J. A. et al., *J. Cell Biol.* 134, 93-102 (1996)). In vitro studies have indicated that membrane binding of rMBDs is also important for membrane stability (Sarkis, J. et al., *FASEB J.* 27, 359-367 (2013); Sarkis, J. et al., *J Biol. Chem.* (2011)). Both rMBDs are in close proximity to the muscle membrane and actin cytoskeleton. R1-3, is near the N-terminus of dystrophin, which interacts with F-actin, while R10-12 overlaps with the actin-binding domain R11-15 (FIG. 3). Simultaneous binding of R11-15 to phospholipid monolayer and F-actin considerably contributes to the stiffness and stability of the lipid monolayer (Sarkis, J. et al., *FASEB J.* 27, 359-367 (2013); Sarkis, J. et al., *J. Biol. Chem.* (2011)). So it is highly likely that the functional role of R1-3 and R10-12 is to tether actin cytoskeleton to the muscle membrane, and thereby strengthen the muscle membrane.

We will generate micro- and mini-dystrophin AAV vectors. Membrane binding of the rMBDs in truncated dystrophins will be disrupted either by cysteine mutations or by incorporating cytosolic rod domains of dystrophin. We will deliver AAV vectors to the tibialis anterior (TA) muscle of Cmah/mdx mice, examine membrane integrity by Evans blue dye uptake, and evaluate TA contractile properties and muscle histopathology. Also we will compare the function of two rMBDs: R1-3 and R101-2, in the context of truncated dystrophins to determine whether two rMBDs have equivalent function.

We will use two well-characterized micro- and mini-dystrophin genes as the backbones. The ΔR4-R23/ΔCT microgene and The ΔH2-R19 mini-gene have been shown to improve muscle function and correct dystrophic pathology in the dystrophic animal models (Harper, S. Q. et al., *Nat. Med.* 8, 253-261 (2002); Liu, M. et al., *Mol Ther* 11, 245-256 (2005); Lai, Y. et al., *Nat. Biotechnol.* 23, 1435-1439 (2005)). Both truncated dystrophins contain one rMBD, R1-3, and one cMBD, the CR domain. The ΔH2-R19 mini-dystrophin also carries another cMBD: the CT domain (FIG. 18). We will make three forms of constructs for the microgene including (1) original R1-3, (2) cysteine-mutated R1-3 and (3) replacement of R1-3 by R4-6. We will also make a similar set of constructs for the ΔH2-R19 minigene. Cysteine mutation or replacement with R4-6 will abolish the membrane binding of the rMBD, R1-3. Therefore, in the resulting truncated dystrophins, only the function of the axis from the ECM to cytoskeleton is maintained, and membrane binding from the rod domain is eliminated (FIG. 18).

Experimental mice and gene delivery. We will use Cmah/mdx double knock out mice, which have a more severe phenotype and shorter life span than mdx mice (Chandrasekharan, K. et al., *Sci Transl Med* 2, 42ra54 (2010)). Microgenes will be delivered to the TA muscle of Cmah/mdx mice by the single AAV vectors, while mini-dystrophins will be delivered by over-lapping AAV vectors as reported before (Odom, G. L. et al., *Mol Ther* 19, 36-45 (2011)). Function of truncated dystrophins and their cysteine mutants will be determined and compared. We will investigate membrane integrity by Evans blue dye uptake, measure muscle force generation and the resistance to eccentric contraction, and examine muscle histopathology, including central nucleation, myofiber size, cross section area, fibrosis and inflammation infiltration, as our published protocols (Lai, Y. et al., *J. Clin. Invest.* 119, 624-635 (2009); Lai, Y. et al., Nat. Biotechnol. 23, 1435-1439 (2005); Lai, Y. et al., *Hum. Mol. Genet.* 23, 3189-3199 (2014)). The experiments outlined above will determine whether membrane binding of R1-3 is important for dystrophin function. To investigate the functional role of another rMBD, R10-12, we will compare it to R1-3 in the context of truncated dystrophins.

Both rMBDs R1-3 and R10-12 have lipid-binding properties, and are in close proximity to the actin-binding domains. However, there are some different aspects between R1-3 and R10-12. First, the rMBD R1-3 is located at the beginning of the rod domain, while the rMBD R10-12 is in the middle of the rod domain. Second, R1-3 is exclusively located at the muscle membrane, while R10-12 is found at both the muscle membrane and cytosol (FIGS. 8 and 10). Third, all therapeutically effective truncated dystrophins only carry a partial or complete R1-3 but not R10-12. It remains unclear whether the difference between R1-3 and R10-12 represents different functional roles.

We choose $\Delta$H2-R23/$\Delta$CT+H3 and $\Delta$H2-R19 micro- and mini-gene as the backbones (FIG. 19). $\Delta$H2-R23/$\Delta$CT+H3 is an enhanced version of $\Delta$R4-R23/$\Delta$CT, in which H2 was replaced with H3 (Banks, G. B. et al., *PLoS Genet.* 6, e1000958 (2010)). R1-3 in $\Delta$H2-R23/$\Delta$CT+H3 will be replaced with R10-12 to generate $\Delta$R1-R9/$\Delta$R13-R23/$\Delta$CT+H3. In $\Delta$H2-R19, we will replace R1-3 with R10-12 to generate $\Delta$R1-R9/$\Delta$R13-R19 mini-dystrophin. To have a fair comparison, the other components of truncated dystrophins are the same (FIG. 19).

We will use AAV gene transfer to express $\Delta$H2-R23/$\Delta$CT+H3, $\Delta$R1-R9/$\Delta$R13-R23/$\Delta$CT+H3, $\Delta$H2-R19 and $\Delta$R1-R9/$\Delta$R13-R19 in the TA muscles of Cmah/mdx mice. The ability of the truncated dystrophins to generate muscle force, maintain membrane integrity and improve histopathology of the dystrophic muscle will be measured as outlined above. These studies will tell us whether R1-3 and R10-12 have equivalent function in micro- and mini-dystrophins.

Dystrophin CR domain not only anchor to β-dystroglycan to form the axis from the ECM to intracellular cytoskeleton, but can assemble the components of DGC at the muscle membrane. Dystrophin deficiency disassembles the DGC components at the muscle membrane. Hence, restoration of the DGC components to the sarcolemma is one criterion for therapeutic outcome of truncated dystrophins.

The non-muscle dystrophin isoform Dp116 contains both cMBDs (CR and CT domain), but is deficient of both rMBDs and actin-binding domains. So Dp116 is unable to interact with F-actin. Due to the presence of both cMBDs, it can restore the DGC. Obviously, Dp116 maintains the DGC function, and loses the mechanical function to connect the ECM and cytoskeleton. In the transgenic mice expressing Dp116, dystrophic histopathology and mechanical function of the muscle were not improved. But restoration of the DGC by Dp116 is found to be crucial for growth and maintenance of muscle mass when Dp116 is expressed in the muscle of dystrophin/utrophin double knockout mice (u-dko) (Judge, L. M. et al., *J. Cell Sci.* 119, 1537-1546 (2006); Judge, L. M. et al., *Hum. Mol. Genet.* 20, 4978-4990 (2011)). These studies suggest that the mechanical function of the CR domain to connect the ECM with cytoskeleton is important for preventing dystrophic pathology, while restoration of the DGC by the CR domain is critical for muscle mass.

Truncated dystrophins without the CR domain cannot prevent dystrophic pathology, despite the presence of the other three MBDs, suggesting that the CT domain cannot compensate for mechanical function of the CR domain. Through our preliminary data, we found that either CR or CT domain alone can restore the DGC components at the muscle membrane (FIG. 17). We will determine if the CT domain can compensate for the CR domain in terms of the function in muscle mass.

We will examine the function of the CT domain in the context of micro-dystrophins. We will use $\Delta$R4-R23/$\Delta$CT microgene as the backbone, and replace the CR domain with the CT domain (FIG. 20).

Experimental mice and gene delivery. We will deliver AAV.$\Delta$R4-R23/$\Delta$CR and AAV.$\Delta$R4-R23/$\Delta$CT microgenes to utrophin/dystrophin double knock-out (u-dko) mice. Since u-dko mice have a short life span, we will perform systemic delivery of AAV viruses to neonatal u-dko mice.

Outcome measurement. Two months following virus injection, the body weight of u-dko mice and muscle mass of TA and Gastro muscles will be recorded. The DGC components will be evaluated by immunostaining and western blot. Contractile properties of TA muscle will be measured.

Both cMBDs, the CR and CT domain, are located at the C-terminal end of dystrophin and can restore the DGC. In certain contexts and embodiments, CR domain is involved in dystrophin function. However, the functional significance of the CT domain is contradictory. Although CT deletion has negligible consequences in transgenic mdx mice (Rafael, J. A. et al., *J. Cell Biol.* 134, 93-102 (1996)), in human patients, partial or complete CT deletion can cause severe DMD phenotype (Suminaga, R. et al., *Pediatr Res* 56, 739-743 (2004); Prior, T. W. et al., *Am. J. Hum. Genet.* 57, 22-33 (1995)), indicating that CT can have important functional roles in human. In this aim, we will address a specific functional role of the CT domain in muscle mass, which will gain more insight into the function of the CT domain.

Despite the identification of R1-3, R10-12 and CT as the new MBDs of dystrophin, it is unclear whether these domains are the smallest region required for membrane binding. In spectrin, lipid-binding motif and ankyrin-binding domain have been mapped to repeats 14 and 15 of β-spectrin (Ipsaro, J. J. et al., *Blood* 113, 5385-5393 (2009); Ipsaro, J. J. et al., *Blood* 115, 4093-4101 (2010); Bok, E. et al., *Cell Biol Int* 31, 1482-1494 (2007)). These results tremendously promote the efforts to solve the structure of repeats 14 and 15 of β-spectrin, which provides the structural and molecular perspective for the interactions of β-spectrin repeats 14 and 15 with lipids and ankyrin (Ipsaro, J. J. et al., *Blood* 113, 5385-5393 (2009); Ipsaro, J. J et al., *Blood* 115, 4093-4101 (2010)). We expect that mapping membrane-binding motifs in dystrophin R1-3, R10-12 and CT should be helpful for the future studies to reveal the structure of dystrophin MBDs, and facilitate our understanding of molecular basis of dystrophin membrane binding.

To date, there exist three functional micro-dystrophins tested in canine dystrophic models and the clinical trial. Only ΔR4-R23/ΔCT micro-dystrophin contains a complete region of R1-3, while ΔR2-R15/ΔR18-R23/ΔCT (Lai, Y. et al., *J Clin. Invest.* 119, 624-635 (2009)) and Δ3900 (Wang, B. et al., *Proc. Natl. Acad. Sci. USA* 97, 13714-13719 (2000)) micro-dystrophin carry only R1 or R1-2, respectively (FIG. 21). But muscle force comparison revealed that there is no apparent difference regarding muscle force improvement between ΔR4-R23/ΔCT and ΔR2-R15/ΔR18-R23/ΔCT, suggesting that a partial region of R1-3 possibly maintains the ability of membrane binding. Mapping membrane-binding motifs in R1-3 will help clarify this issue.

Identification of membrane-binding motifs in R1-3, R10-12, and CT will be important for the development of DMD gene therapy. Given the packaging limit of AAV vectors, the main focus of engineering truncated dystrophins will be maximizing dystrophin function in a minimal sequence. Hence, shortening dystrophin MBDs will be useful for DMD gene therapy.

Both R1-3 and R10-12 are composed of three spectrin-like repeats. First we ask whether the single repeat or bi-repeats of R1-3 and R10-12 maintain the ability of membrane binding. To address this issue, we will split R1-3 and R10-12 into smaller individual repeats, and use AAV.R16/17.GFP construct as the backbone, since our previous study has shown that R16/17.GFP is expressed in the cytosol of myofibers, and R16/17 are an important component of the microgene (Lai, Y. et al., *Proc. Natl. Acad. Sci. USA* 110, 525-530 (2013)). And we will fuse R1, R2, R3, R1-2, R2-3, R1,3 or R10, R11, R12, R10-11, R11-12, R10,12 to R16/17.GFP (FIG. 16), and exploit AAV gene transfer to express the GFP fusion proteins in the muscle of mdx 4cv mice. Membrane binding of the GFP fusion proteins will be determined by the GFP signal and immunostaining with the epitope-specific antibodies. If the single repeat or bi-repeats maintain the membrane-binding ability, they will target the R16/17.GFP to the muscle membrane. The information gathered from these studies will help us determine which repeats in R1-3 and R10-12 have the ability of membrane binding, and will clarify whether the partial R1-3 in some micro-dystrophins conserves membrane binding.

Those repeats with the ability of membrane binding are named as membrane-binding repeats. Each spectrin-like repeat consists of three α-helices. Next, we will proceed to narrow down the membrane-binding motifs to the helices of the membrane-binding repeats. In our previous study, we successfully determined a 10-amino-acid nNOS-binding motif in the first helix of R17, and also found that two upstream and downstream helices that flank nNOS-binding motif are also required for nNOS binding since the flanking helices frame the nNOS-binding motif and make it accessible to nNOS binding (Lai, Y. et al., *Proc. Natl. Acad. Sci. USA* 110, 525-530 (2013)). Here, we will use the same strategy to decide the membrane-binding motifs in membrane-binding repeats.

We will choose AAV constructs that contain membrane-binding repeats as the backbones (FIGS. 19, 20, and 21). Like our previous study, we will replace the individual helix in the membrane-binding repeats with the corresponding helix from R16 to determine which helices in the membrane-binding repeats are involved in membrane binding. For the helices that are involved in membrane binding, we will split each helix into 4-5 parts, each part containing 9-10 amino acids, and replace each part with the corresponding region from R16. Then we will express these mutants by AAV gene transfer in the TA muscle of mdx 4cv mice, and determine the membrane binding of these mutants by the GFP signal and immunostaining. An example of a methodology used to test various constructs is shown (FIG. 23). These studies will further narrow down the membrane-binding motifs in the membrane-binding repeats of R1-3 and R10-12.

We will use the deletion strategy to identify the membrane-binding motif in the CT domain. The construct AAV.CT.GFP shown in FIG. 5 will be used as the backbone. Different partial deletions of the CT domain will be introduced to AAV.CT.GFP construct as outlined in FIG. 18. We will use AAV gene transfer to deliver these constructs to the TA muscle of mdx 4cv mice. The membrane localization of the GFP fusion proteins will be determined by the GFP signal. If we decide which part of the CT domain is responsible for membrane binding, we will split this part into three smaller motifs, and narrow down the membrane-binding region to the smallest motif.

Example 4. Construction of New Dystrophin MBDs into Micro- and Mini-Dystrophin Synthetic Genes and Insertion of Same into AAV Vectors In vitro studies have shown that membrane association from newly discovered MBDs is important for dystrophin function (Sarkis, J. et al., *FASEB J.* 27, 359-367 (2013); Sarkis, J. et al., *J. Biol. Chem.* (2011)). However, currently available micro-dystrophins contain two MBDs: partial or complete R1-3 and the CR domain, while mini-dystrophins ΔH2-R19 and ΔH2-R15 carry three MBDs: R1-3, CR and CT, suggesting that the membrane-binding ability of truncated dystrophins is compromised. Here, we will generate new dystrophin AAV vectors by adding more MBDs.

For initial testing, we will use the ΔR4-R23/ΔCT microgene as the backbone, since ΔR4-R23/ΔCT microgene is the only microgene containing the complete MBD, R1-3 (FIG. 21). The micro-dystrophins are packaged by the single AAV vector, which has a packaging limit of about 4.9 kb. The original size of ΔR4-R23/ΔCT AAV vector is about 4.8 kb, including 3.6 kb micro-dystrophin cDNA, a 523 bp CMV promoter, a 206 bp SV40 PolyA site, 0.3 kb AAV ITRs, and other sequences for 5' and 3' untranslated regions (UTR) and multiple cloning sites. We will free up space for an additional MBD by shortening transcription regulation elements and sequences for UTRs and cloning sites. A shortened muscle-specific promoter and a synthetic PolyA site (49 bp) (Levitt, N. et al., *Genes Dev.* 3, 1019-1025 (1989)) will replace the CMV promoter and SV40 PolyA site. Also the sequences for UTRs and the cloning sites will be shortened by engineering the shorter UTRs, and including the cloning sites into the UTRs. To make the total size of micro-dystrophin AAV vector about 4.9 kb, these changes allow us to add >700 bp more bps in the AR4-R23/ΔCT micro-dystrophin. Since each spectrin-like repeat is about 330 bps and the CT domain is about 792 bps, the spared space can hold two more repeats or one more repeat and half of the CT domain or the whole CT domain. Since the shortest membrane-binding regions are first being identified, only the CT domain can be added to microgenes. For the first test, we will add the CT domain into ΔR4-R23/ΔCT micro-dystrophin without affecting the packaging efficiency of AAV vectors. So the resultant microgene ΔR4-R23 contains three MBDs (FIG. 19).

ΔH2-R19 mini-dystrophin contains three MBDs: R1-3, CR and CT domain. It can restore full muscle force but only partially recover heart hemodynamic function (Bostick, B. et al., *Mol Ther* 17, 253-261 (2009)). So we will use ΔH2-R19 mini-dystrophin as the backbone, and engineer R10-12 into ΔH2-R19 mini-dystrophin to make a new mini-dystrophin with four MBDs (FIG. 19).

These two constructs are two examples for how we will engineer new dystrophin AAV vectors by adding more MBDs into dystrophin AAV vectors. The list of micro- and mini-dystrophin AAV vectors can be expanded once the smallest membrane-binding region is identified from the preceding studies. For example, if rMBDs, R1-3 and R10-12, could be reduced to the single repeat, we can make the micro-dystrophin with two rMBDs and one cMBD, the CR domain. If one half of the CT domain can be trimmed, we could even make new micro-dystrophin AAV vector containing all four MBDs. If the membrane-binding motifs can be reduced to the helices, we can generate a hybrid repeat. For example, R16/17 are essential for nNOS binding. The first helix of R16 can be replaced without affecting nNOS binding. We can engineer the membrane-binding motif from R1-3 or R10-12 into the first helix of R16 to generate a hybrid repeat with two functions.

To examine therapeutic efficacy of new micro- and mini-dystrophins in murine and canine dystrophic models, we will deliver new dystrophin AAV vectors to Cmah/mdx mice and DMD dogs and examine therapeutic efficacy of these new dystrophin AAV vectors. All new dystrophin AAV vectors will be tested in Cmah/mdx first. Contractile properties of TA muscle, ECG and hemodynamic function, membrane integrity and muscle histopathology will be examined as outlined above. From the functional results, one best microgene and one best minigene will be selected for further testing in DMD dogs.

The therapeutic efficacy of new micro- and mini-dystrophins will be tested in DMD dogs. A series of functional studies in canine dystrophic models, including measurements of single muscle force, cardiac function and blood flow (Yang, H. T. et al. *PLoS One* 7, e44438 (2012); Fine, D. M. et al., *Neuromuscul Disord* 21, 453-461 (2011)) can be performed. Micro- and mini-dystrophin AAV vectors will be delivered to 5-6 DMD dogs, respectively. For virus injection in DMD dogs, a transient immunosuppression protocol will be administered. And AAV vectors will be injected to the Extensor Carpi Ulnaris (ECU) muscle of DMD dogs by intramuscular (IM) injection. After five to six months, force generation and the resistance to eccentric contraction of ECU muscle will be evaluated (Yang, H. T. et al., *PLoS One* 7, e44438 (2012); Shin, J. H. et al., *Mol Ther* 21, 750-757 (2013)). Histopathology will be investigated as proposed in the mouse studies.

Despite the role of cysteine residues in membrane binding of R1-3, R10-12 and the CT domain, the shortest membrane-binding region is still unknown. In this aim, we will identify membrane-binding motifs by AAV gene transfer. Hence, the membrane-binding motifs derived from this study will be highly relevant to DMD gene therapy. A previous study has shown that the single repeat R2 has lipid-binding ability (Le Rumeur, E. et al. *Biochim. Biophys. Acta* 1768, 648-654 (2007)) suggesting that the individual repeat from R1-3 can bind to the muscle membrane. So it is likely that the R1-3 membrane-binding region can be shortened.

Currently available truncated dystrophins are not fully functional. We will generate a series of new dystrophin AAV vectors that contain more MBDs to improve their therapeutic effects. First we will examine therapeutic effects of new dystrophin AAV vectors in the mouse model. Only after we confirm that new dystrophin AAV vectors perform better than original dystrophin AAV vectors, we will proceed to test the best candidates in the canine dystrophic model.

Example 5. Restoration of Sarcolemmal nNOS in Mdx Mice by Dystrophin Spectrin-Like Repeats 16 and 17 and Syntrophin PDZ Fusion Protein Duchenne Muscular Dystrophy (DMD) is a genetic disorder that affects sarcolemmal localization of neuronal nitric oxide synthase (nNOS). Sarcolemmal nNOS is required for muscle cells to function properly. In DMD patients, a deficiency in the dystrophin protein leads to a reduction in sarcolemmal nNOS and syntrophin. From a previous study (Lai, Yi, et al. *Journal of Clinical Investigation* (2009): 624-35), recruitment of sarcolemmal nNOS is dependent on dystrophin spectrin-like repeats 16 and 17 (R16/17) and syntrophin PDZ domain.

Muscle wasting diseases such as Duchenne muscular dystrophy (DMD) affect sarcolemmal localization of neuronal nitric oxide synthase (nNOS). Sarcolemmal nNOS is required for muscle cells to function properly. Sarcolemmal localization of nNOS is dependent on its simultaneous binding to dystrophin spectrin-like repeats 16 and 17 (R16/17) and syntrophin PDZ domain. DMD is characterized by a deficiency in dystrophin. In DMD, loss of dystrophin leads to the reduction or loss of syntrophin at the sarcolemma, which further results in the loss of sarcolemmal nNOS. Loss of sarcolemmal neuronal nitric oxide synthase (nNOS) is a salient pathogenic feature in muscle wasting conditions/diseases such as age-related muscle atrophy, cancer cachexia, Duchenne muscular dystrophy (DMD) and many other neuromuscular disorders.

In a previous study, dystrophin R16/17 was expressed in the muscle of a truncated dystrophin transgenic mouse, where syntrophin is present at the membrane. The results showed that sarcolemmal nNOS was recovered successfully, indicating that dystrophin R16/17 and syntrophin PDZ are required for sarcolemmal nNOS.

In this study, we engineered an adeno-associated virus (AAV) vector that can express a dystrophin R16/17-syntrophin PDZ fusion protein. We tested whether the expression of the fusion protein restored sarcolemmal nNOS in the muscle of mdx mice, the DMD mouse model (FIG. 23). PCR-based cloning was used to clone syntrophin PDZ into the AAV.R16/17.GFP.Pal backbone to produce AAV.R16/17.Syn.GFP.Pal construct (FIG. 24). In the vector, a hinge region (GGSG) was inserted between R16/17 and syn PDZ. GFP is a tag that helps detect the R16/17.Syn protein. Pal is the signal for membrane targeting. The AAV plasmid DNA was amplified to produce large amounts of DNA for virus production. We then performed a local injection of the virus into six, ~3.5 month old mdx mice. Each mouse received $1.4*10^{12}$ viral genome particles (vg) into the tibialis anterior and $2.2*10^{12}$ vg into the gastrocnemius muscles. Three weeks later, we harvested the muscle tissues. First, we confirmed the expression of the R16/17-syntrophin PDZ fusion protein in the muscle by fluorescence microscopy for the GFP signal. Then we performed immunostaining and nNOS activity staining to examine if the expression of R16/17-syntrophin PDZ fusion protein can restore sarcolemmal nNOS.

Our results show that sarcolemmal nNOS was recovered successfully with the use of R16/17-syntrophin PDZ fusion protein (FIG. 25). Further testing will be done to examine the therapeutic effects of restoring sarcolemmal nNOS. Restoration of sarcolemmal nNOS has therapeutic use for multiple neuromuscular disorders, such as DMD, and other muscle wasting conditions such as age/inactivity-related muscle atrophy and cancer cachexia.

DMD is a disorder that is characterized by degeneration and regeneration of muscle tissues and premature death most commonly due to cardiac or respiratory failure. In patients suffering from DMD, sarcolemmal nNOS is either reduced or completely lost. Sarcolemmal nNOS plays a crucial role in the upkeep of muscle tissues.

The results from this project show that it is possible to introduce sarcolemmal localization of nNOS in mdx mice with the use of a viral vector. Our next step is to see whether or not the R16/17-syntrophin PDZ fusion protein can recruit nNOS in DBA/mdx mice, a more severe phenotype mouse model of DMD.

Example 6. Description of Sequences Provided in the Sequence Listing

A description of sequences provided herewith in the electronic sequence listing file "17UMC006_SEQ LST_TC167044_ST25.txt" follows below.

SEQ ID NO: 1: Full-length human dystrophin protein sequence

SEQ ID NO: 2: Full-length dystrophin coding region

SEQ ID NO: 3: .DELTA.17-48 (mini-dystrophin with 8.5 repeats and 3 hinges) (This minigene does not carry R16 or R17. It cannot restore nNOS)

SEQ ID NO: 4: .DELTA.H2-R19 (mini-dystrophin with 8 repeats and 3 hinges) (This minigene does not carry R16 or R17. It cannot restore nNOS)

SEQ ID NO: 5: .DELTA.H2-R17 (mini-dystrophin with 10 repeats and 3 hinges) (This minigene does not carry R16 or R17. It cannot restore nNOS)

SEQ ID NO: 6: .DELTA.H2-R16 (mini-dystrophin with 11 repeats and 3 hinges) (This minigene carries R17 but not R16. It cannot restore nNOS)

SEQ ID NO: 7: .DELTA.H2-R15 (mini-dystrophin with 12 repeats and 3 hinges) (This minigene carries both R16 and R17. It can restore nNOS)

SEQ ID NO: 8: .DELTA.H2-R15/.DELTA.R18-19 (mini-dystrophin with 10 repeats and 3 hinges) (This minigene carries both R16 and R17. It can restore nNOS)

SEQ ID NO: 9: .DELTA.H2-R15/.DELTA.17-19 (mini-dystrophin with 9 repeats and 3 hinges) (This minigene carries R16 but not R17. It cannot restore nNOS)

SEQ ID NO: 10: .DELTA.H2-R15/.DELTA.0 (mini-dystrophin with 12 repeats and 3 hinges, no C-terminal domain) (This minigene carries both R16 and R17. It can restore nNOS)

SEQ ID NO: 11: .DELTA.R2-R15/.DELTA.H3-R23/.DELTA.C (micro-dystrophin with 6 repeats and 2 hinges, no C-terminal domain) (This microgene carries both R16 and R17. It can restore nNOS)

SEQ ID NO: 12: .DELTA.R3-R15/.DELTA.R18-23/.DELTA.C (micro-dystrophin with 5 repeats and 2 hinges, no C-terminal domain) (This microgene carries both R16 and R17. It can restore nNOS)

SEQ ID NO: 13: .DELTA.R2-R15/.DELTA.R18-23/.DELTA.C (micro-dystrophin with 4 repeats and 2 hinges, no C-terminal domain) (This microgene carries both R16 and R17. It can restore nNOS)

SEQ ID NO: 14: .DELTA.R3-R15/.DELTA.R17-23/.DELTA.C (micro-dystrophin with 4 repeats and 2 hinges, no C-terminal domain) (This microgene carries R16 but not R17. It cannot restore nNOS)

SEQ ID NO: 15: AV.CMV..DELTA.R2-15/.DELTA.R18-23/.DELTA.C (This AAV vector contains four repeats and two hinges. It carries both R16 and R17 and it can restore nNOS)

SEQ ID NO: 16: AV.CMV..DELTA.R3-15/.DELTA.R18-23/.DELTA.C (This AAV vector contains five repeats and two hinges. It carries both R16 and R17 and it can restore nNOS)

SEQ ID NO: 17: Human dystrophin domain sequence N-terminal domain

SEQ ID NO: 18: Hinge 1

SEQ ID NO: 19: Repeat 1

SEQ ID NO: 20: Repeat 2

SEQ ID NO: 21: Repeat 3

SEQ ID NO: 22: Hinge 1 SEQ ID NO: 23: Repeat 4

SEQ ID NO: 24: Repeat 5

SEQ ID NO: 25: Repeat 6

SEQ ID NO: 26: Repeat 7

SEQ ID NO: 27: Repeat 8

SEQ ID NO: 28: Repeat 9

SEQ ID NO: 29: Repeat 10

SEQ ID NO: 30: Repeat 11

SEQ ID NO: 31: Repeat 12

SEQ ID NO: 32: Repeat 13

SEQ ID NO: 33: Repeat 14

SEQ ID NO: 34: Repeat 15

SEQ ID NO: 35: Repeat 16

SEQ ID NO: 36: Repeat 17

SEQ ID NO: 37: Repeat 18

SEQ ID NO: 38: Repeat 19

SEQ ID NO: 39: Hinge 3

SEQ ID NO: 40: Repeat 20

SEQ ID NO: 41: Repeat 21

SEQ ID NO: 42: Repeat 22

SEQ ID NO: 43: Repeat 23

SEQ ID NO: 44: Repeat 24

SEQ ID NO: 45: Hinge 4

SEQ ID NO: 46: Cysteine-rich domain

SEQ ID NO: 47: C-terminal domain

SEQ ID NO: 48: Full-length canine dystrophin DNA sequence

SEQ ID NO: 49: Full-length canine dystrophin protein sequence

SEQ ID NO: 50: N-terminal domain from 1 aa to 252 aa; total 252 aa of full length human dystrophin protein of 3685 aa)

SEQ ID NO: 51: Mid-rod domain (from 253 aa to 3112 aa; total 2860 aa of full length human dystrophin protein of 3685 aa)

SEQ ID NO: 52: Cysteine-rich domain (from 3113 aa to 3408 aa; total 296 aa of full length human dystrophin protein of 3685 aa)

SEQ ID NO: 53: C-terminal domain (from 3409 aa to 3695 aa; total 277 aa of full length human dystrophin protein of 3685 aa)

-continued

SEQ ID NO: 54: LLNSRWECLRVASME

SEQ ID NO: 55: QRLTEEQCLFSAWLS

SEQ ID NO: 56: WLDNFARCWDNLVQK

SEQ ID NO: 57: CLKLSRKM

SEQ ID NO: 58 R16 peptide sequence (first alpha-helix underlined):
EISYVPSTYLTEITHVSQALLEVEQLLNAPDLCAKDFEDLFKQEESLKNIKDSLQQSSG

RIDIIHSKKTAALQSATPVERVKLQEALSQLDFQWEKVNKMYKDRQGRFDR

SEQ ID NO: 59 first alpha-helix of R16:
PSTYLTEITHVSQALLEVEQL

SEQ ID NO: 60(R10-R11-R12 peptide; MBM underlined):
SIQSAQETEKSLHLIQESLTFIDKQLAAYIADKVDAAQMPQEAQKIQSDLTSHEISLEE

MKKHNQGKEAAQRVLSQIDVAQKKLQDVSMKFRLFQKPANFELRLQESKMILDEV

KMHLPALETKSVEQEVVQSQLNHCVNLYKSLSEVKSEVEMVIKTGRQIVQKKQTEN

PKELDERVTALKLHYNELGAKVTERKQQLEKCLKLSRKMRKEMNVLTEWLAATDM

ELTKRSAVEGMPSNLDSEVAWGKATQKEIEKQKVHLKSITEVGEALKTVLGKKETL

VEDKLSLLNSNWIAVTSRAEEWLNLLLE

SEQ ID NO: 61(R1-R2-R3 peptide; MBM underlined):
SEVNLDRYQTALEEVLSWLLSAEDTLQAQGEISNDVEVVKDQFHTHEGYMMDLTA

HQGRVGNILQLGSKLIGTGKLSEDEETEVQEQMNLLNSRWECLRVASMEKQSNLHR

VLMDLQNQKLKELNDWLTKTEERTRKMEEEPLGPDLEDLKRQVQQHKVLQEDLEQ

EQVRVNSLTHMVVVVDESSGDHATAALEEQLKVLGDRWANICRWTEDRWVLLQDI

LLKWQRLTEEQCLFSAWLSEKEDAVNKIHTTGFKDQNEMLSSLQKLAVLKADLEKK

KQSMGKLYSLKQDLLSTLKNKSVTQKTEAWLDNFARCWDNLVQKLEKSTAQISQ

SEQ ID NO: 62:
GGSG

SEQ ID NO: 63:
GGGS

SEQ ID NO: 64:
GGGGS

SEQ ID NO: 65:
GSAT

SEQ ID NO: 66: (PDZ domain of mouse syntrophin)

SEQ ID NO: 67: (PDZ Domain of Human syntrophin)

REFERENCES

1. Straub, V., Rafael, J. A., Chamberlain, J. S. and Campbell, K. P. (1997) Animal models for muscular dystrophy show different patterns of sarcolemmal disruption. *J. Cell Biol.*, 139, 375-385.
2. Petrof, B. J., Shrager, J. B., Stedman, H. H., Kelly, A. M. and Sweeney, H. L. (1993) Dystrophin protects the sarcolemma from stresses developed during muscle contraction. *Proc. Natl. Acad. Sci. USA*, 90, 3710-3714.
3. Hoffman, E. P., Brown, R. H. J. and Kunkel, L. M. (1987) Dystrophin: the protein product of the Duchenne muscular dystrophy locus. *Cell*, 51, 919-928.
4. Koenig, M. and Kunkel, L. M. (1990) Detailed analysis of the repeat domain of dystrophin reveals four potential hinge segments that can confer flexibility *J. Biol. Chem.*, 265, 4560-4566.
5. Amann, K. J., Renley, B. A. and Ervasti, J. M. (1998) A cluster of basic repeats in the dystrophin rod domain binds F-actin through an electrostatic interaction. *J. Biol. Chem.*, 273, 28419-28423.
6. Rybakova, I. N., Amann, K. J. and Ervasti, J. M. (1996) A new model for the interaction of dystrophin with F-actin. *J. Cell Biol.*, 135, 661-672.
7. Campbell, K. P. and Kahl, S. D. (1989) Association of dystrophin and an integral membrane glycoprotein. *Nature*, 338, 259-262.
8. Jung, D., Yang, B., Meyer, J., Chamberlain, J. S. and Campbell, K. P. (1995) Identification and characterization of the dystrophin anchoring site on beta-dystroglycan. *J. Biol. Chem.*, 270, 27305-27310.
9. Huang, X., Poy, F., Zhang, R., Joachimiak, A., Sudol, M. and Eck, M. J. (2000) Structure of a WW domain containing fragment of dystrophin in complex with beta-dystroglycan. *Nat. Struct. Biol.*, 7, 634-638.

10. Ervasti, J. M. and Campbell, K. P. (1991) Membrane organization of the dystrophin-glycoprotein complex. *Cell*, 66, 1121-1131.
11. Helliwell, T. R., Ellis, J. M., Mountford, R. C., Appleton, R. E. and Morris, G. E. (1992) A truncated dystrophin lacking the C-terminal domains is localized at the muscle membrane. *Am. J. Hum. Genet.*, 50, 508-514.
12. Hoffman, E. P., Garcia, C. A., Chamberlain, J. S., Angelini, C., Lupski, J. R. and Fenwick, R. (1991) Is the carboxyl-terminus of dystrophin required for membrane association? A novel, severe case of Duchenne muscular dystrophy. *Ann. Neurol.*, 30, 605-610.
13. Recan, D., Chafey, P., Leturcq, F., Hugnot, J. P., Vincent, N., Tome, F., Collin, H., Simon, D., Czernichow, P., Nicholson, L. V. and et, A. (1992) Are cysteine-rich and COOH-terminal domains of dystrophin critical for sarcolemmal localization? *J. Clin. Invest.*, 89, 712-716.
14. Le Rumeur, E., Winder, S. J. and Hubert, J. F. (2010) Dystrophin: more than just the sum of its parts. *Biochim. Biophys. Acta*, 1804, 1713-1722.
15. Cox, G. A., Sunada, Y., Campbell, K. P. and Chamberlain, J. S. (1994) Dp71 can restore the dystrophin-associated glycoprotein complex in muscle but fails to prevent dystrophy. *Nat. Genet.*, 8, 333-339.
16. Crawford, G. E., Faulkner, J. A., Crosbie, R. H., Campbell, K. P., Froehner, S. C. and Chamberlain, J. S. (2000) Assembly of the dystrophin-associated protein complex does not require the dystrophin COOH-terminal domain *J. Cell Biol.*, 150, 1399-1410.
17. Rapaport, D., Greenberg, D. S., Tal, M., Yaffe, D. and Nudel, U. (1993) Dp71, the nonmuscle product of the Duchenne muscular dystrophy gene is associated with the cell membrane. *FEBS Lett.*, 328, 197-202.
18. Judge, L. M., Haraguchiln, M. and Chamberlain, J. S. (2006) Dissecting the signaling and mechanical functions of the dystrophin-glycoprotein complex *J. Cell Sci.*, 119, 1537-1546.
19. Rafael, J. A., Cox, G. A., Corrado, K., Jung, D., Campbell, K. P. and Chamberlain, J. S. (1996) Forced expression of dystrophin deletion constructs reveals structure-function correlations. *J. Cell Biol.*, 134, 93-102.
20. Fritz, J. D., Danko, I., Roberds, S. L., Campbell, K. P., Latendresse, J. S. and Wolff, J. A. (1995) Expression of deletion-containing dystrophins in mdx muscle: implications for gene therapy and dystrophin function. *Pediatr Res*, 37, 693-700.
21. Maconochie, M. K., Simpkins, A. H., Damien, E., Coulton, G., Greenfield, A. J. and Brown, S. D. (1996) The cysteine-rich and C-terminal domains of dystrophin are not required for normal costameric localization in the mouse. *Transgenic Res*, 5, 123-130.
22. Gardner, K. L., Kearney, J. A., Edwards, J. D. and Rafael-Fortney, J. A. (2006) Restoration of all dystrophin protein interactions by functional domains in trans does not rescue dystrophy. *Gene Ther*, 13, 744-751.
23. Barnabei, M. S., Sjaastad, F. V., Townsend, D., Bedada, F. B. and Metzger, J. M. (2015) Severe dystrophic cardiomyopathy caused by the enteroviral protease 2A-mediated C-terminal dystrophin cleavage fragment. *Sci Transl Med*, 7, 294ra106.
24. Dunckley, M. G., Wells, K. E., Piper, T. A., Wells, D. J. and Dickson, G. (1994) Independent localization of dystrophin N- and C-terminal regions to the sarcolemma of mdx mouse myofibres in vivo. *J Cell Sci.*, 107, 1469-1475.
25. Hir, S. A., Raguenes-Nicol, C., Paboeuf, G., Nicolas, A., Le Rumeur, E. and Vie, V. (2014) Cholesterol favors the anchorage of human dystrophin repeats 16 to 21 in membrane at physiological surface pressure. *Biochim. Biophys. Acta*, 1838, 1266-1273.
26. DeWolf, C., McCauley, P., Sikorski, A. F., Winlove, C. P., Bailey, A. I., Kahana, E., Pinder, J. C. and Gratzer, W. B. (1997) Interaction of dystrophin fragments with model membranes. *Biophys. 1*, 72, 2599-2604.
27. Le Rumeur, E., Fichou, Y., Pottier, S., Gaboriau, F., Rondeau-Mouro, C., Vincent, M., Gallay, J. and Bondon, A. (2003) Interaction of dystrophin rod domain with membrane phospholipids. Evidence of a close proximity between tryptophan residues and lipids. *J Biol. Chem.*, 278, 5993-6001.
28. Le Rumeur, E., Pottier, S., Da Costa, G., Metzinger, L., Mouret, L., Rocher, C., Fourage, M., Rondeau-Mouro, C. and Bondon, A. (2007) Binding of the dystrophin second repeat to membrane di-oleyl phospholipids is dependent upon lipid packing. *Biochim. Biophys. Acta*, 1768, 648-654.
29. Legardinier, S., Hubert, J. F., Le Bihan, O., Tascon, C., Rocher, C., Raguenes-Nicol, C., Bondon, A., Hardy, S. and Le Rumeur, E. (2008) Sub-domains of the dystrophin rod domain display contrasting lipid-binding and stability properties. *Biochim. Biophys. Acta*, 1784, 672-682.
30. Legardinier, S., Raguenes-Nicol, C., Tascon, C., Rocher, C., Hardy, S., Hubert, J. F. and Le Rumeur, E. (2009) Mapping of the lipid-binding and stability properties of the central rod domain of human dystrophin. *J Mol. Biol.*, 389, 546-558.
31. Lai, Y., Zhao, J., Yue, Y. and Duan, D. (2013) alpha2 and alpha3 helices of dystrophin R16 and R17 frame a microdomain in the alphal helix of dystrophin R17 for neuronal NOS binding. *Proc. Natl. Acad. Sci. USA*, 110, 525-530.
32. Johnson, E. K., Zhang, L., Adams, M. E., Phillips, A., Freitas, M. A., Froehner, S. C., Green-Church, K. B. and Montanaro, F. (2012) Proteomic analysis reveals new cardiac-specific dystrophin-associated proteins. *PLoS One*, 7, e43515.
33. Lai, Y., Thomas, G. D., Yue, Y., Yang, H. T., Li, D., Long, C., Judge, L., Bostick, B., Chamberlain, J. S., Terjung, R. L. and Duan, D. (2009) Dystrophins carrying spectrin-like repeats 16 and 17 anchor nNOS to the sarcolemma and enhance exercise performance in a mouse model of muscular dystrophy. *J. Clin. Invest.*, 119, 624-635.
34. Bennett, V. and Lorenzo, D. N. (2016) An Adaptable Spectrin/Ankyrin-Based Mechanism for Long-Range Organization of Plasma Membranes in Vertebrate Tissues. *Curr Top Membr*, 77, 143-184.
35. Yoshida, M., Hama, H., Ishikawa-Sakurai, M., Imamura, M., Mizuno, Y., Araishi, K., Wakabayashi-Takai, E., Noguchi, S., Sasaoka, T. and Ozawa, E. (2000) Biochemical evidence for association of dystrobrevin with the sarcoglycan-sarcospan complex as a basis for understanding sarcoglycanopathy. *Hum. Mol. Genet.*, 9, 1033-1040.
36. Suzuki, A., Yoshida, M. and Ozawa, E. (1995) Mammalian alpha 1- and beta 1-syntrophin bind to the alternative splice-prone region of the dystrophin COOH terminus. *J. Cell Biol.*, 128, 373-381.
37. Yang, B., Jung, D., Rafael, J. A., Chamberlain, J. S. and Campbell, K. P. (1995) Identification of alpha-syntrophin binding to syntrophin triplet, dystrophin, and utrophin. *J. Biol. Chem.*, 270, 4975-4978.
38. Bunnell, T. M., Jaeger, M. A., Fitzsimons, D. P., Prins, K. W. and Ervasti, J. M. (2008) Destabilization of the dystrophin-glycoprotein complex without functional deficits in alpha-dystrobrevin null muscle. *PLoS One*, 3, e2604.

39. Bajanca, F., Gonzalez-Perez, V., Gillespie, S. J., Beley, C., Garcia, L., Theveneau, E., Sear, R. P. and Hughes, S. M. (2015) In vivo dynamics of skeletal muscle Dystrophin in zebrafish embryos revealed by improved FRAP analysis. Elife, 4, e06541.

40. Shin, J. H., Yue, Y. and Duan, D. (2012) Recombinant adeno-associated viral vector production and purification. *Methods Mol. Biol.*, 798, 267-284.

41. Zhong, L., Li, B., Mah, C. S., Govindasamy, L., Agbandje-McKenna, M., Cooper, M., Herzog, R. W., Zolotukhin, I., Warrington, K. H. J., Weigel-Van Aken, K. A. et al. (2008) Next generation of adeno-associated virus 2 vectors: point mutations in tyrosines lead to high-efficiency transduction at lower doses. *Proc. Natl. Acad. Sci. USA*, 105, 7827-7832.

42. Shin, J. H., Yue, Y., Srivastava, A., Smith, B., Lai, Y. and Duan, D. (2012) A Simplified Immune Suppression Scheme Leads to Persistent Micro-dystrophin Expression in Duchenne Muscular Dystrophy Dogs. *Hum. Gene Ther.*, 23, 202-209.

43. Liadaki, K., Luth, E. S. and Kunkell, L. M. (2007) Co-detection of GFP and dystrophin in skeletal muscle tissue sections. *BioTechniques*, 42, 699-700.

44. Lai, Y., Zhao, J., Yue, Y., Wasala, N. B. and Duan, D. (2014) Partial restoration of cardiac function with APDZ nNOS in aged mdx model of Duchenne cardiomyopathy. *Hum. Mol. Genet.*, 23, 3189-3199.

SUPPLEMENTARY REFERENCES

1. Suzuki, A., Yoshida, M., Yamamoto, H. and Ozawa, E. (1992) Glycoprotein-binding site of dystrophin is confined to the cysteine-rich domain and the first half of the carboxy-terminal domain. *FEBS Lett.*, 308, 154-160.

2. Suzuki, A., Yoshida, M., Hayashi, K., Mizuno, Y., Hagiwara, Y. and Ozawa, E. (1994) Molecular organization at the glycoprotein-complex-binding site of dystrophin. Three dystrophin-associated proteins bind directly to the carboxy-terminal portion of dystrophin. *Eur. J Biochem.*, 220, 283-292.

3. Campbell, K. P. and Kahl, S. D. (1989) Association of dystrophin and an integral membrane glycoprotein. *Nature*, 338, 259-262.

4. Jung, D., Yang, B., Meyer, J., Chamberlain, J. S. and Campbell, K. P. (1995) Identification and characterization of the dystrophin anchoring site on beta-dystroglycan. *J. Biol. Chem.*, 270, 27305-27310.

5. Huang, X., Poy, F., Zhang, R., Joachimiak, A., Sudol, M. and Eck, M. J. (2000) Structure of a WW domain containing fragment of dystrophin in complex with beta-dystroglycan. *Nat. Struct. Biol.*, 7, 634-638.

6. Ishikawa-Sakurai, M., Yoshida, M., Imamura, M., Davies, K. E. and Ozawa, E. (2004) ZZ domain is essentially required for the physiological binding of dystrophin and utrophin to beta-dystroglycan. *Hum. Mol. Genet.*, 13, 693-702.

7. Draviam, R. A., Wang, B., Li, J., Xiao, X. and Watkins, S. C. (2006) Mini-dystrophin efficiently incorporates into the dystrophin protein complex in living cells. *J Muscle Res Cell Motil*, 27, 53-67.

8. Einbond, A. and Sudol, M. (1996) Towards prediction of cognate complexes between the WW domain and proline-rich ligands. *FEBS Lett.*, 384, 1-8.

9. Recan, D., Chafey, P., Leturcq, F., Hugnot, J. P., Vincent, N., Tome, F., Collin, H., Simon, D., Czernichow, P., Nicholson, L. V. and et, A. (1992) Are cysteine-rich and COOH-terminal domains of dystrophin critical for sarcolemmal localization? *J. Clin. Invest.*, 89, 712-716.

10. Hoffman, E. P., Garcia, C. A., Chamberlain, J. S., Angelini, C., Lupski, J. R. and Fenwick, R. (1991) Is the carboxyl-terminus of dystrophin required for membrane association? A novel, severe case of Duchenne muscular dystrophy. *Ann. Neurol.*, 30, 605-610.

11. Helliwell, T. R., Ellis, J. M., Mountford, R. C., Appleton, R. E. and Morris, G. E. (1992) A truncated dystrophin lacking the C-terminal domains is localized at the muscle membrane. *Am. J. Hum. Genet.*, 50, 508-514.

12. Rafael, J. A., Cox, G. A., Corrado, K., Jung, D., Campbell, K. P. and Chamberlain, J. S. (1996) Forced expression of dystrophin deletion constructs reveals structure-function correlations. *J. Cell Biol.*, 134, 93-102.

13. Maconochie, M. K., Simpkins, A. H., Damien, E., Coulton, G., Greenfield, A. J. and Brown, S. D. (1996) The cysteine-rich and C-terminal domains of dystrophin are not required for normal costameric localization in the mouse. *Transgenic Res*, 5, 123-130.

14. Gardner, K. L., Kearney, J. A., Edwards, J. D. and Rafael-Fortney, J. A. (2006) Restoration of all dystrophin protein interactions by functional domains in trans does not rescue dystrophy. *Gene Ther*, 13, 744-751.

15. Barnabei, M. S., Sjaastad, F. V., Townsend, D., Bedada, F. B. and Metzger, J. M. (2015) Severe dystrophic cardiomyopathy caused by the enteroviral protease 2A-mediated C-terminal dystrophin cleavage fragment. *Sci Transl Med*, 7, 294ra106.

16. Dunckley, M. G., Wells, K. E., Piper, T. A., Wells, D. J. and Dickson, G. (1994) Independent localization of dystrophin N- and C-terminal regions to the sarcolemma of mdx mouse myofibres in vivo. *J. Cell Sci.*, 107, 1469-1475.

17. Fritz, J. D., Danko, I., Roberds, S. L., Campbell, K. P., Latendresse, J. S. and Wolff, J. A. (1995) Expression of deletion-containing dystrophins in mdx muscle: implications for gene therapy and dystrophin function. *Pediatr Res*, 37, 693-700.

18. Sarkis, J., Hubert, J. F., Legrand, B., Robert, E., Cheron, A., Jardin, J., Hitti, E., Le Rumeur, E. and Vie, V. (2011) Spectrin-like repeats 11-15 of human dystrophin show adaptations to a lipidic environment. *J. Biol. Chem.*, 286, 30481-30491.

19. Legardinier, S., Raguenes-Nicol, C., Tascon, C., Rocher, C., Hardy, S., Hubert, J. F. and Le Rumeur, E. (2009) Mapping of the lipid-binding and stability properties of the central rod domain of human dystrophin. *J. Mol. Biol.*, 389, 546-558.

20. Legardinier, S., Hubert, J. F., Le Bihan, O., Tascon, C., Rocher, C., Raguenes-Nicol, C., Bondon, A., Hardy, S. and Le Rumeur, E. (2008) Sub-domains of the dystrophin rod domain display contrasting lipid-binding and stability properties. *Biochim. Biophys. Acta*, 1784, 672-682.

21. Le Rumeur, E., Pottier, S., Da Costa, G., Metzinger, L., Mouret, L., Rocher, C., Fourage, M., Rondeau-Mouro, C. and Bondon, A. (2007) Binding of the dystrophin second repeat to membrane di-oleyl phospholipids is dependent upon lipid packing. *Biochim. Biophys. Acta*, 1768, 648-654.

22. Hir, S. A., Raguenes-Nicol, C., Paboeuf, G., Nicolas, A., Le Rumeur, E. and Vie, V. (2014) Cholesterol favors the anchorage of human dystrophin repeats 16 to 21 in membrane at physiological surface pressure. *Biochim. Biophys. Acta*, 1838, 1266-1273.

23. Le Rumeur, E., Fichou, Y., Pottier, S., Gaboriau, F., Rondeau-Mouro, C., Vincent, M., Gallay, J. and Bondon, A. (2003) Interaction of dystrophin rod domain with membrane phospholipids. Evidence of a close proximity between tryptophan residues and lipids. *J. Biol. Chem.,* 278, 5993-6001.
24. Suzuki, A., Yoshida, M. and Ozawa, E. (1995) Mammalian alpha 1- and beta 1-syntrophin bind to the alternative splice-prone region of the dystrophin COOH terminus. *J. Cell Biol.,* 128, 373-381.
25. Yang, B., Jung, D., Rafael, J. A., Chamberlain, J. S. and Campbell, K. P. (1995) Identification of alpha-syntrophin binding to syntrophin triplet, dystrophin, and utrophin. *J. Biol. Chem.,* 270, 4975-4978.
26. Yoshida, M., Hama, H., Ishikawa-Sakurai, M., Imamura, M., Mizuno, Y., Araishi, K., Wakabayashi-Takai, E., Noguchi, S., Sasaoka, T. and Ozawa, E. (2000) Biochemical evidence for association of dystrobrevin with the sarcoglycan-sarcospan complex as a basis for understanding sarcoglycanopathy. *Hum. Mol. Genet.,* 9, 1033-1040.
27. Cox, G. A., Sunada, Y., Campbell, K. P. and Chamberlain, J. S. (1994) Dp71 can restore the dystrophin-associated glycoprotein complex in muscle but fails to prevent dystrophy. *Nat. Genet.,* 8, 333-339.
28. Rapaport, D., Greenberg, D. S., Tal, M., Yaffe, D. and Nudel, U. (1993) Dp71, the nonmuscle product of the Duchenne muscular dystrophy gene is associated with the cell membrane. *FEBS Lett.,* 328, 197-202.
29. Judge, L. M., Haraguchiln, M. and Chamberlain, J. S. (2006) Dissecting the signaling and mechanical functions of the dystrophin-glycoprotein complex *J. Cell Sci.,* 119, 1537-1546.

The inclusion of various references herein is not to be construed as any admission by the Applicant that the references constitute prior art. Applicants expressly reserve their right to challenge any allegations of unpatentability of inventions disclosed herein over the references included herein.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims or otherwise disclosed herein.

The invention claimed is:

1. A synthetic nucleic acid molecule comprising:
   (i) a sequence encoding a fusion protein comprising a nNOS binding domain of dystrophin R16-R17 that is operably linked to a syntrophin PDZ domain,
   wherein the n-terminal alpha-helix, alpha-helix 2, and alpha-helix 3 of the R16 domain are present in the fusion protein and alpha-helix 1, alpha-helix 2, and alpha-helix 3 of the R17 domain are present in the fusion protein; or
   (ii) a sequence encoding a fusion protein comprising a nNOS binding domain of dystrophin R16-R17 that is operably linked to a syntrophin PDZ domain,
   wherein the n-terminal alpha helix of the R16 domain (SEQ ID NO: 59) or a portion thereof is substituted in phase with an alpha helix from another dystrophin repeat; and
   wherein alpha-helix 2 and alpha-helix 3 of the R16 domain are present in the fusion protein and alpha-helix 1, alpha-helix 2, and alpha-helix 3 of the R17 domain are present in the fusion protein.

2. A composition comprising the synthetic nucleic acid molecule of claim 1 and a pharmaceutically acceptable carrier.

3. An isolated host cell comprising the synthetic nucleic acid molecule of claim 1.

4. A single recombinant adeno-associated virus (AAV) vector comprising the synthetic nucleic acid molecule of claim 1, wherein said synthetic nucleic acid molecule is operably linked to an expression cassette and viral inverted terminal repeats (ITRs) in the AAV.

5. A composition comprising the vector of claim 4 and a pharmaceutically acceptable carrier.

6. An isolated host cell comprising the vector of claim 4.

7. A dual recombinant AAV vector system, comprising two AAV vectors, wherein one of the two AAV vectors comprises a part of the synthetic nucleic acid molecule of claim 1, and the other vector comprises the remaining part of said synthetic nucleic acid molecule, wherein the two vectors further comprise sequences that permit recombination with each other to produce said nucleic acid in full length, and wherein the nucleic acid in full length is operably linked to an expression cassette and viral ITRs.

8. A composition comprising the vectors of claim 7 and a pharmaceutically acceptable carrier.

9. An isolated host cell comprising the vectors of claim 7.

10. A lentiviral vector comprising the synthetic nucleic acid molecule of claim 1, wherein the synthetic nucleic acid molecule is operably linked to an expression cassette, 5' and 3' long terminal repeats (LTR), and a psi sequence in the lentiviral vector.

11. A composition comprising the vector of claim 10 and a pharmaceutically acceptable carrier.

12. An isolated host cell comprising the vector of claim 10.

13. A method of increasing the localization of nNOS to the sarcolemma of a subject having a neuromuscular disorder characterized by loss of sarcolemmal neuronal nitric oxide synthase (nNOS) activity, the method comprising administering to the subject a therapeutically effective amount of the synthetic nucleic acid molecule of claim 1.

14. The method of claim 13, wherein the neuromuscular disorder characterized by loss of sarcolemmal nNOS activity is selected from the group consisting of Duchenne muscular dystrophy (DMD), age-related muscle atrophy, and cancer cachexia.

15. The method of claim 13, wherein the neuromuscular disorder characterized by loss of sarcolemmal nNOS activity is selected from the group consisting A of Duchenne muscular dystrophy (DMD), Becker muscular dystrophy (BMD), and X-linked dilated cardiomyopathy (XLDC).

16. The method of claim 13, wherein the synthetic nucleic acid molecule is administered via a lentiviral vector comprising the synthetic nucleic acid molecule, and wherein the nucleic acid molecule is operably linked to an expression cassette, 5' and 3' long terminal repeats (LTR), and a psi sequence in the lentiviral vector.

17. The method of claim 13, wherein the synthetic nucleic acid molecule is administered via a single recombinant adeno-associated virus (AAV) vector comprising said synthetic nucleic acid molecule, and wherein said nucleic acid molecule is operably linked to an expression cassette and viral inverted terminal repeats (ITRs) in the AAV.

18. The method of claim 13, wherein a defective endogenous dystrophin gene of the host cell or a defective portion thereof is edited to provide the synthetic nucleic acid molecule within the host cell's X-chromosome.

19. The method of claim 13, wherein the neuromuscular disorder characterized by loss of sarcolemmal nNOS activity is selected from the group consisting of Duchenne muscular dystrophy (DMD) and Becker muscular dystrophy (BMD).

20. The method of claim 13, wherein the neuromuscular disorder characterized by loss of sarcolemmal nNOS activity is Duchenne muscular dystrophy (DMD).

* * * * *

SEQUENCE LISTING

```
<160> NUMBER OF SEQ ID NOS: 67

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
```

-continued

```
            195                 200                 205
Ile Glu Lys Leu Leu Asp Pro Glu Asp Val Asp Thr Thr Tyr Pro Asp
    210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
    290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Lys Asp Gln Phe His Thr His Glu Gly
    370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
        435                 440                 445
Leu Met Asp Leu Gln Asn Gln Lys Leu Lys Glu Leu Asn Asp Trp Leu
    450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
        515                 520                 525
Leu Glu Glu Gln Leu Lys Val Leu Gly Asp Arg Trp Ala Asn Ile Cys
    530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
        595                 600                 605
Asp Leu Glu Lys Lys Lys Gln Ser Met Gly Lys Leu Tyr Ser Leu Lys
    610                 615                 620
```

-continued

```
Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
690                 695                 700

Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
        1010                1015                1020

Glu Ile Glu Gly Arg Trp Lys Lys Leu Ser Ser Gln Leu Val Glu
        1025                1030                1035
```

His Cys Gln Lys Leu Glu Glu Gln Met Asn Lys Leu Arg Lys Ile
1040            1045                1050

Gln Asn His Ile Gln Thr Leu Lys Lys Trp Met Ala Glu Val Asp
1055            1060                1065

Val Phe Leu Lys Glu Glu Trp Pro Ala Leu Gly Asp Ser Glu Ile
1070            1075                1080

Leu Lys Lys Gln Leu Lys Gln Cys Arg Leu Leu Val Ser Asp Ile
1085            1090                1095

Gln Thr Ile Gln Pro Ser Leu Asn Ser Val Asn Glu Gly Gly Gln
1100            1105                1110

Lys Ile Lys Asn Glu Ala Glu Pro Glu Phe Ala Ser Arg Leu Glu
1115            1120                1125

Thr Glu Leu Lys Glu Leu Asn Thr Gln Trp Asp His Met Cys Gln
1130            1135                1140

Gln Val Tyr Ala Arg Lys Glu Ala Leu Lys Gly Gly Leu Glu Lys
1145            1150                1155

Thr Val Ser Leu Gln Lys Asp Leu Ser Glu Met His Glu Trp Met
1160            1165                1170

Thr Gln Ala Glu Glu Glu Tyr Leu Glu Arg Asp Phe Glu Tyr Lys
1175            1180                1185

Thr Pro Asp Glu Leu Gln Lys Ala Val Glu Glu Met Lys Arg Ala
1190            1195                1200

Lys Glu Glu Ala Gln Gln Lys Glu Ala Lys Val Lys Leu Leu Thr
1205            1210                1215

Glu Ser Val Asn Ser Val Ile Ala Gln Ala Pro Pro Val Ala Gln
1220            1225                1230

Glu Ala Leu Lys Lys Glu Leu Glu Thr Leu Thr Thr Asn Tyr Gln
1235            1240                1245

Trp Leu Cys Thr Arg Leu Asn Gly Lys Cys Lys Thr Leu Glu Glu
1250            1255                1260

Val Trp Ala Cys Trp His Glu Leu Leu Ser Tyr Leu Glu Lys Ala
1265            1270                1275

Asn Lys Trp Leu Asn Glu Val Glu Phe Lys Leu Lys Thr Thr Glu
1280            1285                1290

Asn Ile Pro Gly Gly Ala Glu Glu Ile Ser Glu Val Leu Asp Ser
1295            1300                1305

Leu Glu Asn Leu Met Arg His Ser Glu Asp Asn Pro Asn Gln Ile
1310            1315                1320

Arg Ile Leu Ala Gln Thr Leu Thr Asp Gly Gly Val Met Asp Glu
1325            1330                1335

Leu Ile Asn Glu Glu Leu Glu Thr Phe Asn Ser Arg Trp Arg Glu
1340            1345                1350

Leu His Glu Glu Ala Val Arg Arg Gln Lys Leu Leu Glu Gln Ser
1355            1360                1365

Ile Gln Ser Ala Gln Glu Thr Glu Lys Ser Leu His Leu Ile Gln
1370            1375                1380

Glu Ser Leu Thr Phe Ile Asp Lys Gln Leu Ala Ala Tyr Ile Ala
1385            1390                1395

Asp Lys Val Asp Ala Ala Gln Met Pro Gln Glu Ala Gln Lys Ile
1400            1405                1410

Gln Ser Asp Leu Thr Ser His Glu Ile Ser Leu Glu Glu Met Lys
1415            1420                1425

Lys His Asn Gln Gly Lys Glu Ala Ala Gln Arg Val Leu Ser Gln

-continued

```
            1430                1435                1440
Ile Asp Val Ala Gln Lys Lys Leu Gln Asp Val Ser  Met Lys Phe
    1445                1450                1455
Arg Leu Phe Gln Lys Pro Ala Asn Phe Glu Leu Arg  Leu Gln Glu
    1460                1465                1470
Ser Lys Met Ile Leu Asp Glu Val Lys Met His Leu  Pro Ala Leu
    1475                1480                1485
Glu Thr Lys Ser Val Glu Gln Glu Val Val Gln Ser  Gln Leu Asn
    1490                1495                1500
His Cys Val Asn Leu Tyr Lys Ser Leu Ser Glu Val  Lys Ser Glu
    1505                1510                1515
Val Glu Met Val Ile Lys Thr Gly Arg Gln Ile Val  Gln Lys Lys
    1520                1525                1530
Gln Thr Glu Asn Pro Lys Glu Leu Asp Glu Arg Val  Thr Ala Leu
    1535                1540                1545
Lys Leu His Tyr Asn Glu Leu Gly Ala Lys Val Thr  Glu Arg Lys
    1550                1555                1560
Gln Gln Leu Glu Lys Cys Leu Lys Leu Ser Arg Lys  Met Arg Lys
    1565                1570                1575
Glu Met Asn Val Leu Thr Glu Trp Leu Ala Ala Thr  Asp Met Glu
    1580                1585                1590
Leu Thr Lys Arg Ser Ala Val Glu Gly Met Pro Ser  Asn Leu Asp
    1595                1600                1605
Ser Glu Val Ala Trp Gly Lys Ala Thr Gln Lys Glu  Ile Glu Lys
    1610                1615                1620
Gln Lys Val His Leu Lys Ser Ile Thr Glu Val Gly  Glu Ala Leu
    1625                1630                1635
Lys Thr Val Leu Gly Lys Lys Glu Thr Leu Val Glu  Asp Lys Leu
    1640                1645                1650
Ser Leu Leu Asn Ser Asn Trp Ile Ala Val Thr Ser  Arg Ala Glu
    1655                1660                1665
Glu Trp Leu Asn Leu Leu Leu Glu Tyr Gln Lys His  Met Glu Thr
    1670                1675                1680
Phe Asp Gln Asn Val Asp His Ile Thr Lys Trp Ile  Ile Gln Ala
    1685                1690                1695
Asp Thr Leu Leu Asp Glu Ser Glu Lys Lys Lys Pro  Gln Gln Lys
    1700                1705                1710
Glu Asp Val Leu Lys Arg Leu Lys Ala Glu Leu Asn  Asp Ile Arg
    1715                1720                1725
Pro Lys Val Asp Ser Thr Arg Asp Gln Ala Ala Asn  Leu Met Ala
    1730                1735                1740
Asn Arg Gly Asp His Cys Arg Lys Leu Val Glu Pro  Gln Ile Ser
    1745                1750                1755
Glu Leu Asn His Arg Phe Ala Ala Ile Ser His Arg  Ile Lys Thr
    1760                1765                1770
Gly Lys Ala Ser Ile Pro Leu Lys Glu Leu Glu Gln  Phe Asn Ser
    1775                1780                1785
Asp Ile Gln Lys Leu Leu Glu Pro Leu Glu Ala Glu  Ile Gln Gln
    1790                1795                1800
Gly Val Asn Leu Lys Glu Glu Asp Phe Asn Lys Asp  Met Asn Glu
    1805                1810                1815
Asp Asn Glu Gly Thr Val Lys Glu Leu Leu Gln Arg  Gly Asp Asn
    1820                1825                1830
```

```
Leu Gln Gln Arg Ile Thr Asp Glu Arg Lys Glu Glu Ile Lys
    1835              1840            1845

Ile Lys Gln Gln Leu Leu Gln Thr Lys His Asn Ala Leu Lys Asp
    1850              1855            1860

Leu Arg Ser Gln Arg Arg Lys Lys Ala Leu Glu Ile Ser His Gln
    1865              1870            1875

Trp Tyr Gln Tyr Lys Arg Gln Ala Asp Asp Leu Leu Lys Cys Leu
    1880              1885            1890

Asp Asp Ile Glu Lys Lys Leu Ala Ser Leu Pro Glu Pro Arg Asp
    1895              1900            1905

Glu Arg Lys Ile Lys Glu Ile Asp Arg Glu Leu Gln Lys Lys Lys
    1910              1915            1920

Glu Glu Leu Asn Ala Val Arg Arg Gln Ala Glu Gly Leu Ser Glu
    1925              1930            1935

Asp Gly Ala Ala Met Ala Val Glu Pro Thr Gln Ile Gln Leu Ser
    1940              1945            1950

Lys Arg Trp Arg Glu Ile Glu Ser Lys Phe Ala Gln Phe Arg Arg
    1955              1960            1965

Leu Asn Phe Ala Gln Ile His Thr Val Arg Glu Glu Thr Met Met
    1970              1975            1980

Val Met Thr Glu Asp Met Pro Leu Glu Ile Ser Tyr Val Pro Ser
    1985              1990            1995

Thr Tyr Leu Thr Glu Ile Thr His Val Ser Gln Ala Leu Leu Glu
    2000              2005            2010

Val Glu Gln Leu Leu Asn Ala Pro Asp Leu Cys Ala Lys Asp Phe
    2015              2020            2025

Glu Asp Leu Phe Lys Gln Glu Glu Ser Leu Lys Asn Ile Lys Asp
    2030              2035            2040

Ser Leu Gln Gln Ser Ser Gly Arg Ile Asp Ile Ile His Ser Lys
    2045              2050            2055

Lys Thr Ala Ala Leu Gln Ser Ala Thr Pro Val Glu Arg Val Lys
    2060              2065            2070

Leu Gln Glu Ala Leu Ser Gln Leu Asp Phe Gln Trp Glu Lys Val
    2075              2080            2085

Asn Lys Met Tyr Lys Asp Arg Gln Gly Arg Phe Asp Arg Ser Val
    2090              2095            2100

Glu Lys Trp Arg Arg Phe His Tyr Asp Ile Lys Ile Phe Asn Gln
    2105              2110            2115

Trp Leu Thr Glu Ala Glu Gln Phe Leu Arg Lys Thr Gln Ile Pro
    2120              2125            2130

Glu Asn Trp Glu His Ala Lys Tyr Lys Trp Tyr Leu Lys Glu Leu
    2135              2140            2145

Gln Asp Gly Ile Gly Gln Arg Gln Thr Val Val Arg Thr Leu Asn
    2150              2155            2160

Ala Thr Gly Glu Glu Ile Ile Gln Gln Ser Ser Lys Thr Asp Ala
    2165              2170            2175

Ser Ile Leu Gln Glu Lys Leu Gly Ser Leu Asn Leu Arg Trp Gln
    2180              2185            2190

Glu Val Cys Lys Gln Leu Ser Asp Arg Lys Lys Arg Leu Glu Glu
    2195              2200            2205

Gln Lys Asn Ile Leu Ser Glu Phe Gln Arg Asp Leu Asn Glu Phe
    2210              2215            2220
```

| | | | | | | | | | | | |
|---|---|---|---|---|---|---|---|---|---|---|---|
| Val | Leu | Trp | Leu | Glu | Glu | Ala | Asp | Asn | Ile | Ala | Ser | Ile | Pro | Leu |
| 2225 | | | | 2230 | | | | | 2235 | | | | | |
| Glu | Pro | Gly | Lys | Glu | Gln | Gln | Leu | Lys | Glu | Lys | Leu | Glu | Gln | Val |
| 2240 | | | | | 2245 | | | | | 2250 | | | | |
| Lys | Leu | Leu | Val | Glu | Glu | Leu | Pro | Leu | Arg | Gln | Gly | Ile | Leu | Lys |
| 2255 | | | | | 2260 | | | | | 2265 | | | | |
| Gln | Leu | Asn | Glu | Thr | Gly | Gly | Pro | Val | Leu | Val | Ser | Ala | Pro | Ile |
| 2270 | | | | | 2275 | | | | | 2280 | | | | |
| Ser | Pro | Glu | Glu | Gln | Asp | Lys | Leu | Glu | Asn | Lys | Leu | Lys | Gln | Thr |
| 2285 | | | | | 2290 | | | | | 2295 | | | | |
| Asn | Leu | Gln | Trp | Ile | Lys | Val | Ser | Arg | Ala | Leu | Pro | Glu | Lys | Gln |
| 2300 | | | | | 2305 | | | | | 2310 | | | | |
| Gly | Glu | Ile | Glu | Ala | Gln | Ile | Lys | Asp | Leu | Gly | Gln | Leu | Glu | Lys |
| 2315 | | | | | 2320 | | | | | 2325 | | | | |
| Lys | Leu | Glu | Asp | Leu | Glu | Glu | Gln | Leu | Asn | His | Leu | Leu | Leu | Trp |
| 2330 | | | | | 2335 | | | | | 2340 | | | | |
| Leu | Ser | Pro | Ile | Arg | Asn | Gln | Leu | Glu | Ile | Tyr | Asn | Gln | Pro | Asn |
| 2345 | | | | | 2350 | | | | | 2355 | | | | |
| Gln | Glu | Gly | Pro | Phe | Asp | Val | Gln | Glu | Thr | Glu | Ile | Ala | Val | Gln |
| 2360 | | | | | 2365 | | | | | 2370 | | | | |
| Ala | Lys | Gln | Pro | Asp | Val | Glu | Glu | Ile | Leu | Ser | Lys | Gly | Gln | His |
| 2375 | | | | | 2380 | | | | | 2385 | | | | |
| Leu | Tyr | Lys | Glu | Lys | Pro | Ala | Thr | Gln | Pro | Val | Lys | Arg | Lys | Leu |
| 2390 | | | | | 2395 | | | | | 2400 | | | | |
| Glu | Asp | Leu | Ser | Ser | Glu | Trp | Lys | Ala | Val | Asn | Arg | Leu | Leu | Gln |
| 2405 | | | | | 2410 | | | | | 2415 | | | | |
| Glu | Leu | Arg | Ala | Lys | Gln | Pro | Asp | Leu | Ala | Pro | Gly | Leu | Thr | Thr |
| 2420 | | | | | 2425 | | | | | 2430 | | | | |
| Ile | Gly | Ala | Ser | Pro | Thr | Gln | Thr | Val | Thr | Leu | Val | Thr | Gln | Pro |
| 2435 | | | | | 2440 | | | | | 2445 | | | | |
| Val | Val | Thr | Lys | Glu | Thr | Ala | Ile | Ser | Lys | Leu | Glu | Met | Pro | Ser |
| 2450 | | | | | 2455 | | | | | 2460 | | | | |
| Ser | Leu | Met | Leu | Glu | Val | Pro | Ala | Leu | Ala | Asp | Phe | Asn | Arg | Ala |
| 2465 | | | | | 2470 | | | | | 2475 | | | | |
| Trp | Thr | Glu | Leu | Thr | Asp | Trp | Leu | Ser | Leu | Leu | Asp | Gln | Val | Ile |
| 2480 | | | | | 2485 | | | | | 2490 | | | | |
| Lys | Ser | Gln | Arg | Val | Met | Val | Gly | Asp | Leu | Glu | Asp | Ile | Asn | Glu |
| 2495 | | | | | 2500 | | | | | 2505 | | | | |
| Met | Ile | Ile | Lys | Gln | Lys | Ala | Thr | Met | Gln | Asp | Leu | Glu | Gln | Arg |
| 2510 | | | | | 2515 | | | | | 2520 | | | | |
| Arg | Pro | Gln | Leu | Glu | Glu | Leu | Ile | Thr | Ala | Ala | Gln | Asn | Leu | Lys |
| 2525 | | | | | 2530 | | | | | 2535 | | | | |
| Asn | Lys | Thr | Ser | Asn | Gln | Glu | Ala | Arg | Thr | Ile | Ile | Thr | Asp | Arg |
| 2540 | | | | | 2545 | | | | | 2550 | | | | |
| Ile | Glu | Arg | Ile | Gln | Asn | Gln | Trp | Asp | Glu | Val | Gln | Glu | His | Leu |
| 2555 | | | | | 2560 | | | | | 2565 | | | | |
| Gln | Asn | Arg | Arg | Gln | Gln | Leu | Asn | Glu | Met | Leu | Lys | Asp | Ser | Thr |
| 2570 | | | | | 2575 | | | | | 2580 | | | | |
| Gln | Trp | Leu | Glu | Ala | Lys | Glu | Glu | Ala | Glu | Gln | Val | Leu | Gly | Gln |
| 2585 | | | | | 2590 | | | | | 2595 | | | | |
| Ala | Arg | Ala | Lys | Leu | Glu | Ser | Trp | Lys | Glu | Gly | Pro | Tyr | Thr | Val |
| 2600 | | | | | 2605 | | | | | 2610 | | | | |
| Asp | Ala | Ile | Gln | Lys | Lys | Ile | Thr | Glu | Thr | Lys | Gln | Leu | Ala | Lys |

```
            2615                2620                2625

Asp Leu Arg Gln Trp Gln Thr Asn Val Asp Val Ala Asn Asp Leu
    2630                2635                2640

Ala Leu Lys Leu Leu Arg Asp Tyr Ser Ala Asp Thr Arg Lys
    2645                2650                2655

Val His Met Ile Thr Glu Asn Ile Asn Ala Ser Trp Arg Ser Ile
    2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850

Glu Leu Lys Thr Lys Glu Pro Val Ile Met Ser Thr Leu Glu Thr
    2855                2860                2865

Val Arg Ile Phe Leu Thr Glu Gln Pro Leu Glu Gly Leu Glu Lys
    2870                2875                2880

Leu Tyr Gln Glu Pro Arg Glu Leu Pro Pro Glu Glu Arg Ala Gln
    2885                2890                2895

Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970

His Leu Glu Lys Val Lys Ala Leu Arg Gly Glu Ile Ala Pro Leu
    2975                2980                2985

Lys Glu Asn Val Ser His Val Asn Asp Leu Ala Arg Gln Leu Thr
    2990                2995                3000

Thr Leu Gly Ile Gln Leu Ser Pro Tyr Asn Leu Ser Thr Leu Glu
    3005                3010                3015
```

-continued

```
Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
3170                3175                3180

Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
3215                3220                3225

Cys Asp Gln Arg Arg Leu Gly Leu Leu Leu His Asp Ser Ile Gln
3230                3235                3240

Ile Pro Arg Gln Leu Gly Glu Val Ala Ser Phe Gly Gly Ser Asn
3245                3250                3255

Ile Glu Pro Ser Val Arg Ser Cys Phe Gln Phe Ala Asn Asn Lys
3260                3265                3270

Pro Glu Ile Glu Ala Ala Leu Phe Leu Asp Trp Met Arg Leu Glu
3275                3280                3285

Pro Gln Ser Met Val Trp Leu Pro Val Leu His Arg Val Ala Ala
3290                3295                3300

Ala Glu Thr Ala Lys His Gln Ala Lys Cys Asn Ile Cys Lys Glu
3305                3310                3315

Cys Pro Ile Ile Gly Phe Arg Tyr Arg Ser Leu Lys His Phe Asn
3320                3325                3330

Tyr Asp Ile Cys Gln Ser Cys Phe Phe Ser Gly Arg Val Ala Lys
3335                3340                3345

Gly His Lys Met His Tyr Pro Met Val Glu Tyr Cys Thr Pro Thr
3350                3355                3360

Thr Ser Gly Glu Asp Val Arg Asp Phe Ala Lys Val Leu Lys Asn
3365                3370                3375

Lys Phe Arg Thr Lys Arg Tyr Phe Ala Lys His Pro Arg Met Gly
3380                3385                3390

Tyr Leu Pro Val Gln Thr Val Leu Glu Gly Asp Asn Met Glu Thr
3395                3400                3405
```

| | | | | | | | | | |
|---|---|---|---|---|---|---|---|---|---|
Pro | Val | Thr | Leu | Ile | Asn | Phe | Trp | Pro | Val | Asp | Ser | Ala | Pro | Ala
 | | 3410 | | | | 3415 | | | | 3420

Ser | Ser | Pro | Gln | Leu | Ser | His | Asp | Asp | Thr | His | Ser | Arg | Ile | Glu
 3425 | | | | | 3430 | | | | | 3435

His | Tyr | Ala | Ser | Arg | Leu | Ala | Glu | Met | Glu | Asn | Ser | Asn | Gly | Ser
 3440 | | | | | 3445 | | | | | 3450

Tyr | Leu | Asn | Asp | Ser | Ile | Ser | Pro | Asn | Glu | Ser | Ile | Asp | Asp | Glu
 3455 | | | | | 3460 | | | | | 3465

His | Leu | Leu | Ile | Gln | His | Tyr | Cys | Gln | Ser | Leu | Asn | Gln | Asp | Ser
 3470 | | | | | 3475 | | | | | 3480

Pro | Leu | Ser | Gln | Pro | Arg | Ser | Pro | Ala | Gln | Ile | Leu | Ile | Ser | Leu
 3485 | | | | | 3490 | | | | | 3495

Glu | Ser | Glu | Glu | Arg | Gly | Glu | Leu | Glu | Arg | Ile | Leu | Ala | Asp | Leu
 3500 | | | | | 3505 | | | | | 3510

Glu | Glu | Glu | Asn | Arg | Asn | Leu | Gln | Ala | Glu | Tyr | Asp | Arg | Leu | Lys
 3515 | | | | | 3520 | | | | | 3525

Gln | Gln | His | Glu | His | Lys | Gly | Leu | Ser | Pro | Leu | Pro | Ser | Pro | Pro
 3530 | | | | | 3535 | | | | | 3540

Glu | Met | Met | Pro | Thr | Ser | Pro | Gln | Ser | Pro | Arg | Asp | Ala | Glu | Leu
 3545 | | | | | 3550 | | | | | 3555

Ile | Ala | Glu | Ala | Lys | Leu | Leu | Arg | Gln | His | Lys | Gly | Arg | Leu | Glu
 3560 | | | | | 3565 | | | | | 3570

Ala | Arg | Met | Gln | Ile | Leu | Glu | Asp | His | Asn | Lys | Gln | Leu | Glu | Ser
 3575 | | | | | 3580 | | | | | 3585

Gln | Leu | His | Arg | Leu | Arg | Gln | Leu | Leu | Glu | Gln | Pro | Gln | Ala | Glu
 3590 | | | | | 3595 | | | | | 3600

Ala | Lys | Val | Asn | Gly | Thr | Thr | Val | Ser | Ser | Pro | Ser | Thr | Ser | Leu
 3605 | | | | | 3610 | | | | | 3615

Gln | Arg | Ser | Asp | Ser | Ser | Gln | Pro | Met | Leu | Leu | Arg | Val | Val | Gly
 3620 | | | | | 3625 | | | | | 3630

Ser | Gln | Thr | Ser | Asp | Ser | Met | Gly | Glu | Glu | Asp | Leu | Leu | Ser | Pro
 3635 | | | | | 3640 | | | | | 3645

Pro | Gln | Asp | Thr | Ser | Thr | Gly | Leu | Glu | Glu | Val | Met | Glu | Gln | Leu
 3650 | | | | | 3655 | | | | | 3660

Asn | Asn | Ser | Phe | Pro | Ser | Ser | Arg | Gly | Arg | Asn | Thr | Pro | Gly | Lys
 3665 | | | | | 3670 | | | | | 3675

Pro | Met | Arg | Glu | Asp | Thr | Met
 3680 | | | | | 3685

<210> SEQ ID NO 2
<211> LENGTH: 11058
<212> TYPE: DNA
<213> ORGANISM: Homo sapiens

<400> SEQUENCE: 2

```
atgctttggt gggaagaagt agaggactgt tatgaaagag aagatgttca aaagaaaaca    60
ttcacaaaat gggtaaatgc acaattttct aagtttggga agcagcatat tgagaacctc   120
ttcagtgacc tacaggatgg gaggcgcctc ctagacctcc tcgaaggcct gacagggcaa   180
aaactgccaa agaaaaagg atccacaaga gttcatgccc tgaacaatgt caacaaggca   240
ctgcgggttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaatat catggctgga ttgcaacaaa ccaacagtga aaagattctc   420
```

```
ctgagctggg tccgacaatc aactcgtaat tatccacagg ttaatgtaat caacttcacc    480
accagctggt ctgatggcct ggcttttgaat gctctcatcc atagtcatag gccagaccta   540
tttgactgga atagtgtggt ttgccagcag tcagccacac aacgactgga acatgcattc    600
aacatcgcca gatatcaatt aggcatagag aaactactcg atcctgaaga tgttgatacc   660
acctatccag ataagaagtc catcttaatg tacatcacat cactcttcca agttttgcct   720
caacaagtga gcattgaagc catccaggaa gtggaaatgt tgccaaggcc acctaaagtg   780
actaagaag aacattttca gttacatcat caaatgcact attctcaaca gatcacggtc    840
agtctagcac agggatatga gagaacttct tcccctaagc ctcgattcaa gagctatgcc   900
tacacacagg ctgcttatgt caccacctct gaccctacac ggagcccatt tccttcacag   960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agttttaatg gatctccaga atcagaaact gaaagagttg  1380
aatgactggc taacaaaaac agaagaaaga acaaggaaaa tggaggaaga gcctcttgga  1440
cctgatcttg aagacctaaa acgccaagta caacaacata aggtgcttca agaagatcta  1500
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacat ccttctcaaa  1680
tggcaacgtc ttactgaaga acagtgcctt tttagtgcat ggctttcaga aaaagaagat  1740
gcagtgaaca gattcacac aactggcttt aaagatcaaa atgaaatgtt atcaagtctt  1800
caaaaactgg ccgttttaaa agcggatcta gaaaagaaaa agcaatccat gggcaaactg  1860
tattcactca aacaagatct tcttttcaaca ctgaagaata agtcagtgac ccagaagacg  1920
gaagcatggc tggataactt tgcccggtgt tgggataatt tagtccaaaa acttgaaaag  1980
agtacagcac agatttcaca ggctgtcacc accactcagc catcactaac acagacaact  2040
gtaatggaaa cagtaactac ggtgaccaca agggaacaga tcctggtaaa gcatgctcaa  2100
gaggaacttc caccaccacc tccccaaaag aagaggcaga ttactgtgga ttctgaaatt  2160
aggaaaaggt tggatgttga tataactgaa cttcacagct ggattactcg ctcagaagct  2220
gtgttgcaga gtcctgaatt tgcaatcttt cggaaggaag gcaacttctc agacttaaaa  2280
gaaaaagtca atgccataga gcgagaaaaa gctgagaagt tcagaaaact gcaagatgcc  2340
agcagatcag ctcaggccct ggtggaacag atggtgaatg agggtgttaa tgcagatagc  2400
atcaaacaag cctcagaaca actgaacagc cggtggatcg aattctgcca gttgctaagt  2460
gagagactta actggctgga gtatcagaac aacatcatcg ctttctataa tcagctacaa  2520
caattggagc agatgacaac tactgctgaa aactggttga aaatccaacc caccacccca  2580
tcagagccaa cagcaattaa aagtcagtta aaaatttgta aggatgaagt caaccggcta  2640
tcaggtcttc aacctcaaat tgaacgatta aaaattcaaa gcatagccct gaaagagaaa  2700
ggacaaggac ccatgttcct ggatgcagac tttgtggcct ttacaaatca ttttaagcaa  2760
gtcttttctg atgtgcaggc cagagagaaa gagctacaga caattttttga cactttgcca  2820
```

```
ccaatgcgct atcaggagac catgagtgcc atcaggacat gggtccagca gtcagaaacc    2880
aaactctcca tacctcaact tagtgtcacc gactatgaaa tcatggagca gagactcggg    2940
gaattgcagg ctttacaaag ttctctgcaa gagcaacaaa gtggcctata ctatctcagc    3000
accactgtga aagagatgtc gaagaaagcg ccctctgaaa ttagccggaa atatcaatca    3060
gaatttgaag aaattgaggg acgctggaag aagctctcct cccagctggt tgagcattgt    3120
caaaagctag aggagcaaat gaataaactc cgaaaaattc agaatcacat acaaaccctg    3180
aagaaatgga tggctgaagt tgatgttttt ctgaaggagg aatggcctgc ccttggggat    3240
tcagaaattc taaaaagca gctgaaacag tgcagacttt tagtcagtga tattcagaca    3300
attcagccca gtctaaacag tgtcaatgaa ggtgggcaga agataaagaa tgaagcagag    3360
ccagagtttg cttcgagact tgagacagaa ctcaaagaac ttaacactca gtgggatcac    3420
atgtgccaac aggtctatgc cagaaaggag gccttgaagg gaggtttgga gaaaactgta    3480
agcctccaga aagatctatc agagatgcac gaatggatga cacaagctga agaagagtat    3540
cttgagagag attttgaata taaaactcca gatgaattac agaaagcagt tgaagagatg    3600
aagagagcta agaagaggc ccaacaaaaa gaagcgaaag tgaaactcct tactgagtct    3660
gtaaatagtg tcatagctca agctccacct gtagcacaag aggccttaaa aaaggaactt    3720
gaaactctaa ccaccaacta ccagtggctc tgcactaggc tgaatgggaa atgcaagact    3780
ttggaagaag tttgggcatg ttggcatgag ttattgtcat acttggagaa agcaaacaag    3840
tggctaaatg aagtagaatt taaacttaaa accactgaaa acattcctgg cggagctgag    3900
gaaatctctg aggtgctaga ttcacttgaa aatttgatgc gacattcaga ggataaccca    3960
aatcagattc gcatattggc acagaccota acagatggcg gagtcatgga tgagctaatc    4020
aatgaggaac ttgagacatt taattctcgt tggagggaac tacatgaaga ggctgtaagg    4080
aggcaaaagt tgcttgaaca gagcatccag tctgcccagg agactgaaaa atccttacac    4140
ttaatccagg agtccctcac attcattgac aagcagttgg cagcttatat tgcagacaag    4200
gtggacgcag ctcaaatgcc tcaggaagcc cagaaaatcc aatctgattt gacaagtcat    4260
gagatcagtt tagaagaaat gaagaaacat aatcagggga aggaggctgc ccaaagagtc    4320
ctgtctcaga ttgatgttgc acagaaaaaa ttacaagatg tctccatgaa gtttcgatta    4380
ttccagaaac cagccaattt tgagctgcgt ctacaagaaa gtaagatgat tttagatgaa    4440
gtgaagatgc acttgcctgc attggaaaca aagagtgtgg aacaggaagt agtacagtca    4500
cagctaaatc attgtgtgaa cttgtataaa agtctgagtg aagtgaagtc tgaagtggaa    4560
atggtgataa agactggacg tcagattgta cagaaaaagc agacggaaaa tcccaaagaa    4620
cttgatgaaa gagtaacagc tttgaaattg cattataatg agctgggagc aaaggtaaca    4680
gaaagaaagc aacagttgga gaatgcttg aaattgtccc gtaagatgcg aaaggaaatg    4740
aatgtcttga cagaatggct ggcagctaca gatatggaat tgacaaagag atcagcagtt    4800
gaaggaatgc ctagtaattt ggattctgaa gttgcctggg gaaaggctac tcaaaaagag    4860
attgagaaac agaaggtgca cctgaagagt atcacagagg taggagaggc cttgaaaaca    4920
gttttgggca agaaggagac gttggtgaaa gataaactca gtcttctgaa tagtaactgg    4980
atagctgtca cctcccgagc agaagagtgg ttaaatcttt tgttggaata ccagaaacac    5040
atggaaactt ttgaccagaa tgtggaccac atcacaaagt ggatcattca ggctgacaca    5100
cttttggatg aatcagagaa aaagaaaccc cagcaaaaag aagacgtgct taagcgttta    5160
```

```
aaggcagaac tgaatgacat acgcccaaag gtggactcta cacgtgacca agcagcaaac    5220
ttgatggcaa accgcggtga ccactgcagg aaattagtag agccccaaat ctcagagctc    5280
aaccatcgat ttgcagccat ttcacacaga attaagactg gaaaggcctc cattcctttg    5340
aaggaattgg agcagtttaa ctcagatata caaaaattgc ttgaaccact ggaggctgaa    5400
attcagcagg gggtgaatct gaaagaggaa gacttcaata aagatatgaa tgaagacaat    5460
gagggtactg taaaagaatt gttgcaaaga ggagacaact acaacaaag  aatcacagat    5520 gagagaaaga gagaggaaat aaagataaaa cagcagctgt tacagacaaa acataatgct    5580
ctcaaggatt tgaggtctca aagaagaaaa aaggctctag aaatttctca tcagtggtat    5640
cagtacaaga ggcaggctga tgatctcctg aaatgcttgg atgacattga aaaaaaatta    5700
gccagcctac ctgagcccag agatgaaagg aaaataaagg aaattgatcg ggaattgcag    5760
aagaagaaag aggagctgaa tgcagtgcgt aggcaagctg agggcttgtc tgaggatggg    5820
gccgcaatgg cagtggagcc aactcagatc cagctcagca agcgctggcg ggaaattgag    5880
agcaaatttg ctcagtttcg aagactcaac tttgcacaaa ttcacactgt ccgtgaagaa    5940
acgatgatgg tgatgactga agacatgcct ttggaaattt cttatgtgcc ttctacttat    6000
ttgactgaaa tcactcatgt ctcacaagcc ctattagaag tggaacaact tctcaatgct    6060
cctgacctct gtgctaagga cttgaagat  ctctttaagc aagaggagtc tctgaagaat    6120 ataaagata  gtctacaaca aagctcaggt cggattgaca ttattcatag caagaagaca    6180
gcagcattgc aaagtgcaac gcctgtggaa agggtgaagc tacaggaagc tctctcccag    6240
cttgatttcc aatgggaaaa agttaacaaa atgtacaagg accgacaagg gcgatttgac    6300
agatctgttg agaaatggcg gcgttttcat tatgatataa agatatttaa tcagtggcta    6360
acagaagctg aacagtttct cagaaagaca caaattcctg agaattggga acatgctaaa    6420
tacaaatggt atcttaagga actccaggat ggcattgggc agcggcaaac tgttgtcaga    6480
acattgaatg caactgggga agaaataatt cagcaatcct caaaaacaga tgccagtatt    6540
ctacaggaaa aattgggaag cctgaatctg cggtggcagg aggtctgcaa acagctgtca    6600
gacagaaaaa agaggctaga agaacaaaag aatatcttgt cagaatttca aagagattta    6660
aatgaatttg ttttatggtt ggaggaagca gataacattg ctagtatccc acttgaacct    6720
ggaaaagagc agcaactaaa agaaaagctt gagcaagtca agttactggt ggaagagttg    6780
cccctgcgcc agggaattct caaacaatta aatgaaactg gaggacccgt gcttgtaagt    6840
gctcccataa gcccagaaga gcaagataaa cttgaaaata agctcaagca gacaaatctc    6900
cagtggataa aggtttccag agctttacct gagaaacaag gagaaattga agctcaaata    6960
aaagaccttg ggcagcttga aaaaaagctt gaagaccttg aagagcagtt aaatcatctg    7020
ctgctgtggt tatctcctat taggaatcag ttggaaattt ataaccaacc aaaccaagaa    7080
ggaccatttg acgttcagga aactgaaata gcagttcaag ctaaacaacc ggatgtggaa    7140 gagatttgt  ctaaagggca gcatttgtac aaggaaaaac cagccactca gccagtgaag    7200
aggaagttag aagatctgag ctctgagtgg aaggcggtaa accgtttact tcaagagctg    7260
agggcaaagc agcctgacct agctcctgga ctgaccacta ttggagcctc tcctactcag    7320
actgttactc tggtgacaca acctgtggtt actaaggaaa ctgccatctc caaactagaa    7380
atgccatctt ccttgatgtt ggaggtacct gctctggcag atttcaaccg ggcttggaca    7440
gaacttaccg actggctttc tctgcttgat caagttataa aatcacagag ggtgatggtg    7500
ggtgaccttg aggatatcaa cgagatgatc atcaagcaga aggcaacaat gcaggatttg    7560
```

```
gaacagaggc gtccccagtt ggaagaactc attaccgctg cccaaaattt gaaaaacaag    7620
accagcaatc aagaggctag aacaatcatt acgatcgaa ttgaaagaat tcagaatcag    7680
tgggatgaag tacaagaaca ccttcagaac cggaggcaac agttgaatga aatgttaaag    7740
gattcaacac aatggctgga agctaaggaa gaagctgagc aggtcttagg acaggccaga    7800
gccaagcttg agtcatggaa ggagggtccc tatacagtag atgcaatcca aaagaaaatc    7860
acagaaacca agcagttggc caaagacctc cgccagtggc agacaaatgt agatgtggca    7920
aatgacttgg ccctgaaact tctccgggat tattctgcag atgataccag aaaagtccac    7980
atgataacag agaatatcaa tgcctcttgg agaagcattc ataaaagggt gagtgagcga    8040
gaggctgctt tggaagaaac tcatagatta ctgcaacagt tcccctgga cctggaaaag    8100 tttcttgcct ggcttacaga agctgaaaca actgccaatg tcctacagga tgctacccgt    8160
aaggaaaggc tcctagaaga ctccaaggga gtaaagagc tgatgaaaca atggcaagac    8220
ctccaaggtg aaattgaagc tcacacagat gtttatcaca acctggatga aaacagccaa    8280
aaaatcctga atccctgga aggttccgat gatgcagtcc tgttacaaag acgtttggat    8340
aacatgaact tcaagtggag tgaacttcgg aaaaagtctc tcaacattag gtcccatttg    8400
gaagccagtt ctgaccagtg gaagcgtctg cacctttctc tgcaggaact tctggtgtgg    8460
ctacagctga aagatgatga attaagccgg caggcaccta ttggaggcga cttccagca    8520 gttcagaagc agaacgatgt acatagggcc ttcaagaggg aattgaaaac taaagaacct    8580
gtaatcatga gtactcttga gactgtacga atatttctga cagagcagcc tttggaagga    8640
ctagagaaac tctaccagga gcccagagag ctgcctcctg aggagagagc ccagaatgtc    8700
actcggcttc tacgaaagca ggctgaggag gtcaatactg agtgggaaaa attgaacctg    8760
cactccgctg actggcagag aaaaatagat gagacccttg aaagactcca ggaacttcaa    8820
gaggccacgg atgagctgga cctcaagctg cgccaagctg aggtgatcaa gggatcctgg    8880
cagcccgtgg gcgatctcct cattgactct ctccaagatc acctcgagaa agtcaaggca    8940
cttcgaggag aaattgcgcc tctgaaagag aacgtgagcc acgtcaatga ccttgctcgc    9000
cagcttacca ctttgggcat tcagctctca ccgtataacc tcagcactct ggaagacctg    9060
aacaccagat ggaagcttct gcaggtggcc gtcgaggacc gagtcaggca gctgcatgaa    9120
gcccacaggg actttggtcc agcatctcag cactttcttt ccacgtctgt ccagggtccc    9180
tgggagagag ccatctcgcc aaacaaagtg ccctactata tcaaccacga gactcaaaca    9240
acttgctggg accatcccaa aatgacagag ctctaccagt cttagctga cctgaataat    9300 gtcagattct cagcttatag gactgccatg aaactccgaa gactgcagaa ggcccttgc    9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taagcacat ttggaagaca agtacagata ccttttcaag    9660
caagtggcaa gttcaacagg attttgtgac cagcgcaggc tgggcctcct tctgcatgat    9720
tctatccaaa ttccaagaca gttgggtgaa gttgcatcct tgggggcag taacattgag    9780 ccaagtgtcc ggagctgctt ccaatttgct aataataagc cagagatcga agcggccctc    9840
ttcctagact ggatgagact ggaaccccag tccatggtgt ggctgccgt cctgcacaga    9900
```

-continued

```
gtggctgctg cagaaactgc caagcatcag gccaaatgta acatctgcaa agagtgtcca      9960
atcattggat tcaggtacag gagtctaaag cactttaatt atgacatctg ccaaagctgc     10020 ttttttctg gtcgagttgc aaaaggccat aaaatgcact atcccatggt ggaatattgc      10080
actccgacta catcaggaga agatgttcga ctttgcca aggtactaaa aaacaaattt       10140
cgaaccaaaa ggtattttgc gaagcatccc cgaatgggct acctgccagt gcagactgtc    10200 ttagagggg acaacatgga aactcccgtt actctgatca acttctggcc agtagattct      10260
gcgcctgcct cgtcccctca gctttcacac gatgatactc attcacgcat tgaacattat    10320
gctagcaggc tagcagaaat ggaaaacagc aatggatctt atctaaatga tagcatctct    10380
cctaatgaga gcatagatga tgaacatttg ttaatccagc attactgcca aagtttgaac    10440
caggactccc ccctgagcca gcctcgtagt cctgcccaga tcttgatttc cttagagagt    10500
gaggaaagag gggagctaga gagaatccta gcagatcttg aggaagaaaa caggaatctg    10560
caagcagaat atgaccgtct aaagcagcag cacgaacata aaggcctgtc cccactgccg    10620 tccctcctg aaatgatgcc cacctctccc cagagtcccc gggatgctga gctcattgct     10680
gaggccaagc tactgcgtca acacaaaggc cgcctggaag ccaggatgca atcctggaa     10740 gaccacaata aacagctgga gtcacagtta cacaggctaa ggcagctgct ggagcaaccc   10800
caggcagagg ccaaagtgaa tggcacaacg gtgtcctctc cttctacctc tctacagagg    10860
tccgacagca gtcagcctat gctgctccga gtggttggca gtcaaacttc ggactccatg    10920
ggtgaggaag atcttctcag tcctccccag gacacaagca cagggttaga ggaggtgatg    10980
gagcaactca acaactcctt ccctagttca agaggaagaa ataccctgg aaagccaatg     11040 agagaggaca caatgtag                                                   11058
```

<210> SEQ ID NO 3
<211> LENGTH: 5953
<212> TYPE: DNA
<213> ORGANISM: Artificial Sequence
<220> FEATURE:
<223> OTHER INFORMATION: Synthetic

<400> SEQUENCE: 3

```
atgctttggt gggaagaagt agaggactgt tatgaaagag aagatgttca aaagaaaaca       60
ttcacaaaat gggtaaatgc acaattttct aagtttggga agcagcatat tgagaacctc      120
ttcagtgacc tacaggatgg gaggcgcctc ctagacctcc tcgaaggcct gacagggcaa      180
aaactgccaa agaaaaagg atccacaaga gttcatgccc tgaacaatgt caacaaggca     240
ctgcgggttt tgcagaacaa taatgttgat ttagtgaata ttggaagtac tgacatcgta     300
gatggaaatc ataaactgac tcttggtttg atttggaata taatcctcca ctggcaggtc    360
aaaaatgtaa tgaaaatat catggctgga ttgcaacaaa ccaacagtga aaagattctc     420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttggcagcag tcagccacac aacgactgga acatgcattc   600
aacatcgcca gatatcaatt aggcatagag aaagtactcg atcctgaaga tgttgatacc     660
acctatccag ataagaagtc atcttaatg tacatcacat cactcttcca agttttgcct     720
caacaagtga gcattgaagc catccaggaa gtggaaatgt tgccaaggcc acctaaagtg   780
actaaagaag aacattttca gtacatcatc aaatgcacta ttctcaacag atcacggtca   840
gtctagcaca gggatatgag agaacttctt ccctaagcc tcgattcaag agctatgcct     900
```

```
acacacaggc tgcttatgtc accacctctg accctacacg gagcccattt ccttcacagc    960
atttggaagc tcctgaagac aagtcatttg gcagttcatt gatggagagt gaagtaaacc   1020
tggaccgtta tcaaacagct ttagaagaag tattatcgtg gcttctttct gctgaggaca   1080
cattgcaagc acaaggagag atttctaatg atgtggaagt ggtgaaagac cagtttcata   1140
ctcatgaggg gtacatgatg gatttgacag cccatcaggg ccgggttggt aatattctac   1200
aattgggaag taagctgatt ggaacaggaa aattatcaga agatgaagaa actgaagtac   1260
aagagcagat gaatctccta aattcaagat gggaatgcct cagggtagct agcatggaaa   1320
aacaaagcaa tttacataga gttttaatgg atctccagaa tcagaaactg aaagagttga   1380
atgactggct aacaaaaaca gaagaaagaa caaggaaaat ggaggaagag cctcttggac   1440
ctgatcttga agacctaaaa cgccaagtac aacaacataa ggtgcttcaa gaagatctag   1500
aacaagaaca agtcagggtc aattctctca ctcacatggt ggtggtagtt gatgaatcta   1560
gtggagatca cgcaactgct gctttggaag aacaagttta aggtattggg agatcgatgg   1620
gcaaacatct gtagatggac agaagaccgc tgggttcttt acaagacat ccttctcaaa    1680
tggcaacgtc ttactgaaga acagtgcctt tttagtgcat ggctttcaga aaagaagat    1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt gggataatt tagtccaaaa acttgaaaag    1980
agtacagcac aggaaactga aatagcagtt caagctaaac aaccggatgt ggaagagatt   2040
ttgtctaaag gcagcatttt gtacaaggaa aaaccagcca ctcagccagt gaagaggaag   2100
ttagaagatc tgagctctga gtggaaggcg gtaaaccgtt tacttcaaga gctgagggca   2160
aagcagcctg acctagctcc tggactgacc actattggag cctctcctac tcagactgtt   2220
actctggtga cacaacctgt ggttagtaag gaaactgcca tctccaaact agaaatgcca   2280
tcttccttga tgtttgaggt acctgctctg gcagatttca acggggcttg gacagaactt   2340
accgagtggc tttctctgct tgatcaagtt ataaaatcac agagggtgat ggtgggtgac   2400
cttgaggata tcaacgagat gatcatcaag cagaaggcaa caatgcagga tttggaacag   2460
aggcgtcccc agttggaaga actcattacc gctgcccaaa atttgaaaaa caagaccagc   2520
aatcaagagg ctagaacaat cattacggat cgaattgaaa gaattcagaa tcagtgggat   2580
gaagtacaag aacaccttca gaaccggagg caacagttga tgaaatgtt aaaggattca    2640
acacaatggc tggaagctaa ggaagaagct gagcaggtct taggacaggg cagagccaag   2700
cttgagtcat ggaaggaggg tccctataca gtagatgcaa tccaaaagaa aatcacagaa   2760
accaagcagt tggccaaaga cctccgccag tggcagacaa atgtagatgt ggcaaatgac   2820
ttggcccctga aacttctccg ggattattct gcagatgata ccagaaaagt ccacatgata   2880
acagagaata tcaatgcctc ttggagaagc attcataaaa gggtgagtga gcgagaggct   2940
gctttggaag aaactcatag attactgcaa cagttccccc tggacctgga aaagtttctt   3000
gcctggctta cagaagctga aacaactgcc aatgtcctac aggatgctac ccgtaaggaa   3060
aggctcctag aagactccaa gggagtaaaa gagctgatga acaatggca agacctccaa    3120
ggtgaaattg aagctcacac agatgtttat cacaacctgg atgaaaacag ccaaaaaatc   3180
ctgagatccc tggaaggttc cgatgatgca gtcctgttac aaagacgttt ggataacatg   3240
```

```
aacttcaagt ggagtgaact tcggaaaaag tctctcaaca ttaggtccca tttggaagcc    3300
agttctgacc agtggaagcg tctgcacctt tctctgcagg aacttctggt gtggctacag    3360
ctgaaagatg atgaattaag ccggcaggca cctattggag gcgactttcc agcagttcag    3420
aagcagaacg atgtacatag ggccttcaag agggaattga aaactaaaga acctgtaatc    3480
atgagtactc ttgagactgt acgaatattt ctgacagagc agcctttgga aggactagag    3540
aaactctacc aggagcccag agagctgcct cctgaggaga gagcccagaa tgtcactcgg    3600
cttctacgaa agcaggctga ggaggtcaat actgagtggg aaaaattgaa cctgcactcc    3660
gctgactggc agagaaaaat agatgagacc cttgaaagac tccaggaact tcaagaggcc    3720
acggatgagc tggacctcaa gctgcgccaa gctgaggtga tcaagggatc ctggcagccc    3780
gtgggcgatc tcctcattga ctctctccaa gatcacctcg agaaagtcaa ggcacttcga    3840
ggagaaattg cgcctctgaa agagaacgtg agccacgtca atgaccttgc tcgccagctt    3900
accactttgg gcattcagct ctcaccgtat aacctcagca ctctggaaga cctgaacacc    3960
agatggaagc ttctgcaggt ggccgtcgag gaccgagtca ggcagctgca tgaagcccac    4020
agggactttg gtccagcatc tcagcacttt cttccacgt ctgtccaggg tcggtgggag    4080
agagccatct cgccaaacaa agtgccctac tatatcaacc acgagactca aacaacttgc    4140
tgggaccatc ccaaaatgac agagctctac cagtctttag ctgacctgaa taatgtcaga    4200
ttctcagctt ataggactgc catgaaactc cgaagactgc agaaggccct ttgcttggat    4260
ctcttgagcc tgtcagctgc atgtgatgcc ttggaccagc acaacctcaa gcaaaatgac    4320
cagcccatgg atatcctgca gattattaat tgtttgacca ctatttatga ccgcctggag    4380
caagagcaca caatttggt caacgtccct ctctgcgtgg atatgtgtct gaactggctg    4440
ctgaatgttt atgatacggg acgaacaggg aggatccgtg tcctgtcttt taaaactggc    4500
atcatttccc tgtgtaaagc acatttggaa gacaagtaca gatacctttt caagcaagtg    4560
gcaagttcaa caggatttg tgaccagcgc aggctgggcc tccttctgca tgattctatc    4620
caaattccaa gacagttggg tgaagttgca tcctttgggg gcagtaacat tgagccaagt    4680
gtccggagct gcttccaatt tgctaataat aagccagaga tcgaagcggc cctcttccta    4740
gactggatga gactggaacc ccagtccatg gtgtggctgc ccgtcctgca cagagtggct    4800
gctgcagaaa ctgccaagca tcaggccaaa tgtaacatct gcaaagagtg tccaatcatt    4860
ggattcaggt acaggagtct aaagcacttt aattatgaca tctgccaaag ctgctttttt    4920
tctggtcgag ttgcaaaagg ccataaaatg cactatccca tggtggaata ttgcactccg    4980
actacatcag gagaagatgt tcgagacttt gccaaggtac taaaaaacaa atttcgaacc    5040
aaaaggtatt ttgcgaagca tccccgaatg ggctacctgc cagtgcagac tgtcttagag    5100
ggggacaaca tggaaactcc cgttactctg atcaacttct ggccagtaga ttctgcgcct    5160
gcctcgtccc ctcagctttc acacgatgat actcattcac gcattgaaca ttatgctagc    5220
aggctagcag aaatgaaaaa cagcaatgga tcttatctaa atgatagcat ctctcctaat    5280
gagagcatag atgatgaaca tttgttaatc cagcattact gccaaagttt gaaccaggac    5340
tccccctga gccagcctcg tagtcctgcc cagatcttga tttccttaga gagtgaggaa    5400
agagggagc tagagagaat cctagcagat cttgaggaag aaaacaggaa tctgcaagca    5460
gaatatgacc gtctaaagca gcagcacgaa cataaaggcc tgtccccact gccgtccct    5520
cctgaaatga tgcccacctc tccccagagt ccccgggatg ctgagctcat tgctgaggcc    5580
aagctactgc gtcaacacaa aggccgcctg gaagccagga tgcaaatcct ggaagaccac    5640
```

```
aataaacagc tggagtcaca gttacacagg ctaaggcagg tgctggagca accccaggca    5700
gaggccaaag tgaatggcac aacggtgtcc tctccttcta cctctctaca gaggtccgac    5760
agcagtcagc ctatgctgct ccgagtggtt ggcagtcaaa cttcggactc catgggtgag    5820
gaagatcttc tcagtcgtcc ccaggacaca agcacacgg tagaggaggt gatggagcaa     5880
ctcaacaact cctttcccta gttcaagagg aagaaatacc cctggaaagc caatgagaga    5940
ggacacaatg tag                                                      5953

<210> SEQ ID NO 4
<211> LENGTH: 5749
<212> TYPE: DNA
<213> ORGANISM: Artificial Sequence
<220> FEATURE:
<223> OTHER INFORMATION: Synthetic

<400> SEQUENCE: 4
atgcttggtg ggaagaagta gaggactgtt atgaaagaga agatgttcaa aagaaaacat      60
tcacaaaatg ggtaaatgca caattttcta agtttgggaa gcagcatatt gagaacctct     120
tcagtgacct acaggatggg aggcgcctcc tagacctcct cgaaggcctg acagggcaaa     180
aactgccaaa agaaaaagga tccacaagag ttcatgccct gaacaatgtc aacaaggcac     240
tgcgggtttt gcagaacaat aatgttgatt tagtgaatat ggaagtact gacatcgtag       300 atggaaatca taaactgact cttggtttga tttggaatat aatcctccac tggcaggtca     360
aaaatgtaat gaaaaatatc atggctggat tgcaacaaac caacagtgaa aagattctcc     420
tgagctgggt gcgacaatca actcgtaatt atccacaggt taatgtaatc aacttcacca     480
ccagctggtc tgatggcctg gctttgaatg ctctcatcca tagtcatagg ccagacctat     540
ttgactggaa tagtgtggtt tgccagcagt cagccacaca acgactggaa catgcattca    600
acatcgccag atatcaatta ggcatagaga aactactcga tcctgaagat gttgatacca     660
cctatccaga taagaagtcc atctttaatg tacatcacat cactcttcca agtttttgcct    720 caacaagtga gcattgaagc catccaggaa gtggaaatgt tgccaaggcc acctaaagtg    780 actaagaag aacattttca gttacatcat caaatgcact attctcaaca gatcacggtc      840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tgaacagga aaattatcag aagatgaaga aactgaagta     1260
caagagcaga tgaatctcct aaattcaaga tgggaatgcc tcagggtagc tagcatggaa    1320
aaacaaagca atttacatag agttttaatg atctccagat atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgcttttgaa gaacaactta aggtattggg agatcgatgg    1620
gcaaacatct gtagatggac agaagaccgc tgggttcttt tacaagacat ccttctcaaa    1680
```

```
tgggaacgtc ttactgaaga acagtgcctt tttagtgcat ggctttcaga aaagaagat       1740 gcagtgaaca agattcacac aactggcttt aaagatcaaa atgaaatgtt atcaagtctt      1800
caaaaactgg ccgttttaaa agcggatcta gaaaagaaaa agcaatccat gggcaaactg      1860
tattcactca aacaagatct tctttcaaca ctgaagaata agtcagtgac ccagaagacg      1920
gaagcatggc tggataactt tgcccggtgt tgggataatt tagtccaaaa acttgaaaag      1980
agtacagcac agatttcaca gcagcctgac ctagctcctg gactgaccac tattggagcc      2040
tctcctactc agactgttac tctggtgaca caacctgtgg ttactaagga aactgccatc      2100
tccaaactag aaatgccatc ttccttgatg ttggaggtac ctgctctggc agatttcaac      2160
cgggcttgga cagaacttac cgactggctt tctctgcttg atcaagttat aaaatcacag      2220
agggtgatgg tgggtgacct tgaggatatc aacgagatga tcatcaagca gaaggcaaca      2280
atgcaggatt tggaacagag gcgtccccag ttggaagaac tcattaccgc tgcccaaaat      2340
ttgaaaaaca agaccagcaa tcaagaggct agaacaatca ttacggatcg aattgaaaga      2400
attcagaatc agtgggatga agtacaagaa caccttcaga accggaggca acagttgaat      2460
gaaatgttaa aggattcaac acaatggctg gaagctaagg aagaagctga gcaggtctta      2520
ggacaggcca gagccaagct tgagtcatgg aaggagggtc cctatacagt agatgcaatc      2580
caaaagaaaa tcacagaaac caagcagttg gccaaagacc tccgcgagtg gcagacaaat      2640
gtagatgtgg caaatgactt ggccctgaaa cttctgcggg attattctgc agatgatacc      2700
agaaaagtcc acatgataac agagaatatc aatgcctctt ggagaagcat tcataaaagg      2760
gtgagtgagc gagaggctgc tttggaagaa actcatagat tactgcaaca gttcccctg       2820 gacctggaaa agtttcttgc ctggcttaca gaagctgaaa caactgccaa tgtcctacag      2880
gatgctaccc gtaaggaaag gctcctagaa gactccaagg gagtaaaaga gctgatgaaa      2940
caatggcaag acctccaagg tgaaattgaa gctcacacag atgtttatga caacctggat      3000
gaaaacagcc aaaaaatcct gagatccctg gaaggttccg atgatgcagt cctgttacaa      3060
agacgtttgg ataacatgaa cttcaagtgg agtgaacttc ggaaaaagtc tctcaacatt      3120
aggtcccatt tggaagccag ttctgaccag tggaagcgtc tgcacctttc tctgcaggaa      3180
cttctggtgt ggctacagct gaaagatgat gaattaagcc ggcaggcacc tattggaggc      3240
gactttccag cagttcagaa gcagaacgat gtacataggg ccttcaagag ggaattgaaa      3300
actaaagaac ctgtaatcat gagtactctt gagactgtac gaatatttct gacagagcag      3360
cctttggaag gactagagaa actctaccag gagcccagag agctgcctcc tgaggagaga      3420
gcccagaatg tcactcggct tctacgaaag caggctgagg aggtcaatac tgagtgggaa      3480
aaattgaacc tgcactccgc tgactggcag agaaaaatag atgagaccct tgaaagactc      3540
caggaacttc aagaggccac ggatgagctg gacctcaagc tgcgccaagc tgaggtgatc      3600
aagggatcct ggcagcccgt gggcgatctc ctgattgact ctctccaaga tcacctcgag      3660
aaagtcaagg cacttcgagg agaaattgcg cctctgaaag agaacgtgag cgacgtcaat      3720
gaccttgctc gccagcttac cactttgggc attcagctct caccgtataa cctcagcact      3780
ctggaagacc tgaacaccag atggaagctt ctgcaggtgg ccgtcgagga ccgagtcagg      3840
cagctgcatg aagcccacag ggactttggt ccagcatctc agcactttct ttccacgtct      3900
gtccagggtc cctgggagag agccatctcg ccaaacaaag tgccctacta tatcaaccac      3960
gagactcaaa caacttgctg ggaccatccc aaaatgacag agctctacca gtctttagct      4020
gacctgaata atgtcagatt ctcagcttat aggactgcca tgaaactccg aagactgcag      4080
```

```
aaggcccttt gcttggatct cttgagcctg tcagctgcat gtgatgcctt ggaccagcac    4140
aacctcaagc aaaatgacca gcccatggat atcctgcaga ttattaattg tttgaccact    4200
atttatgacc gcctggagca agagcacaac aatttggtca acgtccctct ctgcgtggat    4260
atgtgtctga actggctgct gaatgtttat gatacgggac gaacagggag gatccgtgtc    4320
ctgtctttaa aagtggcatc atttccctgt gtaaagcaca tttggaagac aagtacagat    4380
accttttcaa gcaagtggca agttcaacag gattttgtga ccagcgcagg ctgggcctcc    4440
ttctgcatga ttctatccaa atccaagaca gttgggtgaa gttgcatcct tgggggcag    4500 taacattgag ccaagtgtcc ggagctgctt ccaatttgct aataataagc cagagatcga    4560
agcggccctc ttcctagact ggatgagact ggaaccccag tccatggtgt ggctgcccgt    4620
cctgcacaga gtggctgctg agaaactgc caagcatcag gccaaatgta acatctgcaa    4680
agagtgtcca atcattggat tcaggtacag gagtctaaag cactttaatt atgacatctg    4740
ccaaagctgc tttttttctg gtcgagttgc aaaaggccat aaaatgcact atcccatggt    4800
ggaatattgc actccgacta catcaggaga agatgttcga actttgcca aggtactaaa    4860 aaacaaattt cgaaccaaaa ggtattttgc gaagcatccc cgaatgggct acctgccagt    4920
gcagactgtc ttagagggg acaacatgga aacgcctgcc tcgtcccctc agctttcaca    4980
cgatgatact cattcacgca ttgaacatta tgctagcagg ctagcagaaa tggaaaacag    5040
caatggatct tatctaaatg atagcatctc tcctaatgag agcatagatg atgaacattt    5100
gttaatccag cattactgcc aaagtttgaa ccaggactcc cccctgagcc agcctcgtag    5160
tcctgcccag atcttgattt ccttagagag tgaggaaaga ggggagctag agagaatcct    5220
agcagatctt gaggaagaaa acaggaatct gcaagcagaa tatgaccgtc taaagcagca    5280
gcacgaacat aaaggcctgt ccccactgcc gtcccctcct gaaatgatgc ccacctctcc    5340
ccagagtccc cgggatgctg agctcattgc tgaggccaag ctactgcgtc aacacaaagg    5400
ccgcctggaa gccaggatgc aaatcctgga agaccacaat aaacagctgg agtcacagtt    5460
acacaggcta aggcagctgc tggagcaacc ccaggcagag gccaaagtga atggcacaac    5520
ggtgtcctct ccttctacct ctctacagag gtccgacagc agtcagccta tgctgctccg    5580
agtggttggc agtcaaactt cggactccat gggtgaggaa gatcttctca gtcctcccca    5640
ggacacaagc acagggttag aggaggtgat ggagcaactc aacaactcct tccctagttg    5700
aagaggaaga aataccctg gaaagccaat gagagaggac acaatgtag               5749
```

<210> SEQ ID NO 5
<211> LENGTH: 6397
<212> TYPE: DNA
<213> ORGANISM: Artificial Sequence
<220> FEATURE:
<223> OTHER INFORMATION: Synthetic

<400> SEQUENCE: 5

```
atgctttggt gggaagaagt agaggactgt tatgaaagag aagatgttca aaagaaaaca      60
ttcacaaaat gggtaaatgc acaatttctt aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
```

```
aaaaatgtaa tgaaaaatat catggctgga ttgcaacaaa ccaacagtga aaagattctc      420
ctgagctggg tccgacaatc aactcgtaat tatccacagg ttaatgtaat caacttcacc      480
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
acctatccag ataagaagtc catcttaatg tacatcacat cactcttcca agttttgcct      720
caacaagtga gcattgaagc catccaggaa gtggaaatgt tgccaaggcc acctaaagtg      780
actaaagaag aacatttttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtgaag tggtgaaaga ccagtttcat      1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaaattcaaga tgggaatgcc tcagggtagc tagcatggaa     1320
aaacaaagca atttacatag agtttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaagacat ccttctcaaa     1680
tggcaacgtc ttactgaaga acagtgcctt tttagtgcat ggctttcaga aaagaagat      1740
gcagtgaaca agattcacac aactggcttt aaagatcaaa atgaaatgtt atcaagtctt     1800
caaaaactgg ccgttttaaa agcggatcta gaaaagaaaa agcaatccat gggcaaactg     1860
tattcactca aacaagatct tctttcaaca ctgaagaata agtcagtgac ccagaagacg     1920
gaagcatggc tggataactt tgcccggtgt tgggataatt tagtccaaaa acttgaaaag     1980
agtacagcac agatttcaca gcaaaagaat atcttgtcag aatttcaaag agatttaaat     2040
gaatttgttt tatggttgga ggaagcagat aacattgcta gtatcccact tgaacctgga     2100
aaagagcagc aactaaaaga aaagcttgag caagtcaagt tactggtgga agagttgccc     2160
ctgcgccagg gaattctcaa acaattaaat gaaactggag gacccgtgct tgtaagtgct     2220
cccataagcc cagaagagca agataaactt gaaaataagc tcaagcagac aaatctccag     2280
tggataaagg tttccagagc tttacctgag aaacaaggag aaattgaagc tcaaataaaa     2340
gaccttgggc agcttgaaaa aaagcttgaa gaccttgaag agcagttaaa tcatctgctg     2400
ctgtggttat ctcgtattag gaatcagttg gaaatttata accaaccaaa ccaagaagga     2460
ccatttgacg ttcaggaaac tgaaatagca gttcaagcta acaaccggaa tgtgaagagc     2520
attttgtcta aagggcagca tttgtacaag gaaaaaccag ccactgagcc agtgaagagg     2580
aagttagaag atctgagctc tgagtggaag gcggtaaacc gtttacttca agagctgagg     2640
gcaaagcagc ctgacctagc tcctggactg accactattg gagcctctcc tactcagact     2700
gttactctgg tgacacaacc tgtggttact aaggaaactg ccatctccaa actagaaatg     2760
```

```
ccatcttcct tgatgttgga ggtacctgct ctggcagatt tcaaccgggc ttggacagaa    2820
cttaccgact ggctttctct gcttgatcaa gttataaaat cacagagggt gatggtgggt    2880
gaccttgagg atatcaacga gatgatcatc aagcagaagg caacaatgca ggatttggaa    2940
cagaggcgtc cccagttgga agaactcatt accgctgccc aaaatttgaa aaacaagacc    3000
agcaatcaag aggctagaac aatcattacg gatcgaattg aaagaattca gaatcagtgg    3060
gatgaagtac aagaacacct tcagaaccgg aggcaacagt tgaatgaaat gttaaaggat    3120
tcaacacaat ggctggaagc taaggaagaa gctgagcagg tcttaggaca ggccagagcc    3180
aagcttgagt catggaagga gggtccctat acagtagatg caatccaaaa gaaaatcaca    3240
gaaaccaagc agttggccaa agacctccgc cagtggcaga caaatgtaga tgtggcaaat    3300
gacttggccc tgaaacttct ccgggattat tctgcagatg ataccagaaa agtccacatg    3360
ataacagaga atatcaatgc ctcttggaga agcattcata aaagggtgag tgagcgagag    3420
gctgctttgg aagaaactca tagattactg caacagttcc ccctggacct ggaaaagttt    3480
cttgcctggc ttacagaagc tgaaacaact gccaatgtcc tacaggatgc tacccgtaag    3540
gaaaggctcc tagaagactc caagggagta aaagagctga tgaaacaatg gcaagacctc    3600
caaggtgaaa ttgaagctca cacagatgtt tatcacaacc tggatgaaaa cagccaaaaa    3660
atcctgagat ccctggaagg ttccgatgat gcagtcctgt tacaaagacg tttggataac    3720
atgaacttca gtggagtgaa acttcggaaa aagtctctca cattaggtcc catttggaa     3780 gccagtctg accagtggaa gcgtctgcac ctttctctgc aggaacttct ggtgtggcta    3840
gagctgaaag atgatgaatt aagccggcag gcacctattg gaggcgactt tccagcagtt    3900
cagaagcaga acgatgtaca tagggccttc aagagggaat tgaaaactaa agaacctgta    3960
atcatgagta ctcttgagac tgtacgaata tttctgacag agcagccttt ggaaggacta    4020
gagaaactct accaggagcc cagagagctg cctcctgagg agagagccca gaatgtcact    4080
cggcttctac gaaagcaggc tgaggaggtc aatactgagt gggaaaaatt gaacctgcac    4140
tccgctgact ggcagagaaa aatagatgag acccttgaaa gactccagga acttcaagag    4200
gccacggatg agctggacct caagctgcgc caagctgagt tgatcaaggg atcctggcag    4260
ccggtgggcg atctcctcat tgactctctc caagatcacc tcgagaaagt caaggcactt    4320
cgaggagaaa ttgcgcctct gaaagagaac gtgagccacg tcaatgacct tgctcgccag    4380
cttaccactt tgggcattca gctctcaccg tataacctca gcactctgga agacctgaac    4440
accagatgga gcttctgca ggtggccgtc gaggaccgag tcaggcagct gcatgaagcc    4500
cacagggact ttggtccagc atctcagcac tttctttcca cgtctgtcca gggtccctgg    4560
gagagagcca tctcgccaaa caaagtgccc tactatatca accacgagac tcaaacaact    4620
tgctgggacc atcccaaaat gacagagctc taccagtctt tagctgacct gaataatgtc    4680
agattctcag cttataggac tgccatgaaa ctccgaagac tgcagaaggc ctttgcttg     4740 gatctcttga gcctgtcagc tgcatgtgat gccttggacc agcacaacct caagcaaaat    4800
gaccagccca tggatatcct gcagattatt aattgtttga ccactattta tgaccgcctg    4860
gagcaagagc acaacaattt ggtcaacgtc cctctctgcg tggatatgtg tctgaactgg    4920
ctgctgaatg tttatgatac gggacgaaca gggaggatcc gtgtcctgtc ttttaaaact    4980
ggcatcattt ccctgtgtaa agcacatttg gaagacaagt acagatacct tttcaagcaa    5040
gtggcaagtt caacaggatt ttgtgaccag cgcaggctgg gcctccttct gcatgattct    5100
```

| | |
|---|---|
| atccaaattc caagacagtt gggtgaagtt gcatcctttg ggggcagtaa cattgagcca | 5160 |
| agtgtccgga gctgcttcca atttgctaat aataagccag agatcgaagc ggccctcttc | 5220 |
| ctagactgga tgagactgga accccagtcc atggtgtggc tgcccgtcct gcacagagtg | 5280 |
| gctgctgcag aaactgccaa gcatcaggcc aaatgtaaca tctgcaaaga gtgtccaatc | 5340 |
| attggattca ggtacaggag tctaaagcac tttaattatg acatctgcca aagctgcttt | 5400 |
| ttttctggtc gagttgcaaa aggccataaa atgcactatc ccatggtgga atattgcact | 5460 |
| ccgactacat caggagaaga tgttcgagac tttgccaagg tactaaaaaa caaatttcga | 5520 |
| accaaaaggt attttgcgaa gcatccccga atgggctacc tgccagtgca gactgtctta | 5580 |
| gaggggggaca acatggaaac gcctgcctcg tcccctcagc tttcacacga tgatactcat | 5640 |
| tcacgcattg aacattatgc tagcaggcta gcagaaatgg aaaacagcaa tggatcttat | 5700 |
| ctaaatgata gcatctctcc taatgagagc atagatgatg aacatttgtt aatccagcat | 5760 |
| tactgccaaa gtttgaacca ggactccccc ctgagccagc tcgtagtcc tgcccagatc | 5820 |
| ttgatttcct tagagagtga ggaaagaggg gagctagaga gaatcctagc agatcttgag | 5880 |
| gaagaaaaca ggaatctgca agcagaatat gaccgtctaa agcagcagca cgaacataaa | 5940 |
| ggcctgtccc cactgccgtc ccctcctgaa atgatgccca cctctcccca gagtccccgg | 6000 |
| gatgctgagc tcattgctga ggccaagcta ctgcgtcaac acaaaggccg cctggaagcc | 6060 |
| aggatgcaaa tcctggaaga ccacaataaa cagctggagt cacagttaca caggctaagg | 6120 |
| cagctgctgg agcaaccccca ggcagaggcc aaagtgaatg cacaacggt gtcctctcct | 6180 |
| tctacctctc tacagaggtc cgacagcagt cagcctatgc tgctccgagt ggttggcagt | 6240 |
| caaacttcgg actccatggg tgaggaagat cttctcagtc ctccccagga cacaagcaca | 6300 |
| gggtttagag gaggtgatgg agcaactcaa caactccttc cctagttcaa gaggaagaaa | 6360 |
| taccctggaa aagccaatga gagaggacac aatgtag | 6397 |

<210> SEQ ID NO 6
<211> LENGTH: 6718
<212> TYPE: DNA
<213> ORGANISM: Artificial Sequence
<220> FEATURE:
<223> OTHER INFORMATION: Synthetic

<400> SEQUENCE: 6

| | |
|---|---|
| atggtttggt gggaagaagt agaggactgt tatgaaagag aagatgttca aagaaaaca | 60 |
| ttcacaaaat gggtaaatgc acaatttcct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata atcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catccttatg tacatcacat cactcttcca agttttgcct | 720 |
| caacaagtga gcattgaagc catccaggaa gtggaaatgt tgccaaggcc acctaaagtg | 780 |

```
actaaagaag aacattttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaagacat ccttctcaaa     1680
tggcaacgtc ttactgaaga acagtgcctt tttagtgcat ggctttcaga aaagaagat     1740 gcagtgaaca agattcacac aactggcttt aaagatcaaa atgaaatgtt atcaagtctt     1800
caaaaactgg ccgttttaaa agcggatcta gaaaagaaaa agcaatccat gggcaaactg     1860
tattcactca acaagatct tcttcaacac tgaagaataa gtcagtgacc cagaagacgg      1920
aagcatggct ggataacttt gcccggtgtt gggataattt agtccaaaaa cttgaaaaga     1980
gtacagcaca gatttcacag tctgttgaga atggcggcg ttttcattat gatataaaga     2040
tatttaatca gtggctaaca gaagctgaag agtttctcag aaagacacaa attcctgaga     2100
attgggaaca tgctaaatac aaatggtatc ttaaggaact ccaggatggc attgggcagc     2160
ggcaaactgt tgtcagaaca ttgaatgcaa ctggggaaga aataattcag caatcctcaa     2220
aaacagatgc cagtattcta caggaaaaat tgggaagcct gaatctgcgg tggcaggagg     2280
tctgcaaaca gctgtcagac agaaaaaaga ggctagaaga acaaaagaat atcttgtcag     2340
aatttcaaag agatttaaat gaatttgttt tatggttgga ggaagcagat aacattgcta     2400
gtatcccact tgaacctgga aaagagcagc aactaaaaga aaagcttgag caagtcaagt     2460
tactggtgga agagttgccc ctgcgccagg gaattctcaa acaattaaat gaaactggag     2520
gacccgtgct tgtaagtgct cccataagcc cagaagagca agataaactt gaaaataagc     2580
tcaagcagac aaatctccag tggataaagg tttccagagc tttacctgag aaacaaggag     2640
aaattgaagc tcaaataaaa gaccttgggc agcttgaaaa aaagcttgaa gaccttgaag     2700
agcagttaaa tcatctgctg ctgtggttat ctcctattag gaatcagttg gaaatttata     2760
accaaccaaa ccaagaagga ccatttgacg ttcaggaaac tgaaatagca gttcaagcta     2820
aacaaccgga tgtggaagag attttgtcta aagggcagca tttgtacaag gaaaaaccag     2880
ccactcagcc agtgaagagg aagttagaag atctgagctc tgagtggaag gcggtaaacc     2940
gtttacttca agagctgagg gcaaagcagc ctgacctagc tcctggactg accactattg     3000
gagcctctcc tactcagact gttactctgg tgacacaacc tgtggttact aaggaaactg     3060
ccatctccaa actagaaatg ccatcttcct tgatgttgga ggtacctgct ctggcagatt     3120
```

```
tcaaccgggc ttggacagaa cttaccgact ggctttctct gcttgatcaa gttataaaat    3180
cacagagggt gatggtgggt gaccttgagg atatcaacga gatgatcatc aagcagaagg    3240
caacaatgca ggatttggaa cagaggcgtc cccagttgga agaactcatt accgctgccc    3300
aaaatttgaa aaacaagacc agcaatcaag aggctagaac aatcattacg gatcgaattg    3360
aaagaattca gaatcagtgg gatgaagtac aagaacacct tcagaaccgg aggcaacagt    3420
tgaatgaaat gttaaaggat tcaacacaat ggctggaagc taaggaagaa gctgagcagg    3480
tcttaggaca ggccagagcc aagcttgagt catggaagga gggtccctat acagtagatg    3540
caatccaaaa gaaaatcaca gaaaccaagc agttggccaa agacctccgc cagtggcaga    3600
caaatgtaga tgtggcaaat gacttggccc tgaaacttct ccgggattat tctgcagatg    3660
ataccagaaa agtccacatg ataacagaga atatcaatgc ctcttggaga agcattcata    3720
aaagggtgag tgagcgagag gctgctttgg aagaaactca tagattactg caacagtccc    3780
cctggacctg gaaaagtttc ttgcctggct tacagaagct gaaacaactg ccaatgtcct    3840
acaggatgct acccgtaagg aaaggctcct agaagactcc aagggagtaa aagagctgat    3900
gaaacaatgg caagacctcc aaggtgaaat tgaagctcac acagatgttt atcacaacct    3960
ggatgaaaac agccaaaaaa tcctgagatc cgtggaaggt tccgatgatg cagtcctgtt    4020
acaaagacgt ttggataaca tgaacttcaa gtggagtgaa cttcggaaaa agtctctcaa    4080
cattggtcc catttggaag ccagttctga ccagtggaag cgtctgcacc tttctctgca    4140
ggaacttctg gtgtggctac agctgaaaga tgatgaatta agccggcagg cacctattgg    4200
aggcgacttt ccagcagttc agaagcagaa cgatgtacat agggccttca agagggaatt    4260
gaaaactaaa gaacctgtaa tcatgagtac tcttgagact gtacgaatat ttctgacaga    4320
gcagcctttg gaaggactag agaaactcta ccaggagccc agagagctgc ctcctgagga    4380
gagagcccag aatgtcactc ggcttctacg aaagcaggct gaggaggtca atactgagtg    4440
ggaaaaattg aacctgcact ccgctgactg gcagagaaaa atagatgaga cccttgaaag    4500
actccaggaa cttcaagagg ccacggatga gctggaactc aagctgcgcc aagctgaggt    4560
gatcaaggga tcctggcagc ccgtgggcga tctcctcatt gactctctcc aagatcacct    4620
cgagaaagtc aaggcacttc gaggagaaat ttgcgcctct gaaagagaac gtgagccacg    4680
tcaatgacct tgctcgccag cttaccactt tgggcattca gctctcaccg tataacctca    4740
gcactctgga agacctgaac accagatgga agcttctgca ggtggccgtc gaggaccgag    4800
tcaggcagct gcatgaagcc cacgggact ttggtccagc atctcagcac tttctttcca    4860
cgtctgtcca gggtccctgg gagagagcca tctcgccaaa caaagtgccc tactatatca    4920
accacgagac tcaaacaact tgctgggacc atcccaaaat gacagagctc taccagtctt    4980
tagctgacct gaataatgtc agattctcag cttataggac tgccatgaaa ctccgaagac    5040
tgcagaaggc cctttgcttg gatctcttga gcctgtcagc tgcatgtgat gccttggacc    5100
agcacaacct caagcaaaat gaccagccca tggatatcct gcagattatt aattgtttga    5160
ccactatttg accgcctg gagcaagagc acaacaattt ggtcaacgtc cctctctgcg    5220
tggatatgtg tctgaactgg ctgctgaatg tttatgatac gggacgaaca gggaggatcc    5280
gtgtcctgtc tttaaaact ggcatcattt ccctgtgtaa agcacatttg gaagacaagt    5340
acagatacct tttcaagcaa gtggcaagtt caacaggatt ttgtgaccag cgcaggctgg    5400
gcctccttct gcatgattct atccaaattc caagacagtt gggtgaagtt gcatcctttg    5460
ggggcagtaa cattgagcca agtgtccgga gctgcttcca atttgctaat aataagccag    5520
```

```
agatcgaagc ggccctcttc ctagactgga tgagactgga accccagtcc atggtgtggc      5580
tgcccgtcct gcacagagtg gctgctgcag aaactgccaa gcatcaggcc aaatgtaaca      5640
tctgcaaaga gtgtccaatc attggatttc aggtacagga gtctaaagca ctttaattat      5700
gacatctgcc aaagctgctt tttttctggt cgagttgcaa aaggccataa aatgcactat      5760
cccatggtgg aatattgcac tccgactaca tcaggagaag atgttcgaga ctttgccaag      5820
gtactaaaaa acaaatttcg aaccaaaagg tattttgcga agcatccccg aatgggctac      5880
ctgccagtgc agactgtctt agaggggac aacatggaaa cgcctgcctc gtcccctgag       5940
cttccacacg atgatactca ttcacgcatt gaacatatgc tagcaggcta gcagaaatgg      6000
aaaacagcaa tggatcttat ctaaatgata gcatctctcc taatgagagc atagatgatg      6060
aacattttgt taatccagca ttactgccaa agtttgaacc aggactcccc cctgagccag      6120
cctcgtagtc ctgcccagat cttgatttcc ttagagagtg aggaaagagg ggagctagag      6180
agaatcctag cagatcttga ggaagaaaac aggaatctgc aagcagaata tgaccgtcta      6240
aagcagcagc acgaacataa aggcctgtcc ccactgccgt cccctcctga aatgatgccc      6300
acgtctcccc agagtccccg ggatgctgag ctcattgctg aggccaagct actgcgtcaa      6360
cacaaaggcc gcctggaagc caggatgcaa atcctggaag accacaataa acagctggag      6420
tcacagttac acaggctaag gcagctgctg gagcaacccc aggcagaggc caaagtgaat      6480
ggcacaacgg tgtcctctcc tttctacctc tctacagagg tccgacagca gtcagcctat      6540
gctgctccga gtggttggca gtcaaacttc ggactccatg ggtgaggaag atcttctcag      6600
tcctccccag gacacaagca cagggttaga ggaggtgatg gagcaactca acaactcctt      6660
ccctagttca agaggaagaa ataccctgg aaagccaatg agagaggaca caatgtag       6718
```

<210> SEQ ID NO 7
<211> LENGTH: 7049
<212> TYPE: DNA
<213> ORGANISM: Artificial Sequence
<220> FEATURE:
<223> OTHER INFORMATION: Synthetic

<400> SEQUENCE: 7

```
atgctttggt gggaagaagt agaggactgt tatgaaagag aagatgttca aaagaaaaca      60
ttcacaaaat gggtaaatgc acaatttct aagtttggga agcagcatat tgagaacctc       120
ttcagtgacc tacaggatgg gaggcgcctc ctagacctcc tcgaaggcct gacagggcaa      180
aaactgccaa agaaaaaagg atccacaaga gttcatgccc tgaacaatgt caacaaggca      240
ctgcgggttt tgcagaacaa taatgttgat ttagtgaata ttggaagtac tgacatcgta      300
gatggaaatc ataaactgac tgttggtttg atttggaata taatcctcca ctggcaggtc      360
aaaaatgtaa tgaaaatat catggctgga ttgcaacaaa ccaacagtga aagattctc       420 ctgagctggg tccgacaatc aactcgtaat tatccacagg ttaatgtaat caacttcacc      480
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
acctatccag ataagaagtc catcttaatg tacatcacat cactcttcca agttttgcct      720
caacaagtga gcattgaagc catccaggaa gtggaaatgt tgccaaggcc acctaaagtg      780
actaaagaag aacattttca gttacatcat caaatgcact attctcaaca gatcacggtc      840
```

```
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttgaa gaacaactta aggtatttgg gagatcgatg     1620
ggcaaacatc tgtagatgga cagaagaccg ctgggttctt ttacaagaca tccttctcaa     1680
atggcaacgt cttactgaag aacagtgcct ttttagtgca tggctttcag aaaaagaaga     1740
tgcagtgaac aagattcaca caactggctt taaagatcaa aatgkaatgt tatcaagtct     1800
tcaaaaagtg gccgttttaa aagcggatct agaaagaaa aagcaatcca tgggcaaact     1860
gtattcactc aaacaagatc ttcttcaac actgaagaat aagtcagtga cccagaagac     1920
ggaagcatgg ctggataact ttgcccggtg ttgggataat ttagtccaaa aacttgaaaa     1980
gagtacagca cagatttcac aggaaatttc ttatgtgcct tctacttatt tgactgaaat     2040
cactcatgtc tcacaagccc tattagaagt ggaacaactt tcaatgctc ctgacctctg     2100
tgctaaggac tttgaagatc tctttaagca agaggagtct ctgaagaata taaaagatag     2160
tctacaacaa agctcaggtc ggattgacat tattcatagc aagaagacag cagcattgca     2220
aagtgcaacg cctgtggaaa gggtgaagct acaggaagct ctctcccagc ttgatttcca     2280
atgggaaaaa gttaacaaaa tgtacaagga ccgacaaggg cgatttgaca gatctgttga     2340
gaaatggcgg cgttttcatt atgatataaa gatatttaat cagtggctaa cagaagctga     2400
acagtttctc agaagacac aaattcctga gaattgggaa catgctaaat acaaatggta     2460
tcttaaggaa ctccaggatg gcattgggca gcggcaaact gttgtcagaa cattgaatgc     2520
aactggggaa gaaataattc agcaatcctc aaaaacagat gccagtattc tacaggaaaa     2580
attgggaagc ctgaatctgc ggtggcagga ggtctgcaaa cagctgtcag acagaaaaaa     2640
gaggctagaa gaacaaaaga atatcttgtc agaatttcaa agagatttaa atgaatttgt     2700
tttatggttg gaggaagcag ataacattgc tagtatccca cttgaacctg gaaaagagca     2760
gcaactaaaa gaaaagcttg agcaagtcaa gttactggtg gaagagttgc ccctgcgcca     2820
gggaattctc aaacaattaa atgaaactgg aggacccgtg cttgtaagtg ctcccataag     2880
cccagaagag caagataaac ttgaaaataa gctcaagcag acaaatctcc agtggataaa     2940
ggtttccaga gctttacctg agaaacaagg agaaattgaa gctcaaataa aagaccttgg     3000
gcagcttgaa aaaaagcttg aagaccttga agagcagtta aatcatctgc tgctgtggtt     3060
atctcctatt aggaatcagt tggaaattta taaccaacca aaccaagaag gaccatttga     3120
cgttcaggaa actgaaatag cagttcaagc taaacaaccg gatgtggaag agattttgtc     3180
taaagggcag catttgtaca aggaaaaacc agccactcag ccagtgaaga ggaagttaga     3240
```

```
agatctgagc tctgagtgga aggcggtaaa ccgtttactt caagagctga gggcaaagca   3300
gcctgaccta gctcctggac tgaccactat tggagcctct cctactcaga ctgttactct   3360
ggtgacacaa cctgtggtta ctaaggaaac tgccatctcc aaactagaaa tgccatcttc   3420
cttgatgttg gaggtacctg ctctggcaga tttcaaccgg gcttggacag aacttaccga   3480
ctggctttct ctgcttgatc aagttataaa atcacagagg gtgatggtgg gtgaccttga   3540
ggatatcaac gagatgatca tcaagcagaa ggcaacaatg caggatttgg aacagaggcg   3600
tcccagttg gaagaactca ttaccgctgg ccaaaatttg aaaaacaaga ccagcaatca   3660
agaggctaga caatcatta cggatcgaat tgaaagaatt cagaatcagt gggatgaagt   3720
acaagaacac cttcagaacc ggaggcaaca gttgaatgaa atgttaaagg attcaacaca   3780
atggctggaa gctaaggaag aagctgagca ggtcttagga caggccagag ccaagcttga   3840
gtcatggaag gagggtccct atacagtaga tgcaatccaa aagaaaatca cagaaaccaa   3900
gcagttggcc aaagacctcc gccagtggca gacaaatgta gatgtggcaa atgacttggc   3960
cctgaaactt ctccgggatt attctgcaga tgataccaga aaagtccaca tgataacaga   4020
gaatatcaat gcctcttgga gaagcattca taaaagggtg agtgagcgag aggctgcttt   4080
ggaagaaact catagattac tgcaacagtt ccccctggac ctggaaaagt ttcttgcctg   4140
gcttacagaa gctgaaacaa ctgccaatgt cctacaggat gctacccgta aggaaaggct   4200
cctagaagac tccaagggag taaaagagct gatgaaacaa tggcaagacc tccaaggtga   4260
aattgaagct cacacagatg tttatcacaa cctggatgaa aacagccaaa aaatcctgag   4320
atccctggaa ggttccgatg atgcagtcct gttacaaaga cgtttggata acatgaactt   4380
caagtggagt gaacttcgga aaagtctct caacattagg tcccatttgg aagccagttc   4440
tgaccagtgg aagcgtctgc acctttctct gcaggaactt ctggtgtggc tacagctgaa   4500
agatgatgaa ttaagccggc aggcacctat tggaggcgac tttccagcag ttcagaagca   4560
gaacgatgta catagggcct tcaagaggga attgaaaact aaagaacctg taatcatgag   4620
tactcttgag actgtacgaa tatttctgac agagcagcct ttggaaggac tagagaaact   4680
ctaccaggag cccagagagc tgcctcctga ggagagagcc cagaatgtca ctcggcttct   4740
acgaaagcag gctgaggagg tcaatactga gtgggaaaaa ttgaacctgc actccgctga   4800
ctggcagaga aaatagatg agaccctga aagactccag gaacttcaag aggccacgga   4860
tgagctggac ctcaagctgc gcgaagctga ggtgatcaag ggatcctggc agcccgtggg   4920
cgatctcctc attgactctc tccaagatca cctcgagaaa gtcaaggcac ttcgaggaga   4980
aattgcgcct ctgaaagaga acgtgagcca cgtcaatgac cttgctcgcc agcttaccac   5040
tttgggcatt cagctctcac cgtataacct cagcactctg gaagacctga acaccagatg   5100
gaagcttctg caggtggccg tcgaggaccg agtcaggcag ctgcatgaag cccacaggga   5160
ctttggtcca gcatctcagc actttctttc cacgtctgtc cagggtccct gggagagagc   5220
catctcgcca aacaaagtgc cctactatat caaccacgag actcaaacaa cttgctggga   5280
ccatcccaaa atgacagagc tctaccagtc tttagctgac ctgaataatg tcagattctc   5340
agcttatagg actgccatga aactccgaag actgcagaag gcccttttgct ggatctctt   5400
gagcctgtca gctgcatgtg atgccttgga ccagcacaac ctcaagcaaa atgaccagcc   5460
catggatatc ctgcagatta ttaattgttt gaccactatt tatgaccgcc tggagcaaga   5520
gcacaacaat ttggtgaacg tgcctctctg cgtggatatg tgtctgaact ggctggtgaa   5580
```

| | |
|---|---|
| tgtttatgat acgggacgaa cagggaggat ccgtgtcctg tcttttaaaa ctggcatcat | 5640 |
| ttccctgtgt aaagcacatt tggaagacaa gtacagatac cttttcaagc aagtgggaag | 5700 |
| ttcaacagga ttttgtgacc agcgcaggct gggcctcctt ctgcatgatt ctatccaaat | 5760 |
| tccaagacag ttgggtgaag ttgcatcctt tgggggcagt aacattgagc caagtgtccg | 5820 |
| gagctgcttc caatttgcta ataataagcc agagatcgaa gcggccctct tcctagactg | 5880 |
| gatgagactg gaaccccagt ccatggtgtg gctgcccgtc ctgcacagag tggctgctgc | 5940 |
| agaaactgcc aagcatcagg ccaaatgtaa catctgcaaa gagtgtccaa tcattggatt | 6000 |
| caggtacagg agtctaaagc actttaatta tgacatctgc caaagctgct ttttttctgg | 6060 |
| tcgagttgca aaaggccata aaatgcacta tcccatggtg gaatattgca ctccgactac | 6120 |
| atcaggagaa gatgttcgag actttgccaa ggtactaaaa aacaaatttc gaaccaaaag | 6180 |
| gtattttgcg aagcatcccc gaatgggcta cctgccagtg cagactgtct tagaggggga | 6240 |
| caacatggaa acgcctgcct cgtcccctca gctttcacag gatgatactc attcacgcat | 6300 |
| tgaacattat gctagcaggc tagcagaaat ggaaaacagc aatggatctt tatctaaatg | 6360 |
| atagcatctc tcctaatgag agcatagatg atgaacattt gttaatccag cattactgcc | 6420 |
| aaagtttgaa ccaggactcc cccctgagcc agcctcgtag tcctgcccag atcttgattt | 6480 |
| ccttagagag tgaggaaaga ggggagctag agagaatcct agcagatctt gaggaagaaa | 6540 |
| acaggaatct gcaagcagaa tatgaccgtc taaagcagca gcacgaacat aaaggcctgt | 6600 |
| ccccactgcc gtcccctcct gaaatgatgc ccacctctcc ccagagtccc cgggatgctg | 6660 |
| agctcattgc tgaggccaag ctactgcgtc aacacaaagg ccgcctggaa gccaggatgc | 6720 |
| aaatcctgga agaccacaat aaacagctgg agtcacagtt acacaggcta aggcagctgg | 6780 |
| tggagcaacc ccaggcagag gccaaagtga atggcacaac ggtgtcctct ccttctacct | 6840 |
| ctctacagag gtccgacagc agtcagccta tgctgctccg agtggttggc agtcaaactt | 6900 |
| cggactccat gggtgaggaa gatcttctca gtcctcccca ggacacaagc acagggttag | 6960 |
| aggaggtgat ggagcaactc aacaactcct tccctagttc aagaggaaga aatacccctg | 7020 |
| gaaagccaat gagagaggac acaatgtag | 7049 |

```
<210> SEQ ID NO 8
<211> LENGTH: 6398
<212> TYPE: DNA
<213> ORGANISM: Artificial Sequence
<220> FEATURE:
<223> OTHER INFORMATION: Synthetic

<400> SEQUENCE: 8
```

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata aatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggcttgaatg ctctcatcca tagtcatagg ccagacctat | 540 |
| ttgactggaa tagtgtggtt tgccagcagt cagccacaca acgactggaa catgcattca | 600 |

```
acatcgccag atatcaatta ggcatagaga aactactcga tcctgaagat gttgatacca    660
cctatccaga taagaagtcc atcttaatgt acatcacatc actcttccaa gttttgcctc    720
aacaagtgag cattgaagcc atccaggaag tggaaatgtt gccaaggcca cctaaagtga    780
ctaaagaaga acattttcag ttacatcatc aaatgcacta ttctcaacag atcacggtca    840
gtctagcaca gggatatgag agaacttctt cccctaaggc tcgattcaag agctatgcct    900
acacacaggc tgcttatgtc accacctctg accctacacg gagcccattt ccttcacagc    960
atttggaagc tcctgaagac aagtcatttg gcagttcatt gatggagagt gaagtaaacc   1020
tggaccgtta tcaaacagct ttagaagaag tattatcgtg gcttctttct gctgaggaca   1080
cattgcaagc acaaggagag atttctaatg atgtggaagt ggtgaaagac cagtttcata   1140
ctcatgaggg gtacatgatg gatttgacag cccatcaggg ccgggttggt aatattctac   1200
aattgggaag taagctgatt ggaacaggaa aattatcaga agatgaagaa actgaagtac   1260
aagagcagat gaatctccta aattcaagat gggaatgcct cagggtagct agcatggaaa   1320
aacaaagcaa tttacataga gttttaatgg atctccagaa tcagaaactg aaagagttga   1380
atgactggct aacaaaaaca gaagaaagaa caaggaaaat ggaggaagag cctcttggac   1440
ctgatcttga agacctaaaa cgccaagtac aacaacataa ggtgcttcaa gaagatctag   1500
aacaagaaca agtcagggtc aattctctca ctcacatggt ggtggtagtt gatgaatcta   1560
gtggagatca cgcaactgct gctttggaag aacaacttaa ggtattggga gatcgatggg   1620
caaacatctg tagatggaca gaagaccgct gggttctttt acaagacatc cttctcaaat   1680
ggcaacgtct tactgaagaa cagtgccttt ttagtgcatg gctttcagaa aaagaagatg   1740
cagtgaacaa gattcacaca actggcttta aagatcaaaa tgaaatgtta tcaagtcttc   1800
aaaaactggc cgttttaaaa gcggatctag aaaagaaaaa gcaatccatg ggcaaactgt   1860
attcactcaa acaagatctt cttccaacac tgaagaataa gtcagtgacc cagaagacgg   1920
aagcatggct ggataacttt gcccggtgtt gggataattt agtccaaaaa cttgaaaaga   1980
gtacagcaca gatttcacag gaaatttctt atgtgccttc tacttatttg actgaaatca   2040
ctcatgtctc acaagcccta ttagaagtgg aacaacttct caatgctcct gacctctgtg   2100
ctaaggactt tgaagatctc tttaagcaag aggagtctct gaagaatata aaagatagtc   2160
tacaacaaag ctcaggtcgg attgacatta ttcatagcaa aagacagca gcattgcaaa   2220 gtgcaacgcc tgtggaaagg gtgaagctac aggaagctct ctcccagctt gatttccaat   2280
gggaaaaagt taacaaaatg tacaaggacc gacaagggcg atttgacaga tctgttgaga   2340
aatggcggcg ttttcattat gatataaaga tatttaatca gtggctaaca gaagctgaac   2400
agtttctcag aaagacacaa attcctgaga attgggaaca tgctaaatac aaatggtatc   2460
ttaaggaact ccaggatggc attgggcagc ggcaaactgt tgtcagaaca ttgaatgcaa   2520
ctggggaaga ataattcag caatcctcaa aaacagatgc cagtattcta caggaaaaat   2580
tgggaagcct gaatctgcgg tggcaggagg tctgcaaaca gctgtcagac agaaaaaaga   2640
ggctagaaga acagcctgac ctagctcctg gactgacgac tattggagcc tctcctactc   2700
agactgttac tctggtgaca caacctgtgg ttactaagga aactgccatc tccaaactag   2760
aaatgccatc ttccttgatg ttggaggtac ctgctctggc agatttcaac cgggcttgga   2820
cagaacttac cgactggctt tctgtgcttg atcaagttat aaaatcacag agggtgatgg   2880
tgggtgacct tgaggatatc aacgagatga tcatcaagca gaaggcaaca atgcaggatt   2940
```

```
                                              -continued
tggaacagag gcgtccccag ttggaagaac tcattaccgc tgcccaaaat ttgaaaaaca   3000
agaccagcaa tcaagaggct agaacaatca ttacggatcg aattgaaaga attcagaatc   3060
agtgggatga agtacaagaa caccttcaga accggaggca acagttgaat gaaatgttaa   3120
aggattcaac acaatggctg gaagctaagg aagaagctga gcaggtctta ggacaggcca   3180
gagccaagct tgagtcatgg aaggagggtc cctatacagt agatgcaatc caaaagaaaa   3240
tcacagaaac caaggagttg gccaaagacc tccgccagtg gcagacaaat gtagatgtgg   3300
caaatgactt ggccctgaaa cttgtccggg attattctgc agatgatacc agaaaagtcc   3360
acatgataac agagaatatc aatgcctctt ggagaagcat tcataaaagg gtgagtgagc   3420
gagaggctgc tttggaagaa actcatagat tactgcaaca gttcccctg  gacctggaaa   3480 agtttcttgc ctggcttaca gaagctgaaa caactgccaa tgtcctacag gatgctaccc   3540
gtaaggaaag gctcctagaa gactccaagg gagtaaaaga gctgatgaaa caatggcaag   3600
acctccaagg tgaaatgaag ctcacacaga tgtttatcac aacctggatg aaaacagcca   3660
aaaaatcctg agatccctgg aaggttccga tgatgcagtc ctgttacaag acgthtggat   3720
aacatgaact tcaagtggag tgaacttcgg aaaaagtctc tcaacattag gtcccatttg   3780
gaagccagtt ctgaccagtg gaagcgtctg cacctttctc tgcaggaact tctggtgtgg   3840
ctacagctga agatgatga  attaagccgg caggcaccta ttggaggcga ctttccagca   3900
gttcagaagc agaacgatgt acatagggcc ttcaagaggg aattgaaaac taagaacct   3960 gtaatcatga gtactcttga gactgtacga atatttctga cagagcagcc tttggaagga   4020
ctagagaaac tctaccagga gcccagagag ctgcctcctg aggagagagc ccagaatgtc   4080
actcggcttc tacgaaagca ggctgaggag gtcaatactg agtgggaaaa attgaacctg   4140
cactccgctg actggcagag aaaaatagat gagacccttg aaagactcca ggaacttcaa   4200
gaggccacgg atgagctgga cctcaagctg cgccaagctg aggtgatcaa gggatcctgg   4260
cagcccgtgg gcgatctcct catgactctc tccaagatca cctcgagaaa gtcaaggcac   4320
ttcgaggaga aattgcgcct ctgaaagaga acgtgagcca cgtcaatgac cttgctcgcc   4380
agcttaccac tttgggcatt cagctctcac cgtataacct cagcactctg aagacctga   4440 acaccagatg gaagcttctg caggtggccg tcgaggaccg agtcaggcag ctgcatgaag   4500
cccacaggga ctttggtcca gcatctcagc actttctttc cacgtctgtc cagggtccct   4560
gggagagagc catctcgcca aacaaagtgc cctactatat caaccacgag actcaaacaa   4620
cttgctggga ccatcccaaa atgacagagc tctaccagtc tttagctgac ctgaataatg   4680
tcagattctc agcttatagg actgccatga aactccgaag actgcagaag gcccttttgct  4740 tggatctctt gagcctgtca gctgcatgtg atgccttgga ccagcacaac ctcaagcaaa   4800
atgaccagcc catggatatc ctgcagatta ttaattgttt gaccactatt tatgaccgcc   4860
tggagcaaga gcacaacaat ttggtcaacg tccctctctg cgtggatatg tgtctgaact   4920
ggctgctgaa tgtttatgat acgggacgaa cagggaggat ccgtgtcctg tcttttaaaa   4980
ctggcatcat ttccctgtgt aaagcacatt tggaagacaa gtacagatac ctttttcaagc  5040 aagtggcaag ttcaacagga ttttgtgacc agcgcaggct gggcctcctt ctgcatgatt   5100
ctatccaaat tccaagacag ttgggtgaag ttgcatcctt tgggggcagt aacattgagc   5160
caagtgtccg gagctgcttc caatttgcta ataataagcc agagatcgaa gcggccctct   5220
tcctagactg gatgagactg gaaccccagt ccatggtgtg gctgccccgtc ctgcacagag   5280 tggctgctgc agaaactgcc aagcatcagg ccaaatgtaa catctgcaaa gagtgtccaa   5340
```

```
tcattggatt caggtacagg agtctaaagc actttaatta tgacatctgc caaagctgct    5400
ttttttctgg tcgagttgca aaaggccata aaatgcacta tcccatggtg gaatattgca    5460
ctccgactac atcaggagaa gatgttcgag actttgccaa ggtactaaaa aacaaatttc    5520
gaaccaaaag gtattttgcg aagcatcccc gaatgggcta cctgccagtg cagactgtct    5580
tagaggggga caacatggaa acgcctgcct cgtcccctca gctttcacac gatgatactc    5640
attcacgcat tgaacattat gctagcaggc tagcagaaat ggaaaacagc aatggatctt    5700
atctaaatga tagcatctct cctaatgaga gcatagatga tgaacatttg ttaatccagc    5760
attactgcca aagtttgaac caggactccc ccctgagcca gcctcgtagt cctgcccaga    5820
tcttgatttc cttagagagt gaggaaagag gggagctaga gaatccta gcagatcttg       5880 aggaagaaaa caggaatctg caagcagaat atgaccgtct aaagcagcag cacgaacata    5940
aaggcctgtc cccactgccg tcccctcctg aaatgatgcc cacctctccc cagagtcccc    6000
gggatgctga gctcattgct gaggccaagc tactgcgtca acacaaaggc cgcgtggaag    6060
ccaggatgca atcctggaa gaccacaata aacagctgga gtcacagtta cacaggctaa      6120
ggcagctgct ggagcaaccc caggcagagg ccaaagtgaa tggcacaacg gtgtcctctc    6180
cttctacctc tctacagagg tccgacagca gtcagcctat gctgctccga gtggttggca    6240
gtcaaacttc ggactccatg ggtgaggaag atcttctcag tcctcccag gacacaagca       6300 cagggttaga ggaggtgatg gagcaactca acaactcctt ccctagttca agaggaagaa    6360 ataccccctgg aaagccaatg agagaggaca caatgtag                            6398
```

<210> SEQ ID NO 9
<211> LENGTH: 6078
<212> TYPE: DNA
<213> ORGANISM: Artificial Sequence
<220> FEATURE:
<223> OTHER INFORMATION: Synthetic

<400> SEQUENCE: 9

```
atgctttggt gggaagaagt agaggactgt tatgaaagag aagatgttca aaagaaaaca       60
ttcacaaaat gggtaaatgc acaatttcct aagtttggga agcagcatat tgagaacctc     120
ttcagtgacc tacaggatgg gaggcgcctc ctagacctcc tcgaaggcct gacagggcaa     180
aaactgccaa agaaaaagg atccacaaga gttcatgccc tgaagaatgt caacaaggca      240
ctgcgggttt tgcagaacaa taatgttgat ttagtgaata ttggaagtac tgagatcgta     300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta   540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct   720
caacaagtga gcattgaagc catccaggaa gtggaaatgt gccaaggcc acctaaagtg     780 actaaagaag aacattttca gttacatcat caaatgcact attctcaaca gatcacggtc    840
agtctagcac agggatatga gagaacttct tcccctaagc ctcgattcaa gagctatgcc   900
tacacacagg ctgcttatgt caccacctct gaccctacac ggagcccatt tccttcacag   960
```

-continued

```
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcaggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga cagtgccttt tttagtgcat ggctttcaga aaaagaagat    1740
gcagtgaaca agattcacac aactggcttt aaagatcaaa atgaaatgtt atcaagtctt    1800
caaaaactgg ccgttttaaa agcggatcta gaaaagaaaa agcaatccat gggcaaactg    1860
tattcactca aacaagatct tcttcaaca ctgaagaata agtcagtgac ccagaagacg    1920
gaagcatggc tggataactt tgcccggtgt gggataattt agtccaaaaa cttgaaaaga    1980
gtacagcaca gatttcacag gaaattctta tgtgccttct acttatttga ctgaaatcac    2040
tcatgtctca caagccctat tagaagtgga acaacttctc aatgctcctg acctctgtgc    2100
taaggacttt gaagatctct ttaagcaaga ggagtctctg aagaatataa aagatagtct    2160
acaacaaagc tcaggtcgga ttgacattat tcatagcaag aagacagcag cattgcaaag    2220
tgcaacgcct gtggaaaggg tgaagctaca ggaagctctc tcccagcttg atttccaatg    2280
ggaaaaagtt aacaaaatgt acaaggaccg acaagggcga tttgacagac agcctgacct    2340
agctcctgga ctgaccacta ttggagcctc tcctactcag actgttactc tggtgacaca    2400
acctgtggtt actaaggaaa ctgccatctc caaactagaa atgccatctt ccttgatgtt    2460
ggaggtacct gctctggcag atttcaaccg ggcttggaca gaacttaccg actggctttc    2520
tctgcttgat caagttataa aatcacagag ggtgatggtg ggtgaccttg aggatatcaa    2580
cgagatgatc atcaagcaga aggcaacaat gcaggatttg aacagaggc gtccccagtt    2640 ggaagaactc attaccgctg cccaaaattt gaaaaacaag accagcaatc aagaggctag    2700
aacaatcatt acggatcgaa ttgaaagaat tcagaatcag tgggatgaag tacaagaaca    2760
ccttcagaac cggaggcaac agttgaatga aatgttaaag gattcaacac aatggctgga    2820
agctaaggaa gaagctgagc aggtcttagg acaggccaga gccaagcttg agtcatggaa    2880
ggagggtccc tatacagtag atgcaatcca aagaaaatc acagaaacca agcagttggc    2940
caaagacctc cgccagtggc agacaaatgt agatgtggca aatgacttgg ccctgaaact    3000
tctccgggat tattctgcag atgataccag aaaagtccac atgataacag agaatatcaa    3060
tgcctcttgg agaagcattc ataaaagggt gagtgagcga gaggctgctt tggaagaaac    3120
tcatagatta ctgcaacagt tccccctgga cctggaaaag tttcttgcct ggcttacaga    3180
agctgaaaca actgccaatg tcctacagga tgctacccgt aaggaaaggc tcctagaaga    3240
ctccaaggga gtaaaagagc tgatgaaaca atggcaagac ctccaaggtg aaattgaagc    3300
tcacacagat gtttatcaca acctggatga aaacagccaa aaaatcctga gatccctgga    3360
```

```
aggttccgat gatgcagtcc tgttacaaag acgtttggat aacatgaact tcaagtggag    3420
tgaacttcgg aaaaagtctc tcaacattag gtcccatttg gaagccagtt ctgaccagtg    3480
gaagcgtctg cacctttctc tgcaggaact tctggtgtgg ctacagctga aagatgatga    3540
attaagccgg caggcaccta ttggaggcga ctttccagca gttcagaagc agaacgatgt    3600
acatagggcc ttcaagaggg aattgaaaac taaagaacct gtaatcatga gtactctgag    3660
actgtacgaa tatttctgac agagcagcct ttggaaggac tagagaaact ctaccaggag    3720
cccagagagc tgcctcctga ggagagagcc cagaatgtca ctcggcttct acgaaagcag    3780
gctgaggagg tcaatactga gtgggaaaaa ttgaacctgc actccgctga ctggcagaga    3840
aaaatagatg agacccttga aagactccag gaacttcaag aggccacgga tgagctggac    3900
ctcaagctgc gccaagctga ggtgatcaag ggatcctggc agcccgtggg cgatctcctc    3960
attgactctc tccaagatca cctcgagaaa gtcaaggcac ttcgaggaga aattgcgcct    4020
ctgaaagaga acgtgagcca cgtcaatgac cttgctcgcc agcttaccac tttggggatt    4080
cagctctcac cgtataacct cagcactctg gaagacctga acaccagatg gaagcttctg    4140
caggtggccg tcgaggacgg agtcaggcag gtgcatgaag cccacaggga ctttggtcca    4200
gcatgtcagc actttctttc cacgtctgtc cagggtccct gggagagagc catctcgcca    4260
aacaaagtgc cctactatat caaccacgag actcaaacaa cttgctggga ccatcccaaa    4320
atgacagagc tctaccagtc tttagctgac ctgaataatg tcagattctc agcttatagg    4380
actgccatga aactccgaag actgcagaag gcccttttgct tggatctctt gagcctgtca    4440
gctgcatgtg atgccttgga ccagcacaac ctcaagcaaa atgaccagcc catggatatc    4500
ctgcagatta ttaattgttt gaccactatt tatgaccgcc tggagcaaga gcacaacaat    4560
ttggtcaacg tccctctctg cgtggatatg tgtctgaact ggctgctgaa tgtttatgat    4620
acgggacgaa cagggaggat ccgtgtcctg tcttttaaaa ctggcatcat ttccctgtgt    4680
aaagcacatt tggaagacaa gtacagatac cttttcaagc aagtggcaag ttcaacagga    4740
ttttgtgacc agcgcaggct gggcctcctt ctgcatgatt ctatccaaat tccaagacag    4800
ttgggtgaag ttgcatcctt tggggcagt aacattgagc caagtgtccg gagctgcttc    4860
caatttgcta ataataagcc agagatcgaa gcggccctct tcctagactg gatgagactg    4920
gaaccccagt ccatggtgtg gctgcccgtc ctgcacagag tggctgctgc agaaactgcc    4980
aagcatcagg ccaaatgtaa catctgcaaa gagtgtccaa tcattggatt caggtacagg    5040
agtctaaagc actttaatta tgacatctgc caaagctgct ttttttctgg tcgagttgca    5100
aaaggccata aaatgcacta tcccatggtg gaatattgca ctccgactac atcaggagaa    5160
gatgttcgag actttgccaa ggtactaaaa aacaaatttc gaagcaaaag gtattttgcg    5220
aagcatcccc gaatgggcta cctgccagtg cagactgtct tagagggga caacatggaa    5280 acgcctgcct cgtcccctca gctttcacac gatgatactc attcacgcat gaacattat    5340 gctagcaggc tagcagaaat ggaaaacagc aatggatctt atctaaatga tagcatctct    5400
cctaatgaga gcatagatga tgaacatttg ttaatccagc attactgcca aagtttgaac    5460
caggactccc ccctgagcca gctcgtagt cctgcccaga tcttgatttc cttagagagt    5520
gaggaaagag gggagctaga gagaatccta gcagatcttg aggaagaaaa caggaatctg    5580
caagcagaat atgaccgtct aaagcagcag cacgaacata aaggcctgtc cccactgccg    5640 tccctcctg aaatgatgcc cacctctccc cagagtcccc gggatgctga gctcattgct    5700
```

| | |
|---|---|
| gaggccaagc tactgcgtca acacaaaggc cgcctggaag ccaggatgca atcctggaa | 5760 |
| gaccacaata aacagctgga gtcacagtta cacaggctaa ggcagctgct ggagcaaccc | 5820 |
| caggcagagg ccaaagtgaa tggcacaacg gtgtcctctc cttctacctc tctacagagg | 5880 |
| tccgacagca gtcagcctat gctgctccga gtggttggca gtcaaacttc ggactccatg | 5940 |
| ggtgaggaag atcttctcag tcctccccag gacacaagca caggggttaga ggaggtgatg | 6000 |
| gagcaactca caactccctt ccctagttga agaggaagaa ataccctgg aaagccaatg | 6060 |
| agagaggaca caatgtag | 6078 |

<210> SEQ ID NO 10
<211> LENGTH: 6264
<212> TYPE: DNA
<213> ORGANISM: Artificial Sequence
<220> FEATURE:
<223> OTHER INFORMATION: Synthetic

<400> SEQUENCE: 10

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct acagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat gatggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca agttttgcct | 720 |
| caacaagtga gcattgaagc catccaggaa gtggaaatgt tgccaaggcc acctaaagtg | 780 |
| actaaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttcttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaatttatca agatgaagaa aaactgaagt | 1260 |
| acaagagcag atgaatctcc taaattcaag atgggaatgc ctcagggtag ctagcatgga | 1320 |
| aaaacaaagc aatttacata gagttttaat ggatctccag aatcagaaac tgaaagagtt | 1380 |
| gaatgactgg ctaacaaaaa cagaagaaag aacaaggaaa atggaggaag agcctcttgg | 1440 |
| acctgatctt gaagacctaa acgccaagt acaacaacat aaggtgcttc aagaagatct | 1500 |
| agaacaagaa caagtcaggg tcaattctct cactcacatg gtggtggtag ttgatgaatc | 1560 |
| tagtggagat cacgcaactg ctgctttgga agaacaactt aaggtattgg agatcgatg | 1620 |
| ggcaaacatc tgtagatgga cagaagaccg ctgggttctt ttacaagaca tccttctcaa | 1680 |

```
atggcaacgt cttactgaag aacagtgcct ttttagtgca tggctttcag aaaaagaaga   1740
tgcagtgaac aagattcaca caactggctt taaagatcaa aatgaaatgt tatcaagtct   1800
tcaaaaactg gccgttttaa agcggatct agaaaagaaa aagcaatcca tgggcaaact    1860
gtattcactc aaacaagatc ttctttcaac actgaagaat aagtcagtga cccagaagac   1920
ggaagcatgg ctggataact ttgcccggtg ttgggataat ttagtccaaa aacttgaaaa   1980
gagtacagca cagatttcac aggaaatttc ttatgtgcct tctacttatt tgactgaaat   2040
cactcatgtc tcacaagccc tattagaagt ggaacaactt ctcaatgctc ctgacctctg   2100
tgctaaggac tttgaagatc tctttaagca agaggagtct ctgaagaata taaaagatag   2160
tctacaacaa agctcaggtc ggattgacat tattcatagc aagaagacag cagcattgca   2220
aagtgcaacg cctgtggaaa gggtgaagct acaggaagct ctctcccagc ttgatttcca   2280
atgggaaaaa gttaacaaaa tgtacaagga cggacaaggg cgatttgaca gatctgttga   2340
gaaatggcgg cgttttcatt atgatataaa gatatttaat cagtggctaa cagaagctga   2400
acagtttctc agaaagacac aaaattcctga gaattgggaa catgctaaat acaaatggta   2460
tcttaaggaa ctccaggatg gcattgggca gcggcaaact gttgtcagaa cattgaatgc   2520
aactggggaa gaaataattc agcaatcctc aaaaacagat gccagtattc tacaggaaaa   2580
attgggaagc ctgaatctgc ggtggcagga ggtctgcaaa cagctgtcag acagaaaaaa   2640
gaggctagaa gaacaaaaga atatcttgtc agaatttcaa agagatttaa atgaatttgt   2700
tttatggttg gaggaagcag ataacattgc tagtatccca cttgaacctg aaaagagca   2760
gcaactaaaa gaaaagcttg agcaagtcaa gttactggtg aagagttgc ccctgcgcca    2820
gggaattctc aaacaattaa atgaaactgg aggacccgtg cttgtaagtg ctcccataag   2880
cccagaagag caagataaac ttgaaaataa gctcaagcag acaaatctcc agtggataaa   2940
ggtttccaga gctttacctg agaaacaagg agaaattgaa gctcaaataa agaccttgg   3000
gcagcttgaa aaaaagcttg aagaccttga agagcagtta aatcatctgc tgctgtggtt   3060
atctcctatt aggaatcagt tggaaattta taaccaacca aaccaagaag gaccatttga   3120
cgttcaggaa actgaaatag cagttcaagc taaacaaccg gatgtggaag agtttttgtc   3180
taaagggcag catttgtaca aggaaaaacc agccactcag ccagtgaaga ggaagttaga   3240
agatctgagc tctgagtgga aggcggtaaa ccgtttactt caagagctga gggcaaagca   3300
gcctgaccta gctcctggac tgaccactat tggagcctct cctactcaga ctgttactct   3360
ggtgacacaa cctgtggtta ctaaggaaac tgccatctcc aaactagaaa tgccatcttc   3420
cttgatgttg gaggtacctg ctctggcaga tttcaaccgg gcttggacag aacttaccga   3480
ctggctttct ctgcttgatc aagttataaa atcacagagg gtgatggtgg gtgaccttga   3540
ggatatcaac gagatgatca tcaagcagaa ggcaacaatg caggatttgg aacagaggcg   3600
tcccagttg gaagaactca ttaccgctgc ccaaaatttg aaaaacaaga ccagcaatca   3660
agaggctaga acaatcatta cggatcgaat tgaaagaatt cagaatcagt gggatgaagt   3720
acaagaacac cttcagaacc ggaggcaaca gttgaatgaa atgttaaagg attcaacaca   3780
atggctggaa gctaaggaag aagctgagca ggtcttagga caggccagag ccaagcttga   3840
gtcatggaag gagggtccct atacagtaga tgcaatccaa aagaaaatca cagaaaccaa   3900
gcagttggcc aaagacctcc gccagtggca gacaaatgta gatgtggcaa atgacttggc   3960
cctgaaactt ctccgggatt attctgcaga tgataccaga aaagtccaca tgataacaga   4020
```

```
gaatatcaat gcctcttgga gaagcattca taaaagggtg agtgagcgag aggctgcttt    4080
ggaagaaact catagattac tgcaacagtt cccctggac ctggaaaagt ttcttgcctg    4140
gcttacagaa gctgaaacaa ctgccaatgt cctacaggat gctacccgta aggaaaggct    4200
cctagaagac tccaagggag taaaagagct gatgaaacaa tggcaagacc tccaaggtga    4260
aattgaagct cacacagatg tttatcacaa cctggatgaa acagccaaa aaatcctgag    4320 atccctggaa ggttccgatg atgcagtcct gttacaaaga cgtttggata acatgaactt    4380
caagtggagt gaacttcgga aaaagtctct caacattagg tcccatttgg aagccagttc    4440
tgaccagtgg aagcgtctgc acctttctct gcaggaactt ctggtgtggc tacagctgaa    4500
agatgatgaa ttaagccggc aggcacctat tggaggcgac tttccagcag ttcagaagca    4560
gaacgatgta cataggcct tcaagaggga attgaaaact aaagaacctg taatcatgag    4620
tactctgaga ctgtacgaat atttctgaca gagcagcctt tggaaggact agagaaactc    4680
taccaggagc ccagagagct gcctcctgag gagagagccc agaatgtcac tcggcttcta    4740
cgaaagcagg ctgaggaggt caatactgag tgggaaaaat tgaacctgca ctccgctgac    4800
tggcagagaa aaatagatga gacccttgaa agactccagg aacttcaaga ggccacggat    4860
gagctggacc tcaagctgcg ccaagctgag gtgatcaagg atcctggca gcccgtgggc    4920 gatctcctca ttgactctct ccaagatcac ctcgagaaag tcaaggcact tcgaggagaa    4980
attgcgcctc tgaaagagaa cgtgagccac gtcaatgacc ttgctcgcca gcttaccact    5040
ttgggcattc agctctcacc gtataacctc agcactctgg aagacctgaa caccagatgg    5100
aagcttctgc aggtggccgt cgaggaccga gtcaggcagc tgcatgaagc ccacagggac    5160
tttggtccag catctcagca cttttcttcc acgtctgtcc agggtccctg ggagagagcc    5220
atctcgccaa acaaagtgcc ctactatatc aaccacgaga ctcaaacaac ttgctgggac    5280
catcccaaaa tgacagagct ctaccagtct ttagctgacc tgaataatgt cagattctca    5340
gcttatagga ctgccatgaa actccgaaga ctgcagaagg ccctttgctt ggatctcttg    5400
agcctgtcag ctgcatgtga tgccttggac cagcacaacc tcaagcaaaa tgaccagccc    5460
atggatatcc tgcagattat taattgtttg accactattt atgaccgcct ggagcaagag    5520
cacaacaatt tggtcaacgt ccctctctgc gtggatatgt gtctgaactg ctgctgaat    5580 gtttatgata cgggacgaac agggaggatc cgtgtcctgt cttttaaaac tggcatcatt    5640
tccctgtgta aagcacattt ggaagacaag tacagatacc ttttcaagca agtggcaagt    5700
tcaacaggat tttgtgacca gcgcaggctg ggcctccttc tgcatgattc tatccaaatt    5760
ccaagacagt tgggtgaagt tgcatccttt gggggcagta acattgagcc aagtgtccgg    5820
agctgcttcc aatttgctaa taataagcca gagatcgaag cggccctctt cctagactgg    5880
atgagactgg aaccccagtc catggtgtgg ctgcccgtcc tgcacagagt ggctgctgca    5940
gaaactgcca agcatcaggc caaatgtaac atctgcaaag agtgtccaat cattggattc    6000
aggtacagga gtctaaagca ctttaattat gacatctgcc aaagctgctt tttttctggt    6060
cgagttgcaa aaggccataa aatgcactat cccatggtgg aatattgcac tccgactaca    6120
tcaggagaag atgttcgaga ctttgccaag gtactaaaaa acaaatttcg aaccaaaagg    6180
tattttgcga agcatccccg aatgggctac ctgccagtgc agactgtctt agagggggac    6240
aacatggaaa ctgacacaat gtag                                          6264
```

<210> SEQ ID NO 11
<211> LENGTH: 4078

<212> TYPE: DNA
<213> ORGANISM: Artificial Sequence
<220> FEATURE:
<223> OTHER INFORMATION: Synthetic

<400> SEQUENCE: 11

| | | | | | |
|---|---|---|---|---|---|
| atgctttggt | gggaagaagt | agaggactgt | tatgaaagag | aagatgttca | aaagaaaaca | 60 |
| ttcacaaaat | gggtaaatgc | acaattttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaaatat | catggctgga | ttgcaacaaa | ccaacagtga | aaagattctc | 420 |
| ctgagctggg | tccgacaatc | aactcgtaat | tatccagagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttctttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agaaatttct | tatgtgcctt | ctacttattt | gactgaaatc | 1380 |
| actcatgtct | cacaagccct | attagaagtg | aacaacttc | tcaatgctcc | tgacctctgt | 1440 |
| gctaaggact | ttgaagatct | ctttaagcaa | gaggagtctc | tgaagaatat | aaaagatagt | 1500 |
| ctacaacaaa | gctcaggtcg | gattgacatt | attcatagca | agaagacagc | agcattgcaa | 1560 |
| agtgcaacgc | ctgtggaaag | ggtgaagcta | caggaagctc | tctcccagct | tgatttcgaa | 1620 |
| tgggaaaaag | ttaacaaaat | gtacaaggac | cgacaagggc | gatttgacag | atctgttgag | 1680 |
| aaatggcggc | gttttcatta | tgatataaag | atatttaatc | agtggctaac | agaagctgaa | 1740 |
| cagtttctca | gaaagacaca | aattcctgag | aattgggaac | atgctaaata | caaatggtat | 1800 |
| cttaaggaac | tccaggatgg | cattgggcag | cggcaaactg | ttgtcagaac | attgaatgca | 1860 |
| actggggaag | aaataattca | gcaatcctca | aaaacagatg | ccagtattct | acaggaaaaa | 1920 |
| ttgggaagcc | tgaatctgcg | gtggcaggag | gtctgcaaac | agctgtcaga | cagaaaaaag | 1980 |
| aggctagaag | aacaaagaa | tatcttgtca | gaatttcaaa | gagatttaaa | tgaatttgtt | 2040 |
| ttatggttgg | aggaagcaga | taacattgct | agtatcccac | ttgaacctgg | aaaagagcag | 2100 |
| caactaaaag | aaaagcttga | gcaagtcaag | ttactggtgg | aagagttgcc | cctgcgccag | 2160 |

-continued

| | |
|---|---|
| ggaattctca acaattaaa tgaaactgga ggacccgtgc ttgtaagtgc tcccataagc | 2220 |
| ccagaagagc aagataaact tgaaaataag ctcaagcaga caaatctcca gtggataaag | 2280 |
| gtttccagag ctttacgtga gaaagaagga gaaattgaag ctcaaataaa agaccttggg | 2340 |
| cagcttgaaa aaaagcttga agaccttgaa gagcagttaa atcatctgct gctgtggtta | 2400 |
| tctcctatta ggaatcagtt ggaaatttat aaccaaccaa accaagaagg accatttgac | 2460 |
| gttcaggaaa ctgaaatagc agtcaagcta acaaccgga tgtggaagag attttgtcta | 2520 |
| aagggcagca tttgtacaag gaaaaaccag ccactcagcc agtgaagagg aagttagaag | 2580 |
| atctgagctc tgagtggaag gcggtaaacc gtttacttca agagctgagg gcaaagaccc | 2640 |
| ttgaaagact ccaggaactt caagaggcca cggatgagct ggacctcaag ctgcgccaag | 2700 |
| ctgaggtgat caagggatcc tggcagcccg tgggcgatct cctcattgac tctctccaag | 2760 |
| atcacctcga gaaagtcaag gcacttcgag agaaattgc gcctctgaaa gagaacgtga | 2820 |
| gccacgtcaa tgaccttgct cgccagctac cactttgggc attcagctct caccgtataa | 2880 |
| cctcagcact ctggaagacc tgaacaccag atggaagctt ctgcaggtgg ccgtcgagga | 2940 |
| ccgagtcagg cagctgcatg aagcccacag ggactttggt ccagcatctc agcactttct | 3000 |
| ttccacgtct gtccagggtc cctgggagag agccatctcg ccaaacaaag tgccctacta | 3060 |
| tatcaaccac gagactcaaa caacttgctg ggaccatccc aaaatgacag agctctacca | 3120 |
| gtctttagct gacctgaata atgtcagatt ctcagcttat aggactgcca tgaaactccg | 3180 |
| aagactgcag aaggcccttt gcttggatct cttgagcctg tcagctgcat gtgatgcctt | 3240 |
| ggaccagcac aacctcaagc aaaatgacca gcccatggat atcctgcaga ttattaattg | 3300 |
| tttgagcact atttatgacc gcctggagca agagcacaac aatttggtca acgtccctct | 3360 |
| ctgcgtggat atgtgtctga actggctgct gaatgtttat gatacgggac gaacagggag | 3420 |
| gatccgtgtc ctgtcttta aaactggcat catttccctg tgtaaagcac atttggaaga | 3480 |
| caagtacaga tacctttttca agcaagtggc aagttcaaca ggattttgtg accagcgcag | 3540 |
| gctgggcctc cttctgcatg attctatcca aattccaaga cagttgggtg aagttgcatc | 3600 |
| ctttgggggc agtaacattg agccaagtgt ccggagctgc ttccaatttg ctaataataa | 3660 |
| gccagagatc gaagcggccc tcttcctaga ctggatgaga ctggaacccc agtccatggt | 3720 |
| gtggctgccc gtcctgcaca gagtggctgc tgcagaaact gccaagcatc aggccaaatg | 3780 |
| taacatctgc aaagagtgtc caatcattgg attcaggtac aggagtctaa agcactttaa | 3840 |
| ttatgacatc tgccaaagct gcttttttc tggtcgagtt gcaaaaggcc ataaaatgca | 3900 |
| ctatcccatg gtggaatatt gcactccgac tacatcagga agagatgttc gagactttgc | 3960 |
| caaggtacta aaaaacaaat tcgaaccaa aaggtatttt gcgaagcatc cccgaatggg | 4020 |
| ctacctgcca gtgcagactg tcttagaggg ggacaacatg gaaactgaca caatgtag | 4078 |

<210> SEQ ID NO 12
<211> LENGTH: 3761
<212> TYPE: DNA
<213> ORGANISM: Artificial Sequence
<220> FEATURE:
<223> OTHER INFORMATION: Synthetic

<400> SEQUENCE: 12

| | |
|---|---|
| atgctttggt gggaagaagt agaggactgt tatgaaagag aagatgttca aaagaaaaca | 60 |
| ttcacaaaat gggtaaatgc acaatttttct aagtttggga agcagcatat tgagaacctc | 120 |
| ttcagtgacc tacaggatgg gaggcgcctc ctagacctcc tcgaaggcct gacagggcaa | 180 |

```
aaactgccaa aagaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg taatgtaatc aacttcacca    480
ccagctggtc tgatggcctg gctttgaatg ctctcatcca tagtcatagg ccagacctat    540
ttgactggaa tagtgtggtt tgccagcagt cagccacaca acgactggaa catgcattca    600
acatcgccag atatcaatta ggcatagaga aactactcga tcctgaagat gttgatacca    660
cctatccaga taagaagtcc atcttaatgt acatcacatc actcttccaa gttttgcctc    720
aacaagtgag cattgaagcc atccaggaag tggaaatgtt gccaaggcca cctaaagtga    780
ctaaagaaga acattttcag ttacatcatc aaatgcacta ttctcaacag atcacggtca    840
gtctagcaca gggatatgag agaacttctt cccctaagcc tcgattcaag agctatgcct    900
acacacaggc tgcttatgtc accacctctg accctacacg gagcccattt ccttcacagc    960
atttggaagc tcctgaagac aagtcatttg gcagttcatt gatggagagt gaagtaaacc    1020
tggaccgtta tcaaacagct ttagaagaag tattatcgtg gcttctttct gctgaggaca    1080
cattgcaagc acaaggagag atttctaatg atgtggaagt ggtgaaagac cagtttcata    1140
ctcatgaggg gtacatgatg gatttgacag cccatcaggg ccgggttggt aatattctac    1200
aattgggaag taagctgatt ggaacaggaa aattatcaga agatgaagaa actgaagtac    1260
aagagcagat gaatctccta aattcaagat gggaatgcct cagggtagct agcatggaaa    1320
aacaaagcaa tttacataga gttttaatgg atctccagaa tcagaaactg aaagagttga    1380
atgactggct aacaaaaaca gaagaaagaa caaggaaaat ggaggaagag cctcttggac    1440
ctgatcttga agacctaaaa cgccaagtac aacaacataa ggtgcttcaa gaagatctag    1500
aacaagaaca agtcagggtc aattctctca ctcacatggt ggtggtagtt gatgaatcta    1560
gtggagatca cgcaactgct gctttggaag aacaacttaa ggtattggga gatcgatggg    1620
caaacatctg tagatggaca gaagaccgct gggttctttt acaagacgaa atttcttatg    1680
tgccttctac ttatttgact gaaatcactc atgtctcaca agccctatta gaagtggaac    1740
aacttctcaa tgctcctgac ctctgtgcta aggactttga agatctcttt aagcaagagg    1800
agtctctgaa gaatataaaa gatagtctac aacaaagctc aggtcggatt gacattattc    1860
atagcaagaa gacagcagca ttgcaaagtg caacgcctgt ggaaagggtg aagctacagg    1920
aagctctctc ccagcttgat ttccaatggg aaaagttaa caaaatgtac aaggaccgac    1980
aagggcgatt tgacagatct gttgagaaat ggcggcgttt tcattatgat ataaagatat    2040
ttaatcagtg gctaacagaa gctgaacagt ttctcagaaa gacacaaatt cctgagaatt    2100
gggaacatgc taaatacaaa tggtatctta aggaactcca ggatggcatt gggcagcggc    2160
aaactgttgt cagaacattg aatgcaactg gggaagaaat aattcagcaa tcctcaaaaa    2220
cagatgccag tattctacag gaaaaattgg gaagcctgaa tctgcggtgg caggaggtct    2280
gcaaacagct gtcagacaga aaaaagaggc tagaagaaac ccttgaaaga ctccaggaac    2340
ttcaagaggc cacggatgag ctggacctca agctgcgcca agctgaggtg atcaagggat    2400
cctggcagcc cgtgggcgat ctcctcattg actctctcca agatcacctc gagaaagtca    2460
aggcacttcg aggagaaatt gcgcctctga agagaacgt gagccacgtc aatgaccttg    2520
```

```
ctcgccagct taccactttg ggcattcagc tctcaccgta taacctcagc actctggaag    2580
acctgaacac cagatggaag cttctgcagg tggccgtcga ggaccgagtc aggcagctgc    2640
atgaagccca cagggacttt ggtccagcat ctcagcactt tctttccacg tctgtccagg    2700
gtccctggga gagagccatc tcgccaaaca aagtgcccta ctatatcaac cacgagactc    2760
aaacaacttg ctgggaccat cccaaaatga cagagctcta ccagtcttta gctgacctga    2820
ataatgtcag attctcagct tataggactg ccatgaaact ccgaagactg cagaaggccc    2880
tttgcttgga tctcttgagc ctgtcagctg catgtgatgc cttggaccag cacaacctca    2940
agcaaaatga ccagcccatg gatatcctgc agattattaa ttgtttgacc actatttatg    3000
accgcctgga gcaagagcac aacaatttgg tcaacgtccc tctctgcgtg gatatgtgtc    3060
tgaactggct gctgaatgtt tatgatacgg acgaacaggg gaggatccgt gtcctgtctt    3120
ttaaaactgg catcatttcc ctgtgtaaag cacatttgga agacaagtac agatacctttt  3180 tcaagcaagt ggcaagttca acaggatttt gtgaccagcg caggctgggc ctccttctgc    3240
atgattctat ccaaattcca agacagttgg gtgaagttgc atcctttggg ggcagtaaca    3300
ttgagccaag tgtccggagc tgcttccaat ttgctaataa taagccagag atcgaagcgg    3360
ccctcttcct agactggatg agactggaac cccagtccat ggtgtggctg cccgtcctgc    3420
acagagtggc tgctgcagaa actgccaagc atcaggccaa atgtaacatc tgcaaagagt    3480
gtccaatcat tggattcagg tacaggagtc taaagcactt taattatgac atctgccaaa    3540
gctgcttttt ttctggtcga gttgcaaaag gccataaaat gcactatccc atggtggaat    3600
attgcactcc gactacatca ggagaagatg ttcgagactt tgccaaggta ctaaaaaaca    3660
aatttcgaac caaaaggtat tttgcgaagc atccccgaat gggctacctg ccagtgcaga    3720
ctgtcttaga gggggacaac atggaaactg acacaatgta g                       3761
```

<210> SEQ ID NO 13
<211> LENGTH: 3434
<212> TYPE: DNA
<213> ORGANISM: Artificial Sequence
<220> FEATURE:
<223> OTHER INFORMATION: Synthetic

<400> SEQUENCE: 13

```
atgctttggt gggaagaagt agaggactgt tatgaaagag aagatgttca aagaaaaaca      60
ttcacaaaat gggtaaatgc acaatttttct aagtttggga agcagcatat tgagaacctc    120
ttcagtgacc tacaggatgg gaggcgcctc ctagacctcc tcgaaggcct acagggcaa     180 aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaggcc acctaaagtg    780 actaaagaag aacattttca gttacatcat caaatgcact attctcaaca gatcacggtc    840
```

```
agtctagcac agggatatga gagaacttct tccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca attacataga gaaatttctt atgtgccttc tacttatttg actgaaatca     1380
ctcatgtctc acaagcccta ttagaagtgg aacaacttct caatgctcct gacctctgtg     1440
ctaaggactt tgaagatctc tttaagcaag aggagtctct gaagaatata aagatagtc      1500
tacaacaaag ctcaggtcgg attgacatta ttcatagcaa aagacagca gcattgcaaa      1560
gtgcaacgcc tgtggaaagg gtgaagctac aggaagctct ctcccagctt gatttccaat     1620
gggaaaaagt taacaaaatg tacaaggacc gacaagggcg atttgacaga tctgttgaga     1680
aatggcggcg ttttcattat gatataaaga tatttaatca gtggctaaca aagctgaac      1740
agtttctcag aaagacacaa attcctgaga attgggaaca tgctaaatac aaatggtatc     1800
ttaaggaact ccaggatggc attgggcagc ggcaaactgt tgtcagaaca ttgaatgcaa     1860
ctggggaaga ataattcag caatcctcaa aaacagatgc cagtattcta caggaaaaat      1920
tgggaagcct gaatctgcgg tggcaggagg tctgcaaaca gctgtcagac agaaaaaaga    1980
ggctagaaga aacccttgaa agactccagg aacttcaaga ggccacggat gagctggacc    2040
tcaagctgcg ccaagctgag gtgatcaagg gatcctggca gcccgtgggc gatctcctca    2100
ttgactctct ccaagatcac ctcgagaaag tcaaggcact tcgaggagaa attgcgcctc    2160
tgaaagagaa cgtgagccac gtcaatgacc ttgctcgcca gcttaccact ttgggcattc    2220
agctctcacc gtataacctc agcactctgg aagacctgaa caccagatgg aagcttctgc    2280
aggtggccgt cgaggaccga gtcaggcagc tgcatgaagc ccacagggac tttggtccag    2340
catctcagca cttctcttcc acgtctgtcc agggtccctg ggagagagcc atctcgccaa    2400
acaaagtgcc ctactatatc aaccacgaga ctcaaacaac ttgctgggac gatccccaaa    2460
tgacagagct ctaccagtct ttagctgacc tgaataatgt cagattctca gcttatagga    2520
ctgccatgaa actccgaaga ctgcagaagg cccttttgctt ggatctcttg agcctgtcag    2580
ctgcatgtga tgccttggac cagcacaacc tcaagcaaaa tgaccagccc atggatatcc    2640
tgcagattat taattgtttg accactattt atgaccgcct ggagcaagag cacaacaatt    2700
tggtcaacgt ccctctctgc gtggatatgt gtctgaactg gctgctgaat gtttatgata    2760
cgggacgaac agggaggatc cgtgtcctgt cttttaaaac tggcatcatt tccctgtgta    2820
aagcacattt ggaagacaag tacagatacc ttttcaagca agtggcaagt tcaacaggat    2880
tttgtgacca gcgcaggctg ggcctccttc tgcatgattc tatccaaatt ccaagacagt    2940
tgggtgaagt tgcatccttt gggggcagta acattgagcc aagtgtccgg agctgcttcc    3000
aatttgctaa taataagcca gagatcgaag cggccctctt cctagactgg atgagactgg    3060
aaccccagtc catggtgtgg ctgccgtcc tgcacagagt ggctgctgca gaaactgcca    3120
agcatcaggc caaatgtaac atctgcaaag agtgtccaat cattggattc aggtacagga    3180
```

| | |
|---|---|
| gtctaaagca ctttaattat gacatctgcc aaagctgctt tttttctggt cgagttgcaa | 3240 |
| aaggccataa aatgcactat cccatggtgg aatattgcac tccgactaca tcaggagaag | 3300 |
| atgttcgaga ctttgccaag gtactaaaaa acaaatttcg aaccaaaagg tattttgcga | 3360 |
| agcatccccg aatgggctac ctgccagtgc agactgtctt agaggggggac aacatggaaa | 3420 |
| ctgacacaat gtag | 3434 |

<210> SEQ ID NO 14
<211> LENGTH: 3439
<212> TYPE: DNA
<213> ORGANISM: Artificial Sequence
<220> FEATURE:
<223> OTHER INFORMATION: Synthetic

<400> SEQUENCE: 14

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttggcagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca agttttgcct | 720 |
| caacaagtga gcatgaagcc atccaggaag tggaaatgtt gccaaggcca cctaaagtga | 780 |
| ctaaagaaga acattttcag ttacatcatc aaatgcacta ttctcaacag atcacggtca | 840 |
| gtctagcaca gggatatgag agaacttctt cccctaagcc tcgattcaag agctatgcct | 900 |
| acacacaggc tgcttatgtc accacctctg accctacacg gagcgcattt ccttcacagc | 960 |
| atttggaagc tcctgaagac aagtcatttg gcagttcatt gatggagagt gaagtaaacc | 1020 |
| tggaccgtta tcaaacagct ttagaagaag tattatcgtg gcttctttct gctgaggaca | 1080 |
| cattgcaagc acaaggagag atttctaatg atgtggaagt ggtgaaagac cagtttcata | 1140 |
| ctcatgaggg gtacatgatg gatttgacag cccatcaggg ccgggttggt aatattctac | 1200 |
| aattgggaag taagctgatt ggaacaggaa aattatcaga agatgaagaa actgaagtac | 1260 |
| aagagcagat gaatctccta aattcaagat gggaatgcct cagggtagct agcatggaaa | 1320 |
| aacaaagcaa tttacataga gttttaatgg atctccagaa tcagaaactg aaagagttga | 1380 |
| atgactggct aacaaaaaca gaagaaagaa caaggaaaat ggaggaagag cctcttggac | 1440 |
| ctgatcttga agacctaaaa cgccaagtac aacaacataa ggtgcttcaa gaagatctag | 1500 |
| aacaagaaca agtcagggtc aattctctca ctcacatggt ggtggtagtt gatgaatcta | 1560 |
| gtggagatca cgcaactgct gctttggaag aacaacttaa ggtattggga gatcgatggg | 1620 |
| caaacatctg tagatggaca gaagaccgct gggttctttt acaagacgaa atttcttatg | 1680 |
| tgccttctac ttatttgact gaaatcactc atgtctcaca gcccattaa gaagtggaac | 1740 |
| aacttctcaa tgctcctgac ctctgtgcta aggactttga agatctcttt aagcaagagg | 1800 |

-continued

```
agtctctgaa gaatataaaa gatagtctac aacaaagctc aggtcggatt gacattattc    1860
atagcaagaa gacagcagca ttgcaaagtg caacgcctgt ggaaagggtg aagctacagg    1920
aagctctctc ccagcttgat ttccaatggg aaaaagttaa caaatgtac aaggaccgac     1980 aagggcgatt tgacagaacc cttgaaagac tccaggaact tcaagaggcc acggatgagc    2040
tggacctcaa gctgcgccaa gctgaggtga tcaagggatc ctggcagccc gtgggcgatc    2100
tcctcattga ctctctccaa gatcacctcg agaaagtcaa ggcacttcga ggagaaattg    2160
cgcctctgaa agagaacgtg agccacgtca atgaccttgc tcgccagctt accactttgg    2220
gcattcagct ctcaccgtat aacctcagca ctctggaaga cctgaacacc agatggaagc    2280
ttctgcaggt ggccgtcgag gaccgagtca ggcagctgca tgaagcccac agggactttg    2340
gtccagcatc tcagcacttt cttttccacgt ctgtccaggg tccctgggag agagccatct    2400
cgccaaacaa agtgccctac tatatcaacc acgagactca aacaacttgc tgggaccatc    2460
ccaaaatgac agagctctac cagtctttag ctgacctgaa taatgtcaga ttctcagctt    2520
ataggactgc catgaaactc cgaagactgc agaaggccct ttgcttggat ctcttgagcc    2580
tgtcagctgc atgtgatgcc ttggaccagc acaacctcaa gcaaaatgac cagcccatgg    2640
atatcctgca gattattaat tgtttgacca ctatttatga ccgcctggag caagagcaca    2700
acaatttggt caacgtccct ctctgcgtgg atatgtgtct gaactggctg ctgaatgttt    2760
atgatacggg acgaacaggg aggatccgtg tcctgtcttt taaaactggc atcatttccc    2820
tgtgtaaagc acatttggaa gacaagtaca gatacctttt caagcaagtg gcaagtcaac    2880
aggattttgt gaccagcgca ggctgggcct ccttctgcat gattctatcc aaattccaag    2940
acagttgggt gaagttgcat cctttggggg cagtaacatt gaggcaagtg tccggagctg    3000
cttccaattt gctaataata agccagagat cgaagcggcc ctcttcctag actggatgag    3060
actggaaccc cagtccatgg tgtggctgcc cgtcctgcac agagtggctg ctgcagaaac    3120
tgccaagcat caggccaaat gtaacatctg caaagagtgt ccaatcattg gattcaggta    3180
caggagtcta aagcactta attatgacat ctgccaaagc tgcttttttt ctggtcgagt    3240
tgcaaaaggc cataaaatgc actatcccat ggtggaatat tgcactccga ctacatcagg    3300
agaagatgtt cgagactttg ccaaggtact aaaaaacaaa tttcgaacca aaaggtattt    3360
tgcgaagcat ccccgaatgg gctacctgcc agtgcagact gtcttagagg gggacaacat    3420
ggaaactgac acaatgtag                                                 3439
```

<210> SEQ ID NO 15
<211> LENGTH: 8312
<212> TYPE: DNA
<213> ORGANISM: Artificial Sequence
<220> FEATURE:
<223> OTHER INFORMATION: Synthetic
<400> SEQUENCE: 15

```
cattaatgaa tcggccaacg cgcggggaga ggcggtttgc gtattgggcg ctcttccgct      60
tcctcgctca ctgactcgct gcgctcggtc gttcggctgc ggcgagcggt atcagctcac     120
tcaaaggcgg taatacggtt atccacagaa tcaggggata acgcaggaaa gaacatgtga     180
gcaaaaggcc agcaaaaggc caggaaccgt aaaaaggccg cgttgctggc gtttttccata     240 ggctccgccc cctgacgag catcacaaaa atcgacgctc aagtcagagg tggcgaaacc     300
cgacaggact ataaagatac caggcgtttc cccctggaag ctccctcgtg cgctctcctg     360
```

```
ttccgaccct gccgcttacc ggatacctgt ccgcctttct cccttcggga agcgtggcgc    420
tttctcatag ctcacgctgt aggtatctca gttcggtgta ggtcgttcgc tccaagctgg    480
gctgtgtgca cgaacccccc gttcagcccg accgctgcgc cttatccggt aactatcgtc    540
ttgagtccaa cccggtaaga cacgacttat cgccactggc agcagccact ggtaacagga    600
ttagcagagc gaggtatgta ggcggtgcta cagagttctt gaagtggtgg cctaactacg    660
gctacactag aaggacagta tttggtatct gcgctctgct gaagccagtt accttcggaa    720
aaagagttgg tagctcttga tccggcaaac aaaccaccgc tggtagcggt ggtttttttg    780
tttgcaagca gcagattacg cgcagaaaaa aaggatctca agaagatcct ttgatctttt    840
ctacggggtc tgacgctcag tggaacgaaa actcacgtta agggattttg gtcatgagat    900
tatcaaaaag gatcttcacc tagatccttt taaattaaaa atgaagtttt aaatcaatct    960
aaagtatata tgagtaaact tggtctgaca gttaccaatg cttaatcagt gaggcaccta   1020
tctcagcgat ctgtctattt cgttcatcca tagttgcctg actccccgtc gtgtagataa   1080
ctacgatacg ggagggctta ccatctggcc ccagtgctgc aatgataccg cgagacccac   1140
gctgaccggc tccagattta tcagcaataa accagccagc cggaagggcc gagcgcagaa   1200
gtggtcctgc aagtttatcc gcctccatcc agtgtattaa ttgttgccgg gaagctagag   1260
taagtagttc gccagttaat agtttgcgca acgttgttgc cattgctaca ggcatcgtgg   1320
tgtcaggctc gtcgtttggt atggcttcat tcagctccgg ttcccaacga tcaaggcgag   1380
ttacatgatc ccccatgttg tgcaaaaaag cggttagctc cttcggtcct ccgatcgttg   1440
tcagaagtaa gttggccgca gtgttatcac tcatggttat ggcagcactg cataattctc   1500
ttactgtcat gccatccgta agatgctttt ctgtgactgg tgagtactca accaagtcat   1560
tctgagaata gtgtatgcgg cgaccgagtt gctcttgccc ggcgtcaata cgggataata   1620
ccgcgccaca tagcagaact ttaaaagtgc tcatcattgg aaaacgttct cggggcgaaa   1680
aactctcaag gatcttaccg ctgttgagat ccagtcgatg taacccactc gtgcacccaa   1740
ctgatcttca gcatctttta ctttcaccag cgtttctggg tgagcaaaaa caggaaggca   1800
aaatgccgca aaaagggaa taaggcgac acggaaatgt tgatactcat actcttcctt   1860
tttcaatatt attgaagcat ttatcagggt tattgtctca tgagcggata catatttgaa   1920
tgtatttaga aaataaaca aatagggggtt ccgcgcacat ttccccgaaa agtgccacct   1980
gacgtctaag aaaccattat tatcatgaca ttaacctata aaaataggcg tatcacgagg   2040 cccttttcgtc tcgcgcgttt cggtgatgac ggtgaaaagc tctgacacat gcagctcccg   2100
gagacggtca cagcttgtct gtaagcggat gccgggagca gacaagcccg tcagggcgcg   2160
tcagcgggtg ttggcgggtg tcggggctgg cttaactatg cggcatcaga gcagattgta   2220
ctgagagtgc accatatgcg gtgtgaaata ccgcacagat gcgtaaggag aaaataccgc   2280
atcaggaatt ccaacatcca ataaatcata caggcaaggc aaagaattag caaaattaag   2340
caataaagcc tcagagcata aagctaaatc ggttgtacca aaaacattat gaccctgtaa   2400
tacttttgcg ggagaagcct ttatttcaac gcaaggataa aaattttttag aaccctcata   2460 tattttaaat gcaatgcctg agtaatgtgt aggtaaagat tcaaacgggt gagaaaggcc   2520
ggagacagtc aaatcaccat caatatgata ttcaaccgtt ctagctgata aattcatgcc   2580
ggagagggta gctattttttg agaggtctct acaaaggcta tcaggtcatt gcctgagagt   2640
ctggagcaaa caagagaatc gatgaacggt aatcgtaaaa ctagcatgtc aatcatatgt   2700
accccggttg ataatcagaa aagccccaaa aacaggaaga ttgtataagc aaatatttaa   2760
```

```
attgtaaacg ttaatatttt gttaaaattc gcgttaaatt tttgtaaatc agctcatttt    2820
ttaaccaata ggccgaaatc ggcaaaatcc cttataaatc aaaagaatag accgagatag    2880
ggttgagtgt tgttccagtt tggaacaaga gtccactatt aaagaacgtg gactccaacg    2940
tcaaagggcg aaaaaccgtc tatcagggcg atggcccact acgtgaacca tcaccctaat    3000 caagttttt ggggtcgagg tgccgtaaag cactaaatcg gaaccctaaa gggagccccc     3060
gatttagagc ttgacgggga agccggcga acgtggcgag aaaggaaggg aagaaagcga     3120
aaggagcggg cgctagggcg ctggcaagtg tagcggtcac gctgcgcgta accaccacac    3180
ccgccgcgct taatgcgccg ctacaggcg cgtactatgg ttgctttgac gagcaggtat     3240
aacgtgcttt cctcgttaga atcagagcgg gagctaaaca ggaggccgat taagggatt    3300 ttagacagga acgtacgcc agaatcctga gaagtgtttt tataatcagt gaggccaccg     3360
agtaaaagag tctgtcgatc acgcaaatta accgttgtcg caatacttct ttgattagta    3420
ataacatcac ttgcctgagt agaagaactc aaactatcgg ccttgctggt aatatccaga    3480
acaatattac cgccagccat tgcaagagga aaaacgctca tggaaatacc tacattttga    3540
cgctcaatcg tctggaattc cattcgccat tcaggctgcg caactgttgg gaagggcgat    3600
cggtgcgggc ctcttcgcta ttacgccagc tggcgcgctc gctcgctcac tgaggccgcc    3660
cgggcaaagc ccgggcgtcg ggcgaccttt ggtcgcccgg cctcagtgag cgagcgagcg    3720
cgcagagagg gagtggccaa ctccatcact aggggttcct tgtagttaat gattaacccg    3780
ccatgctact tatctacggc cgcggtaccg cgttacataa cttacggtaa atggcccgcc    3840
tggctgaccg cccaacgacc cccgcccatt gacgtcaata atgacgtatg ttcgcatagt    3900
aacgccaata gggactttcc attgacgtca atgggtggag tatttacggt aaactgccca    3960
cttggcagta catcaagtgt atcatatgcc aagtacgccc cctattgacg tcaatgacgg    4020
taaatggccc gcctggcatt atgcccagta catgacctta tgggactttc ctacttggca    4080
gtacatctac gtattagtca tcgctattac catggtgatg cggttttggc agtacatcaa    4140
tgggcgtgga tagcggtttg actcacgggg atttccaagt ctccaccca ttgacgtcaa      4200 tgggagtttg ttttggcacc aaaatcaacg ggactttcca aaatgtcgta acaactccgc    4260
cccattgacg caaatgggcg gtaggcgtgt acggtgggag gtctatataa gcagagctcg    4320
tttagtgaac cgtctagacg gccgcggttt tttttatcgc tgccttgata tacactttcc    4380
accatgcttt ggtgggaaga agtagaggac tgttatgaaa gagaagatgt tcaaaagaaa    4440
acattcacaa aatgggtaaa tgcacaattt tctaagtttg ggaagcagca tattgagaac    4500
ctcttcagtg acctacagga tgggaggggc ctcctagacc tcctcgaagg cctgacaggg    4560
caaaaactgc caaagaaaa aggatccaca agagttcatg ccctgaacaa tgtcaacaag    4620
gcactgcggg ttttgcagaa caataatgtt gatttagtga atattggaag tactgacatc    4680
gtagatggaa atcataaact gactcttggt ttgatttgga atataatcct ccactggcag    4740
gtcaaaaatg taatgaaaaa tatcatggct ggattgcaac aaaccaacag tgaaaagatt    4800
ctcctgagct gggtccgaca atcaactcgt aattatccac aggttaatgt aatcaacttc    4860
accaccagct ggtctgatgg cctggctttg aatgctctca tccatagtca taggccagac    4920
ctatttgact ggaatagtgt ggtttgccag cagtcagcca cacaacgact ggaacatgca    4980
ttcaacatcg ccagatatca attaggcata gagaaactac tcgatcctga agatgttgat    5040
accacctatc cagataagaa gtccatctta atgtacatca catcactctt ccaagttttg    5100
```

```
cctcaacaag tgagcattga agccatccag gaagtggaaa tgttgccaag gccacctaaa    5160
gtgactaaag aagaacattt tcagttacat catcaaatgc actattctca acagatcacg    5220
gtcagtctag cacagggata tgagagaact tcttccccta agcctcgatt caagagctat    5280
gcctacacac aggctgctta tgtcaccacc tctgaccta cacggagccc atttccttca     5340
cagcatttgg aagctcctga agacaagtca tttggcagtt cattgatgga gagtgaagta    5400
aacctggacc gttatcaaac agcttttagaa gaagtattat cgtggcttct ttctgctgag   5460
gacacattgc aagcacaagg agagatttct aatgatgtgg aagtggtgaa agaccagttt    5520
catactcatg aggggtacat gatggatttg acagcgcatc agggccgggt tggtaatatt    5580
ctacaattgg gaagtaagct gattggaaca ggaaaattat cagaagatga agaaactgaa    5640
gtacaagagc agatgaatct cctaaattca agatgggaat gcctcagggt agctagcatg    5700
gaaaaacaaa gcaatttaca tagagaaatt tcttatgtgc cttctactta tttgactgaa    5760
atcactcatg tctcacaagc cctattagaa gtgaacaac ttctcaatgc tcctgacctc     5820
tgtgctaagg actttgaaga tctctttaag caagaggagt ctctgaagaa tataaaagat    5880
agtctacaac aaagctcagg tcggattgac attattcata gcaagaagac agcagcattg    5940
caaagtgcaa cgcctgtgga aagggtgaag ctacaggaag ctctctccga gcttgatttc    6000
caatgggaaa aagttaacaa aatgtacaag gaccgacaag ggcgatttga cagatctgtt    6060
gagaaatggc ggcgttttca ttatgatata agatattta atcagtggct aacagaagct     6120
gaacagtttc tcagaaagag acaaattcct gagaattggg aacatgctaa atacaaatgg    6180
tatcttaagg aactccagga tggcattggg cagcggcaaa ctgttgtcag aacattgaat    6240
gcaactgggg aagaaataat tcagcaatcc tcaaaaacag atgccagtat tctacaggaa    6300
aaattgggaa gcctgaatct gcggtggcag gaggtctgca aacagctgtc agacagaaaa    6360
aagaggctag aagaaaccct tgaaagactc caggaacttc aagaggccac ggatgaggtg    6420
gacctcaagc tgcgccaagc tgaggtgatc aagggatcct ggcagcccgt gggcgatctc    6480
ctcattgact ctctccaaga tcacctcgag aaagtcaagg cacttcgagg agaaattgcg    6540
cctctgaaag agaacgtgag ccacgtcaat gaccttgctc gccagcttac cactttgggc    6600
attcagctct caccgtataa cctcagcact ctggaagacc tgaacaccag atggaagctt    6660
ctgcaggtgg ccgtcgagga ccgagtcagg cagctgcatg aagcccacag ggactttggt    6720
ccagcatctc agcactttct ttccacgtct gtccagggtc cctgggagag agccatctcg    6780
ccaaacaaag tgccctacta tatcaaccac gagactcaaa caacttgctg ggaccatccc    6840
aaaatgacag agctctacca gtctttagct gacctgaata atgtcagatt ctcagcttat    6900
aggactgcca tgaaactccg aagactgcag aaggcccttt gcttggatct cttgagcctg    6960
tcagctgcat gtgatgcctt ggaccagcac aacctcaagc aaaatgacca gcccatggat    7020
atcctgcaga ttattaattg tttgaccact atttatgacc gcctggagca agagcacaac    7080
aatttggtca acgtccctct ctgcgtggat atgtgtctga actggctgct gaatgtttat    7140
gatacgggac gaacagggag gatccgtgtc ctgtcttta aaactggcat catttccctg     7200
tgtaaagcac atttggaaga caagtacaga taccttttca gcaagtggc aagttcaaca    7260 ggattttgtg accagcgcag gctgggcctc cttctgcatg attctatcca aattccaaga    7320
cagttgggtg aagttgcatc ctttgggggc agtaacattg agccaagtgt ccggagctgc    7380
ttccaatttg ctaataataa gccagagatc gaagcggccc tcttcctaga ctggatgaga    7440
ctggaacccc agtccatggt gtggctgccc gtcctgcaca gagtggctgc tgcagaaact    7500
```

| | |
|---|---:|
| gccaagcatc aggccaaatg taacatctgc aaagagtgtc caatcattgg attcaggtac | 7560 |
| aggagtctaa agcactttaa ttatgacatc tgccaaagct gcttttttc tggtcgagtt | 7620 |
| gcaaaaggcc ataaaatgca ctatcccatg gtggaatatt gcactccgac tacatcagga | 7680 |
| gaagatgttc gagactttgc caaggtacta aaaaacaaat ttcgaaccaa aaggtatttt | 7740 |
| gcgaagcatc cccgaatggg ctacctgcca gtgcagactg tcttagaggg ggacaacatg | 7800 |
| gaaactgaca caatgtagga agtcttttcc acatggcaga tgatttgggc agagcgatgg | 7860 |
| agtccttagt atcagtcatg acagatgaag aaggagcaga ataaatgttt tacaactcct | 7920 |
| gattcccgca tgcggccgat ccagacatga taagatacat tgatgagttt ggacaaacca | 7980 |
| caactagaat gcagtgaaaa aaatgcttta tttgtgaaat ttgtgatgct attgctttat | 8040 |
| ttgtaaccat tataagctgc aataaacaag ttaacaacaa caattgcatt cattttatgt | 8100 |
| ttcaggttca gggggaggtg tgggaggttt tttgcggccg tagataagta gcatggcggg | 8160 |
| ttaatcatta actacaagga acccctagtg atggagttgg ccactccctc tctgcgcgct | 8220 |
| cgctcgctca ctgaggccgg gcgaccaaag gtcgcccgac gcccgggctt tgcccgggcg | 8280 |
| gcctcagtga gcgagcgagc gcgcagctgc tg | 8312 |

<210> SEQ ID NO 16
<211> LENGTH: 8293
<212> TYPE: DNA
<213> ORGANISM: Artificial Sequence
<220> FEATURE:
<223> OTHER INFORMATION: Synthetic

<400> SEQUENCE: 16

| | |
|---|---:|
| cattaatgaa tcggccaacg cgcggggaga ggcggtttgc gtattgggcg ctcttccgct | 60 |
| tcctcgctca ctgactcgct gcgctcggtc gttcggctgc ggcgagcggt atcagctcac | 120 |
| tcaaaggcgg taatacggtt atccacagaa tcaggggata acgcaggaaa gaacatgtga | 180 |
| gcaaaaggcc agcaaaaggc caggaaccgt aaaaaggccg cgttgctggc gtttttccat | 240 |
| aggctccgcc cccctgacga gcatcacaaa aatcgacgct caagtcagag gtggcgaaac | 300 |
| ccgacaggac tataaagata ccaggcgttt ccccctggaa gctccctcgt gcgctctcct | 360 |
| gttccgaccc tgccgcttac cggatacctg tccgcctttc tcccttcggg aagcgtggcg | 420 |
| ctttctcata gctcacgctg taggtatctc agttcggtgt aggtcgttcg ctccaagctg | 480 |
| ggctgtgtgc acgaaccccc cgttcagccc gaccgctgcg ccttatccgg taactatcgt | 540 |
| cttgagtcca acccggtaag acacgactta tcgccactgg cagcagccac tggtaacagg | 600 |
| attagcagag cgaggtatgt aggcggtgct acagagttct tgaagtggtg gcctaactac | 660 |
| ggctacacta gaaggacagt atttggtatc tgcgctctgc tgaagccagt taccttcgga | 720 |
| aaaagagttg gtagctcttg atccggcaaa caaaccaccg ctggtagcgg tggttttttt | 780 |
| gtttgcaagc agcagattac gcgcagaaaa aaaggatctc aagaagatcc tttgatcttt | 840 |
| tctacggggt ctgacgctca gtggaacgaa aactcacgtt aagggatttt ggtcatgaga | 900 |
| ttatcaaaaa ggatcttcac ctagatcctt ttaaattaaa aatgaagttt taaatcaatc | 960 |
| taaagtatat atgagtaaac ttggtctgac agttaccaat gcttaatcag tgaggcacct | 1020 |
| atctgagcga tctgtctatt tcgttcatcc atagttgcct gactccccgt cgtgtagata | 1080 |
| actacgatac gggagggctt accatctggc cccagtgctg caatgatacc gcgagaccca | 1140 |
| cgctgaccgg ctccagattt atcagcaata aaccagccag ccggaagggc cgagcgcaga | 1200 |

```
agtggtcctg caactttatc cgcctccatc cagtctatta attgttgccg ggaagctaga    1260
gtaagtagtt cgccagttaa tagtttgcgc aacgttgttg ccattgctac aggcatcgtg    1320
gtgtcacgct cgtcgtttgg tatggcttca ttcagctccg gttcccaacg atcaaggcga    1380
gttacatgat cccccatgtt gtgcaaaaaa gcggttagct ccttcggtcc tccgatcgtt    1440
gtcagaagta agttggccgc agtgttatca ctcatggtta tggcagcact gcataattct    1500
cttactgtca tgccatccgt aagatgcttt tctgtgactg gtgagtactc aaccaagtca    1560
ttctgagaat agtgtatgcg gcgaccgagt tgctcttgcc cggcgtcaat aggggataat    1620
accgcgccac atagcagaac tttaaaagtg ctcatcattg gaaaacgttc ttcggggcga    1680
aaactctcaa ggatcttacc gctgttgaga tccagttcga tgtaacccac tcgtgcaccc    1740
aactgatctt cagcatcttt tactttcacc agcgtttctg ggtgagcaaa aacaggaagg    1800
caaaatgccg caaaaaaggg aataagggcg acacggaaat gttgaatact catactcttc    1860 cttttcaat attattgaag catttatcag ggttattgtc tcatgagcgg atacatattt     1920
gaatgtattt agaaaaataa acaaataggg gttccgcgca catttccccg aaaagtgcca    1980
cctgacgtct aagaaaccat tattatcatg acattaacct ataaaaatag gcgtatcacg    2040
aggccctttc gtctcgcgcg tttcggtgat gacggtgaaa acctctgaca catgcagctc    2100
ccggagacgg tcacagcttg tctgtaagcg gatgccggga gcagacaagc ccgtcagggc    2160
gcgtcagcgg gtgttggcgg gtgtcggggc tggcttaact atgcggcatc agagcagatt    2220
gtactgagag tgcaccatat gcggtgtgaa ataccgcaca gatgcgtaag gagaaaatac    2280
cgcatcagga attccaacat ccaataaatc atacaggcaa ggcaaagaat tagcaaaatt    2340
aagcaataaa gcctcagagc ataaagctaa atcggttgta ccaaaaacat tatgaccctg    2400
taatactttt gcgggagaag cctttatttc aacgcaagga taaaatttt tagaaccctc     2460 atatatttta aatgcaatgc ctgagtaatg tgtaggtaaa gattcaaacg ggtgagaaag    2520
gccggagaca gtcaaatcac catcaatatg atattcaacc gttctagctg ataaattcat    2580
gccggagagg gtagctattt tgagaggtc tctacaaagg ctatcaggtc attgcctgag     2640
agtctggagc aaacaagaga atcgatgaac ggtaatcgta aaactagcat gtcaatcata    2700
tgtaccccgg ttgataatca gaaaagcccc aaaaacagga agattgtata agcaaatatt    2760
taaattgtaa acgttaatat tttgttaaaa ttcgcgttaa attttttgtta aatcagctca    2820 ttttttaacc aataggccga aatcggcaaa atcccttata aatcaaaaga atagaccgag    2880
atagggttga gtgttgttcc agtttggaac aagagtccac tattaaagaa cgtggactcc    2940
aacgtcaaag ggcgaaaaac cgtctatcag ggcgatggcc cactacgtga accatcaccc    3000
taatcaagtt ttttggggtc gaggtgccgt aaagcactaa atcggaaccc taaagggagc    3060
ccccgattta gagcttgacg gggaaagccg gcgaacgtgg cgagaaagga agggaagaaa    3120
gcgaaaggag cgggcgctag ggcgctggca agtgtagcgg tcacgctgcg cgtaaccacc    3180
acacccgccg cgcttaatgc gccgctacag ggcgcgtact atggttgctt tgacgagcac    3240
gtataacgtg ctttcctcgt tagaatcaga gcgggagcta acaggaggc cgattaaagg     3300 gattttagac aggaacggta cgccagaatc ctgagaagtg ttttttataat cagtgaggcc    3360 accgagtaaa agagtctgtc catcacgcaa attaaccgtt gtcgcaatac ttcttgatta    3420
gtaataacat cacttgcctg agtagaagaa ctcaaactat cggccttgct ggtaatatcc    3480
agaacaatat taccgccagc cattgcaaca ggaaaaacgc tcatggaaat acctacattt    3540
tgacgctcaa tcgtctggaa ttccattcgc cattcaggct gcgcaactgt tgggaagggc    3600
```

```
gatcggtgcg ggcctcttcg ctattacgcc agctggcgcg ctcgctcgct cactgaggcc   3660
gccggggcaa agcccgggcg tcgggcgacc tttggtcgcc cggcctcagt gagcgagcga   3720
gcgcgcagag agggagtggc caactccatc actaggggtt ccttgtagtt aatgattaac   3780
ccgccatgct acttatctac ggccgcggta ccactcacgg ggatttccaa gtctccaccc   3840
cattgacgtc aatgggagtt tgttttggca ccaaaatcaa cgggactttc caaaatgtcg   3900
taataacccc gccccgttga cgcaaatggg cggtaggcgt gtacggtggg aggtctatat   3960
aagcagagct cgtttagtga accgtctcta gacggccgcg ttttttttta tcgctgcctt   4020
gatatacact ttccaccatg ctttggtggg aagaagtaga ggactgttat gaaagagaag   4080
atgttcaaaa gaaacattc acaaaatggg taaatgcaca attttctaag tttgggaagc    4140
agcatattga gaacctcttc agtgacctac aggatgggag gcgcctccta gacctcctcg   4200
aaggcctgac agggcaaaaa ctgccaaaag aaaaggatc cacaagagtt catgccctga    4260
acaatgtcaa caaggcactg cgggttttgc agaacaataa tgttgattta gtgaatattg   4320
gaagtactga catcgtagat ggaaatcata aactgactct tggtttgatt tggaatataa   4380
tcctccactg gcaggtcaaa aatgtaatga aaaatatcat ggctggattg caacaaacca   4440
acagtgaaaa gattctcctg agctgggtcc gacaatcaac tcgtaattat ccacaggtta   4500
atgtaatcaa cttcaccacc agctggtctg atggcctggc tttgaatgct ctcatccata   4560
gtcataggcc agacctattt gactggaata gtgtggtttg ccagcagtca gccacacaac   4620
gactggaaca tgcattcaac atcgccagat atcaattagg catagagaaa ctactcgatc   4680
ctgaagatgt tgataccacc tatccagata agaagtccat cttaatgtac atcacatcac   4740
tcttccaagt tttgcctcaa caagtgagca ttgaagccat ccaggaagtg gaaatgttgc   4800
caaggccacc taaagtgact aaagaagaac attttcagtt acatcatcaa atgcactatt   4860
ctcaacagat cacggtcagt ctagcacagg gatatgagag aagttcttcc cctaagcctc   4920
gattcaagag ctatgcctac acacaggctg cttatgtcac cacctctgac cctacacgga   4980
gcccatttcc ttcacagcat ttggaagctc ctgaagacaa gtcatttggc agttcattga   5040
tggagagtga agtaaacctg gaccgttatc aaacagcttt agaagaagta ttatcgtggc   5100
ttctttctgc tgaggacaca ttgcaagcac aaggagagat ttctaatgat gtggaagtgg   5160
tgaaagacca gtttcatact catgagggt acatgatgga tttgacagcc catcagggcc    5220
gggttggtaa tattctacaa ttgggaagta agctgattgg aacaggaaaa ttatcagaag   5280
atgaagaaac tgaagtacaa gagcagatga atctcctaaa ttcaagatgg gaatgcctca   5340
gggtagctag catggaaaaa caaagcaatt tacatagagt tttaatggat ctccagaatc   5400
agaaactgaa agagttgaat gactggctaa caaaaacaga agaagaaca aggaaaatgg    5460 aggaagagcc tcttggacct gatcttgaag acctaaaacg gcaagtacaa caacataagg   5520
tgcttcaaga agatcagaa caagaacaag tcagggtcaa ttctctcact cacatggtgg    5580
tggtagttga tgaatctagt ggagatcacg caactgctgc tttggaagaa caacttaagg   5640
tattgggaga tcgatgggca acatctgta gatggacaga agaccgctgg gttctttta     5700 aagacgaaat ttcttatgtg ccttctactt atttgactga aatcactcat gtctcacaag   5760
ccctattaga agtggaacaa cttctcaatg ctcctgacct ctgtgctaag gactttgaag   5820
atctctttaa gcaagaggag tctctgaaga atataaaaga tagtctacaa caaagctcag   5880
gtcggattga cattattcat agcaagaaga cagcagcatt gcaaagtgca acgcctgtgg   5940
```

```
aaagggtgaa gctacaggaa gctctctccc agcttgattt ccaatgggaa aaagttaaca      6000
aaatgtacaa ggaccgacaa gggcgatttg acagatctgt tgagaaatgg cggcgttttc      6060
attatgatat aaagatattt aatcagtggc taacagaagc tgaacagttt ctcagaaaga      6120
cacaaattcc tgagaattgg gaacatgcta aatacaaatg gtatcttaag gaactccagg      6180
atggcattgg gcagcggcaa actgttgtca gaacattgaa tgcaactggg gaagaaataa      6240
ttcagcaatc gtcaaaaaca gatgccagta ttctacagga aaaattggga agcctgaatc      6300
tgcggtggca ggaggtctgc aaacagctgt cagacagaaa aagaggcta aagaaaccc      6360 ttgaaagact ccaggaactt caagaggcca cggatgagct ggacctcaag ctgcgccaag      6420
ctgaggtgat caagggatcc tggcagcccg tgggcgatct cctcattgac tctctccaag      6480
atcacctcga gaaagtcaag gcacttcgag gagaaattgc gcctctgaaa gagaacgtga      6540
gccacgtcaa tgaccttgct cgccagctta ccactttggg cattcaggtc tcacggtata      6600
acctcagcac tctggaagac ctgaacacca gatggaagct tctgcaggtg gccgtcgagg      6660
accgagtcag gcagctgcat gaagcccaca gggactttgg tccagcatct cagcactttc      6720
tttccacgtc tgtccagggt ccctgggaga gagccatctc gccaaacaaa gtgccctact      6780
atatcaacca cgagactcaa acaacttgct gggaccatcc caaaatgaca gagctctacc      6840
agtctttagc tgacctgaat aatgtcagat tctcagctta taggactgcc atgaaactcc      6900
gaagactgca gaaggccctt tgcttggatc tcttgagcct gtcagctgca tgtgatgcct      6960
tggaccagca aacctcaag caaaatgacc agcccatgga tatcctgcag attattaatt      7020
gtttgaccac tatttatgac cgcctggagc aagagcacaa caatttggtc aacgtccctc      7080
tctgcgtgga tatgtgtctg aactggctgc tgaatgttta tgatacggga cgaacaggga      7140
ggatccgtgt cctgtctttt aaaactggca tcatttccct gtgtaaagca catttggaag      7200
acaagtacag ataccttttc aagcaagtgg caagttcaac aggattttgt gaccagcgca      7260
ggctgggcct cctctgcat gattctatcc aaattccaag acagttgggt gaagttgcat      7320
cctttggggg cagtaacatt gagccaagtg tccggagctg cttccaattt gctaataata      7380
agccagagat cgaagcggcc ctcttcctag actggatgag actggaaccg cagtccatgg      7440
tgtggctgcc cgtcctgcac agagtggctg ctgcagaaac tgccaagcat caggccaaat      7500
gtaacatctg caaagagtgt ccaatcattg gattcaggta caggagtcta aagcacttta      7560
attatgacat ctgccaaagc tgcttttttt ctggtcgagt tgcaaaaggc cataaaatgc      7620
actatcccat ggtggaatat tgcactccga ctacatcagg agaagatgtt cgagactttg      7680
ccaaggtact aaaaaacaaa tttcgaacca aaaggtattt tgcgaagcat ccccgaatgg      7740
gctacctgcc agtgcagact gtcttagagg gggacaacat ggaaactgac acaatgtagg      7800
aagtcttttc cacatggcag atgatttggg cagagcgatg gagtccttag tatcagtcat      7860
gacagatgaa gaaggagcag aataaatgtt ttacaactcc tgattcccgc atgcggccga      7920
tccagacatg ataagataca ttgatgagtt tggacaaacc acaactagaa tgcagtgaaa      7980
aaaatgcttt atttgtgaaa tttgtgatgc tattgcttta tttgtaacca ttataagctg      8040
caataaacaa gttaacaaca acaattgcat tcattttatg tttcaggttc agggggaggt      8100
gtgggaggtt ttttgcggcc gtagataagt agcatggcgg gttaatcatt aactacaagg      8160
aacccctagt gatggagttg gccactccct ctctgcgcgc tcggtcgctc actgaggccg      8220
ggcgaccaaa ggtcgcccga cgcccgggct tgcccgggc ggcctcagtg agcgagcgag      8280
cgcgcagctg ctg                                                        8293
```

<210> SEQ ID NO 17
<211> LENGTH: 756
<212> TYPE: DNA
<213> ORGANISM: Homo sapiens

<400> SEQUENCE: 17

```
atgctttggt gggaagaagt agaggactgt tatgaaagag aagatgttca aaagaaaaca      60
ttcacaaaat gggtaaatgc acaattttct aagtttggga agcagcatat tgagaacctc     120
ttcagtgacc tacaggatgg gaggcgcctc ctagacctcc tcgaaggcct gacagggcaa     180
aaactgccaa agaaaaagg atccacaaga gttcatggcc tgaacaatgt caacaaggca     240
ctgcgggttt tgcagaacaa taatgttgat ttagtgaata ttggaagtac tgacatcgta     300
gatggaaatc ataaactgac tcttggtttg atttggaata taatcctcca ctggcaggtc     360
aaaaatgtaa tgaaaatat catggctgga ttgcaacaaa ccaacagtga aaagattctc     420
ctgagctggg tccgacaatc aactcgtaat tatccacagg ttaatgtaat caacttcacc     480
accagctggt ctgatggcct ggctttgaat gctctcatcc atagtcatag ccagaccta      540
tttgactgga atagtgtggt ttgccagcag tcagccacac aacgactgga acatgcattc     600
aacatcgcca gatatcaatt aggcatagag aaactactcg atcctgaaga tgttgatacc     660
acctatccag ataagaagtc catcttaatg tacatcacat cactcttcca agttttgcct     720
caacaagtga gcattgaagc catccaggaa gtggaa                               756
```

<210> SEQ ID NO 18
<211> LENGTH: 252
<212> TYPE: DNA
<213> ORGANISM: Homo sapiens

<400> SEQUENCE: 18

```
atgttgccaa ggccacctaa agtgactaaa gaagaacatt ttcagttaca tcatcaaatg      60
cactattctc aacagatcac ggtcagtcta gcacagggat atgagagaac ttcttcccct     120
aagcctcgat tcaagagcta tgcctacaca caggctgctt atgtcaccac ctctgaccct     180
acacggagcc catttccttc acagcatttg gaagctcctg aagacaagtc atttggcagt     240
tcattgatgg ag                                                         252
```

<210> SEQ ID NO 19
<211> LENGTH: 333
<212> TYPE: DNA
<213> ORGANISM: Homo sapiens

<400> SEQUENCE: 19

```
agtgaagtaa acctggaccg ttatcaaaca gctttagaag aagtattatc gtggcttctt      60
tctgctgagg acacattgca agcacaagga gagatttcta atgatgtgga agtggtgaaa     120
gaccagtttc atactcatga ggggtacatg atggatttga cagcccatca gggccgggtt     180
ggtaatattc tacaattggg aagtaagctg attggaacag aaaattatc agaagatgaa     240
gaaactgaag tacaagagca gatgaatctc ctaaattcaa gatgggaatg cctcagggta     300
gctagcatgg aaaaacaaag caatttacat aga                                  333
```

<210> SEQ ID NO 20
<211> LENGTH: 327
<212> TYPE: DNA
<213> ORGANISM: Homo sapiens

```
<400> SEQUENCE: 20
gttttaatgg atctccagaa tcagaaactg aaagagttga atgactggct aacaaaaaca    60
gaagaaagaa caaggaaaat ggaggaagag cctcttggac ctgatcttga agacctaaaa   120
cgccaagtac aacaacataa ggtgcttcaa gaagatctag aacaagaaca agtcagggtc   180
aattctctca ctcacatggt ggtggtagtt gatgaatcta gtggagatca cgcaactgct   240
gctttggaag aacaacttaa ggtattggga gatcgatggg caaacatctg tagatggaca   300
gaagaccgct gggttctttt acaagac                                       327

<210> SEQ ID NO 21
<211> LENGTH: 333
<212> TYPE: DNA
<213> ORGANISM: Homo sapiens

<400> SEQUENCE: 21
atccttctca aatggcaacg tcttactgaa gaacagtgcc ttttagtgc  atggctttca    60 gaaaagaag  atgcagtgaa caagattcac acaactggct ttaaagatca aaatgaaatg   120
ttatcaagtc ttcaaaaact ggccgtttta aagcggatc  tagaaaagaa aaagcaatcc   180
atgggcaaac tgtattcact caaacaagat cttctttcaa cactgaagaa taagtcagtg   240
acccagaaga cggaagcatg gctggataac tttgcccggt gttgggataa tttagtccaa   300
aaacttgaaa agagtacagc acagatttca cag                                333

<210> SEQ ID NO 22
<211> LENGTH: 150
<212> TYPE: DNA
<213> ORGANISM: Homo sapiens

<400> SEQUENCE: 22
gctgtcacca ccactcagcc atcactaaca cagacaactg taatggaaac agtaactacg    60
gtgaccacaa gggaacagat cctggtaaag catgctcaag aggaacttcc accaccacct   120
ccccaaaaga agaggcagat tactgtggat                                    150

<210> SEQ ID NO 23
<211> LENGTH: 262
<212> TYPE: DNA
<213> ORGANISM: Homo sapiens

<400> SEQUENCE: 23
tctgaaatta ggaaaaggtt ggatgttgat ataactgaac ttcacagctg gattactcgc    60
tcagaagctg tgttgcagag tcctgaattt gcaatctttc ggaaggaagg caacttctca   120
gacttaaaag aaaagtcaa  tgccatagag cgagaaaaag ctgagaagtt cagaaaactg   180
caagatgcca gcagatcagc tcaggccctg gtggaacaga tggtgaatga gggtgttaat   240
gcagatagca tcaaacaagc ct                                            262

<210> SEQ ID NO 24
<211> LENGTH: 389
<212> TYPE: DNA
<213> ORGANISM: Homo sapiens

<400> SEQUENCE: 24
cagaacaact gaacagccgg tggatcgaat tctgccagtt gctaagtgag agacttaact    60
ggctggagta tcagaacaac atcatcgctt tctataatca gctacaacaa ttggagcaga   120
tgacaactac tgctgaaaac tggttgaaaa tccaacccac caccccatca gagccaacag   180
```

| | |
|---|---|
| caattaaaag tcagttaaaa atttgtaagg atgaagtcaa ccggctatca ggtcttcaac | 240 |
| ctcaaattga acgattaaaa attcaaagca tagccctgaa agagaaagga caaggaccca | 300 |
| tgttcctgga tgcagacttt gtggccttta caaatcattt taagcaagtc ttttctgatg | 360 |
| tgcaggccag agagaaagag ctacagaca | 389 |

<210> SEQ ID NO 25
<211> LENGTH: 333
<212> TYPE: DNA
<213> ORGANISM: Homo sapiens

<400> SEQUENCE: 25

| | |
|---|---|
| atttttgaca ctttgccacc aatgcgctat caggagacca tgagtgccat caggacatgg | 60 |
| gtccagcagt cagaaaccaa actctccata cctcaactta gtgtcaccga ctatgaaatc | 120 |
| atggagcaga gactcgggga attgcaggct ttacaaagtt ctctgcaaga gcaacaaagt | 180 |
| ggcctatact atctcagcac cactgtgaaa gagatgtcga agaaagcgcc ctctgaaatt | 240 |
| agccggaaat atcaatcaga atttgaagaa attgagggac gctggaagaa gctctcctcc | 300 |
| cagctggttg agcattgtca aaagctagag gag | 333 |

<210> SEQ ID NO 26
<211> LENGTH: 327
<212> TYPE: DNA
<213> ORGANISM: Homo sapiens

<400> SEQUENCE: 26

| | |
|---|---|
| caaatgaata aactccgaaa aattcagaat cacatacaaa ccctgaagaa atggatggct | 60 |
| gaagttgatg ttttttctgaa ggaggaatgg cctgcccttg gggattcaga aattctaaaa | 120 |
| aagcagctga acagtgcag acttttagtc agtgatattc agacaattca gcccagtcta | 180 |
| aacagtgtca atgaaggtgg gcagaagata aagaatgaag cagagccaga gtttgcttcg | 240 |
| agacttgaga cagaactcaa agaacttaac actcagtggg atcacatgtg ccaacaggtc | 300 |
| tatgccagaa aggaggcctt gaaggga | 327 |

<210> SEQ ID NO 27
<211> LENGTH: 327
<212> TYPE: DNA
<213> ORGANISM: Homo sapiens

<400> SEQUENCE: 27

| | |
|---|---|
| ggtttggaga aaactgtaag cctccagaaa gatctatcag agatgcacga atggatgaca | 60 |
| caagctgaag aagagtatct tgagagagat tttgaatata aaactccaga tgaattacag | 120 |
| aaagcagttg aagagatgaa gagagctaaa gaagaggccc aacaaaaaga agcgaaagtg | 180 |
| aaactcctta ctgagtctgt aaatagtgtc atagctcaag ctccacctgt agcacaagag | 240 |
| gccttaaaaa aggaacttga aactctaacc accaactacc agtggctctg cactaggctg | 300 |
| aatgggaaat gcaagacttt ggaagaa | 327 |

<210> SEQ ID NO 28
<211> LENGTH: 312
<212> TYPE: DNA
<213> ORGANISM: Homo sapiens

<400> SEQUENCE: 28

| | |
|---|---|
| gtttgggcat gttggcatga gttattgtca tacttggaga aagcaaacaa gtggctaaat | 60 |

```
gaagtagaat ttaaacttaa aaccactgaa acattcctg gcggagctga ggaaatctct    120
gaggtgctag attcacttga aaatttgatg cgacattcag aggataaccc aaatcagatt    180
cgcatattgg cacagaccct aacagatggc ggagtcatgg atgagctaat caatgaggaa    240
cttgagacat ttaattctcg ttggagggaa ctacatgaag aggctgtaag gaggcaaaag    300
ttgcttgaac ag                                                        312

<210> SEQ ID NO 29
<211> LENGTH: 288
<212> TYPE: DNA
<213> ORGANISM: Homo sapiens

<400> SEQUENCE: 29
agcatccagt ctgcccagga gactgaaaaa tccttacact taatccagga gtccctcaca     60
ttcattgaca agcagttggc agcttatatt gcagacaagg tggacgcagc tcaaatgcct    120
caggaagccc agaaaatcca atctgatttg acaagtcatg agatcagttt agaagaaatg    180
aagaaacata atcaggggaa ggaggctgcc caaagagtcc tgtctcagat tgatgttgca    240
cagaaaaaat acaagatgt ctccatgaag tttcgattat ccagaaaa                  288

<210> SEQ ID NO 30
<211> LENGTH: 315
<212> TYPE: DNA
<213> ORGANISM: Homo sapiens

<400> SEQUENCE: 30
ccagccaatt ttgagctgcg tctacaagaa agtaagatga ttttagatga agtgaagatg     60
cacttgcctg cattggaaac aaagagtgtg gaacaggaag tagtacagtc acagctaaat    120
cattgtgtga acttgtataa aagtctgagt gaagtgaagt ctgaagtgga aatggtgata    180
aagactggac gtcagattgt acagaaaaag cagacggaaa atcccaaaga acttgatgaa    240
agagtaacag ctttgaaatt gcattataat gagctgggag caaaggtaac agaaagaaag    300
caacagttgg agaaa                                                     315

<210> SEQ ID NO 31
<211> LENGTH: 324
<212> TYPE: DNA
<213> ORGANISM: Homo sapiens

<400> SEQUENCE: 31
tgcttgaaat tgtcccgtaa gatgcgaaag gaaatgaatg tcttgacaga atggctggca     60
gctacagata tggaattgac aaagagatca gcagttgaag gaatgcctag taatttggat    120
tctgaagttg cctggggaaa ggctactcaa aaagagattg agaaacagaa ggtgcacctg    180
aagagtatca cagaggtagg agaggccttg aaaacagttt tgggcaagaa ggagacgttg    240
gtggaagata aactcagtct tctgaatagt aactggatag ctgtcacctc ccgagcagaa    300
gagtggttaa atcttttgtt ggaa                                           324

<210> SEQ ID NO 32
<211> LENGTH: 306
<212> TYPE: DNA
<213> ORGANISM: Homo sapiens

<400> SEQUENCE: 32
taccagaaac acatggaaac ttttgaccag aatgtggacc acatcacaaa gtggatcatt     60
caggctgaca cacttttgga tgaatcagag aaaaagaaac cccagcaaaa agaagacgtg    120
```

```
cttaagcgtt taaaggcaga actgaatgac atacgcccaa aggtggactc tacacgtgac      180
caagcagcaa acttgatggc aaaccgcggt gaccactgca ggaaattagt agagccccaa      240
atctcagagc tcaaccatcg atttgcagcc atttcacaca gaattaagac tggaaaggcc      300
tccatt                                                                306
```

<210> SEQ ID NO 33
<211> LENGTH: 288
<212> TYPE: DNA
<213> ORGANISM: Homo sapiens

<400> SEQUENCE: 33

```
cctttgaagg aattggagca gtttaactca gatatacaaa aattgcttga accactggag       60
gctgaaattc agcaggggt gaatctgaaa gaggaagact tcaataaaga tatgaatgaa      120
gacaatgagg gtactgtaaa agaattgttg caaagaggag acaacttaca acaaagaatc      180
acagatgaga gaaagagaga ggaaataaag ataaaacagc agctgttaca gacaaaacat      240
aatgctctca aggatttgag gtctcaaaga agaaaaaagg ctctagaa                  288
```

<210> SEQ ID NO 34
<211> LENGTH: 297
<212> TYPE: DNA
<213> ORGANISM: Homo sapiens

<400> SEQUENCE: 34

```
atttctcatc agtggtatca gtacaagagg caggctgatg atctcctgaa atgcttggat       60
gacattgaaa aaaattagc cagcctacct gagcccagag atgaaaggaa aataaaggaa      120
attgatcggg aattgcagaa gaagaaagag gagctgaatg cagtgcgtag gcaagctgag      180
ggcttgtctg aggatggggc cgcaatggca gtggagccaa ctcagatcca gctcagcaag      240
cgctggcggg aaattgagag caaatttgct cagtttcgaa gactcaactt tgcacaa       297
```

<210> SEQ ID NO 35
<211> LENGTH: 384
<212> TYPE: DNA
<213> ORGANISM: Homo sapiens

<400> SEQUENCE: 35

```
attcacactg tccgtgaaga aacgatgatg gtgatgactg aagacatgcc tttggaaatt       60
tcttatgtgc cttctactta tttgactgaa atcactcatg tctcacaagc cctattagaa      120
gtggaacaac ttctcaatgc tcctgacctc tgtgctaagg actttgaaga tctctttaag      180
caagaggagt ctctgaagaa tataaaagat agtctacaac aaagctcagg tcggattgac      240
attattcata gcaagaagac agcagcattg caaagtgcaa cgcctgtgga aagggtgaag      300
ctacaggaag ctctctccca gcttgatttc caatgggaaa agttaacaa aatgtacaag      360 gaccgacaag ggcgatttga caga                                            384
```

<210> SEQ ID NO 36
<211> LENGTH: 321
<212> TYPE: DNA
<213> ORGANISM: Homo sapiens

<400> SEQUENCE: 36

```
tctgttgaga aatggcggcg ttttcattat gatataaaga tatttaatca gtggctaaca       60
gaagctgaac agtttctcag aaagacacaa attcctgaga attgggaaca tgctaaatac      120
```

```
aaatggtatc ttaaggaact ccaggatggc attgggcagc ggcaaactgt tgtcagaaca      180
ttgaatgcaa ctggggaaga aataattcag caatcctcaa aaacagatgc cagtattcta      240
caggaaaaat tgggaagcct gaatctgcgg tggcaggagg tctgcaaaca gctgtcagac      300
agaaaaaaga ggctagaaga a                                                321

<210> SEQ ID NO 37
<211> LENGTH: 330
<212> TYPE: DNA
<213> ORGANISM: Homo sapiens

<400> SEQUENCE: 37
caaaagaata tcttgtcaga atttcaaaga gatttaaatg aatttgtttt atggttggag       60
gaagcagata acattgctag tatcccactt gaacctggaa aagagcagca actaaaagaa      120
aagcttgagc aagtcaagtt actggtggaa gagttgcccc tgcgccaggg aattctcaaa      180
caattaaatg aaactggagg acccgtgctt gtaagtgctc ccataagccc agaagagcaa      240
gataaacttg aaataagct caagcagaca atctccagt ggataaaggt ttccagagct       300
ttacctgaga acaaggaga aattgaagct                                        330

<210> SEQ ID NO 38
<211> LENGTH: 315
<212> TYPE: DNA
<213> ORGANISM: Homo sapiens

<400> SEQUENCE: 38
caaataaaag accttgggca gcttgaaaaa aagcttgaag accttgaaga gcagttaaat       60
catctgctgc tgtggttatc tcctattagg aatcagttgg aaatttataa ccaaccaaac      120
caagaaggac catttgacgt tcaggaaact gaaatagcag ttcaagctaa acaaccggat      180
gtggaagaga ttttgtctaa agggcagcat ttgtacaagg aaaaaccagc cactcagcca      240
gtgaagagga agttagaaga tctgagctct gagtggaagg cggtaaaccg tttacttcaa      300
gagctgaggg caaag                                                       315

<210> SEQ ID NO 39
<211> LENGTH: 141
<212> TYPE: DNA
<213> ORGANISM: Homo sapiens

<400> SEQUENCE: 39
cagcctgacc tagctcctgg actgaccact attggagcct ctcctactca gactgttact       60
ctggtgacac aacctgtggt tactaaggaa actgccatct ccaaactaga aatgccatct      120
tccttgatgt tggaggtacc t                                                141

<210> SEQ ID NO 40
<211> LENGTH: 321
<212> TYPE: DNA
<213> ORGANISM: Homo sapiens

<400> SEQUENCE: 40
gctctggcag atttcaaccg ggcttggaca gaacttaccg actggctttc tctgcttgat       60
caagttataa aatcacagag ggtgatggtg ggtgaccttg aggatatcaa cgagatgatc      120
atcaagcaga aggcaacaat gcaggatttg aacagaggc gtccccagtt ggaagaactc      180
attaccgctg cccaaaattt gaaaacaag accagcaatc aagaggctag aacaatcatt      240
acggatcgaa ttgaaagaat tcagaatcag tgggatgaag tacaagaaca ccttcagaac      300
```

```
cggaggcaac agttgaatga a                                            321
```

<210> SEQ ID NO 41
<211> LENGTH: 327
<212> TYPE: DNA
<213> ORGANISM: Homo sapiens

<400> SEQUENCE: 41

```
atgttaaagg attcaacaca atggctggaa gctaaggaag aagctgagca ggtcttagga    60
caggccagag ccaagcttga gtcatggaag gagggtccct atacagtaga tgcaatccaa   120
aagaaaatca cagaaaccaa gcagttggcc aaagacctcc gccagtggca gacaaatgta   180
gatgtggcaa atgacttggc cctgaaactt ctccgggatt attctgcaga tgataccaga   240
aaagtccaca tgataacaga gaatatcaat gcctcttgga gaagcattca taaaagggtg   300
agtgagcgag aggctgcttt ggaagaa                                      327
```

<210> SEQ ID NO 42
<211> LENGTH: 348
<212> TYPE: DNA
<213> ORGANISM: Homo sapiens

<400> SEQUENCE: 42

```
actcatagat tactgcaaca gttccccctg gacctggaaa agtttcttgc ctggcttaca    60
gaagctgaaa caactgccaa tgtcctacag gatgctaccc gtaaggaaag gctcctagaa   120
gactccaagg gagtaaaaga gctgatgaaa caatggcaag acctccaagg tgaaattgaa   180
gctcacacag atgttttatca caacctggat gaaaacagcc aaaaaatcct gagatccctg   240
gaaggttccg atgatgcagt cctgttacaa agacgtttgg ataacatgaa cttcaagtgg   300
agtgaacttc ggaaaaagtc tctcaacatt aggtcccatt tggaagcc               348
```

<210> SEQ ID NO 43
<211> LENGTH: 387
<212> TYPE: DNA
<213> ORGANISM: Homo sapiens

<400> SEQUENCE: 43

```
agttctgacc agtggaagcg tctgcacctt tctctgcagg aacttctggt gtggctacag    60
ctgaaagatg atgaattaag ccggcaggca cctattggag gcgactttcc agcagttcag   120
aagcagaacg atgtacatag ggccttcaag agggaattga aaactaaaga acctgtaatc   180
atgagtactc ttgagactgt acgaatattt ctgacagagc agcctttgga aggactagag   240
aaactctacc aggagcccag agagctgcct cctgaggaga gagcccagaa tgtcactcgg   300
cttctacgaa agcaggctga ggaggtcaat actgagtggg aaaaattgaa cctgcactcc   360
gctgactggc agagaaaaat agatgag                                      387
```

<210> SEQ ID NO 44
<211> LENGTH: 327
<212> TYPE: DNA
<213> ORGANISM: Homo sapiens

<400> SEQUENCE: 44

```
acccttgaaa gactccagga acttcaagag gccacggatg agctggacct caagctgcgc    60
caagctgagg tgatcaaggg atcctggcag cccgtgggcg atctcctcat tgactctctc   120
caagatcacc tcgagaaagt caaggcactt cgaggagaaa ttgcgcctct gaaagagaac   180
```

| | |
|---|---|
| gtgagccacg tcaatgacct tgctcgccag cttaccactt tgggcattca gctctcaccg | 240 |
| tataacctca gcactctgga agacctgaac accagatgga agcttctgca ggtggccgtc | 300 |
| gaggaccgag tcaggcagct gcatgaa | 327 |

<210> SEQ ID NO 45
<211> LENGTH: 216
<212> TYPE: DNA
<213> ORGANISM: Homo sapiens

<400> SEQUENCE: 45

| | |
|---|---|
| gcccacaggg actttggtcc agcatctcag cactttcttt ccacgtctgt ccagggtccc | 60 |
| tgggagagag ccatctcgcc aaacaaagtg ccctactata tcaaccacga gactcaaaca | 120 |
| acttgctggg accatcccaa aatgacagag ctctaccagt cttttagctga cctgaataat | 180 |
| gtcagattct cagcttatag gactgccatg aaactc | 216 |

<210> SEQ ID NO 46
<211> LENGTH: 888
<212> TYPE: DNA
<213> ORGANISM: Homo sapiens

<400> SEQUENCE: 46

| | |
|---|---|
| cgaagactgc agaaggccct ttgcttggat ctcttgagcc tgtcagctgc atgtgatgcc | 60 |
| ttggaccagc acaacctcaa gcaaaatgac cagcccatgg atatcctgca gattattaat | 120 |
| tgtttgacca ctatttatga ccgcctggag caagagcaca caatttggt caacgtccct | 180 |
| ctctgcgtgg atatgtgtct gaactggctg ctgaatgttt atgatacggg acgaacaggg | 240 |
| aggatccgtg tcctgtcttt taaaactggc atcatttccc tgtgtaaagc acatttggaa | 300 |
| gacaagtaca gatacctttt caagcaagtg gcaagttcaa caggattttg tgaccagcgc | 360 |
| aggctgggcc tccttctgca tgattctatc caaattccaa gacagttggg tgaagttgca | 420 |
| tcctttgggg gcagtaacat tgagccaagt gtccggagct gcttccaatt tgctaataat | 480 |
| aagccagaga tcgaagcggc cctcttccta gactggatga gactggaacc ccagtccatg | 540 |
| gtgtggctgc ccgtcctgca cagagtggct gctgcagaaa ctgccaagca tcaggccaaa | 600 |
| tgtaacatct gcaaagagtg tccaatcatt ggattcaggt acaggagtct aaagcacttt | 660 |
| aattatgaca tctgccaaag ctgctttttt tctggtcgag ttgcaaaagg ccataaaatg | 720 |
| cactatccca tggtggaata ttgcactccg actacatcag gagaagatgt tcgagacttt | 780 |
| gccaaggtac taaaaaacaa atttcgaacc aaaaggtatt ttgcgaagca tccccgaatg | 840 |
| ggctacctgc cagtgcagac tgtcttagag ggggacaaca tggaaact | 888 |

<210> SEQ ID NO 47
<211> LENGTH: 834
<212> TYPE: DNA
<213> ORGANISM: Homo sapiens

<400> SEQUENCE: 47

| | |
|---|---|
| cccgttactc tgatcaactt ctggccagta gattctgcgc ctgcctcgtc ccctcagctt | 60 |
| tcacacgatg atactcattc acgcattgaa cattatgcta gcaggctagc agaaatggaa | 120 |
| aacagcaatg gatcttatct aaatgatagc atctctccta atgagagcat agatgatgaa | 180 |
| catttgttaa tccagcatta ctgccaaagt ttgaaccagg actccccct gagccagcct | 240 |
| cgtagtcctg cccagatctt gatttcctta gagagtgagg aaagagggga gctagagaga | 300 |
| atcctagcag atcttgagga agaaaacagg aatctgcaag cagaatatga ccgtctaaag | 360 |

```
cagcagcacg aacataaagg cctgtcccca ctgccgtccc ctcctgaaat gatgcccacc    420
tctccccaga gtccccggga tgctgagctc attgctgagg ccaagctact gcgtcaacac    480
aaaggccgcc tggaagccag gatgcaaatc ctggaagacc acaataaaca gctggagtca    540
cagttacaca ggctaaggca gctgctggag caacccgagg cagaggccaa agtgaatggc    600
acaacggtgt cctctccttc tacctctcta cagaggtccg acagcagtca gcctatgctg    660
ctccgagtgg ttggcagtca aacttcggac tccatgggtg aggaagatct tctcagtcct    720
ccccaggaca caagcacagg gttagaggag gtgatggagc aactcaacaa ctccttccct    780
agttcaagag gaagaaatac ccctggaaag ccaatgagag aggacacaat gtag          834
```

<210> SEQ ID NO 48
<211> LENGTH: 11044
<212> TYPE: DNA
<213> ORGANISM: Canis familiaris

<400> SEQUENCE: 48

```
atgctttggt gggaagaagt agaggactgt tatgaaagag aagatgttca aaagaaaaca     60
ttcacaaaat gggtaaatgc acagttttct aagtttggga agcagcacat agagaacctc    120
ttcagtgacc tacaggatgg gagacgcctc ctagaccttt tggaaggcct gacagggcaa    180
aaactgccaa agaaaaagg atccacaaga gttcatgccc tgaacaatgt caacaaggca    240
ctgcgcgtct tgcagaaaaa taatgttgat ttagtgaaca ttggaagtac tgacatagta    300
gatggaaatc acaaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtcat taacttcacc    480
accagctggt ctgatggcct ggcttttgaac gctctcatcc acagtcatag gccagacctg    540
tttgattgga atagtgtggt ttgccagcag tcagccacac aacgcctgga acatgcattc    600
aacattgcca atatcaatt aggcatagag aaactgcttg atcctgaaga tgttgccacc    660
acttatccag ataagaagtc catcttaatg tatatcacat cactcttcca agttttgcct    720
caacaagtga gcattgaagc catccaggaa gtggaaatgt tgccaaggcc atctcaagtt    780
actagagaag aacattttca gatacatcat caaatgcact attctcaaca gatcacagtc    840
agtctagcac agggatatga acgagcccct tcctttccta gcctcggtt caagagctat    900 gcctacacac aggctgctta tgtcaccact tctgacccca cacggagccc acttccttca    960
cagcatttgg aaactcctga agacaagtca tttggccggt cattgacaga gaccgaagca   1020
aacctggaca gttatcaaac agctttggaa gaagtactct cgtggcttct ttcagctgag   1080
gatgcactgc aagcccaagg agagatttct aatgatgtcg aagaagtgaa agaacaattt   1140
catactcatg agggatatat gatggacttg acatcccatc agggacgggt cggtaatgtt   1200
ctccaactgg gaagtcaact gattggaaca gggaaattat cagaagatga gaaaccgaa   1260 gtgcaggaac aaatgaatct cctcaattca agatgggaat gcctcagggt agctagcatg   1320
gaaaaacaaa gcaatttaca taagttcta atggatctcc agaatcagca actgaaagag   1380
ttaaatgact ggctaaccaa aacagaagag agaacaagga aaatggagaa ggagcccctt   1440
ggacctgata ttgaagacct aaaacgccaa gtacaacaac ataaggtgct tcaagaagac   1500
ttagaacagg aacaagtcag ggtcaattcc ctcactcata tggtggtggt agtcgatgaa   1560
tctagtggag accatgcaac tgctgctttg gaagaacaac ttaaggtact gggagatcga   1620
```

-continued

| | |
|---|---|
| tgggcaaaca tctgtaggtg acagaagat cgctgggttc ttttacaaga catcctccta | 1680 |
| aaatggcagc gttttactga agaacagtgc cttttagtg catggctttc ggagaaggaa | 1740 |
| gatgcagtga acaagattca cacaactggc tttaaggatc aaagtgaagt gttatcaaat | 1800 |
| cttcagaaac tggctgtctt aaaaacagat ctggaaaaga agaagcaaac catggacaaa | 1860 |
| ctctgctcac tcaaccaaga ccttctttca gcgctgaaaa acacagtggt agcccacaag | 1920 |
| atggaagcat ggctggacaa cttgcccag cgctgggata tttagtcca gaaacttgaa | 1980 |
| aaaagttcag cacagatttc acaggctgtc accaccactc agccatcact aacacagaca | 2040 |
| actgtaatgg aaacagtaac tatggtgacc acgagggaac acatcttggt aaagcatgcc | 2100 |
| caagaggaac tgccaccacc accccctcag aagaagaggc agattatcgt ggattctgaa | 2160 |
| attaggaaaa ggttggatgt cgatataact gaacttcaca gttggattac tcgttcagaa | 2220 |
| gctgtgttgc agagtcctga atttgcaatc tatcggaagg aaggcaactt ctcagaccct | 2280 |
| aaagaaaaag tcaatgccat agagcgagaa aaagccgaga agttcagaaa actgcaagat | 2340 |
| gccagcagat cagctcaggc cctggtggaa cagatggtga atgagggtgt taatgctgac | 2400 |
| agcatcaaac aagcctccga caactgaacc agccggtgga tagagttctg ccaattgcta | 2460 |
| agcgagagac ttaactggct ggagtatcag aacaacatca tcactttcta taatcagcta | 2520 |
| caacaattgg agcagatgac aactactgct gaaaactggt tgaaaaccca gcctaccacc | 2580 |
| acatcagagc caacagcaat taaaagccag ttaaaaattt gtaaggatga aatcaaccga | 2640 |
| ctgtcagctc ttcagcctca aatcgagcga ttaaaaattc aaagcatagc cctgaaagag | 2700 |
| aaaggacaag ggccaatgtt cctggatgca gactttgtgg cctttacaaa tcatttaac | 2760 |
| caagtctttg ctgatgtgca ggcaagagaa aaagagctac aaacaatttt tgacagtttg | 2820 |
| ccacccatgc gctatcagga gactatgagt accatcctga catggatcca gcagtcagaa | 2880 |
| accaaactct ctatacctca ggttactgtc actgaatatg acatcatgga acagagactc | 2940 |
| ggagagctac aggctttaca aagctctctg caagagcaac aaaatggcct aaactatctc | 3000 |
| agcaccactg tgaaagagat gtcaaagaaa gcaccactgt ctgatattag tcggaaatat | 3060 |
| caatcagaat ttgaagagat tgaggacgt tggaagaagc tgtcttccca gctggttgaa | 3120 |
| cattgtcaaa agttggagga gcaaatggct aaacttcgaa aaattcagaa tcacataaaa | 3180 |
| actctgaaga aatggatcac tgaagtcgat gttttcctga aggaggaatg gcctgccctt | 3240 |
| ggggattcag aaattctgaa aagacagctg aaacagtgca ggctttagt caatgacatt | 3300 |
| cagaccatcc agcctagtct caacagtgtc aatgaagggg ctcagaagat gaagaatgaa | 3360 |
| gcagaaccag agtttgctgg cagacttgag acagagctcc gagaacttaa cacccagtgg | 3420 |
| gattacatgt gccgccaggt ctatgccagg aaggaagcct taaaggagg ttttggataa | 3480 |
| aactgtaagt cttcagaaag atctgtcaga gatgcatgag tggatgacac aagctgaaga | 3540 |
| agaataccta gagagagatt tcgaatacaa gaccctgat gaattacaga cagcagttga | 3600 |
| agagatgaag agagctaaag aagaggccca gcaaaaagaa gcaaagtgaa aactcctaac | 3660 |
| cgagtccgtc aatagtgtca tagctcaggc tccacctgca gcacaagagg ccttaaaaaa | 3720 |
| ggaacttgac actctcacca ccaactacca gtggctctgc accaggctca atggcaaatg | 3780 |
| caagaccttg gaagaagttt gggcgtgctg gcatgagtta ttgtcctact ggagaaggc | 3840 |
| aaacaagtgg ctaagtgaag tagaagtcaa gcttaaaacc actgaaaata tttctggggg | 3900 |
| agctgaggaa atcgccgagg tgcttgattc gcttgaaaat ttgatgcaac attcagagga | 3960 |
| taacccgaat cagattcgca tattggcaca gaccttgaca gatggtggag tcatggatga | 4020 |

```
actgatcaat gaggagcttg agacatttaa ttctcgttgg agagaactcc atgaagaggc      4080
tgtgaggagg caaaagttgc ttgagcagag tatccagtcg gcccaggaga tagaaaaatc      4140
cttgcactta attcaggagt ccctctcttc cattgacaag cagttggcag cttatattgc      4200
tgacaaagtg gatgcagctc agatgcctca ggaagcccag aaaatccaat cagatttgac      4260
aagtcatgag atcagtttag aagaaatgaa gaaacataac cagggaaagg agactgccca      4320
aagggtacta tcccaaattg atgtggcaca gaaaaaattg caggatgttt ccatgaagtt      4380
tcgattattc cagaagccag ccaattttga gcagcgccta caagaaagta aatgattttt      4440
agatgaagtg aagatgcatt tacctgcgtt ggaaacaaag agtgtggaac aggaagtagt      4500
acagtcacag ttaaatcatt gtgtgaactt gtataaaagt ctgagtgaag tgaagtctga      4560
agtggaaatg gtaataaaaa ctggacgtca gattgtacag aagaagcaga cggaaaaccc      4620
gaaagagctt gatgaaagag ttacagcttt gaaattgcat tataatgagc tgggagcaaa      4680
ggtgacagaa agaaagcaac agttggaaaa atgcttgaaa ttgtcccgta agatgcgaaa      4740
ggaaatgaat gccctgacag aatggctggc agctacagat atggaactga caaagagatc      4800
ggcagttgaa ggaatgccta gtaatttgga ttctgaagtt gcctggggaa aggctactca      4860
gaaagagatt gagaaacaga aggttcacct aaagagtgtc acagaggtag gagaggcctt      4920
gaaacggttt ttgggcaaga aggaaatgtt ggtggaagat aaactgagtc ttctgaatag      4980
taactggata gccgtcactt cccgagcaga agagtggtta aaccttttat tggaatacca      5040
gaaacacatg gaaactttg accagaatgt ggattacatc acaaactgga tcattcaggc      5100
tgatgcactt ttggatgaat ctgagaaaaa gaaacctcag caaaagaag acatacttaa      5160
gcgtttaaag gctgaaatga atgacatacg tccaaaggtg gattctacac gtgaccaagc      5220
agcaaacctg atggcaaacc gcggcgacca ctgcaggaaa gtagtagagc ccaaaatctc      5280
agagctcaac catcgatttg cagccatttc tcacagaatt aagactggaa aggcctccat      5340
tcctttgaag gaattggagc agtttaactc agatatacaa aaattgcttg aaccactgga      5400
ggctgaaatt cagcaggggg tgaatctgaa agaggaagac ttcaataaag atatgagtga      5460
agacaatgag ggtactgtaa aagaattgtt gcaaagagga gacaacttac aacaaagaat      5520
cacagatgag agaaagcgag aggaaataaa gataaaacaa cagctgttac agacaaaaca      5580
taatgctctc aaggatttga ggtctcaaag aagaaaaaag gctctagaaa tttctcacca      5640
gtggtatcag tacaagaggc aggctgatga tctcctgaaa tgcttggatg acattgaaaa      5700
aaaattagcc agcctacctg aacccagaga tgaaggaaa ataaaggaaa ttgatcgtga      5760
attgcagaag aagaaagagg agctgaatgc agtgcgtagg caagctgagg gcttgtctga      5820
ggatggggcc gcaatggcag tggagccaac tcagatccag ctcagcaagc gctggcggga      5880
aattgagagc aaatttgctc agtttcgaag actcaacttt gcacaaattc acactgtcca      5940
tgaagagtca gtggtggcga tgactgaaga catgcctttg gaaatttctt atgtgccttc      6000
tacttacctg actgagatca ctcatgtctc acaagcccta tcagaagtgg aagagcttct      6060
taatgctccc gacctttgtg ctcaagattt tgaagatctc tttaaacaag aggaatcctt      6120
gaagaacata aaagacagcc tgcaacaaat ctcaggtcgg attgacatca ttcacaataa      6180
aaagacagca gcattgcaca gtgccactcc tgcagaaagg gcaaagctcc aggaagctct      6240
ctcacggctt gatttccaat gggaaagagt taacaatatg tacaaggacc gacaagggag      6300
atttgacaga tctgtggaaa aatggcggcg gtttcattat gatatgaaga tacttaatca      6360
```

```
atggctaaca gaagctgaac agtttctcaa aaagacacaa attcctgaga attgggaaca    6420
tgccaaatac aaatggtatc ttaaggaact ccaggatggc attggacagc ggcaaagtgt    6480
tgtcagggta ttgaatgcaa ctggggaaga aataattcaa cagtcctcaa aaacagatgc    6540
cagtattctc caagaaaaac tgggaagcct gaatctgcgg tggcaggagg tctgcaaaca    6600
gctggcagaa agaaaaaaga ggctagagga acagaagaat atcttgtcag aatttcaaag    6660
agatgtaaat gaatttgttt tatggttgga agaagcggga aacgttgcta atattccact    6720
tgaacctgga aatgagcagc agctaaaaga aaaacttgaa caagtcaagt tactggcaga    6780
agagttgccc ctgcgccagg gaattctaaa acaattaaat gaaactggag gaacagtgct    6840
tgtaagtgct cccctaagcc cagaagagca agataaactt gaaataagc tcaagcagac    6900
aaatcttcag tggataaagg tttctagaaa tctgcctgag aagcaagaag aaattgaggc    6960
acacgtaaaa gaccttggac agctggaaga gcagttaaat catctgcttc tatggctgtc    7020
tcctattagg aatcagttgg aaatttacaa tcagccaaat caaacaggac catttgacat    7080
caaggaaatt gaagtagcag ttcaagctaa acagccggat gtggaaggga ttttgtctaa    7140
agggcagcat ttgtacaagg aaaaaccagc cactcagcca gcgaagagaa agctggaaga    7200
tctcagctct gattggaagg tggtaactca gttgcttcaa gagctgcggg caaagcaacc    7260
tggcccagct cctggactga ccactgtcag agcccctccc agtcagactg ttactctggt    7320
gacacaaccc gcggttacca aggaaactgc catctccaaa ctagaaatgc catcttcatt    7380
gctgttggag gtacctgcac tggcagattt caaccgagct tggacagaac ttaccgactg    7440
gctgtctctg cttgatcgag ttataaaatc acagagggtg atggtgggtg atcttgaaga    7500
cattaacgag atgatcatca agcagaaggc aacgctgcag gatttggaac agaggcgccc    7560
ccagttggaa gaactcatta ccgctgccca gaatttgaaa acaagaccaa gcaatcaaga    7620
ggctagaaca atcattactg atcgaattga agaattcag agtcagtggg atgaagtaca    7680
ggaacatctt cagaaccgga ggctacagtt gactgaaatg ttaaaggatt ccacacaatg    7740
gctggaagct aaagaggagg ctgagcaggt gttggggcag gccagagcca gcttgagtc    7800
atggaaggag gctccctaca cagtagatgc aatccaaaag aaaatcacag aaaccaagca    7860
gttggccaaa gacctccgcc agtggcagat aaatgtagat gttgcaaatg atttggcact    7920
gaaacttctc cgagattatt ctgcagatga taccagaaaa gtacacatga taacagagaa    7980
catcaatgcc tcttgggcaa gcatccataa aagattgagt gagcgagagg ctgctctgga    8040
agaaacccac agattactgc aacagttccc cttggacctg gagaagttcc ttgcctggct    8100
tacagaagcc gaaacaactg ccaacgtcct gcaggatgcc acccataagg aaaggcttct    8160
agaagattcc aagggagtaa gagagctgat gaaacaatgg caagacctcc aaggagaaat    8220
cgaagctcac acagatatct atcacaacct ggacgaaaat ggccaaaaag tcctgagatc    8280
cctgaaggt tctgacgatg cagccttgtt gcaaagacgt ttggataaca tgaacttcaa    8340
gtggagcgaa cttcggaaaa agtctctcaa cattaggtct cacttggaag ccagttctga    8400
ccagtggaag cgtctgcacc tttctcttca ggaacttctg gtatggctcc agctgaaaga    8460
tgatgagtta gccggcagg cacccattgg aggagacttt ccagcggtgc agaagcagaa    8520
tgatgtacac agggccttca gagggaatt gaaaacgaaa gaacctgtaa tcatgagtac    8580
tcttgagact gtacgaatat ttctgacaga gcagccttta gaaggactag agaaactcta    8640
ccaggagccc agagagctgc ctcctgaaga gagagcccag aatgtcacac ggctcctacg    8700
aaagcaagct gaggaggtca acactcagtg ggaaaaactg aacgtgcact ctgcagactg    8760
```

```
gcagagaaaa atagacgagg ccctcgaaag actccaggag cttcaggaag caacagatga    8820
gctggatctc aaactacgtc aggcagaggt gatcaaagga tcctggcagc ctgtgggtga    8880
cctcctcatt gactctctcc aagatcacct cgaaaaagtc aaggcgcttc gaggagaaat    8940
tacacctctg aaagagaatg tcagctacgt caatgacctt gctcgccaac tcactacgtt    9000
gggcattcag ctgtcaccat ataacctcaa cactctggaa gacctgaaca ccagatggaa    9060
gcttctgcag gtggccattg aggaccgcat caggcagctg catgaagcgc acgggactt    9120 tggaccagcc tcccagcact tcctttccac ttctgtccag ggtccctggg agagagccat    9180
ctcaccaaac aaagtgccct actatatcaa ccacgagacc caaacaactt gctgggacca    9240
tcccaaaatg acagagctct accagtcttt agctgacctg aataatgtca ggttctcagc    9300
ttacaggact gccatgaaac tccgaagact gcagaaggcc ctttgcttgg atctcttgag    9360
cctatcggct gcatgcgatg ccttggacca gcacaacctc aagcaaaatg accagcccat    9420
ggatatcctg caggtcatta actgtctgac cactatttat gatcgcctag agcaagagca    9480
caacaatctg gtcaacgtcc ctctctgcgt ggatatgtgt ctcaattggc tgctgaatgt    9540
ttatgacacg ggacgaacgg ggaggatccg ggtcctgtct tttaaaactg gcatcatttc    9600
tctgtgtaaa gcccatttgg aagacaagta cagatacctc ttcaagcaag tggcaagttc    9660
gacaggattt tgtgaccagc gcaggctggg cctcctcctg catgactcta tccagatccc    9720
aagacagttg ggtgaagtcg catcgttcgg gggcagtaac attgagccga gtgtcaggag    9780
ctgcttccag tttgctaata ataagcctga gatcgaagcg gccctcttcc tagactggat    9840
gcgcctggag ccccagtcca tggtgtggct gcctgtcctg caccgagtgg ctgccgcgga    9900
aactgccaag caccaggcca agtgcaacat ctgcaaggag tgtcccatca tcggattcag    9960
gtacaggagt ctaaagcact ttaattatga catctggcaa agttgctttt tttctggtcg   10020
agttgcaaaa ggccataaaa tgcactatcc catggtggaa tactgcactc cgactacatc   10080
gggagaagat gtccgtgact tgccaaggt actaaaaaac aaatttcgaa ccaaaaggta   10140
ttttgcgaag catccccgaa tgggctacct gccagtgcag actgtcttag agggggacaa   10200
catgaaaact cctgtcactc tgatcaactt ctggccggta gattctgcgc ctgcctcgtc   10260
ccctcagctt tcacacgatg atactcattc acgcattgag cattatgcta gcaggctaaa   10320
aaaaatggaa aacagcaatg gatcttatct aaatgatagc atctctccta atgagagcat   10380
agatgatgaa catttgttaa tccagcatta ctggcgaagt ttgaaccagg aatccccct   10440 gagccagcct cgtagtcctg cccagatctt gatttcctta gagagtgagg aaagagggga   10500
gctagagaga atcctagcag atcttgaggg gagaaacaga aatctgcaag cagagtatga   10560
tcgtctaaag cagcagcatg aacacaaagg cctgtcccca ctgccatccc ctcctgaaat   10620
gatgcctact tctcccccaaa gtccccggga tgctgagctc atcgctgagg ccaagctgct   10680
gcgtcaacac aaaggccgcc tggaagccag gatgcaaatc cttgaagacc ataacaaaca   10740
actggaatcc cagttacaca ggctcaggca gctgctggag caaccccagg cagaggccaa   10800
ggtgaatggt acaacggtgt cttctccttc tacctctctt cagaggtcag atagcagtca   10860
gcctatgctg ctccgggtgg tcggcagtca gacttcagaa tccatgggcg aggaagacct   10920
gctcagccct ccccaggaca caagcacagg gttagaggaa gtgatggagc agctcaacca   10980
ctccttccct agttccagag gaagaaatac ccctgggaag ccaatgagag aggacacaat   11040
gtag                                                                11044
```

```
<210> SEQ ID NO 49
<211> LENGTH: 3680
<212> TYPE: PRT
<213> ORGANISM: Canis familiaris

<400> SEQUENCE: 49

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Lys Tyr Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Ser Gln Val Thr Arg Glu Glu His Phe Gln Ile His His Gln Met
            260                 265                 270

His Tyr Ser Gln Gln Ile Thr Val Ser Leu Ala Gln Gly Tyr Glu Arg
        275                 280                 285

Ala Pro Ser Phe Pro Lys Pro Arg Phe Lys Ser Tyr Ala Tyr Thr Gln
    290                 295                 300

Ala Ala Tyr Val Thr Thr Ser Asp Pro Thr Arg Ser Pro Leu Pro Ser
305                 310                 315                 320

Gln His Leu Glu Thr Pro Glu Asp Lys Ser Phe Gly Arg Ser Leu Thr
                325                 330                 335

Glu Thr Glu Ala Asn Leu Asp Ser Tyr Gln Thr Ala Leu Glu Glu Val
            340                 345                 350

Leu Ser Trp Leu Leu Ser Ala Glu Asp Ala Leu Gln Ala Gln Gly Glu
        355                 360                 365

Ile Ser Asn Asp Val Glu Glu Val Lys Glu Gln Phe His Thr His Glu
    370                 375                 380
```

```
Gly Tyr Met Met Asp Leu Thr Ser His Gln Arg Val Gly Asn Val
385                 390                 395                 400

Leu Gln Leu Gly Ser Gln Leu Ile Gly Thr Gly Lys Leu Ser Glu Asp
                405                 410                 415

Glu Glu Thr Glu Val Gln Glu Gln Met Asn Leu Leu Asn Ser Arg Trp
            420                 425                 430

Glu Cys Leu Arg Val Ala Ser Met Glu Lys Gln Ser Asn Leu His Lys
        435                 440                 445

Val Leu Met Asp Leu Gln Asn Gln Gln Leu Lys Glu Leu Asn Asp Trp
    450                 455                 460

Leu Thr Lys Thr Glu Arg Thr Arg Lys Met Glu Lys Glu Pro Leu
465                 470                 475                 480

Gly Pro Asp Ile Glu Asp Leu Lys Arg Gln Val Gln Gln His Lys Val
                485                 490                 495

Leu Gln Glu Asp Leu Glu Gln Glu Gln Val Arg Val Asn Ser Leu Thr
            500                 505                 510

His Met Val Val Val Asp Glu Ser Ser Gly Asp His Ala Thr Ala
        515                 520                 525

Ala Leu Glu Glu Gln Leu Lys Val Leu Gly Asp Arg Trp Ala Asn Ile
530                 535                 540

Cys Arg Trp Thr Glu Asp Arg Trp Val Leu Leu Gln Asp Ile Leu Leu
545                 550                 555                 560

Lys Trp Gln Arg Phe Thr Glu Glu Gln Cys Leu Phe Ser Ala Trp Leu
                565                 570                 575

Ser Glu Lys Glu Asp Ala Val Asn Lys Ile His Thr Thr Gly Phe Lys
            580                 585                 590

Asp Gln Ser Glu Val Leu Ser Asn Leu Gln Lys Leu Ala Val Leu Lys
        595                 600                 605

Thr Asp Leu Glu Lys Lys Lys Gln Thr Met Asp Lys Leu Cys Ser Leu
    610                 615                 620

Asn Gln Asp Leu Leu Ser Ala Leu Lys Asn Thr Val Val Ala His Lys
625                 630                 635                 640

Met Glu Ala Trp Leu Asp Asn Phe Ala Gln Arg Trp Asp Asn Leu Val
                645                 650                 655

Gln Lys Leu Glu Lys Ser Ser Ala Gln Ile Ser Gln Ala Val Thr Thr
            660                 665                 670

Thr Gln Pro Ser Leu Thr Gln Thr Thr Val Met Glu Thr Val Thr Met
        675                 680                 685

Val Thr Thr Arg Glu His Ile Leu Val Lys His Ala Gln Glu Glu Leu
    690                 695                 700

Pro Pro Pro Pro Pro Gln Lys Lys Arg Gln Ile Ile Val Asp Ser Glu
705                 710                 715                 720

Ile Arg Lys Arg Leu Asp Val Asp Ile Thr Glu Leu His Ser Trp Ile
                725                 730                 735

Thr Arg Ser Glu Ala Val Leu Gln Ser Pro Glu Phe Ala Ile Tyr Arg
            740                 745                 750

Lys Glu Gly Asn Phe Ser Asp Leu Lys Glu Lys Val Asn Ala Ile Glu
        755                 760                 765

Arg Glu Lys Ala Glu Lys Phe Arg Lys Leu Gln Asp Ala Ser Arg Ser
    770                 775                 780

Ala Gln Ala Leu Val Glu Gln Met Val Asn Glu Gly Val Asn Ala Asp
785                 790                 795                 800
```

-continued

```
Ser Ile Lys Gln Ala Ser Glu Gln Leu Asn Ser Arg Trp Ile Glu Phe
            805                 810                 815

Cys Gln Leu Leu Ser Glu Arg Leu Asn Trp Leu Glu Tyr Gln Asn Asn
            820                 825                 830

Ile Ile Thr Phe Tyr Asn Gln Leu Gln Gln Leu Glu Gln Met Thr Thr
            835                 840                 845

Thr Ala Glu Asn Trp Leu Lys Thr Gln Pro Thr Thr Thr Ser Glu Pro
850                 855                 860

Thr Ala Ile Lys Ser Gln Leu Lys Ile Cys Lys Asp Glu Ile Asn Arg
865                 870                 875                 880

Leu Ser Ala Leu Gln Pro Gln Ile Glu Arg Leu Lys Ile Gln Ser Ile
                885                 890                 895

Ala Leu Lys Glu Lys Gly Gln Gly Pro Met Phe Leu Asp Ala Asp Phe
            900                 905                 910

Val Ala Phe Thr Asn His Phe Asn Gln Val Phe Ala Asp Val Gln Ala
            915                 920                 925

Arg Glu Lys Glu Leu Gln Thr Ile Phe Asp Ser Leu Pro Pro Met Arg
930                 935                 940

Tyr Gln Glu Thr Met Ser Thr Ile Leu Thr Trp Ile Gln Gln Ser Glu
945                 950                 955                 960

Thr Lys Leu Ser Ile Pro Gln Val Thr Val Thr Glu Tyr Asp Ile Met
                965                 970                 975

Glu Gln Arg Leu Gly Glu Leu Gln Ala Leu Gln Ser Ser Leu Gln Glu
            980                 985                 990

Gln Gln Asn Gly Leu Asn Tyr Leu Ser Thr Thr Val Lys Glu Met Ser
            995                 1000                1005

Lys Lys Ala Pro Leu Ser Asp Ile Ser Arg Lys Tyr Gln Ser Glu
            1010                1015                1020

Phe Glu Glu Ile Glu Gly Arg Trp Lys Lys Leu Ser Ser Gln Leu
            1025                1030                1035

Val Glu His Cys Gln Lys Leu Glu Glu Gln Met Ala Lys Leu Arg
            1040                1045                1050

Lys Ile Gln Asn His Ile Lys Thr Leu Lys Lys Trp Ile Thr Glu
            1055                1060                1065

Val Asp Val Phe Leu Lys Glu Glu Trp Pro Ala Leu Gly Asp Ser
            1070                1075                1080

Glu Ile Leu Lys Arg Gln Leu Lys Gln Cys Arg Leu Leu Val Asn
            1085                1090                1095

Asp Ile Gln Thr Ile Gln Pro Ser Leu Asn Ser Val Asn Glu Gly
            1100                1105                1110

Ala Gln Lys Met Lys Asn Glu Ala Glu Pro Glu Phe Ala Gly Arg
            1115                1120                1125

Leu Glu Thr Glu Leu Arg Glu Leu Asn Thr Gln Trp Asp Tyr Met
            1130                1135                1140

Cys Arg Gln Val Tyr Ala Arg Lys Glu Ala Leu Lys Gly Gly Leu
            1145                1150                1155

Asp Lys Thr Val Ser Leu Gln Lys Asp Leu Ser Glu Met His Glu
            1160                1165                1170

Trp Met Thr Gln Ala Glu Glu Glu Tyr Leu Glu Arg Asp Phe Glu
            1175                1180                1185

Tyr Lys Thr Pro Asp Glu Leu Gln Thr Ala Val Glu Glu Met Lys
            1190                1195                1200

Arg Ala Lys Glu Glu Ala Gln Gln Lys Glu Ala Lys Val Lys Leu
```

```
            1205                1210                1215

Leu Thr Glu Ser Val Asn Ser Val Ile Ala Gln Ala Pro Pro Ala
        1220                1225                1230

Ala Gln Glu Ala Leu Lys Lys Glu Leu Asp Thr Leu Thr Thr Asn
        1235                1240                1245

Tyr Gln Trp Leu Cys Thr Arg Leu Asn Gly Lys Cys Lys Thr Leu
        1250                1255                1260

Glu Glu Val Trp Ala Cys Trp His Glu Leu Leu Ser Tyr Leu Glu
        1265                1270                1275

Lys Ala Asn Lys Trp Leu Ser Glu Val Glu Val Lys Leu Lys Thr
        1280                1285                1290

Thr Glu Asn Ile Ser Gly Gly Ala Glu Glu Ile Ala Glu Val Leu
        1295                1300                1305

Asp Ser Leu Glu Asn Leu Met Gln His Ser Glu Asp Asn Pro Asn
        1310                1315                1320

Gln Ile Arg Ile Leu Ala Gln Thr Leu Thr Asp Gly Gly Val Met
        1325                1330                1335

Asp Glu Leu Ile Asn Glu Glu Leu Glu Thr Phe Asn Ser Arg Trp
        1340                1345                1350

Arg Glu Leu His Glu Glu Ala Val Arg Arg Gln Lys Leu Leu Glu
        1355                1360                1365

Gln Ser Ile Gln Ser Ala Gln Glu Ile Glu Lys Ser Leu His Leu
        1370                1375                1380

Ile Gln Glu Ser Leu Ser Ser Ile Asp Lys Gln Leu Ala Ala Tyr
        1385                1390                1395

Ile Ala Asp Lys Val Asp Ala Ala Gln Met Pro Gln Glu Ala Gln
        1400                1405                1410

Lys Ile Gln Ser Asp Leu Thr Ser His Glu Ile Ser Leu Glu Glu
        1415                1420                1425

Met Lys Lys His Asn Gln Gly Lys Glu Thr Ala Gln Arg Val Leu
        1430                1435                1440

Ser Gln Ile Asp Val Ala Gln Lys Lys Leu Gln Asp Val Ser Met
        1445                1450                1455

Lys Phe Arg Leu Phe Gln Lys Pro Ala Asn Phe Glu Gln Arg Leu
        1460                1465                1470

Gln Glu Ser Lys Met Ile Leu Asp Glu Val Lys Met His Leu Pro
        1475                1480                1485

Ala Leu Glu Thr Lys Ser Val Glu Gln Glu Val Val Gln Ser Gln
        1490                1495                1500

Leu Asn His Cys Val Asn Leu Tyr Lys Ser Leu Ser Glu Val Lys
        1505                1510                1515

Ser Glu Val Glu Met Val Ile Lys Thr Gly Arg Gln Ile Val Gln
        1520                1525                1530

Lys Lys Gln Thr Glu Asn Pro Lys Glu Leu Asp Glu Arg Val Thr
        1535                1540                1545

Ala Leu Lys Leu His Tyr Asn Glu Leu Gly Ala Lys Val Thr Glu
        1550                1555                1560

Arg Lys Gln Gln Leu Glu Lys Cys Leu Lys Leu Ser Arg Lys Met
        1565                1570                1575

Arg Lys Glu Met Asn Ala Leu Thr Glu Trp Leu Ala Ala Thr Asp
        1580                1585                1590

Met Glu Leu Thr Lys Arg Ser Ala Val Glu Gly Met Pro Ser Asn
        1595                1600                1605
```

-continued

Leu Asp Ser Glu Val Ala Trp Gly Lys Ala Thr Gln Lys Glu Ile
1610                1615                1620

Glu Lys Gln Lys Val His Leu Lys Ser Val Thr Glu Val Gly Glu
1625                1630                1635

Ala Leu Lys Thr Val Leu Gly Lys Lys Glu Met Leu Val Glu Asp
1640                1645                1650

Lys Leu Ser Leu Leu Asn Ser Asn Trp Ile Ala Val Thr Ser Arg
1655                1660                1665

Ala Glu Glu Trp Leu Asn Leu Leu Leu Glu Tyr Gln Lys His Met
1670                1675                1680

Glu Thr Phe Asp Gln Asn Val Asp Tyr Ile Thr Asn Trp Ile Ile
1685                1690                1695

Gln Ala Asp Ala Leu Leu Asp Glu Ser Glu Lys Lys Lys Pro Gln
1700                1705                1710

Gln Lys Glu Asp Ile Leu Lys Arg Leu Lys Ala Glu Met Asn Asp
1715                1720                1725

Ile Arg Pro Lys Val Asp Ser Thr Arg Asp Gln Ala Ala Asn Leu
1730                1735                1740

Met Ala Asn Arg Gly Asp His Cys Arg Lys Val Val Glu Pro Lys
1745                1750                1755

Ile Ser Glu Leu Asn His Arg Phe Ala Ala Ile Ser His Arg Ile
1760                1765                1770

Lys Thr Gly Lys Ala Ser Ile Pro Leu Lys Glu Leu Glu Gln Phe
1775                1780                1785

Asn Ser Asp Ile Gln Lys Leu Leu Glu Pro Leu Glu Ala Glu Ile
1790                1795                1800

Gln Gln Gly Val Asn Leu Lys Glu Glu Asp Phe Asn Lys Asp Met
1805                1810                1815

Ser Glu Asp Asn Glu Gly Thr Val Lys Glu Leu Leu Gln Arg Gly
1820                1825                1830

Asp Asn Leu Gln Gln Arg Ile Thr Asp Glu Arg Lys Arg Glu Glu
1835                1840                1845

Ile Lys Ile Lys Gln Gln Leu Leu Gln Thr Lys His Asn Ala Leu
1850                1855                1860

Lys Asp Leu Arg Ser Gln Arg Arg Lys Lys Ala Leu Glu Ile Ser
1865                1870                1875

His Gln Trp Tyr Gln Tyr Lys Arg Gln Ala Asp Asp Leu Leu Lys
1880                1885                1890

Cys Leu Asp Asp Ile Glu Lys Lys Leu Ala Ser Leu Pro Glu Pro
1895                1900                1905

Arg Asp Glu Arg Lys Ile Lys Glu Ile Asp Arg Glu Leu Gln Lys
1910                1915                1920

Lys Lys Glu Glu Leu Asn Ala Val Arg Arg Gln Ala Glu Gly Leu
1925                1930                1935

Ser Glu Asp Gly Ala Ala Met Ala Val Glu Pro Thr Gln Ile Gln
1940                1945                1950

Leu Ser Lys Arg Trp Arg Glu Ile Glu Ser Lys Phe Ala Gln Phe
1955                1960                1965

Arg Arg Leu Asn Phe Ala Gln Ile His Thr Val His Glu Glu Ser
1970                1975                1980

Val Val Ala Met Thr Glu Asp Met Pro Leu Glu Ile Ser Tyr Val
1985                1990                1995

```
Pro Ser Thr Tyr Leu Thr Glu Ile Thr His Val Ser Gln Ala Leu
    2000            2005            2010

Ser Glu Val Glu Glu Leu Leu Asn Ala Pro Asp Leu Cys Ala Gln
    2015            2020            2025

Asp Phe Glu Asp Leu Phe Lys Gln Glu Glu Ser Leu Lys Asn Ile
    2030            2035            2040

Lys Asp Ser Leu Gln Gln Ile Ser Gly Arg Ile Asp Ile Ile His
    2045            2050            2055

Asn Lys Lys Thr Ala Ala Leu His Ser Ala Thr Pro Ala Glu Arg
    2060            2065            2070

Ala Lys Leu Gln Glu Ala Leu Ser Arg Leu Asp Phe Gln Trp Glu
    2075            2080            2085

Arg Val Asn Asn Met Tyr Lys Asp Arg Gln Gly Arg Phe Asp Arg
    2090            2095            2100

Ser Val Glu Lys Trp Arg Arg Phe His Tyr Asp Met Lys Ile Leu
    2105            2110            2115

Asn Gln Trp Leu Thr Glu Ala Glu Gln Phe Leu Lys Lys Thr Gln
    2120            2125            2130

Ile Pro Glu Asn Trp Glu His Ala Lys Tyr Lys Trp Tyr Leu Lys
    2135            2140            2145

Glu Leu Gln Asp Gly Ile Gly Gln Arg Gln Ser Val Val Arg Val
    2150            2155            2160

Leu Asn Ala Thr Gly Glu Glu Ile Ile Gln Gln Ser Ser Lys Thr
    2165            2170            2175

Asp Ala Ser Ile Leu Gln Glu Lys Leu Gly Ser Leu Asn Leu Arg
    2180            2185            2190

Trp Gln Glu Val Cys Lys Gln Leu Ala Glu Arg Lys Lys Arg Leu
    2195            2200            2205

Glu Glu Gln Lys Asn Ile Leu Ser Glu Phe Gln Arg Asp Val Asn
    2210            2215            2220

Glu Phe Val Leu Trp Leu Glu Glu Ala Asp Asn Val Ala Asn Ile
    2225            2230            2235

Pro Leu Glu Pro Gly Asn Glu Gln Gln Leu Lys Glu Lys Leu Glu
    2240            2245            2250

Gln Val Lys Leu Leu Ala Glu Glu Leu Pro Leu Arg Gln Gly Ile
    2255            2260            2265

Leu Lys Gln Leu Asn Glu Thr Gly Gly Thr Val Leu Val Ser Ala
    2270            2275            2280

Pro Leu Ser Pro Glu Glu Gln Asp Lys Leu Glu Asn Lys Leu Lys
    2285            2290            2295

Gln Thr Asn Leu Gln Trp Ile Lys Val Ser Arg Asn Leu Pro Glu
    2300            2305            2310

Lys Gln Glu Glu Ile Glu Ala His Val Lys Asp Leu Gly Gln Leu
    2315            2320            2325

Glu Glu Gln Leu Asn His Leu Leu Leu Trp Leu Ser Pro Ile Arg
    2330            2335            2340

Asn Gln Leu Glu Ile Tyr Asn Gln Pro Asn Gln Thr Gly Pro Phe
    2345            2350            2355

Asp Ile Lys Glu Ile Glu Val Ala Val Gln Ala Lys Gln Pro Asp
    2360            2365            2370

Val Glu Gly Ile Leu Ser Lys Gly Gln His Leu Tyr Lys Glu Lys
    2375            2380            2385

Pro Ala Thr Gln Pro Ala Lys Arg Lys Leu Glu Asp Leu Ser Ser
```

```
                2390                2395                2400

Asp Trp Lys Val Val Thr Gln Leu Leu Gln Glu Leu Arg Ala Lys
    2405                2410                2415

Gln Pro Gly Pro Ala Pro Gly Leu Thr Thr Val Arg Ala Pro Pro
    2420                2425                2430

Ser Gln Thr Val Thr Leu Val Thr Gln Pro Ala Val Thr Lys Glu
    2435                2440                2445

Thr Ala Ile Ser Lys Leu Glu Met Pro Ser Ser Leu Leu Leu Glu
    2450                2455                2460

Val Pro Ala Leu Ala Asp Phe Asn Arg Ala Trp Thr Glu Leu Thr
    2465                2470                2475

Asp Trp Leu Ser Leu Leu Asp Arg Val Ile Lys Ser Gln Arg Val
    2480                2485                2490

Met Val Gly Asp Leu Glu Asp Ile Asn Glu Met Ile Ile Lys Gln
    2495                2500                2505

Lys Ala Thr Leu Gln Asp Leu Glu Gln Arg Arg Pro Gln Leu Glu
    2510                2515                2520

Glu Leu Ile Thr Ala Ala Gln Asn Leu Lys Asn Lys Thr Ser Asn
    2525                2530                2535

Gln Glu Ala Arg Thr Ile Ile Thr Asp Arg Ile Glu Arg Ile Gln
    2540                2545                2550

Ser Gln Trp Asp Glu Val Gln Glu His Leu Gln Asn Arg Arg Leu
    2555                2560                2565

Gln Leu Thr Glu Met Leu Lys Asp Ser Thr Gln Trp Leu Glu Ala
    2570                2575                2580

Lys Glu Glu Ala Glu Gln Val Leu Gly Gln Ala Arg Ala Lys Leu
    2585                2590                2595

Glu Ser Trp Lys Glu Ala Pro Tyr Thr Val Asp Ala Ile Gln Lys
    2600                2605                2610

Lys Ile Thr Glu Thr Lys Gln Leu Ala Lys Asp Leu Arg Gln Trp
    2615                2620                2625

Gln Ile Asn Val Asp Val Ala Asn Asp Leu Ala Leu Lys Leu Leu
    2630                2635                2640

Arg Asp Tyr Ser Ala Asp Asp Thr Arg Lys Val His Met Ile Thr
    2645                2650                2655

Glu Asn Ile Asn Ala Ser Trp Ala Ser Ile His Lys Arg Leu Ser
    2660                2665                2670

Glu Arg Glu Ala Ala Leu Glu Glu Thr His Arg Leu Leu Gln Gln
    2675                2680                2685

Phe Pro Leu Asp Leu Glu Lys Phe Leu Ala Trp Leu Thr Glu Ala
    2690                2695                2700

Glu Thr Thr Ala Asn Val Leu Gln Asp Ala Thr His Lys Glu Arg
    2705                2710                2715

Leu Leu Glu Asp Ser Lys Gly Val Arg Glu Leu Met Lys Gln Trp
    2720                2725                2730

Gln Asp Leu Gln Gly Glu Ile Glu Ala His Thr Asp Ile Tyr His
    2735                2740                2745

Asn Leu Asp Glu Asn Gly Gln Lys Val Leu Arg Ser Leu Glu Gly
    2750                2755                2760

Ser Asp Asp Ala Ala Leu Leu Gln Arg Arg Leu Asp Asn Met Asn
    2765                2770                2775

Phe Lys Trp Ser Glu Leu Arg Lys Lys Ser Leu Asn Ile Arg Ser
    2780                2785                2790
```

```
His Leu Glu Ala Ser Ser Asp Gln Trp Lys Arg Leu His Leu Ser
    2795            2800                2805

Leu Gln Glu Leu Leu Val Trp Leu Gln Leu Lys Asp Asp Glu Leu
    2810            2815                2820

Ser Arg Gln Ala Pro Ile Gly Gly Asp Phe Pro Ala Val Gln Lys
    2825            2830                2835

Gln Asn Asp Val His Arg Ala Phe Lys Arg Glu Leu Lys Thr Lys
    2840            2845                2850

Glu Pro Val Ile Met Ser Thr Leu Glu Thr Val Arg Ile Phe Leu
    2855            2860                2865

Thr Glu Gln Pro Leu Glu Gly Leu Glu Lys Leu Tyr Gln Glu Pro
    2870            2875                2880

Arg Glu Leu Pro Pro Glu Glu Arg Ala Gln Asn Val Thr Arg Leu
    2885            2890                2895

Leu Arg Lys Gln Ala Glu Glu Val Asn Thr Gln Trp Glu Lys Leu
    2900            2905                2910

Asn Val His Ser Ala Asp Trp Gln Arg Lys Ile Asp Glu Ala Leu
    2915            2920                2925

Glu Arg Leu Gln Glu Leu Gln Glu Ala Thr Asp Glu Leu Asp Leu
    2930            2935                2940

Lys Leu Arg Gln Ala Glu Val Ile Lys Gly Ser Trp Gln Pro Val
    2945            2950                2955

Gly Asp Leu Leu Ile Asp Ser Leu Gln Asp His Leu Glu Lys Val
    2960            2965                2970

Lys Ala Leu Arg Gly Glu Ile Thr Pro Leu Lys Glu Asn Val Ser
    2975            2980                2985

Tyr Val Asn Asp Leu Ala Arg Gln Leu Thr Thr Leu Gly Ile Gln
    2990            2995                3000

Leu Ser Pro Tyr Asn Leu Asn Thr Leu Glu Asp Leu Asn Thr Arg
    3005            3010                3015

Trp Lys Leu Leu Gln Val Ala Ile Glu Asp Arg Ile Arg Gln Leu
    3020            3025                3030

His Glu Ala His Arg Asp Phe Gly Pro Ala Ser Gln His Phe Leu
    3035            3040                3045

Ser Thr Ser Val Gln Gly Pro Trp Glu Arg Ala Ile Ser Pro Asn
    3050            3055                3060

Lys Val Pro Tyr Tyr Ile Asn His Glu Thr Gln Thr Thr Cys Trp
    3065            3070                3075

Asp His Pro Lys Met Thr Glu Leu Tyr Gln Ser Leu Ala Asp Leu
    3080            3085                3090

Asn Asn Val Arg Phe Ser Ala Tyr Arg Thr Ala Met Lys Leu Arg
    3095            3100                3105

Arg Leu Gln Lys Ala Ile Cys Leu Asp Leu Leu Ser Leu Ser Ala
    3110            3115                3120

Ala Cys Asp Ala Leu Asp Gln His Asn Leu Lys Gln Asn Asp Gln
    3125            3130                3135

Pro Asn Asp Ile Leu Gln Val Ile Asn Cys Leu Thr Thr Ile Tyr
    3140            3145                3150

Asp Arg Leu Glu Gln Glu His Asn Asn Leu Val Asn Val Pro Leu
    3155            3160                3165

Cys Val Asp Met Cys Leu Asn Trp Leu Leu Asn Val Tyr Asp Thr
    3170            3175                3180
```

```
Gly Arg Thr Gly Arg Ile Arg Val Leu Ser Phe Lys Thr Gly Ile
3185                3190                3195

Ile Ser Leu Cys Lys Ala His Leu Glu Asp Lys Tyr Arg Tyr Leu
3200                3205                3210

Phe Lys Gln Val Ala Ser Ser Thr Gly Phe Cys Asp Gln Arg Arg
3215                3220                3225

Leu Gly Leu Leu Leu His Asp Ser Ile Gln Ile Pro Arg Gln Leu
3230                3235                3240

Gly Glu Val Ala Ser Phe Gly Gly Ser Asn Ile Glu Pro Ser Val
3245                3250                3255

Arg Ser Cys Phe Gln Phe Ala Asn Asn Lys Pro Glu Ile Glu Ala
3260                3265                3270

Ala Leu Phe Leu Asp Trp Met Arg Leu Glu Pro Gln Ser Met Val
3275                3280                3285

Trp Leu Pro Val Leu His Arg Val Ala Ala Glu Thr Ala Lys
3290                3295                3300

His Gln Ala Lys Cys Asn Ile Cys Lys Glu Cys Pro Ile Ile Gly
3305                3310                3315

Phe Arg Tyr Arg Ser Leu Lys His Phe Asn Tyr Asp Ile Cys Gln
3320                3325                3330

Ser Cys Phe Phe Ser Gly Arg Val Ala Lys Gly His Lys Met His
3335                3340                3345

Tyr Pro Met Val Glu Tyr Cys Thr Pro Thr Thr Ser Gly Glu Asp
3350                3355                3360

Val Arg Asp Phe Ala Lys Val Leu Lys Asn Lys Phe Arg Thr Lys
3365                3370                3375

Arg Tyr Phe Ala Lys His Pro Arg Met Gly Tyr Leu Pro Val Gln
3380                3385                3390

Thr Val Leu Glu Gly Asp Asn Met Glu Thr Pro Val Thr Leu Ile
3395                3400                3405

Asn Phe Trp Pro Val Asp Ser Ala Pro Ala Ser Ser Pro Gln Leu
3410                3415                3420

Ser His Asp Asp Thr His Ser Arg Ile Glu His Tyr Ala Ser Arg
3425                3430                3435

Leu Lys Lys Met Glu Asn Ser Asn Gly Ser Tyr Leu Asn Asp Ser
3440                3445                3450

Ile Ser Pro Asn Glu Ser Ile Asp Asp Glu His Leu Leu Ile Gln
3455                3460                3465

His Tyr Trp Arg Ser Leu Asn Gln Glu Ser Pro Leu Ser Gln Pro
3470                3475                3480

Arg Ser Pro Ala Gln Ile Leu Ile Ser Leu Glu Ser Glu Glu Arg
3485                3490                3495

Gly Glu Leu Glu Arg Ile Leu Ala Asp Leu Glu Gly Arg Asn Arg
3500                3505                3510

Asn Leu Gln Ala Glu Tyr Asp Arg Leu Lys Gln Gln His Glu His
3515                3520                3525

Lys Gly Leu Ser Pro Leu Pro Ser Pro Pro Glu Met Met Pro Thr
3530                3535                3540

Ser Pro Gln Ser Pro Arg Asp Ala Glu Leu Ile Ala Glu Ala Lys
3545                3550                3555

Leu Leu Arg Gln His Lys Gly Arg Leu Glu Ala Arg Met Gln Ile
3560                3565                3570

Leu Glu Asp His Asn Lys Gln Leu Glu Ser Gln Leu His Arg Leu
```

```
              3575                3580                3585

Arg Gln Leu Leu Glu Gln Pro Gln Ala Glu Ala Lys Val Asn Gly
        3590                3595                3600

Thr Thr Val Ser Ser Pro Ser Thr Ser Leu Gln Arg Ser Asp Ser
    3605                3610                3615

Ser Gln Pro Met Leu Leu Arg Val Val Gly Ser Gln Thr Ser Glu
    3620                3625                3630

Ser Met Gly Glu Glu Asp Leu Leu Ser Pro Pro Gln Asp Thr Ser
    3635                3640                3645

Thr Gly Leu Glu Glu Val Met Glu Gln Leu Asn His Ser Phe Pro
    3650                3655                3660

Ser Ser Arg Gly Arg Asn Thr Pro Gly Lys Pro Met Arg Glu Asp
    3665                3670                3675

Thr Met
    3680

<210> SEQ ID NO 50
<211> LENGTH: 251
<212> TYPE: PRT
<213> ORGANISM: Homo sapiens

<400> SEQUENCE: 50

Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Val Met Lys Asn Ile Met Ala
        115                 120                 125

Gly Leu Gln Gln Thr Asn Ser Glu Lys Ile Leu Leu Ser Trp Val Arg
    130                 135                 140

Gln Ser Thr Arg Asn Tyr Pro Gln Val Asn Val Ile Asn Phe Thr Thr
145                 150                 155                 160

Ser Trp Ser Asp Gly Leu Ala Leu Asn Ala Leu Ile His Ser His Arg
                165                 170                 175

Pro Asp Leu Phe Asp Trp Asn Ser Val Val Cys Gln Gln Ser Ala Thr
            180                 185                 190

Gln Arg Leu Glu His Ala Phe Asn Ile Ala Arg Tyr Gln Leu Gly Ile
        195                 200                 205

Glu Lys Leu Leu Asp Pro Glu Asp Val Asp Thr Thr Tyr Pro Asp Lys
    210                 215                 220

Lys Ser Ile Leu Met Tyr Ile Thr Ser Leu Phe Gln Val Leu Pro Gln
225                 230                 235                 240

Gln Val Ser Ile Glu Ala Ile Gln Glu Val Glu
                245                 250
```

<210> SEQ ID NO 51
<211> LENGTH: 2860
<212> TYPE: PRT
<213> ORGANISM: Homo sapiens

<400> SEQUENCE: 51

```
Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser Glu Val Asn Leu Asp Arg Tyr Gln Thr Ala Leu
                85                  90                  95

Glu Glu Val Leu Ser Trp Leu Leu Ser Ala Glu Asp Thr Leu Gln Ala
            100                 105                 110

Gln Gly Glu Ile Ser Asn Asp Val Glu Val Val Lys Asp Gln Phe His
        115                 120                 125

Thr His Glu Gly Tyr Met Met Asp Leu Thr Ala His Gln Gly Arg Val
    130                 135                 140

Gly Asn Ile Leu Gln Leu Gly Ser Lys Leu Ile Gly Thr Gly Lys Leu
145                 150                 155                 160

Ser Glu Asp Glu Glu Thr Glu Val Gln Glu Gln Met Asn Leu Leu Asn
                165                 170                 175

Ser Arg Trp Glu Cys Leu Arg Val Ala Ser Met Glu Lys Gln Ser Asn
            180                 185                 190

Leu His Arg Val Leu Met Asp Leu Gln Asn Gln Lys Leu Lys Glu Leu
        195                 200                 205

Asn Asp Trp Leu Thr Lys Thr Glu Glu Arg Thr Arg Lys Met Glu Glu
    210                 215                 220

Glu Pro Leu Gly Pro Asp Leu Glu Asp Leu Lys Arg Gln Val Gln Gln
225                 230                 235                 240

His Lys Val Leu Gln Glu Asp Leu Glu Gln Glu Gln Val Arg Val Asn
                245                 250                 255

Ser Leu Thr His Met Val Val Val Asp Glu Ser Ser Gly Asp His
            260                 265                 270

Ala Thr Ala Ala Leu Glu Glu Gln Leu Lys Val Leu Gly Asp Arg Trp
        275                 280                 285

Ala Asn Ile Cys Arg Trp Thr Glu Asp Arg Trp Val Leu Leu Gln Asp
    290                 295                 300

Ile Leu Leu Lys Trp Gln Arg Leu Thr Glu Glu Gln Cys Leu Phe Ser
305                 310                 315                 320

Ala Trp Leu Ser Glu Lys Glu Asp Ala Val Asn Lys Ile His Thr Thr
                325                 330                 335

Gly Phe Lys Asp Gln Asn Glu Met Leu Ser Ser Leu Lys Leu Ala
            340                 345                 350

Val Leu Lys Ala Asp Leu Glu Lys Lys Gln Ser Met Gly Lys Leu
        355                 360                 365

Tyr Ser Leu Lys Gln Asp Leu Leu Ser Thr Leu Lys Asn Lys Ser Val
    370                 375                 380
```

```
Thr Gln Lys Thr Glu Ala Trp Leu Asp Asn Phe Ala Arg Cys Trp Asp
385                 390                 395                 400

Asn Leu Val Gln Lys Leu Glu Lys Ser Thr Ala Gln Ile Ser Gln Ala
            405                 410                 415

Val Thr Thr Thr Gln Pro Ser Leu Thr Gln Thr Thr Val Met Glu Thr
        420                 425                 430

Val Thr Thr Val Thr Thr Arg Glu Gln Ile Leu Val Lys His Ala Gln
        435                 440                 445

Glu Glu Leu Pro Pro Pro Pro Gln Lys Lys Arg Gln Ile Thr Val
    450                 455                 460

Asp Ser Glu Ile Arg Lys Arg Leu Asp Val Asp Ile Thr Glu Leu His
465                 470                 475                 480

Ser Trp Ile Thr Arg Ser Glu Ala Val Leu Gln Ser Pro Glu Phe Ala
                485                 490                 495

Ile Phe Arg Lys Glu Gly Asn Phe Ser Asp Leu Lys Glu Lys Val Asn
            500                 505                 510

Ala Ile Glu Arg Glu Lys Ala Glu Lys Phe Arg Lys Leu Gln Asp Ala
            515                 520                 525

Ser Arg Ser Ala Gln Ala Leu Val Glu Gln Met Val Asn Glu Gly Val
530                 535                 540

Asn Ala Asp Ser Ile Lys Gln Ala Ser Glu Gln Leu Asn Ser Arg Trp
545                 550                 555                 560

Ile Glu Phe Cys Gln Leu Leu Ser Glu Arg Leu Asn Trp Leu Glu Tyr
                565                 570                 575

Gln Asn Asn Ile Ile Ala Phe Tyr Asn Gln Leu Gln Gln Leu Glu Gln
            580                 585                 590

Met Thr Thr Thr Ala Glu Asn Trp Leu Lys Ile Gln Pro Thr Thr Pro
            595                 600                 605

Ser Glu Pro Thr Ala Ile Lys Ser Gln Leu Lys Ile Cys Lys Asp Glu
            610                 615                 620

Val Asn Arg Leu Ser Gly Leu Gln Pro Gln Ile Glu Arg Leu Lys Ile
625                 630                 635                 640

Gln Ser Ile Ala Leu Lys Glu Lys Gly Gln Gly Pro Met Phe Leu Asp
                645                 650                 655

Ala Asp Phe Val Ala Phe Thr Asn His Phe Lys Gln Val Phe Ser Asp
                660                 665                 670

Val Gln Ala Arg Glu Lys Glu Leu Gln Thr Ile Phe Asp Thr Leu Pro
            675                 680                 685

Pro Met Arg Tyr Gln Glu Thr Met Ser Ala Ile Arg Thr Trp Val Gln
            690                 695                 700

Gln Ser Glu Thr Lys Leu Ser Ile Pro Gln Leu Ser Val Thr Asp Tyr
705                 710                 715                 720

Glu Ile Met Glu Gln Arg Leu Gly Glu Leu Gln Ala Leu Gln Ser Ser
                725                 730                 735

Leu Gln Glu Gln Gln Ser Gly Leu Tyr Tyr Leu Ser Thr Thr Val Lys
            740                 745                 750

Glu Met Ser Lys Lys Ala Pro Ser Glu Ile Ser Arg Lys Tyr Gln Ser
            755                 760                 765

Glu Phe Glu Glu Ile Glu Gly Arg Trp Lys Lys Leu Ser Ser Gln Leu
            770                 775                 780

Val Glu His Cys Gln Lys Leu Glu Glu Gln Met Asn Lys Leu Arg Lys
785                 790                 795                 800
```

```
Ile Gln Asn His Ile Gln Thr Leu Lys Lys Trp Met Ala Glu Val Asp
                805                 810                 815

Val Phe Leu Lys Glu Glu Trp Pro Ala Leu Gly Asp Ser Glu Ile Leu
        820                 825                 830

Lys Lys Gln Leu Lys Gln Cys Arg Leu Leu Val Ser Asp Ile Gln Thr
    835                 840                 845

Ile Gln Pro Ser Leu Asn Ser Val Asn Glu Gly Gly Gln Lys Ile Lys
850                 855                 860

Asn Glu Ala Glu Pro Glu Phe Ala Ser Arg Leu Glu Thr Glu Leu Lys
865                 870                 875                 880

Glu Leu Asn Thr Gln Trp Asp His Met Cys Gln Gln Val Tyr Ala Arg
            885                 890                 895

Lys Glu Ala Leu Lys Gly Gly Leu Glu Lys Thr Val Ser Leu Gln Lys
        900                 905                 910

Asp Leu Ser Glu Met His Glu Trp Met Thr Gln Ala Glu Glu Glu Tyr
    915                 920                 925

Leu Glu Arg Asp Phe Glu Tyr Lys Thr Pro Asp Glu Leu Gln Lys Ala
    930                 935                 940

Val Glu Glu Met Lys Arg Ala Lys Glu Ala Gln Gln Lys Glu Ala
945                 950                 955                 960

Lys Val Lys Leu Leu Thr Glu Ser Val Asn Ser Val Ile Ala Gln Ala
            965                 970                 975

Pro Pro Val Ala Gln Glu Ala Leu Lys Lys Glu Leu Glu Thr Leu Thr
            980                 985                 990

Thr Asn Tyr Gln Trp Leu Cys Thr Arg Leu Asn Gly Lys Cys Lys Thr
        995                 1000                1005

Leu Glu Glu Val Trp Ala Cys Trp His Glu Leu Leu Ser Tyr Leu
    1010                1015                1020

Glu Lys Ala Asn Lys Trp Leu Asn Glu Val Glu Phe Lys Leu Lys
    1025                1030                1035

Thr Thr Glu Asn Ile Pro Gly Gly Ala Glu Glu Ile Ser Glu Val
    1040                1045                1050

Leu Asp Ser Leu Glu Asn Leu Met Arg His Ser Glu Asp Asn Pro
    1055                1060                1065

Asn Gln Ile Arg Ile Leu Ala Gln Thr Leu Thr Asp Gly Gly Val
    1070                1075                1080

Met Asp Glu Leu Ile Asn Glu Glu Leu Glu Thr Phe Asn Ser Arg
    1085                1090                1095

Trp Arg Glu Leu His Glu Glu Ala Val Arg Arg Gln Lys Leu Leu
    1100                1105                1110

Glu Gln Ser Ile Gln Ser Ala Gln Glu Thr Glu Lys Ser Leu His
    1115                1120                1125

Leu Ile Gln Glu Ser Leu Thr Phe Ile Asp Lys Gln Leu Ala Ala
    1130                1135                1140

Tyr Ile Ala Asp Lys Val Asp Ala Ala Gln Met Pro Gln Glu Ala
    1145                1150                1155

Gln Lys Ile Gln Ser Asp Leu Thr Ser His Glu Ile Ser Leu Glu
    1160                1165                1170

Glu Met Lys Lys His Asn Gln Gly Lys Glu Ala Ala Gln Arg Val
    1175                1180                1185

Leu Ser Gln Ile Asp Val Ala Gln Lys Lys Leu Gln Asp Val Ser
    1190                1195                1200

Met Lys Phe Arg Leu Phe Gln Lys Pro Ala Asn Phe Glu Leu Arg
```

```
                  1205                1210                1215
Leu Gln Glu Ser Lys Met Ile Leu Asp Glu Val Lys Met His Leu
    1220                1225                1230
Pro Ala Leu Glu Thr Lys Ser Val Gln Glu Val Val Gln Ser
    1235                1240                1245
Gln Leu Asn His Cys Val Asn Leu Tyr Lys Ser Leu Ser Glu Val
    1250                1255                1260
Lys Ser Glu Val Glu Met Val Ile Lys Thr Gly Arg Gln Ile Val
    1265                1270                1275
Gln Lys Lys Gln Thr Glu Asn Pro Lys Glu Leu Asp Glu Arg Val
    1280                1285                1290
Thr Ala Leu Lys Leu His Tyr Asn Glu Leu Gly Ala Lys Val Thr
    1295                1300                1305
Glu Arg Lys Gln Gln Leu Glu Lys Cys Leu Lys Leu Ser Arg Lys
    1310                1315                1320
Met Arg Lys Glu Met Asn Val Leu Thr Glu Trp Leu Ala Ala Thr
    1325                1330                1335
Asp Met Glu Leu Thr Lys Arg Ser Ala Val Glu Gly Met Pro Ser
    1340                1345                1350
Asn Leu Asp Ser Glu Val Ala Trp Gly Lys Ala Thr Gln Lys Glu
    1355                1360                1365
Ile Glu Lys Gln Lys Val His Leu Lys Ser Ile Thr Glu Val Gly
    1370                1375                1380
Glu Ala Leu Lys Thr Val Leu Gly Lys Lys Glu Thr Leu Val Glu
    1385                1390                1395
Asp Lys Leu Ser Leu Leu Asn Ser Asn Trp Ile Ala Val Thr Ser
    1400                1405                1410
Arg Ala Glu Glu Trp Leu Asn Leu Leu Leu Glu Tyr Gln Lys His
    1415                1420                1425
Met Glu Thr Phe Asp Gln Asn Val Asp His Ile Thr Lys Trp Ile
    1430                1435                1440
Ile Gln Ala Asp Thr Leu Leu Asp Glu Ser Glu Lys Lys Lys Pro
    1445                1450                1455
Gln Gln Lys Glu Asp Val Leu Lys Arg Leu Lys Ala Glu Leu Asn
    1460                1465                1470
Asp Ile Arg Pro Lys Val Asp Ser Thr Arg Asp Gln Ala Ala Asn
    1475                1480                1485
Leu Met Ala Asn Arg Gly Asp His Cys Arg Lys Leu Val Glu Pro
    1490                1495                1500
Gln Ile Ser Glu Leu Asn His Arg Phe Ala Ala Ile Ser His Arg
    1505                1510                1515
Ile Lys Thr Gly Lys Ala Ser Ile Pro Leu Lys Glu Leu Glu Gln
    1520                1525                1530
Phe Asn Ser Asp Ile Gln Lys Leu Leu Glu Pro Leu Glu Ala Glu
    1535                1540                1545
Ile Gln Gln Gly Val Asn Leu Lys Glu Glu Asp Phe Asn Lys Asp
    1550                1555                1560
Met Asn Glu Asp Asn Glu Gly Thr Val Lys Glu Leu Leu Gln Arg
    1565                1570                1575
Gly Asp Asn Leu Gln Gln Arg Ile Thr Asp Glu Arg Lys Arg Glu
    1580                1585                1590
Glu Ile Lys Ile Lys Gln Gln Leu Leu Gln Thr Lys His Asn Ala
    1595                1600                1605
```

```
Leu Lys Asp Leu Arg Ser Gln Arg Arg Lys Ala Leu Glu Ile
    1610            1615            1620

Ser His Gln Trp Tyr Gln Tyr Lys Arg Gln Ala Asp Asp Leu Leu
    1625            1630            1635

Lys Cys Leu Asp Asp Ile Glu Lys Lys Leu Ala Ser Leu Pro Glu
    1640            1645            1650

Pro Arg Asp Glu Arg Lys Ile Lys Glu Ile Asp Arg Glu Leu Gln
    1655            1660            1665

Lys Lys Lys Glu Glu Leu Asn Ala Val Arg Arg Gln Ala Glu Gly
    1670            1675            1680

Leu Ser Glu Asp Gly Ala Ala Met Ala Val Glu Pro Thr Gln Ile
    1685            1690            1695

Gln Leu Ser Lys Arg Trp Arg Glu Ile Glu Ser Lys Phe Ala Gln
    1700            1705            1710

Phe Arg Arg Leu Asn Phe Ala Gln Ile His Thr Val Arg Glu Glu
    1715            1720            1725

Thr Met Met Val Met Thr Glu Asp Met Pro Leu Glu Ile Ser Tyr
    1730            1735            1740

Val Pro Ser Thr Tyr Leu Thr Glu Ile Thr His Val Ser Gln Ala
    1745            1750            1755

Leu Leu Glu Val Glu Gln Leu Leu Asn Ala Pro Asp Leu Cys Ala
    1760            1765            1770

Lys Asp Phe Glu Asp Leu Phe Lys Gln Glu Glu Ser Leu Lys Asn
    1775            1780            1785

Ile Lys Asp Ser Leu Gln Gln Ser Ser Gly Arg Ile Asp Ile Ile
    1790            1795            1800

His Ser Lys Lys Thr Ala Ala Leu Gln Ser Ala Thr Pro Val Glu
    1805            1810            1815

Arg Val Lys Leu Gln Glu Ala Leu Ser Gln Leu Asp Phe Gln Trp
    1820            1825            1830

Glu Lys Val Asn Lys Met Tyr Lys Asp Arg Gln Gly Arg Phe Asp
    1835            1840            1845

Arg Ser Val Glu Lys Trp Arg Arg Phe His Tyr Asp Ile Lys Ile
    1850            1855            1860

Phe Asn Gln Trp Leu Thr Glu Ala Glu Gln Phe Leu Arg Lys Thr
    1865            1870            1875

Gln Ile Pro Glu Asn Trp Glu His Ala Lys Tyr Lys Trp Tyr Leu
    1880            1885            1890

Lys Glu Leu Gln Asp Gly Ile Gly Gln Arg Gln Thr Val Val Arg
    1895            1900            1905

Thr Leu Asn Ala Thr Gly Glu Glu Ile Ile Gln Gln Ser Ser Lys
    1910            1915            1920

Thr Asp Ala Ser Ile Leu Gln Glu Lys Leu Gly Ser Leu Asn Leu
    1925            1930            1935

Arg Trp Gln Glu Val Cys Lys Gln Leu Ser Asp Arg Lys Lys Arg
    1940            1945            1950

Leu Glu Glu Gln Lys Asn Ile Leu Ser Glu Phe Gln Arg Asp Leu
    1955            1960            1965

Asn Glu Phe Val Leu Trp Leu Glu Glu Ala Asp Asn Ile Ala Ser
    1970            1975            1980

Ile Pro Leu Glu Pro Gly Lys Glu Gln Gln Leu Lys Glu Lys Leu
    1985            1990            1995
```

```
Glu Gln Val Lys Leu Leu Val Glu Glu Leu Pro Leu Arg Gln Gly
2000                2005                2010

Ile Leu Lys Gln Leu Asn Glu Thr Gly Pro Val Leu Val Ser
2015                2020                2025

Ala Pro Ile Ser Pro Glu Gln Asp Lys Leu Glu Asn Lys Leu
2030                2035                2040

Lys Gln Thr Asn Leu Gln Trp Ile Lys Val Ser Arg Ala Leu Pro
2045                2050                2055

Glu Lys Gln Gly Glu Ile Glu Ala Gln Ile Lys Asp Leu Gly Gln
2060                2065                2070

Leu Glu Lys Lys Leu Glu Asp Leu Glu Glu Gln Leu Asn His Leu
2075                2080                2085

Leu Leu Trp Leu Ser Pro Ile Arg Asn Gln Leu Glu Ile Tyr Asn
2090                2095                2100

Gln Pro Asn Gln Glu Gly Pro Phe Asp Val Gln Glu Thr Glu Ile
2105                2110                2115

Ala Val Gln Ala Lys Gln Pro Asp Val Glu Glu Ile Leu Ser Lys
2120                2125                2130

Gly Gln His Leu Tyr Lys Glu Lys Pro Ala Thr Gln Pro Val Lys
2135                2140                2145

Arg Lys Leu Glu Asp Leu Ser Ser Glu Trp Lys Ala Val Asn Arg
2150                2155                2160

Leu Leu Gln Glu Leu Arg Ala Lys Gln Pro Asp Leu Ala Pro Gly
2165                2170                2175

Leu Thr Thr Ile Gly Ala Ser Pro Thr Gln Thr Val Thr Leu Val
2180                2185                2190

Thr Gln Pro Val Val Thr Lys Glu Thr Ala Ile Ser Lys Leu Glu
2195                2200                2205

Met Pro Ser Ser Leu Met Leu Glu Val Pro Ala Leu Ala Asp Phe
2210                2215                2220

Asn Arg Ala Trp Thr Glu Leu Thr Asp Trp Leu Ser Leu Leu Asp
2225                2230                2235

Gln Val Ile Lys Ser Gln Arg Val Met Val Gly Asp Leu Glu Asp
2240                2245                2250

Ile Asn Glu Met Ile Ile Lys Gln Lys Ala Thr Met Gln Asp Leu
2255                2260                2265

Glu Gln Arg Arg Pro Gln Leu Glu Glu Leu Ile Thr Ala Ala Gln
2270                2275                2280

Asn Leu Lys Asn Lys Thr Ser Asn Gln Glu Ala Arg Thr Ile Ile
2285                2290                2295

Thr Asp Arg Ile Glu Arg Ile Gln Asn Gln Trp Asp Glu Val Gln
2300                2305                2310

Glu His Leu Gln Asn Arg Arg Gln Gln Leu Asn Glu Met Leu Lys
2315                2320                2325

Asp Ser Thr Gln Trp Leu Glu Ala Lys Glu Glu Ala Glu Gln Val
2330                2335                2340

Leu Gly Gln Ala Arg Ala Lys Leu Glu Ser Trp Lys Glu Gly Pro
2345                2350                2355

Tyr Thr Val Asp Ala Ile Gln Lys Lys Ile Thr Glu Thr Lys Gln
2360                2365                2370

Leu Ala Lys Asp Leu Arg Gln Trp Gln Thr Asn Val Asp Val Ala
2375                2380                2385

Asn Asp Leu Ala Leu Lys Leu Leu Arg Asp Tyr Ser Ala Asp Asp
```

|   |   |   |   |   |   |   |   |   |   |
|---|---|---|---|---|---|---|---|---|---|
|     2390      |     |     |     |     2395 |     |     |     2400 |     |     |
| Thr | Arg | Lys | Val | His | Met | Ile | Thr | Glu | Asn | Ile | Asn | Ala | Ser | Trp |

Thr Arg Lys Val His Met Ile Thr Glu Asn Ile Asn Ala Ser Trp
          2405                     2410                    2415

Arg Ser Ile His Lys Arg Val Ser Glu Arg Glu Ala Ala Leu Glu
          2420                     2425                    2430

Glu Thr His Arg Leu Leu Gln Gln Phe Pro Leu Asp Leu Glu Lys
          2435                     2440                    2445

Phe Leu Ala Trp Leu Thr Glu Ala Glu Thr Thr Ala Asn Val Leu
          2450                     2455                    2460

Gln Asp Ala Thr Arg Lys Glu Arg Leu Leu Glu Asp Ser Lys Gly
          2465                     2470                    2475

Val Lys Glu Leu Met Lys Gln Trp Gln Asp Leu Gln Gly Glu Ile
          2480                     2485                    2490

Glu Ala His Thr Asp Val Tyr His Asn Leu Asp Glu Asn Ser Gln
          2495                     2500                    2505

Lys Ile Leu Arg Ser Leu Glu Gly Ser Asp Asp Ala Val Leu Leu
          2510                     2515                    2520

Gln Arg Arg Leu Asp Asn Met Asn Phe Lys Trp Ser Glu Leu Arg
          2525                     2530                    2535

Lys Lys Ser Leu Asn Ile Arg Ser His Leu Glu Ala Ser Ser Asp
          2540                     2545                    2550

Gln Trp Lys Arg Leu His Leu Ser Leu Gln Glu Leu Leu Val Trp
          2555                     2560                    2565

Leu Gln Leu Lys Asp Asp Glu Leu Ser Arg Gln Ala Pro Ile Gly
          2570                     2575                    2580

Gly Asp Phe Pro Ala Val Gln Lys Gln Asn Asp Val His Arg Ala
          2585                     2590                    2595

Phe Lys Arg Glu Leu Lys Thr Lys Glu Pro Val Ile Met Ser Thr
          2600                     2605                    2610

Leu Glu Thr Val Arg Ile Phe Leu Thr Glu Gln Pro Leu Glu Gly
          2615                     2620                    2625

Leu Glu Lys Leu Tyr Gln Glu Pro Arg Glu Leu Pro Pro Glu Glu
          2630                     2635                    2640

Arg Ala Gln Asn Val Thr Arg Leu Leu Arg Lys Gln Ala Glu Glu
          2645                     2650                    2655

Val Asn Thr Glu Trp Glu Lys Leu Asn Leu His Ser Ala Asp Trp
          2660                     2665                    2670

Gln Arg Lys Ile Asp Glu Thr Leu Glu Arg Leu Gln Glu Leu Gln
          2675                     2680                    2685

Glu Ala Thr Asp Glu Leu Asp Leu Lys Leu Arg Gln Ala Glu Val
          2690                     2695                    2700

Ile Lys Gly Ser Trp Gln Pro Val Gly Asp Leu Leu Ile Asp Ser
          2705                     2710                    2715

Leu Gln Asp His Leu Glu Lys Val Lys Ala Leu Arg Gly Glu Ile
          2720                     2725                    2730

Ala Pro Leu Lys Glu Asn Val Ser His Val Asn Asp Leu Ala Arg
          2735                     2740                    2745

Gln Leu Thr Thr Leu Gly Ile Gln Leu Ser Pro Tyr Asn Leu Ser
          2750                     2755                    2760

Thr Leu Glu Asp Leu Asn Thr Arg Trp Lys Leu Leu Gln Val Ala
          2765                     2770                    2775

Val Glu Asp Arg Val Arg Gln Leu His Glu Ala His Arg Asp Phe
          2780                     2785                    2790

```
Gly Pro Ala Ser Gln His Phe Leu Ser Thr Ser Val Gln Gly Pro
    2795                2800                2805

Trp Glu Arg Ala Ile Ser Pro Asn Lys Val Pro Tyr Tyr Ile Asn
    2810                2815                2820

His Glu Thr Gln Thr Thr Cys Trp Asp His Pro Lys Met Thr Glu
    2825                2830                2835

Leu Tyr Gln Ser Leu Ala Asp Leu Asn Asn Val Arg Phe Ser Ala
    2840                2845                2850

Tyr Arg Thr Ala Met Lys Leu
    2855                2860

<210> SEQ ID NO 52
<211> LENGTH: 296
<212> TYPE: PRT
<213> ORGANISM: Homo sapiens

<400> SEQUENCE: 52

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
            20                  25                  30

Met Asp Ile Leu Gln Ile Ile Asn Cys Leu Thr Thr Ile Tyr Asp Arg
        35                  40                  45

Leu Glu Gln Glu His Asn Asn Leu Val Asn Val Pro Leu Cys Val Asp
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
```

<210> SEQ ID NO 53
<211> LENGTH: 277
<212> TYPE: PRT
<213> ORGANISM: Homo sapiens

<400> SEQUENCE: 53

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Asp Glu His Leu Leu Ile
    50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95

Glu Leu Glu Arg Ile Leu Ala Asp Leu Glu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175

Gln Leu Glu Ser Gln Leu His Arg Leu Arg Gln Leu Leu Glu Gln Pro
            180                 185                 190

Gln Ala Glu Ala Lys Val Asn Gly Thr Thr Val Ser Ser Pro Ser Thr
        195                 200                 205

Ser Leu Gln Arg Ser Asp Ser Ser Gln Pro Met Leu Leu Arg Val Val
    210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
            260                 265                 270

Arg Glu Asp Thr Met
        275

<210> SEQ ID NO 54
<211> LENGTH: 15
<212> TYPE: PRT
<213> ORGANISM: Homo sapiens

<400> SEQUENCE: 54

Leu Leu Asn Ser Arg Trp Glu Cys Leu Arg Val Ala Ser Met Glu
1               5                   10                  15

<210> SEQ ID NO 55
<211> LENGTH: 15
<212> TYPE: PRT

<213> ORGANISM: Homo sapiens

<400> SEQUENCE: 55

Gln Arg Leu Thr Glu Glu Gln Cys Leu Phe Ser Ala Trp Leu Ser
1               5                   10                  15

<210> SEQ ID NO 56
<211> LENGTH: 15
<212> TYPE: PRT
<213> ORGANISM: Homo sapiens

<400> SEQUENCE: 56

Trp Leu Asp Asn Phe Ala Arg Cys Trp Asp Asn Leu Val Gln Lys
1               5                   10                  15

<210> SEQ ID NO 57
<211> LENGTH: 8
<212> TYPE: PRT
<213> ORGANISM: Homo sapiens

<400> SEQUENCE: 57

Cys Leu Lys Leu Ser Arg Lys Met
1               5

<210> SEQ ID NO 58
<211> LENGTH: 110
<212> TYPE: PRT
<213> ORGANISM: Homo sapiens

<400> SEQUENCE: 58

Glu Ile Ser Tyr Val Pro Ser Thr Tyr Leu Thr Glu Ile Thr His Val
1               5                   10                  15

Ser Gln Ala Leu Leu Glu Val Glu Gln Leu Leu Asn Ala Pro Asp Leu
            20                  25                  30

Cys Ala Lys Asp Phe Glu Asp Leu Phe Lys Gln Glu Glu Ser Leu Lys
        35                  40                  45

Asn Ile Lys Asp Ser Leu Gln Gln Ser Ser Gly Arg Ile Asp Ile Ile
    50                  55                  60

His Ser Lys Lys Thr Ala Ala Leu Gln Ser Ala Thr Pro Val Glu Arg
65                  70                  75                  80

Val Lys Leu Gln Glu Ala Leu Ser Gln Leu Asp Phe Gln Trp Glu Lys
                85                  90                  95

Val Asn Lys Met Tyr Lys Asp Arg Gln Gly Arg Phe Asp Arg
            100                 105                 110

<210> SEQ ID NO 59
<211> LENGTH: 21
<212> TYPE: PRT
<213> ORGANISM: Homo sapiens

<400> SEQUENCE: 59

Pro Ser Thr Tyr Leu Thr Glu Ile Thr His Val Ser Gln Ala Leu Leu
1               5                   10                  15

Glu Val Glu Gln Leu
            20

<210> SEQ ID NO 60
<211> LENGTH: 309
<212> TYPE: PRT
<213> ORGANISM: Homo sapiens

<400> SEQUENCE: 60

Ser Ile Gln Ser Ala Gln Thr Glu Lys Ser Leu His Leu Ile Gln
1               5                   10                  15

Glu Ser Leu Thr Phe Ile Asp Lys Gln Leu Ala Ala Tyr Ile Ala Asp
            20                  25                  30

Lys Val Asp Ala Ala Gln Met Pro Gln Glu Ala Gln Lys Ile Gln Ser
        35                  40                  45

Asp Leu Thr Ser His Glu Ile Ser Leu Glu Glu Met Lys Lys His Asn
    50                  55                  60

Gln Gly Lys Glu Ala Ala Gln Arg Val Leu Ser Gln Ile Asp Val Ala
65                  70                  75                  80

Gln Lys Lys Leu Gln Asp Val Ser Met Lys Phe Arg Leu Phe Gln Lys
                85                  90                  95

Pro Ala Asn Phe Glu Leu Arg Leu Gln Glu Ser Lys Met Ile Leu Asp
            100                 105                 110

Glu Val Lys Met His Leu Pro Ala Leu Glu Thr Lys Ser Val Glu Gln
        115                 120                 125

Glu Val Val Gln Ser Gln Leu Asn His Cys Val Asn Leu Tyr Lys Ser
    130                 135                 140

Leu Ser Glu Val Lys Ser Glu Val Glu Met Val Ile Lys Thr Gly Arg
145                 150                 155                 160

Gln Ile Val Gln Lys Lys Gln Thr Glu Asn Pro Lys Glu Leu Asp Glu
                165                 170                 175

Arg Val Thr Ala Leu Lys Leu His Tyr Asn Glu Leu Gly Ala Lys Val
            180                 185                 190

Thr Glu Arg Lys Gln Gln Leu Glu Lys Cys Leu Lys Leu Ser Arg Lys
        195                 200                 205

Met Arg Lys Glu Met Asn Val Leu Thr Glu Trp Leu Ala Ala Thr Asp
    210                 215                 220

Met Glu Leu Thr Lys Arg Ser Ala Val Glu Gly Met Pro Ser Asn Leu
225                 230                 235                 240

Asp Ser Glu Val Ala Trp Gly Lys Ala Thr Gln Lys Glu Ile Glu Lys
                245                 250                 255

Gln Lys Val His Leu Lys Ser Ile Thr Glu Val Gly Glu Ala Leu Lys
            260                 265                 270

Thr Val Leu Gly Lys Lys Glu Thr Leu Val Glu Asp Lys Leu Ser Leu
        275                 280                 285

Leu Asn Ser Asn Trp Ile Ala Val Thr Ser Arg Ala Glu Glu Trp Leu
    290                 295                 300

Asn Leu Leu Leu Glu
305

<210> SEQ ID NO 61
<211> LENGTH: 331
<212> TYPE: PRT
<213> ORGANISM: Homo sapiens

<400> SEQUENCE: 61

Ser Glu Val Asn Leu Asp Arg Tyr Gln Thr Ala Leu Glu Glu Val Leu
1               5                   10                  15

Ser Trp Leu Leu Ser Ala Glu Asp Thr Leu Gln Ala Gln Gly Glu Ile
            20                  25                  30

Ser Asn Asp Val Glu Val Val Lys Asp Gln Phe His Thr His Glu Gly
        35                  40                  45

Tyr Met Met Asp Leu Thr Ala His Gln Gly Arg Val Gly Asn Ile Leu

```
              50                  55                  60
Gln Leu Gly Ser Lys Leu Ile Gly Thr Gly Lys Leu Ser Glu Asp Glu
 65                  70                  75                  80

Glu Thr Glu Val Gln Glu Gln Met Asn Leu Leu Asn Ser Arg Trp Glu
                 85                  90                  95

Cys Leu Arg Val Ala Ser Met Glu Lys Gln Ser Asn Leu His Arg Val
            100                 105                 110

Leu Met Asp Leu Gln Asn Gln Lys Leu Lys Glu Leu Asn Asp Trp Leu
        115                 120                 125

Thr Lys Thr Glu Glu Arg Thr Arg Lys Met Glu Glu Pro Leu Gly
    130                 135                 140

Pro Asp Leu Glu Asp Leu Lys Arg Gln Val Gln Gln His Lys Val Leu
145                 150                 155                 160

Gln Glu Asp Leu Glu Gln Glu Gln Val Arg Val Asn Ser Leu Thr His
                165                 170                 175

Met Val Val Val Asp Glu Ser Ser Gly Asp His Ala Thr Ala Ala
            180                 185                 190

Leu Glu Glu Gln Leu Lys Val Leu Gly Asp Arg Trp Ala Asn Ile Cys
        195                 200                 205

Arg Trp Thr Glu Asp Arg Trp Val Leu Leu Gln Asp Ile Leu Leu Lys
    210                 215                 220

Trp Gln Arg Leu Thr Glu Glu Gln Cys Leu Phe Ser Ala Trp Leu Ser
225                 230                 235                 240

Glu Lys Glu Asp Ala Val Asn Lys Ile His Thr Thr Gly Phe Lys Asp
                245                 250                 255

Gln Asn Glu Met Leu Ser Ser Leu Gln Lys Leu Ala Val Leu Lys Ala
            260                 265                 270

Asp Leu Glu Lys Lys Lys Gln Ser Met Gly Lys Leu Tyr Ser Leu Lys
        275                 280                 285

Gln Asp Leu Leu Ser Thr Leu Lys Asn Lys Ser Val Thr Gln Lys Thr
    290                 295                 300

Glu Ala Trp Leu Asp Asn Phe Ala Arg Cys Trp Asp Asn Leu Val Gln
305                 310                 315                 320

Lys Leu Glu Lys Ser Thr Ala Gln Ile Ser Gln
                325                 330

<210> SEQ ID NO 62
<211> LENGTH: 4
<212> TYPE: PRT
<213> ORGANISM: Homo sapiens

<400> SEQUENCE: 62

Gly Gly Ser Gly
1

<210> SEQ ID NO 63
<211> LENGTH: 4
<212> TYPE: PRT
<213> ORGANISM: Homo sapiens

<400> SEQUENCE: 63

Gly Gly Gly Ser
1

<210> SEQ ID NO 64
<211> LENGTH: 5
<212> TYPE: PRT
```

<213> ORGANISM: Homo sapiens

<400> SEQUENCE: 64

Gly Gly Gly Gly Ser
1               5

<210> SEQ ID NO 65
<211> LENGTH: 4
<212> TYPE: PRT
<213> ORGANISM: Homo sapiens

<400> SEQUENCE: 65

Gly Ser Ala Thr
1

<210> SEQ ID NO 66
<211> LENGTH: 96
<212> TYPE: PRT
<213> ORGANISM: Mus musculus

<400> SEQUENCE: 66

Leu Leu Leu Gln Arg Arg Val Thr Val Arg Lys Ala Asp Ala Gly
1               5                   10                  15

Gly Leu Gly Ile Ser Ile Lys Gly Gly Arg Glu Asn Lys Met Pro Ile
            20                  25                  30

Leu Ile Ser Lys Ile Phe Lys Gly Leu Ala Ala Asp Gln Thr Glu Ala
        35                  40                  45

Leu Phe Val Gly Asp Ala Ile Leu Ser Val Asn Gly Glu Asp Leu Ser
    50                  55                  60

Ser Ala Thr His Asp Glu Ala Val Gln Ala Leu Lys Lys Thr Gly Lys
65                  70                  75                  80

Glu Val Val Leu Glu Val Lys Tyr Met Lys Gln Val Ser Pro Tyr Phe
                85                  90                  95

<210> SEQ ID NO 67
<211> LENGTH: 96
<212> TYPE: PRT
<213> ORGANISM: Homo sapiens

<400> SEQUENCE: 67

Leu Leu Leu Gln Arg Arg Val Thr Val Arg Lys Ala Asp Ala Gly
1               5                   10                  15

Gly Leu Gly Ile Ser Ile Lys Gly Gly Arg Glu Asn Lys Met Pro Ile
            20                  25                  30

Leu Ile Ser Lys Ile Phe Lys Gly Leu Ala Ala Asp Gln Thr Glu Ala
        35                  40                  45

Leu Phe Val Gly Asp Ala Ile Leu Ser Val Asn Gly Glu Asp Leu Ser
    50                  55                  60

Ser Ala Thr His Asp Glu Ala Val Gln Val Leu Lys Lys Thr Gly Lys
65                  70                  75                  80

Glu Val Val Leu Glu Val Lys Tyr Met Lys Asp Val Ser Pro Tyr Phe
                85                  90                  95